US011872337B2

(12) United States Patent
Wyeth et al.

(10) Patent No.: US 11,872,337 B2
(45) Date of Patent: Jan. 16, 2024

(54) FLUID PREPARATION AND TREATMENT DEVICES METHODS AND SYSTEMS

(71) Applicant: NxStage Medical, Inc., Lawrence, MA (US)

(72) Inventors: Mark T. Wyeth, Andover, MA (US); Gregory Yantz, Boxford, MA (US); Ciro A. de la Vega, Amesbury, MA (US)

(73) Assignee: NxStage Medical, Inc., Lawrence, MA (US)

( * ) Notice: Subject to any disclaimer, the term of this patent is extended or adjusted under 35 U.S.C. 154(b) by 711 days.

(21) Appl. No.: 16/288,725

(22) Filed: Feb. 28, 2019

(65) Prior Publication Data

US 2019/0262522 A1 Aug. 29, 2019

Related U.S. Application Data

(60) Provisional application No. 62/676,098, filed on May 24, 2018, provisional application No. 62/636,404, filed on Feb. 28, 2018.

(51) Int. Cl.
*A61M 1/28* (2006.01)
*A61M 1/16* (2006.01)
(Continued)

(52) U.S. Cl.
CPC ............ *A61M 1/287* (2013.01); *A61M 1/154* (2022.05); *A61M 1/155* (2022.05); *A61M 1/156* (2022.05);
(Continued)

(58) Field of Classification Search
CPC ........ A61M 1/28; A61M 1/284; A61M 1/287; A61M 1/288; A61M 1/1664;
(Continued)

(56) References Cited

U.S. PATENT DOCUMENTS 2,369,070 A 2/1945 Nielsen
2,575,447 A 11/1951 Gossick
(Continued)

FOREIGN PATENT DOCUMENTS

CA 2544144 10/2012
CA 2791816 12/2013
(Continued)

OTHER PUBLICATIONS

English language abstract for Swedish application publication No. SE 198300739 A, published Aug. 13, 1983.
(Continued)

*Primary Examiner* — Krishnan S Menon
(74) *Attorney, Agent, or Firm* — Potomac Law Group, PLLC

(57) ABSTRACT

Methods, device, and systems for preparing peritoneal dialysis fluid and/or administering a peritoneal dialysis treatment are disclosed. In embodiments, peritoneal dialysis fluid is prepared at a point of use automatically using a daily sterile disposable fluid circuit and one or more long-term concentrate containers that are changed only after multiple days (e.g. weekly). The daily disposable may have concentrate containers that are initially empty and are filled from the long-term concentrate containers once per day at the beginning of a treatment.

3 Claims, 57 Drawing Sheets

(51) Int. Cl.
*A61M 1/26* (2006.01)
*A61M 1/14* (2006.01)
*C02F 1/44* (2023.01)
*C02F 103/02* (2006.01)

(52) U.S. Cl.
CPC .......... *A61M 1/159* (2022.05); *A61M 1/1524* (2022.05); *A61M 1/1562* (2022.05); *A61M 1/1565* (2022.05); *A61M 1/1664* (2014.02); *A61M 1/1666* (2014.02); *A61M 1/1672* (2014.02); *A61M 1/1674* (2014.02); *A61M 1/1696* (2013.01); *A61M 1/267* (2014.02); *A61M 1/28* (2013.01); *A61M 1/288* (2014.02); *A61M 2205/05* (2013.01); *A61M 2205/12* (2013.01); *A61M 2205/126* (2013.01); *A61M 2205/127* (2013.01); *A61M 2205/128* (2013.01); *A61M 2205/215* (2013.01); *A61M 2205/3334* (2013.01); *A61M 2205/3344* (2013.01); *A61M 2205/3569* (2013.01); *A61M 2205/702* (2013.01); *A61M 2205/8212* (2013.01); *C02F 1/444* (2013.01); *C02F 2103/026* (2013.01); *C02F 2201/005* (2013.01); *C02F 2209/03* (2013.01)

(58) Field of Classification Search
CPC .............. A61M 1/1666; A61M 1/1672; A61M 1/1674; A61M 1/1696; A61M 2205/12; A61M 2205/126; A61M 2205/127; A61M 2205/128
See application file for complete search history.

(56) References Cited

U.S. PATENT DOCUMENTS

| | | |
|---|---|---|
| 2,874,351 A | 2/1959 | John |
| 3,490,591 A | 1/1970 | Jones et al. |
| 3,526,834 A | 9/1970 | Brown |
| 3,786,810 A | 1/1974 | Pannier et al. |
| 3,847,809 A | 11/1974 | Kopf |
| 4,138,639 A | 2/1979 | Hutchins |
| 4,161,264 A | 7/1979 | Malmgren et al. |
| 4,209,391 A | 6/1980 | Lipps et al. |
| 4,338,190 A | 7/1982 | Kraus et al. |
| 4,396,382 A | 8/1983 | Goldhaber |
| 4,412,834 A | 11/1983 | Kulin et al. |
| 4,420,752 A | 12/1983 | Davis et al. |
| 4,432,759 A | 2/1984 | Gross et al. |
| 4,432,765 A | 2/1984 | Oscarsson |
| 4,435,171 A | 3/1984 | Goldberg et al. |
| 4,439,179 A | 3/1984 | Lueders et al. |
| 4,439,188 A | 3/1984 | Dennehey et al. |
| 4,440,207 A | 4/1984 | Genatempo et al. |
| 4,447,230 A | 5/1984 | Gula et al. |
| 4,479,760 A | 10/1984 | Bilstad et al. |
| 4,489,535 A | 12/1984 | Veltman |
| 4,526,572 A | 7/1985 | Donnan et al. |
| 4,553,552 A | 11/1985 | Valdespino et al. |
| 4,585,436 A | 4/1986 | Davis et al. |
| 4,605,895 A | 8/1986 | Park |
| 4,617,115 A | 10/1986 | Vantard |
| 4,618,343 A | 10/1986 | Polaschegg |
| 4,636,204 A | 1/1987 | Christopherson et al. |
| 4,655,742 A | 4/1987 | Vantard |
| 4,657,529 A | 4/1987 | Prince et al. |
| 4,663,006 A | 5/1987 | Yao et al. |
| 4,670,007 A | 6/1987 | Wheeldon et al. |
| 4,702,829 A | 10/1987 | Polaschegg et al. |
| 4,747,822 A | 5/1988 | Peabody |
| 4,747,950 A | 5/1988 | Guinn |
| 4,797,191 A | 1/1989 | Metzner et al. |
| 4,823,833 A | 4/1989 | Hogan et al. |
| 4,825,168 A | 4/1989 | Ogawa et al. |
| 4,846,950 A | 7/1989 | Yao et al. |
| 4,857,199 A | 8/1989 | Cortial |
| 4,876,515 A | 10/1989 | Ball |
| 4,954,782 A | 9/1990 | Ball |
| 4,997,570 A | 3/1991 | Polaschegg |
| 5,004,535 A | 4/1991 | Bosko et al. |
| 5,062,774 A | 11/1991 | Kramer et al. |
| 5,087,245 A | 2/1992 | Doan |
| 5,141,493 A | 8/1992 | Jacobsen et al. |
| 5,225,783 A | 7/1993 | Suzuki et al. |
| 5,326,476 A | 7/1994 | Grogan et al. |
| 5,336,173 A | 8/1994 | Folden |
| 5,344,392 A | 9/1994 | Senninger et al. |
| 5,346,472 A | 9/1994 | Keshaviah et al. |
| 5,442,969 A | 8/1995 | Troutner et al. |
| 5,485,083 A | 1/1996 | Pulice |
| 5,486,286 A | 1/1996 | Peterson et al. |
| 5,522,998 A | 6/1996 | Polaschegg |
| 5,567,320 A | 10/1996 | Goux et al. |
| 5,570,026 A | 10/1996 | Buffaloe, IV et al. |
| 5,628,908 A | 5/1997 | Kamen et al. |
| 5,631,552 A | 5/1997 | Ogawa et al. |
| 5,650,071 A | 7/1997 | Brugger et al. |
| 5,674,390 A | 10/1997 | Matthews et al. |
| 5,725,773 A | 3/1998 | Polaschegg |
| 5,800,383 A | 9/1998 | Chandler et al. |
| 5,836,933 A | 11/1998 | Buttitta et al. |
| 5,865,764 A | 2/1999 | Moorhead |
| 5,895,578 A | 4/1999 | Simard et al. |
| 5,900,136 A | 5/1999 | Gotsu et al. |
| 5,925,011 A | 7/1999 | Faict et al. |
| 5,932,110 A | 8/1999 | Shah et al. |
| 5,938,634 A | 8/1999 | Packard |
| 5,945,449 A | 8/1999 | Purcell et al. |
| 6,036,680 A | 3/2000 | Horne et al. |
| 6,129,699 A | 10/2000 | Haight et al. |
| 6,136,201 A | 10/2000 | Shah et al. |
| 6,139,754 A | 10/2000 | Hartranft et al. |
| 6,156,797 A | 12/2000 | Kubo et al. |
| 6,168,578 B1 | 1/2001 | Diamond |
| 6,196,991 B1 | 3/2001 | Keilman |
| 6,228,047 B1 | 5/2001 | Dadson |
| 6,241,943 B1 | 6/2001 | Wieslander et al. |
| 6,254,567 B1 | 7/2001 | Treu et al. |
| 6,270,673 B1 | 8/2001 | Belt et al. |
| 6,280,634 B1 | 8/2001 | Shah et al. |
| 6,327,895 B1 | 12/2001 | Jeppsson et al. |
| 6,391,404 B1 | 5/2002 | Rosenbaum et al. |
| 6,409,699 B1 | 6/2002 | Ash |
| 6,423,029 B1 | 7/2002 | Elsberry |
| 6,460,592 B1 | 10/2002 | Sano et al. |
| 6,463,979 B1 | 10/2002 | Sano et al. |
| 6,471,855 B1 | 10/2002 | Odak et al. |
| 6,488,647 B1 | 12/2002 | Miura et al. |
| 6,489,785 B2 | 12/2002 | McAllister |
| 6,491,658 B1 | 12/2002 | Miura et al. |
| 6,492,336 B1 | 12/2002 | Mahiout |
| 6,503,062 B1 | 1/2003 | Gray et al. |
| 6,537,976 B1 | 3/2003 | Gupta |
| 6,585,682 B1 | 7/2003 | Haraldsson et al. |
| 6,591,126 B2 | 7/2003 | Roeper et al. |
| 6,595,948 B2 | 7/2003 | Suzuki et al. |
| 6,605,214 B1 | 8/2003 | Taylor |
| 6,610,206 B1 | 8/2003 | Callan et al. |
| 6,626,862 B1 | 9/2003 | Duchon et al. |
| 6,645,191 B1 | 11/2003 | Knerr et al. |
| 6,648,906 B2 | 11/2003 | Lasheras et al. |
| 6,666,842 B1 | 12/2003 | Sakai |
| 6,689,275 B1 | 2/2004 | Gupta |
| 6,705,372 B2 | 3/2004 | Sano et al. |
| 6,738,052 B1 | 5/2004 | Manke et al. |
| 6,749,580 B2 | 6/2004 | Work et al. |
| 6,758,975 B2 | 7/2004 | Peabody et al. |
| 6,769,231 B2 | 8/2004 | Danby |
| 6,803,363 B2 | 10/2004 | Polaschegg |
| 6,808,369 B2 | 10/2004 | Gray et al. |
| 6,814,869 B2 | 11/2004 | Brandl et al. |
| 6,861,033 B2 | 3/2005 | Mullins et al. |
| 6,877,713 B1 | 4/2005 | Gray et al. |

(56) References Cited

U.S. PATENT DOCUMENTS

| | | |
|---|---|---|
| 6,887,214 B1 | 5/2005 | Levin |
| 6,889,713 B2 | 5/2005 | Navis |
| 6,911,014 B2 | 6/2005 | Wentling et al. |
| 6,912,917 B2 | 7/2005 | Brugger et al. |
| 6,929,751 B2 | 8/2005 | Bowman et al. |
| 6,981,977 B2 | 1/2006 | Herweck et al. |
| 6,986,752 B2 | 1/2006 | McGuckin et al. |
| 6,995,563 B2 | 2/2006 | Talutis |
| 7,013,928 B2 | 3/2006 | Navis |
| 7,033,539 B2 | 4/2006 | Krensky et al. |
| 7,053,059 B2 | 5/2006 | Zieske et al. |
| 7,057,400 B2 | 6/2006 | Gaignet |
| 7,067,061 B2 | 6/2006 | Bosetto et al. |
| 7,083,719 B2 | 8/2006 | Bowman et al. |
| 7,119,305 B2 | 10/2006 | Sano et al. |
| 7,138,088 B2 | 11/2006 | Wariar et al. |
| 7,175,606 B2 | 2/2007 | Bowman, Jr. et al. |
| 7,214,228 B2 | 5/2007 | Crabtree |
| 7,235,589 B2 | 6/2007 | Hausheer |
| 7,243,893 B2 | 7/2007 | Sobue et al. |
| 7,250,619 B2 | 7/2007 | Taylor et al. |
| 7,320,676 B2 | 1/2008 | Miesel |
| 7,354,190 B2 | 4/2008 | Demers et al. |
| 7,410,475 B2 | 8/2008 | Krensky et al. |
| 7,421,316 B2 | 9/2008 | Gray et al. |
| 7,441,108 B2 | 10/2008 | Fisher et al. |
| 7,459,054 B2 | 12/2008 | Landherr et al. |
| 7,544,301 B2 | 6/2009 | Shah et al. |
| 7,559,483 B2 | 7/2009 | Hickle et al. |
| 7,559,524 B2 | 7/2009 | Gray et al. |
| 7,559,913 B1 | 7/2009 | Jeppsson et al. |
| 7,641,753 B2 | 1/2010 | Gao et al. |
| 7,670,491 B2 | 3/2010 | Callan et al. |
| 7,686,279 B2 | 3/2010 | Nerbonne et al. |
| 7,758,552 B2 | 7/2010 | Zoltan et al. |
| 7,763,013 B2 | 7/2010 | Baldwin et al. |
| 7,803,628 B2 | 9/2010 | Glocker |
| 7,837,666 B2 | 11/2010 | Jensen et al. |
| 7,842,002 B2 | 11/2010 | Mantle |
| 7,847,564 B2 | 12/2010 | Rossi |
| 7,857,805 B2 | 12/2010 | Raines |
| 7,862,530 B2 | 1/2011 | Callan et al. |
| 7,867,214 B2 | 1/2011 | Childers et al. |
| 7,883,725 B2 | 2/2011 | Shah et al. |
| 7,892,423 B2 | 2/2011 | Rohde et al. |
| 7,901,376 B2 | 3/2011 | Steck et al. |
| 7,905,853 B2 | 3/2011 | Chapman et al. |
| 7,905,855 B2 | 3/2011 | Childers |
| 7,935,074 B2 | 5/2011 | Plahey et al. |
| 7,955,295 B2 | 6/2011 | Lee et al. |
| 7,988,469 B2 | 8/2011 | Biewer et al. |
| 7,993,050 B2 | 8/2011 | Demers et al. |
| 8,034,017 B2 | 10/2011 | Petersen |
| 8,083,709 B2 | 12/2011 | Childers et al. |
| 8,088,094 B2 | 1/2012 | Hamada et al. |
| 8,096,969 B2 | 1/2012 | Roberts et al. |
| 8,105,487 B2 | 1/2012 | Fulkerson et al. |
| 8,147,696 B1 | 4/2012 | Pandya |
| 8,178,040 B2 | 5/2012 | Brauer |
| 8,202,547 B2 | 6/2012 | Shah et al. |
| 8,222,229 B2 | 7/2012 | Kiribayashi et al. |
| 8,246,826 B2 | 8/2012 | Wilt et al. |
| 8,287,724 B2 | 10/2012 | Slepicka et al. |
| 8,297,954 B2 | 10/2012 | Moubayed |
| 8,298,167 B2 | 10/2012 | Peters et al. |
| 8,298,170 B2 | 10/2012 | Lundtveit et al. |
| 8,308,128 B2 | 11/2012 | Mackal |
| 8,348,904 B2 | 1/2013 | Petersen |
| 8,361,009 B2 | 1/2013 | Lee et al. |
| 8,367,731 B2 | 2/2013 | Wieslander et al. |
| 8,375,797 B2 | 2/2013 | Beden et al. |
| 8,382,447 B2 | 2/2013 | Wang et al. |
| 8,393,690 B2 | 3/2013 | Grant et al. |
| 8,398,590 B2 | 3/2013 | Sternberg et al. |
| 8,414,686 B2 | 4/2013 | Gura et al. |
| 8,414,768 B2 | 4/2013 | Shah et al. |
| 8,431,086 B2 | 4/2013 | Lurvey et al. |
| 8,444,593 B2 | 5/2013 | Hamada et al. |
| 8,449,496 B2 | 5/2013 | Hamada et al. |
| 8,460,544 B2 | 6/2013 | Völker |
| 8,474,784 B2 | 7/2013 | Kashmirian et al. |
| 8,491,184 B2 | 7/2013 | Kamen et al. |
| 8,500,676 B2 | 8/2013 | Jansson et al. |
| 8,501,009 B2 | 8/2013 | Peterson et al. |
| 8,516,902 B2 | 8/2013 | Beavis et al. |
| 8,529,496 B2 | 9/2013 | Britton et al. |
| 8,540,886 B2 | 9/2013 | Hedmann et al. |
| 8,556,225 B2 | 10/2013 | Gray |
| 8,560,510 B2 | 10/2013 | Brueggerhoff et al. |
| 8,587,516 B2 | 11/2013 | Kopychev et al. |
| 8,597,229 B2 | 12/2013 | Pan |
| 8,600,772 B2 | 12/2013 | Bacon |
| 8,613,739 B2 | 12/2013 | Sobue |
| 8,641,685 B2 | 2/2014 | Mansour et al. |
| 8,671,996 B2 | 3/2014 | Weilhoefer et al. |
| 8,678,224 B2 | 3/2014 | D'Ayot et al. |
| 8,685,251 B2 | 4/2014 | Smejtek et al. |
| 8,698,741 B1 | 4/2014 | Wang et al. |
| 8,708,992 B2 | 4/2014 | Kobayashi et al. |
| 8,728,056 B2 | 5/2014 | Colantonio et al. |
| 8,731,726 B2 | 5/2014 | Gray et al. |
| 8,740,864 B2 | 6/2014 | Hoang et al. |
| 8,741,131 B2 | 6/2014 | Bedingfield et al. |
| 8,747,370 B2 | 6/2014 | Feith et al. |
| 8,758,626 B2 | 6/2014 | Wong |
| 8,764,702 B2 | 7/2014 | Childers et al. |
| 8,774,885 B2 | 7/2014 | Abreu |
| 8,777,892 B2 | 7/2014 | Sandford et al. |
| 8,789,558 B2 | 7/2014 | Volker |
| 8,801,652 B2 | 8/2014 | Landherr et al. |
| 8,801,677 B2 | 8/2014 | Wallin |
| 8,808,595 B2 | 8/2014 | Babrowicz et al. |
| 8,813,769 B2 | 8/2014 | Gastauer et al. |
| 8,815,095 B2 | 8/2014 | Micheli |
| 8,828,232 B2 | 9/2014 | Shah et al. |
| 8,834,718 B2 | 9/2014 | Randall et al. |
| 8,834,719 B2 | 9/2014 | Childers et al. |
| 8,838,395 B2 | 9/2014 | Matsiev et al. |
| 8,840,581 B2 | 9/2014 | McGill et al. |
| 8,858,792 B2 | 10/2014 | Ding et al. |
| 8,869,612 B2 | 10/2014 | Chen et al. |
| 8,870,812 B2 | 10/2014 | Alberti et al. |
| 8,875,748 B2 | 11/2014 | Beden et al. |
| 8,876,753 B2 | 11/2014 | Roberts et al. |
| 8,882,700 B2 | 11/2014 | Chapman et al. |
| 8,924,458 B2 | 12/2014 | Levin et al. |
| 8,926,550 B2 | 1/2015 | Plahey et al. |
| 8,926,551 B2 | 1/2015 | Lo et al. |
| 8,930,213 B2 | 1/2015 | Gotlib et al. |
| 8,945,042 B2 | 2/2015 | Lee et al. |
| 8,961,444 B2 | 2/2015 | Chapman et al. |
| 8,961,466 B2 | 2/2015 | Steinbach |
| 8,980,070 B2 | 3/2015 | Nishio et al. |
| 8,989,906 B2 | 3/2015 | Gray et al. |
| 8,992,454 B2 | 3/2015 | Anand |
| 8,992,777 B2 | 3/2015 | Doyle |
| 9,004,886 B2 | 4/2015 | Beck et al. |
| 9,014,775 B2 | 4/2015 | Bennett et al. |
| 9,022,969 B2 | 5/2015 | Helmore et al. |
| 9,044,544 B2 | 6/2015 | Lo et al. |
| 9,060,727 B2 | 6/2015 | Saikley et al. |
| 9,066,968 B2 | 6/2015 | Ohta et al. |
| 9,067,017 B2 | 6/2015 | Tan et al. |
| 9,069,886 B2 | 6/2015 | Shimizu et al. |
| 9,108,031 B2 | 8/2015 | Brandenburger et al. |
| 9,112,245 B2 | 8/2015 | Yen |
| 9,132,220 B2 | 9/2015 | Kugelmann et al. |
| 9,138,523 B2 | 9/2015 | Burnett et al. |
| 9,152,918 B1 | 10/2015 | McNair |
| 9,153,002 B2 | 10/2015 | Jones et al. |
| 9,162,044 B2 | 10/2015 | Traversaz |
| 9,165,112 B2 | 10/2015 | Doyle et al. |
| 9,180,238 B2 | 11/2015 | Bedingfield et al. |
| 9,198,830 B2 | 12/2015 | Kugelmann et al. |

(56) References Cited

U.S. PATENT DOCUMENTS

| | | |
|---|---|---|
| 9,199,070 B2 | 12/2015 | Wegener et al. |
| 9,216,247 B2 | 12/2015 | Callan et al. |
| 9,217,702 B2 | 12/2015 | Sullivan |
| 9,242,035 B2 | 1/2016 | Karoor |
| 9,254,356 B2 | 2/2016 | Shah et al. |
| 9,254,358 B2 | 2/2016 | Volker |
| 9,274,073 B2 | 3/2016 | Nier et al. |
| 9,284,960 B2 | 3/2016 | Chappel et al. |
| 9,308,309 B2 | 4/2016 | Hedmann et al. |
| 9,310,232 B2 | 4/2016 | Heide et al. |
| 9,319,110 B2 | 4/2016 | Kopychev et al. |
| 9,320,680 B2 | 4/2016 | Schröder |
| 9,345,871 B2 | 5/2016 | Guala |
| 9,358,332 B2 | 6/2016 | McGill et al. |
| 9,381,290 B2 | 7/2016 | Yu et al. |
| 9,393,356 B2 | 7/2016 | Karoor et al. |
| 9,408,958 B2 | 8/2016 | Wang et al. |
| 9,427,518 B2 | 8/2016 | Brueckner |
| 9,433,768 B2 | 9/2016 | Tekeste et al. |
| 9,440,016 B2 | 9/2016 | Lin et al. |
| 9,440,019 B2 | 9/2016 | Falkenhagen et al. |
| 9,470,220 B2 | 10/2016 | Becker |
| 9,471,754 B2 | 10/2016 | Mastalli et al. |
| 9,474,841 B2 | 10/2016 | Volker |
| 9,495,511 B2 | 11/2016 | Harrington et al. |
| 9,500,188 B2 | 11/2016 | Ly et al. |
| 9,514,131 B1 | 12/2016 | Bochenko et al. |
| 9,519,969 B1 | 12/2016 | Kusens |
| 9,539,387 B2 | 1/2017 | Fini et al. |
| 9,555,232 B2 | 1/2017 | Davis et al. |
| 9,593,679 B2 | 3/2017 | Gray et al. |
| 9,610,518 B2 | 4/2017 | Kamen et al. |
| 9,616,163 B2 | 4/2017 | Wong et al. |
| 9,629,993 B2 | 4/2017 | Klewinghaus |
| 9,651,511 B2 | 5/2017 | Howell et al. |
| 9,669,145 B2 | 6/2017 | Günther et al. |
| 9,677,555 B2 | 6/2017 | Kamen et al. |
| 9,687,646 B2 | 6/2017 | Sobue et al. |
| 9,694,125 B2 | 7/2017 | Plahey et al. |
| 9,694,126 B2 | 7/2017 | Hedmann et al. |
| 9,700,711 B2 | 7/2017 | Grant et al. |
| 9,724,270 B2 | 8/2017 | Bonnal et al. |
| 9,724,298 B2 | 8/2017 | Nilsson et al. |
| 9,724,505 B2 | 8/2017 | Williams et al. |
| 10,973,968 B2 | 4/2021 | Rohde |
| 2001/0005487 A1 | 6/2001 | Kamibayashi et al. |
| 2002/0045851 A1 | 4/2002 | Suzuki et al. |
| 2002/0072718 A1 | 6/2002 | Brugger et al. |
| 2002/0087126 A1 | 7/2002 | Quah |
| 2002/0120227 A1 | 8/2002 | Childers et al. |
| 2002/0123715 A1 | 9/2002 | Sorenson et al. |
| 2002/0162778 A1 | 11/2002 | Peabody et al. |
| 2003/0065284 A1 | 4/2003 | Briggs |
| 2003/0086794 A1 | 5/2003 | Gray et al. |
| 2003/0143352 A1 | 7/2003 | Yang et al. |
| 2003/0153865 A1 | 8/2003 | Connell et al. |
| 2003/0217976 A1 | 11/2003 | Bowman et al. |
| 2003/0218623 A1 | 11/2003 | Krensky et al. |
| 2004/0019312 A1 | 1/2004 | Childers et al. |
| 2004/0031756 A1 | 2/2004 | Suzuki et al. |
| 2004/0040620 A1 | 3/2004 | Brauer et al. |
| 2004/0078024 A1 | 4/2004 | Peluso et al. |
| 2004/0087890 A1 | 5/2004 | Sakai |
| 2004/0099521 A1 | 5/2004 | Demers et al. |
| 2004/0108223 A1 | 6/2004 | Jansson |
| 2004/0111294 A1 | 6/2004 | McNally et al. |
| 2004/0215129 A1 | 10/2004 | Edgson et al. |
| 2004/0215336 A1 | 10/2004 | Udipi et al. |
| 2004/0221643 A1 | 11/2004 | Ehwald et al. |
| 2004/0254513 A1 | 12/2004 | Shang et al. |
| 2005/0006296 A1 | 1/2005 | Sullivan et al. |
| 2005/0020507 A1 | 1/2005 | Zieske et al. |
| 2005/0082226 A1 | 4/2005 | Bene et al. |
| 2005/0089994 A1 | 4/2005 | Neftel |
| 2005/0094483 A1 | 5/2005 | Demers et al. |
| 2005/0094485 A1 | 5/2005 | Demers et al. |
| 2005/0095154 A1 | 5/2005 | Tracey et al. |
| 2005/0126998 A1 | 6/2005 | Childers |
| 2005/0131141 A1 | 6/2005 | Poss et al. |
| 2005/0167363 A1 | 8/2005 | Taylor |
| 2005/0173344 A1 | 8/2005 | Bowman et al. |
| 2005/0202395 A1 | 9/2005 | Edrich et al. |
| 2005/0209563 A1 | 9/2005 | Hopping et al. |
| 2005/0211373 A1 | 9/2005 | Tomasetti et al. |
| 2005/0224372 A1 | 10/2005 | Sasso et al. |
| 2005/0244909 A1 | 11/2005 | Hamada et al. |
| 2005/0283132 A1 | 12/2005 | Stanus et al. |
| 2006/0005886 A1 | 1/2006 | Parrino et al. |
| 2006/0015015 A1 | 1/2006 | Kawamoto et al. |
| 2006/0161107 A1 | 7/2006 | Mantle |
| 2006/0172954 A1 | 8/2006 | Jensen et al. |
| 2006/0189923 A1 | 8/2006 | Neftel et al. |
| 2006/0195064 A1 | 8/2006 | Plahey et al. |
| 2007/0007208 A1 | 1/2007 | Brugger et al. |
| 2007/0043317 A1 | 2/2007 | Sugawara |
| 2007/0048161 A1 | 3/2007 | Moubayed |
| 2007/0088314 A1 | 4/2007 | Gollier et al. |
| 2007/0106197 A1 | 5/2007 | Lauman et al. |
| 2007/0106247 A1 | 5/2007 | Burnett et al. |
| 2007/0112297 A1 | 5/2007 | Plahey et al. |
| 2007/0149913 A1 | 6/2007 | Busby et al. |
| 2007/0179422 A1 | 8/2007 | Schnell et al. |
| 2007/0194792 A1 | 8/2007 | Quackenbush et al. |
| 2007/0213651 A1 | 9/2007 | Busby et al. |
| 2007/0213654 A1 | 9/2007 | Lundtveit et al. |
| 2007/0213665 A1 | 9/2007 | Curtin et al. |
| 2007/0253463 A1 | 11/2007 | Perry et al. |
| 2007/0276328 A1 | 11/2007 | Childers et al. |
| 2007/0287966 A1 | 12/2007 | Keeley |
| 2008/0015492 A1 | 1/2008 | Biesel |
| 2008/0023135 A1 | 1/2008 | Ivansons et al. |
| 2008/0027374 A1 | 1/2008 | Jensen et al. |
| 2008/0031746 A9 | 2/2008 | Gray et al. |
| 2008/0058712 A1 | 3/2008 | Plahey |
| 2008/0065006 A1 | 3/2008 | Roger et al. |
| 2008/0097283 A1 | 4/2008 | Plahey |
| 2008/0101969 A1 | 5/2008 | Moubayed |
| 2008/0112258 A1 | 5/2008 | Demers et al. |
| 2008/0125693 A1 | 5/2008 | Gavin et al. |
| 2008/0138223 A1 | 6/2008 | Lanigan et al. |
| 2008/0161751 A1 | 7/2008 | Plahey et al. |
| 2008/0183126 A1 | 7/2008 | Landherr et al. |
| 2008/0183127 A1 | 7/2008 | Landherr et al. |
| 2008/0200865 A1 | 8/2008 | Bedingfield |
| 2008/0200866 A1 | 8/2008 | Prisco et al. |
| 2008/0200867 A1 | 8/2008 | Bedingfield |
| 2008/0200868 A1 | 8/2008 | Alberti et al. |
| 2008/0200869 A1 | 8/2008 | Bedingfield |
| 2008/0208195 A1 | 8/2008 | Shores et al. |
| 2008/0216898 A1 | 9/2008 | Grant et al. |
| 2008/0230450 A1 | 9/2008 | Burbank et al. |
| 2008/0240929 A1 | 10/2008 | Kamen et al. |
| 2008/0243211 A1 | 10/2008 | Cartwright et al. |
| 2008/0253427 A1 | 10/2008 | Kamen et al. |
| 2008/0253911 A1 | 10/2008 | Demers et al. |
| 2008/0273996 A1 | 11/2008 | Gray et al. |
| 2008/0275382 A1 | 11/2008 | Biesel et al. |
| 2009/0007642 A1 | 1/2009 | Busby et al. |
| 2009/0008306 A1 | 1/2009 | Cicchello et al. |
| 2009/0009290 A1 | 1/2009 | Kneip et al. |
| 2009/0012447 A1 | 1/2009 | Huitt et al. |
| 2009/0012451 A1 | 1/2009 | Sobue et al. |
| 2009/0012452 A1 | 1/2009 | Slepicka et al. |
| 2009/0012453 A1 | 1/2009 | Childers et al. |
| 2009/0012455 A1 | 1/2009 | Childers et al. |
| 2009/0012458 A1 | 1/2009 | Childers et al. |
| 2009/0012460 A1 | 1/2009 | Steck et al. |
| 2009/0012464 A1 | 1/2009 | Martin et al. |
| 2009/0024096 A1 | 1/2009 | Hai et al. |
| 2009/0054873 A1 | 2/2009 | Landherr et al. |
| 2009/0078592 A1 | 3/2009 | Jensen et al. |
| 2009/0082758 A1 | 3/2009 | Gill et al. |
| 2009/0095679 A1 | 4/2009 | Demers et al. |
| 2009/0098215 A1 | 4/2009 | Riser et al. |

(56) References Cited

U.S. PATENT DOCUMENTS

| | | |
|---|---|---|
| 2009/0101549 A1 | 4/2009 | Kamen et al. |
| 2009/0112151 A1 | 4/2009 | Chapman et al. |
| 2009/0143723 A1 | 6/2009 | Szpara et al. |
| 2009/0149810 A1 | 6/2009 | Ring et al. |
| 2009/0169872 A1 | 7/2009 | Krongauz et al. |
| 2009/0173682 A1 | 7/2009 | Robinson et al. |
| 2009/0177149 A1 | 7/2009 | Childers et al. |
| 2009/0182263 A1 | 7/2009 | Burbank et al. |
| 2009/0185920 A1 | 7/2009 | Lanigan et al. |
| 2009/0196776 A1 | 8/2009 | Moubayed |
| 2009/0198170 A1 | 8/2009 | Childers et al. |
| 2009/0206023 A1 | 8/2009 | Rohde et al. |
| 2009/0212178 A1 | 8/2009 | Westberg |
| 2009/0213521 A1 | 8/2009 | Bedingfield |
| 2009/0218290 A1 | 9/2009 | Poss et al. |
| 2009/0222119 A1 | 9/2009 | Plahey et al. |
| 2009/0223899 A1 | 9/2009 | Poss et al. |
| 2009/0232908 A1 | 9/2009 | Zhou |
| 2009/0264854 A1 | 10/2009 | Jensen et al. |
| 2009/0275881 A1 | 11/2009 | Lo et al. |
| 2009/0275883 A1 | 11/2009 | Chapman et al. |
| 2009/0277276 A1 | 11/2009 | Evering et al. |
| 2009/0294339 A1 | 12/2009 | Biewer et al. |
| 2009/0295591 A1 | 12/2009 | Bedingfield |
| 2009/0299272 A1 | 12/2009 | Hopping et al. |
| 2009/0299273 A1 | 12/2009 | Lee et al. |
| 2010/0004588 A1 | 1/2010 | Yeh et al. |
| 2010/0004589 A1 | 1/2010 | Hedmann et al. |
| 2010/0004590 A1 | 1/2010 | Hedmann et al. |
| 2010/0005416 A1 | 1/2010 | Hedmann et al. |
| 2010/0010423 A1 | 1/2010 | Yu et al. |
| 2010/0010424 A1 | 1/2010 | Yu et al. |
| 2010/0010425 A1 | 1/2010 | Yu et al. |
| 2010/0010426 A1 | 1/2010 | Childers et al. |
| 2010/0010427 A1 | 1/2010 | Yu et al. |
| 2010/0010428 A1 | 1/2010 | Yu et al. |
| 2010/0016802 A1 | 1/2010 | Tambourgi et al. |
| 2010/0019686 A1 | 1/2010 | Gutierrez |
| 2010/0028170 A1 | 2/2010 | Schneeberger et al. |
| 2010/0028208 A1 | 2/2010 | Shekalim et al. |
| 2010/0038322 A1 | 2/2010 | Hedmann et al. |
| 2010/0049158 A1 | 2/2010 | Roger |
| 2010/0051552 A1 | 3/2010 | Rohde et al. |
| 2010/0063445 A1 | 3/2010 | Sternberg et al. |
| 2010/0069817 A1 | 3/2010 | Falkvall et al. |
| 2010/0078387 A1 | 4/2010 | Wong |
| 2010/0084326 A1 | 4/2010 | Takesawa |
| 2010/0087777 A1 | 4/2010 | Hopping et al. |
| 2010/0096329 A1 | 4/2010 | Kotanko et al. |
| 2010/0100027 A1 | 4/2010 | Schilthuizen et al. |
| 2010/0100034 A1 | 4/2010 | Wich-Heiter |
| 2010/0114012 A1 | 5/2010 | Sandford et al. |
| 2010/0129247 A1 | 5/2010 | Lauer |
| 2010/0130918 A1 | 5/2010 | Elahi |
| 2010/0130919 A1 | 5/2010 | Elahi |
| 2010/0133153 A1 | 6/2010 | Beden et al. |
| 2010/0137782 A1 | 6/2010 | Jansson et al. |
| 2010/0168652 A1 | 7/2010 | Landherr et al. |
| 2010/0169513 A1 | 7/2010 | Levin |
| 2010/0185132 A1 | 7/2010 | Han et al. |
| 2010/0187476 A1 | 7/2010 | Yugari et al. |
| 2010/0191180 A1 | 7/2010 | Childers et al. |
| 2010/0191181 A1 | 7/2010 | Childers et al. |
| 2010/0192686 A1 | 8/2010 | Kamen et al. |
| 2010/0197817 A1 | 8/2010 | Bui et al. |
| 2010/0204765 A1 | 8/2010 | Hall et al. |
| 2010/0217178 A1 | 8/2010 | Lo et al. |
| 2010/0217179 A1 | 8/2010 | Lo et al. |
| 2010/0217180 A1 | 8/2010 | Akonur et al. |
| 2010/0222735 A1 | 9/2010 | Plahey et al. |
| 2010/0224492 A1 | 9/2010 | Ding et al. |
| 2010/0229978 A1 | 9/2010 | Zhou |
| 2010/0241062 A1 | 9/2010 | Morris et al. |
| 2010/0252490 A1 | 10/2010 | Fulkerson et al. |
| 2010/0252702 A1 | 10/2010 | Spang et al. |
| 2010/0258690 A1 | 10/2010 | Kleitsch et al. |
| 2010/0296953 A1 | 11/2010 | Gray |
| 2010/0308243 A1 | 12/2010 | Bedingfield |
| 2010/0312174 A1 | 12/2010 | Hoffman |
| 2010/0314314 A1 | 12/2010 | Ding et al. |
| 2010/0326916 A1 | 12/2010 | Wrazel et al. |
| 2010/0331768 A1 | 12/2010 | Hedmann et al. |
| 2011/0000902 A1 | 1/2011 | Hedmann et al. |
| 2011/0004152 A1 | 1/2011 | Brady et al. |
| 2011/0010101 A1 | 1/2011 | Lo et al. |
| 2011/0015610 A1 | 1/2011 | Plahey et al. |
| 2011/0017665 A1 | 1/2011 | Updyke et al. |
| 2011/0034866 A1 | 2/2011 | Zhang et al. |
| 2011/0038755 A1 | 2/2011 | Pesci et al. |
| 2011/0040242 A1 | 2/2011 | Fallon et al. |
| 2011/0040243 A1 | 2/2011 | Busby et al. |
| 2011/0040244 A1 | 2/2011 | Busby et al. |
| 2011/0046533 A1 | 2/2011 | Stefani et al. |
| 2011/0054397 A1 | 3/2011 | Schneeberger |
| 2011/0064608 A1 | 3/2011 | Lee et al. |
| 2011/0085923 A1 | 4/2011 | Gray et al. |
| 2011/0092893 A1 | 4/2011 | Demers et al. |
| 2011/0092895 A1 | 4/2011 | Yardimci et al. |
| 2011/0093294 A1 | 4/2011 | Elahi et al. |
| 2011/0098635 A1 | 4/2011 | Helmore et al. |
| 2011/0105979 A1 | 5/2011 | Schlaeper et al. |
| 2011/0105981 A1 | 5/2011 | Wagner et al. |
| 2011/0114559 A1 | 5/2011 | Fislage et al. |
| 2011/0131058 A1 | 6/2011 | McNally et al. |
| 2011/0132838 A1 | 6/2011 | Curtis et al. |
| 2011/0137236 A1 | 6/2011 | Prisco et al. |
| 2011/0137237 A1 | 6/2011 | Prisco et al. |
| 2011/0138936 A1 | 6/2011 | Collins et al. |
| 2011/0141116 A1 | 6/2011 | Dalesch et al. |
| 2011/0144557 A1 | 6/2011 | Childers et al. |
| 2011/0144569 A1 | 6/2011 | Britton et al. |
| 2011/0158823 A1 | 6/2011 | Wang et al. |
| 2011/0160649 A1 | 6/2011 | Pan |
| 2011/0163033 A1 | 7/2011 | Chapman et al. |
| 2011/0166507 A1 | 7/2011 | Childers et al. |
| 2011/0171713 A1 | 7/2011 | Bluchel et al. |
| 2011/0184339 A1 | 7/2011 | Tan |
| 2011/0184340 A1 | 7/2011 | Tan et al. |
| 2011/0186517 A1 | 8/2011 | Hedmann et al. |
| 2011/0189048 A1 | 8/2011 | Curtis et al. |
| 2011/0190691 A1 | 8/2011 | Cazzini |
| 2011/0192796 A1 | 8/2011 | Smejtek et al. |
| 2011/0196289 A1 | 8/2011 | Plahey et al. |
| 2011/0198350 A1 | 8/2011 | Meisberger et al. |
| 2011/0218486 A1 | 9/2011 | Huitt et al. |
| 2011/0224603 A1 | 9/2011 | Richter |
| 2011/0230822 A1 | 9/2011 | Lee et al. |
| 2011/0249916 A1 | 10/2011 | Herrenbauer et al. |
| 2011/0257124 A1 | 10/2011 | Fenn et al. |
| 2011/0262555 A1 | 10/2011 | Riser et al. |
| 2011/0264042 A1 | 10/2011 | Shang et al. |
| 2011/0266221 A1 | 11/2011 | Ware et al. |
| 2011/0275984 A1 | 11/2011 | Biewer et al. |
| 2011/0284377 A1 | 11/2011 | Rohde |
| 2011/0286167 A1 | 11/2011 | Winkler |
| 2011/0288480 A1 | 11/2011 | Bedingfield et al. |
| 2011/0300231 A1 | 12/2011 | Peterson et al. |
| 2011/0309019 A1 | 12/2011 | Ahrens |
| 2012/0001762 A1 | 1/2012 | Turner et al. |
| 2012/0022440 A1 | 1/2012 | Childers et al. |
| 2012/0029325 A1 | 2/2012 | Neftel |
| 2012/0029937 A1 | 2/2012 | Neftel et al. |
| 2012/0030933 A1 | 2/2012 | Lanigan et al. |
| 2012/0031826 A1 | 2/2012 | Childers et al. |
| 2012/0035533 A1 | 2/2012 | Britton et al. |
| 2012/0058328 A1 | 3/2012 | Tourvieille et al. |
| 2012/0065581 A1 | 3/2012 | Childers et al. |
| 2012/0067805 A1 | 3/2012 | Childers et al. |
| 2012/0071815 A1 | 3/2012 | Childers et al. |
| 2012/0071816 A1 | 3/2012 | Busby et al. |
| 2012/0074060 A1 | 3/2012 | Lass |
| 2012/0078168 A1 | 3/2012 | Veneroni et al. |
| 2012/0082576 A1 | 4/2012 | Beck et al. |
| 2012/0089085 A1 | 4/2012 | Childers et al. |

(56) References Cited

U.S. PATENT DOCUMENTS

| | | |
|---|---|---|
| 2012/0095392 A1 | 4/2012 | Jensen et al. |
| 2012/0105850 A1 | 5/2012 | Slepicka |
| 2012/0116294 A1 | 5/2012 | Boenig et al. |
| 2012/0132574 A1 | 5/2012 | Ware et al. |
| 2012/0145615 A1 | 6/2012 | Rohde et al. |
| 2012/0150102 A1 | 6/2012 | Childers et al. |
| 2012/0179133 A1 | 7/2012 | Bedingfield et al. |
| 2012/0185267 A1 | 7/2012 | Kamen et al. |
| 2012/0185619 A1 | 7/2012 | Levin |
| 2012/0199205 A1 | 8/2012 | Eyrard et al. |
| 2012/0205306 A1 | 8/2012 | Reich et al. |
| 2012/0209169 A1 | 8/2012 | Morris et al. |
| 2012/0211422 A1 | 8/2012 | Thys |
| 2012/0212434 A1 | 8/2012 | Bluemler et al. |
| 2012/0212455 A1 | 8/2012 | Kloeffel |
| 2012/0215151 A1 | 8/2012 | Han et al. |
| 2012/0215159 A1 | 8/2012 | Childers et al. |
| 2012/0226237 A1 | 9/2012 | Russo |
| 2012/0230844 A1 | 9/2012 | Farrell et al. |
| 2012/0232469 A1 | 9/2012 | Medina |
| 2012/0238525 A1 | 9/2012 | Leypoldt et al. |
| 2012/0241367 A1 | 9/2012 | Childers et al. |
| 2012/0248017 A1 | 10/2012 | Beiriger et al. |
| 2012/0259275 A1 | 10/2012 | Jensen et al. |
| 2012/0265145 A1 | 10/2012 | Mefti et al. |
| 2012/0271226 A1 | 10/2012 | Farrell et al. |
| 2012/0271273 A1 | 10/2012 | Childers et al. |
| 2012/0273354 A1 | 11/2012 | Orhan et al. |
| 2012/0283629 A1 | 11/2012 | Childers et al. |
| 2012/0310150 A1 | 12/2012 | Brandl et al. |
| 2012/0318740 A1 | 12/2012 | Ekdahl et al. |
| 2013/0006171 A1 | 1/2013 | Griessmann et al. |
| 2013/0020237 A1 | 1/2013 | Wilt et al. |
| 2013/0030356 A1 | 1/2013 | Ding et al. |
| 2013/0030404 A1 | 1/2013 | Gerlach et al. |
| 2013/0037142 A1 | 2/2013 | Farrell |
| 2013/0037461 A1 | 2/2013 | Biewer et al. |
| 2013/0037465 A1 | 2/2013 | Heyes et al. |
| 2013/0056419 A1 | 3/2013 | Curtis |
| 2013/0072895 A1 | 3/2013 | Kreischer et al. |
| 2013/0075309 A1 | 3/2013 | West et al. |
| 2013/0079705 A1 | 3/2013 | Cazzini |
| 2013/0079706 A1 | 3/2013 | Childers et al. |
| 2013/0085437 A1 | 4/2013 | Deshpande |
| 2013/0085451 A1 | 4/2013 | Sheu |
| 2013/0106609 A1 | 5/2013 | Singh et al. |
| 2013/0126430 A1* | 5/2013 | Kenley ............... B01D 65/02 210/638 |
| 2013/0131581 A1 | 5/2013 | Lundtveit et al. |
| 2013/0131583 A1 | 5/2013 | Chapman et al. |
| 2013/0138037 A1 | 5/2013 | Lee et al. |
| 2013/0150781 A1 | 6/2013 | Busby et al. |
| 2013/0153048 A1 | 6/2013 | Schwalm |
| 2013/0158469 A1 | 6/2013 | Hopping et al. |
| 2013/0165848 A1 | 6/2013 | Sebesta et al. |
| 2013/0167052 A1 | 6/2013 | Niesslein et al. |
| 2013/0172806 A1 | 7/2013 | Griessmann et al. |
| 2013/0177455 A1 | 7/2013 | Kamen et al. |
| 2013/0180905 A1 | 7/2013 | Wong |
| 2013/0186759 A1 | 7/2013 | Lin et al. |
| 2013/0190681 A1 | 7/2013 | Jansson et al. |
| 2013/0193041 A1 | 8/2013 | Rohde |
| 2013/0195792 A1 | 8/2013 | Chan et al. |
| 2013/0204173 A1 | 8/2013 | Kelly et al. |
| 2013/0205873 A1 | 8/2013 | Wagner et al. |
| 2013/0211322 A1 | 8/2013 | Degen et al. |
| 2013/0245530 A1 | 9/2013 | Brandl et al. |
| 2013/0245531 A1 | 9/2013 | Brandl et al. |
| 2013/0248448 A1 | 9/2013 | Shah et al. |
| 2013/0248449 A1 | 9/2013 | Kelly et al. |
| 2013/0263650 A1 | 10/2013 | Nier et al. |
| 2013/0272902 A1 | 10/2013 | Chappel |
| 2013/0277306 A1 | 10/2013 | Chapman et al. |
| 2013/0310726 A1 | 11/2013 | Miller et al. |
| 2013/0310735 A1 | 11/2013 | Yu et al. |
| 2013/0310736 A1 | 11/2013 | Hedmann et al. |
| 2013/0313191 A1* | 11/2013 | Wolf ..................... C02F 9/00 210/638 |
| 2013/0317795 A1 | 11/2013 | Akonur et al. |
| 2013/0324915 A1 | 12/2013 | (Krensky) Britton et al. |
| 2013/0330208 A1 | 12/2013 | Ly et al. |
| 2013/0331774 A1 | 12/2013 | Farrell et al. |
| 2013/0331775 A1 | 12/2013 | Britton et al. |
| 2013/0334138 A1 | 12/2013 | Cicchello et al. |
| 2013/0338102 A1 | 12/2013 | Martis et al. |
| 2013/0345621 A1 | 12/2013 | Cicchello et al. |
| 2013/0346099 A1 | 12/2013 | Yu et al. |
| 2013/0346102 A1 | 12/2013 | Yu et al. |
| 2014/0010691 A1 | 1/2014 | Lanigan et al. |
| 2014/0018272 A1 | 1/2014 | Thoea et al. |
| 2014/0018727 A1 | 1/2014 | Burbank et al. |
| 2014/0021115 A1 | 1/2014 | Ellegaard |
| 2014/0027380 A1 | 1/2014 | Childers et al. |
| 2014/0031631 A1 | 1/2014 | Hall et al. |
| 2014/0046150 A1 | 2/2014 | Gagel et al. |
| 2014/0046248 A1 | 2/2014 | Fini et al. |
| 2014/0052044 A1 | 2/2014 | Crnkovich et al. |
| 2014/0074018 A1 | 3/2014 | Childers et al. |
| 2014/0098359 A1 | 4/2014 | Gross et al. |
| 2014/0129250 A1 | 5/2014 | Daniel et al. |
| 2014/0148409 A1 | 5/2014 | Ohta et al. |
| 2014/0188040 A1 | 7/2014 | Busby et al. |
| 2014/0207055 A1 | 7/2014 | Junod et al. |
| 2014/0216994 A1 | 8/2014 | Ki |
| 2014/0217029 A1 | 8/2014 | Meyer et al. |
| 2014/0217030 A1 | 8/2014 | Meyer et al. |
| 2014/0249683 A1 | 9/2014 | Gray et al. |
| 2014/0263063 A1 | 9/2014 | Jones et al. |
| 2014/0288947 A1 | 9/2014 | Simpson et al. |
| 2014/0291218 A1 | 10/2014 | Bluchel et al. |
| 2014/0299545 A1 | 10/2014 | Wrazel et al. |
| 2014/0316332 A1 | 10/2014 | Lo et al. |
| 2014/0360594 A1 | 12/2014 | Lee et al. |
| 2015/0005699 A1 | 1/2015 | Burbank et al. |
| 2015/0014249 A1 | 1/2015 | Alberti et al. |
| 2015/0051536 A1 | 2/2015 | Mendels et al. |
| 2015/0088053 A1 | 3/2015 | Lundtveit et al. |
| 2015/0093450 A1 | 4/2015 | Riser et al. |
| 2015/0129055 A1 | 5/2015 | Byler |
| 2015/0133854 A1 | 5/2015 | Zhu et al. |
| 2015/0159643 A1 | 6/2015 | Koob |
| 2015/0196698 A1 | 7/2015 | Grant et al. |
| 2015/0197431 A1 | 7/2015 | Shiki |
| 2015/0204807 A1 | 7/2015 | Kamen et al. |
| 2015/0209500 A1 | 7/2015 | Lin et al. |
| 2015/0231571 A1 | 8/2015 | Volker |
| 2015/0233367 A1 | 8/2015 | Shimogata et al. |
| 2015/0273471 A1 | 10/2015 | Manzella et al. |
| 2015/0276742 A1 | 10/2015 | Henrie |
| 2015/0335808 A1 | 11/2015 | White et al. |
| 2015/0359956 A1 | 12/2015 | Gray et al. |
| 2016/0030654 A1 | 2/2016 | Singh et al. |
| 2016/0051949 A1 | 2/2016 | Jansson et al. |
| 2016/0097382 A1 | 4/2016 | Kamen et al. |
| 2016/0106904 A1 | 4/2016 | Cicchello et al. |
| 2016/0153444 A1 | 6/2016 | Chappel et al. |
| 2016/0193399 A1 | 7/2016 | Wallace et al. |
| 2016/0206804 A1 | 7/2016 | Holmer et al. |
| 2016/0239637 A1 | 8/2016 | Miller et al. |
| 2016/0245277 A1 | 8/2016 | Lanigan et al. |
| 2016/0271312 A1 | 9/2016 | Lance et al. |
| 2016/0310653 A1 | 10/2016 | Wang et al. |
| 2016/0319954 A1 | 11/2016 | Smith |
| 2016/0346451 A1 | 12/2016 | Stonger et al. |
| 2016/0362234 A1 | 12/2016 | Peret et al. |
| 2016/0367794 A1 | 12/2016 | Bedingfield |
| 2017/0043079 A1 | 2/2017 | Jensen et al. |
| 2017/0112992 A1 | 4/2017 | Plahey et al. |
| 2017/0157310 A1 | 6/2017 | Scarpaci et al. |
| 2017/0232175 A1 | 8/2017 | Burbank et al. |
| 2017/0281846 A1 | 10/2017 | Manda et al. |
| 2017/0319768 A1 | 11/2017 | Szpara et al. |
| 2017/0319769 A1 | 11/2017 | Wieslander et al. |
| 2017/0319770 A1 | 11/2017 | Fitzgerald et al. |

(56) References Cited

U.S. PATENT DOCUMENTS

| | | | |
|---|---|---|---|
| 2017/0333609 A1 | 11/2017 | O'Brien et al. | |
| 2018/0021501 A1 | 1/2018 | Gerber et al. | |
| 2018/0043079 A1 | 2/2018 | Gerber et al. | |
| 2018/0066648 A1 | 3/2018 | Kamen et al. | |
| 2018/0078692 A1 | 3/2018 | Cicchello et al. | |
| 2018/0093031 A1 | 4/2018 | Crawford et al. | |
| 2018/0106246 A1 | 4/2018 | Kamen et al. | |
| 2018/0128259 A1 | 5/2018 | Kamen et al. | |

FOREIGN PATENT DOCUMENTS

| | | |
|---|---|---|
| CA | 2832661 | 8/2016 |
| CN | 201150709 | 11/2008 |
| CN | 201710718 U | 1/2011 |
| CN | 201806987 U | 4/2011 |
| CN | 101901000 B | 11/2011 |
| CN | 102258942 A | 11/2011 |
| CN | 202116617 U | 1/2012 |
| CN | 102363054 A | 2/2012 |
| CN | 202355628 U | 8/2012 |
| CN | 202379834 U | 8/2012 |
| CN | 202478260 U | 10/2012 |
| CN | 202505852 U | 10/2012 |
| CN | 202542986 U | 11/2012 |
| CN | 102989047 A | 3/2013 |
| CN | 202822485 U | 3/2013 |
| CN | 204723486 U | 10/2015 |
| CN | 105013031 A | 11/2015 |
| CN | 204824277 U | 12/2015 |
| DE | 2838414 A1 | 3/1980 |
| DE | 4308586 C1 | 5/1994 |
| DE | 19546027 C1 | 4/1997 |
| DE | 29918801 U1 | 3/2000 |
| DE | 69725104 | 7/2004 |
| DE | 102007020573 A1 | 11/2008 |
| DE | 102007053752 A1 | 5/2009 |
| DE | 102008045422 A1 | 3/2010 |
| DE | 102009037917 A1 | 2/2011 |
| DE | 102010009816 A1 | 9/2011 |
| DE | 102010033241 A1 | 2/2012 |
| DE | 102010053903 A1 | 6/2012 |
| DE | 102011103325 A1 | 12/2012 |
| DE | 102012004673 A1 | 9/2013 |
| DE | 102012007412 A1 | 10/2013 |
| DE | 102013103223 A1 | 10/2014 |
| DE | 102013013414 | 1/2015 |
| DE | 102013013415 A1 | 2/2015 |
| DE | 102013016204 A1 | 4/2015 |
| DE | 102013018444 A1 | 5/2015 |
| DE | 102014201714 A1 | 8/2015 |
| DE | 102014004476 A1 | 10/2015 |
| DE | 102014013152 A1 | 3/2016 |
| DE | 102015010418 A1 | 2/2017 |
| EP | 100682 A1 | 2/1984 |
| EP | 0104460 A2 | 4/1984 |
| EP | 0112104 A2 | 6/1984 |
| EP | 049673 B1 | 9/1985 |
| EP | 0265352 A1 | 4/1988 |
| EP | 0367252 A2 | 5/1990 |
| EP | 0611227 A1 | 8/1994 |
| EP | 0711569 A1 | 5/1996 |
| EP | 0763367 A1 | 3/1997 |
| EP | 0778033 A2 | 6/1997 |
| EP | 0813880 A1 | 12/1997 |
| EP | 1187642 A1 | 3/2002 |
| EP | 1314442 A1 | 5/2003 |
| EP | 0846470 B1 | 9/2003 |
| EP | 1346749 A2 | 9/2003 |
| EP | 1048316 B1 | 10/2003 |
| EP | 0971674 B1 | 12/2003 |
| EP | 0914093 B1 | 2/2004 |
| EP | 1438981 A2 | 7/2004 |
| EP | 1438982 A2 | 7/2004 |
| EP | 0970699 B1 | 9/2005 |
| EP | 0994739 B1 | 9/2005 |
| EP | 0958832 B1 | 1/2006 |
| EP | 1648536 A2 | 4/2006 |
| EP | 1066068 B1 | 7/2006 |
| EP | 1677900 A2 | 7/2006 |
| EP | 1351726 B1 | 2/2007 |
| EP | 1382359 B1 | 2/2007 |
| EP | 1110564 B1 | 5/2007 |
| EP | 1236685 B1 | 8/2007 |
| EP | 1867359 A2 | 12/2007 |
| EP | 1938849 A2 | 7/2008 |
| EP | 1191960 B1 | 9/2008 |
| EP | 1582227 B1 | 11/2008 |
| EP | 1218039 B1 | 2/2009 |
| EP | 1641473 B1 | 4/2010 |
| EP | 1357958 B1 | 8/2010 |
| EP | 2289577 A1 | 3/2011 |
| EP | 1432462 B1 | 5/2011 |
| EP | 2350897 A2 | 8/2011 |
| EP | 2402047 A1 | 1/2012 |
| EP | 1509231 B1 | 2/2012 |
| EP | 1465687 B2 | 5/2012 |
| EP | 2446910 A1 | 5/2012 |
| EP | 1195171 B1 | 8/2012 |
| EP | 2503150 A1 | 9/2012 |
| EP | 2510958 A1 | 10/2012 |
| EP | 2517742 A2 | 10/2012 |
| EP | 1735028 B1 | 7/2013 |
| EP | 2656785 A1 | 10/2013 |
| EP | 2689790 A1 | 1/2014 |
| EP | 2712648 B1 | 3/2015 |
| EP | 1878430 B1 | 4/2016 |
| EP | 2114487 B1 | 4/2016 |
| EP | 2131891 B1 | 4/2016 |
| EP | 2173433 B1 | 5/2016 |
| FR | 2594340 A1 | 8/1987 |
| GB | 2312055 B | 7/2000 |
| JP | S59166156 A | 9/1984 |
| JP | 60155952 A | 8/1985 |
| JP | S61008057 A | 1/1986 |
| JP | H05502614 A | 5/1993 |
| JP | 2001511400 A | 8/2001 |
| JP | 2002539896 A | 11/2002 |
| JP | 2003024435 A | 1/2003 |
| JP | 2003509126 A | 3/2003 |
| JP | 2003205031 A | 7/2003 |
| JP | 2004518462 A | 6/2004 |
| JP | 2006181386 A | 7/2006 |
| JP | 2006218037 A | 8/2006 |
| JP | 2002355305 B | 2/2008 |
| JP | 2008119509 A | 5/2008 |
| JP | 03150035 U | 4/2009 |
| JP | 2009131573 A | 6/2009 |
| JP | 2009139091 A | 6/2009 |
| JP | 2009142436 A | 7/2009 |
| JP | 2009533092 A | 9/2009 |
| JP | 2009539522 A | 11/2009 |
| JP | 2009279110 A | 12/2009 |
| JP | 2009279532 A | 12/2009 |
| JP | 2010502405 A | 1/2010 |
| JP | 2010042312 A | 2/2010 |
| JP | 2010088759 A | 4/2010 |
| JP | 2010099631 A | 5/2010 |
| JP | 2010131495 A | 6/2010 |
| JP | 2010175285 A | 8/2010 |
| JP | 2010214132 A | 9/2010 |
| JP | 2010238013 A | 10/2010 |
| JP | 2010532217 A | 10/2010 |
| JP | 2010279423 A | 12/2010 |
| JP | 2011056395 A | 3/2011 |
| JP | 2011067535 A | 4/2011 |
| JP | 2011120713 A | 6/2011 |
| JP | 2011131209 A | 7/2011 |
| JP | 2011188996 A | 9/2011 |
| JP | 2011189190 A | 9/2011 |
| JP | 2011207867 A | 10/2011 |
| JP | 2011217965 A | 11/2011 |
| JP | 2011241174 A | 12/2011 |
| JP | 2012011260 A | 1/2012 |
| JP | 2012071287 A | 4/2012 |

(56) References Cited

FOREIGN PATENT DOCUMENTS

| | | |
|---|---|---|
| JP | 2012075572 A | 4/2012 |
| JP | 2012075573 A | 4/2012 |
| JP | 2012075574 A | 4/2012 |
| JP | 2012075575 A | 4/2012 |
| JP | 2012210382 A | 11/2012 |
| JP | 2012223248 A | 11/2012 |
| JP | 2012228285 A | 11/2012 |
| JP | 2013006128 A | 1/2013 |
| JP | 2013048894 A | 3/2013 |
| JP | 2013048895 A | 3/2013 |
| JP | 2013202231 A | 10/2013 |
| JP | 2014014645 A | 1/2014 |
| JP | 2014519345 A | 8/2014 |
| JP | 2014184380 A | 10/2014 |
| JP | 2014184384 A | 10/2014 |
| JP | 2014184410 A | 10/2014 |
| JP | 2014184411 A | 10/2014 |
| JP | 2015517834 A | 6/2015 |
| JP | 2017000802 A | 1/2017 |
| JP | 2017006538 A | 1/2017 |
| JP | 6080937 B1 | 2/2017 |
| JP | 2018027256 A | 2/2018 |
| JP | 2018050751 A | 4/2018 |
| KR | 20120118906 A | 10/2012 |
| TW | M411244 U | 9/2011 |
| WO | 1983002060 A1 | 6/1983 |
| WO | 1984000137 A1 | 1/1984 |
| WO | 1984000340 A1 | 2/1984 |
| WO | 9203202 A2 | 3/1992 |
| WO | 1992003202 A2 | 3/1992 |
| WO | 1994020154 A1 | 9/1994 |
| WO | 1996025214 A1 | 8/1996 |
| WO | 1997007837 A1 | 3/1997 |
| WO | 1998032480 A1 | 7/1998 |
| WO | 1999006082 A1 | 2/1999 |
| WO | 2000057833 A1 | 10/2000 |
| WO | 2000057935 A1 | 10/2000 |
| WO | 0119413 A1 | 3/2001 |
| WO | 2001032237 A1 | 5/2001 |
| WO | 2001058509 A1 | 8/2001 |
| WO | 0232476 A2 | 4/2002 |
| WO | 2002066099 A2 | 8/2002 |
| WO | 2004006992 A1 | 1/2004 |
| WO | 2004009156 A2 | 1/2004 |
| WO | 2004043566 A2 | 5/2004 |
| WO | 2005009511 A2 | 2/2005 |
| WO | 2005042139 A1 | 5/2005 |
| WO | 2005089832 A2 | 9/2005 |
| WO | 2007061368 A1 | 5/2007 |
| WO | 2007091217 A1 | 8/2007 |
| WO | 2007103411 A2 | 9/2007 |
| WO | 2007118235 A2 | 10/2007 |
| WO | 2007144427 A2 | 12/2007 |
| WO | 2007148443 A1 | 12/2007 |
| WO | 2008086619 A1 | 7/2008 |
| WO | 2008106440 A1 | 9/2008 |
| WO | 2008154435 A2 | 12/2008 |
| WO | 2009005900 A1 | 1/2009 |
| WO | 2009094182 A2 | 7/2009 |
| WO | 2009094183 A1 | 7/2009 |
| WO | 2009094186 A2 | 7/2009 |
| WO | 2009127683 A1 | 10/2009 |
| WO | 2009134881 A1 | 11/2009 |
| WO | 2010002830 A2 | 1/2010 |
| WO | 2010009867 A1 | 1/2010 |
| WO | 2010020380 A1 | 2/2010 |
| WO | 2010024963 A1 | 3/2010 |
| WO | 2010031424 A1 | 3/2010 |
| WO | 2010059959 A2 | 5/2010 |
| WO | 2010121751 A2 | 10/2010 |
| WO | 2010143693 A1 | 12/2010 |
| WO | 2011017215 A1 | 2/2011 |
| WO | 2011052348 A1 | 5/2011 |
| WO | 2011065222 A1 | 6/2011 |
| WO | 2011091998 A1 | 8/2011 |
| WO | 2011113615 A1 | 9/2011 |
| WO | 2011132165 A1 | 10/2011 |
| WO | 2012049261 A1 | 4/2012 |
| WO | 2012087798 A2 | 6/2012 |
| WO | 2012095829 A2 | 7/2012 |
| WO | 2012148781 A1 | 11/2012 |
| WO | 2012163537 A1 | 12/2012 |
| WO | 2012172818 A1 | 12/2012 |
| WO | 2012176135 A1 | 12/2012 |
| WO | 2013000569 A1 | 1/2013 |
| WO | 2013012744 A2 | 1/2013 |
| WO | 2013019179 A1 | 2/2013 |
| WO | 2013019994 A2 | 2/2013 |
| WO | 2013040420 A2 | 3/2013 |
| WO | 2013051927 A1 | 4/2013 |
| WO | 2013057109 A1 | 4/2013 |
| WO | 2013110919 A1 | 8/2013 |
| WO | 2013114063 A1 | 8/2013 |
| WO | 2013121162 A1 | 8/2013 |
| WO | 2013135386 A1 | 9/2013 |
| WO | 2013135388 A1 | 9/2013 |
| WO | 2013159935 A1 | 10/2013 |
| WO | 2013163949 A1 | 11/2013 |
| WO | 2013185080 A1 | 12/2013 |
| WO | 2013191344 A1 | 12/2013 |
| WO | 2014009111 A1 | 1/2014 |
| WO | 2014053858 A1 | 4/2014 |
| WO | 2014081367 A1 | 5/2014 |
| WO | 2014106010 A1 | 7/2014 |
| WO | 2014124186 A2 | 8/2014 |
| WO | 2014155120 A1 | 10/2014 |
| WO | 2014162489 A1 | 10/2014 |
| WO | 2015050752 A1 | 4/2015 |
| WO | 2015177606 A1 | 11/2015 |
| WO | 2015188154 A1 | 12/2015 |
| WO | 2016049542 A2 | 3/2016 |
| WO | 2016059634 A2 | 4/2016 |
| WO | 2016049542 A3 | 5/2016 |
| WO | 2016080883 A1 | 5/2016 |
| WO | 2016088072 A1 | 6/2016 |
| WO | 2016091366 A1 | 6/2016 |
| WO | 2016095026 A1 | 6/2016 |
| WO | 2016193930 A1 | 12/2016 |
| WO | 2016206949 A1 | 12/2016 |
| WO | 2017193065 A1 | 11/2017 |
| WO | 2018041760 A1 | 3/2018 |
| WO | 2018115028 A1 | 6/2018 |

OTHER PUBLICATIONS

Examination Report for United Kingdom Patent Application No. 1316544.4 dated Nov. 1, 2017.
Extended European Search Report dated Apr. 2, 2019 for European Patent Application No. 18215332.0.
Extended European Search Report for European Application No. 17170146 dated Jul. 25, 2017.
Extended European Search Report for European Application No. 17170151.9 dated Aug. 22, 2017.
Extended European Search Report for European Patent Application No. 12760085.6 dated Sep. 25, 2015.
Extended European Search Report for European Patent Application No. 12871735.2 dated Oct. 15, 2015.
International Search Report and Written Opinion dated Oct. 24, 2018 issued in International Patent Application No. PCT/US2018/039188.
International Search Report and Written Opinion for International Application No. PCT/US2012/30350 dated Sep. 13, 2012.
International Search Report and Written Opinion for International Application No. PCT/US2012/56781 dated Apr. 4, 2013.
Notice of Reasons for Refusal dated Nov. 15, 2018 for Japanese Patent Application No. 2018-071806.
Office Action for Chinese Patent Application No. 201280015466.8 dated Apr. 20, 2015 (with translation).
Office Action for Japanese Patent Application No. 2014-501276 dated Mar. 1, 2016 (with translation).

(56) References Cited

OTHER PUBLICATIONS

Office Action for Japanese Patent Application No. 2015-503186 dated Jun. 6, 2017 (with translation).
Office Action in Japanese Patent Application No. 2015-503186 dated Aug. 2, 2016 (with translation).
Partial Supplementary European Search Report for European Patent Application No. 12760085.6 dated Jun. 1, 2015.
Extended European Search Report for European Patent Application No. 19166992.8 dated Aug. 2, 2019.
Extended European Search Report issued in EP Application 19173274.2 dated Jul. 29, 2019.
International Search Report and Written Opinion dated Sep. 6, 2019 and issued in International Application No. PCT/US2019/019967.
Extended European Search Report dated Oct. 22, 2019 for European Patent Application No. 19167042.1.
Office Action (Communication Pursuant to Article 94(3) EPC) dated Jun. 24, 2020 for European Patent Application No. 19173274.2.
Office Action dated Aug. 4, 2020, issued in JP App No. 2019-063926.
Communication under Rule 71(3) EPC dated Apr. 23, 2020, issued in EP 19 166 992.8.
Office Action dated Mar. 24, 2020 issued in JP Patent App. No. 2019-063926.
Extended European Search Report dated Feb. 17, 2021 for European Patent Application No. 18821268.2.
Office Action (Notice of Reasons for Refusal) dated Mar. 1, 2022 for Japanese Patent Application No. 2020-200127.
Agar, "An Obituary for Baxter's Vivia Home HD Machine," Home Dialysis Central, 2016, pp. 1-11, Home Dialysis Central, Madison, Wisconsin.
Agar, "Technology: What's Coming," Nocturnal Haemodialysis Program, Barwon Health, 2012, pp. 1-8, www.nocturnaldialysis.org/technology_whats_coming.html.
Fassbinder, "Experience with the Genius hemodialysis system," Kidney Blood Press Res., 2003, vol. 26(2), pp. 96-99 (Abstract only), Karger, Basel, Switzerland.
Heroux, "Aksys—Dialysis Technologists," Dialysis Technologists, 2005, pp. 1-5, https://www.tapatalk.com/groups/dialysistechnologists39151/aksys-t607.html.
Nellstrand et al., "The Aksys personal hemodialysis system," Seminars in Dialysis, 2004, vol. 17(2), Abstract only, Wiley, Hoboken, New Jersey.
Office Action (Communication Pursuant to Article 94(3) EPC) dated May 10, 2021, issued in European Application No. 18215332.0.
Office Action (Examination Report No. 1) dated Jun. 1, 2021 for Australian Patent Application No. 2019228526.
Office Action (Examination Report No. 1) dated Jun. 1, 2021 for Australian Patent Application No. 2020244565.
Office Action (Examination Report No. 1) dated Jun. 1, 2021 for Australian Patent Application No. 2020244566.
Office Action (Examination Report No. 1) dated Jun. 1, 2021 for Australian Patent Application No. 2020244567.
Office Action (Notice of Reasons for Refusal) dated Aug. 9, 2022 for Japanese Patent Application No. 2020-545472.
Office Action (Notice of Reasons for Refusal) dated Mar. 22, 2022 for Japanese Patent Application No. 2020-545472.
Office Action (Notice of Reasons for Refusal) dated Oct. 11, 2022 for Japanese Patent Application No. 2020-200127.
Office Action (Notification of Examination) issued in German Application No. 112012001381.6 dated Mar. 30, 2022.
Office Action (Pre-Appeal Examination Report) dated Feb. 9, 2021 for Japanese Patent Application No. 2019-063926.
Office Action for Japanese Patent Application No. 2020-200127, dated Apr. 11, 2023.
Office Action dated Aug. 9, 2022 in Japanese Patent Application No. 2020-545472.
Schlaeper et al., "The Fresenius Medical Care Home Hemodialysis System," Seminars in Dialysis, 2004, vol. 17 (2), pp. 159-161, Wiley, Hoboken, New Jersey.
Unknown, "4008 H—Hemodialysis Machine Operating Instructions," Fresenius Medical Care AG, Software Version 4.3, May 1, 2005, pp. 1-365.
Unknown, "4008 S—Hemodialysis Machine Operating Instructions," Fresenius Medical Care, Software Version 4.5, Oct. 1, 2011, pp. 1-368.
Unknown, "4400HX Hot Water Disinfection Water Treatment Solutions for Hemodialysis," MAR CAR Purification—A Cantel Medical Company, 2006, 4 pages.
Unknown, "Aquaboss EcoRO Dia 70—Portable water treatment for hemodialysis," Lauer Membran Wassertechnik, 2008, Rev. 4.53, Software version 4.00_12, pp. 1-144.
Unknown, "AquaUNO Single Station Reverse Osmosis Unit—Operation Instructions," Fresenius Medical Care, Jul. 1, 2006, Software Version: V2.05, pp. 1-116.
Unknown, "Baxter nixes Vivia home hemodialysis machine," Nephrology News & Issues, 2016, p. 1, Healio, https://www.healio.com/news/nephrology/20180227/baxter-nixes-vivia-home-hemodialysis-machine.
Unknown, "Conversion/Retrofit Kit—No. M37525—Connection of an AguaUNO or AquaC UNO H to a 4008" Fresenius Medical Care, 2012, pp. 1-8.
Unknown, "User and service manual—Single place reverse osmosis system—RO 4008," DWA GmbH & Co. KG, Oct. 1, 2008, pp. 1-39.
Unknown, "User Interface Design—PHD Personal Hemodialysis System for Aksys," Brochure, Stream Product Development, Inc., 2020, North Chelmsford, Massachusetts.
Unknown, "Xcorporeal, Inc Announces the XCR-6 Dialysis Platform for Self-Directed Kidney Hemodialysis," Med Device Online, 2008, pp. 1-2, Business Wire, San Francisco, California, https://www.meddeviceonline.com/doc/xcorporeal-inc-announces-the-xcr-6-dialysis-0001.
Extended European Search Report dated Oct. 18, 2021, issued in European Application No. 19760761.7.
Office Action (Communication Pursuant to Article 94(3) EPC) dated Aug. 11, 2022 for European Patent Application No. 19167042.1.
Office Action for Japanese Patent Application No. 2014-501276 dated Aug. 9, 2022 (includes English translation).

\* cited by examiner

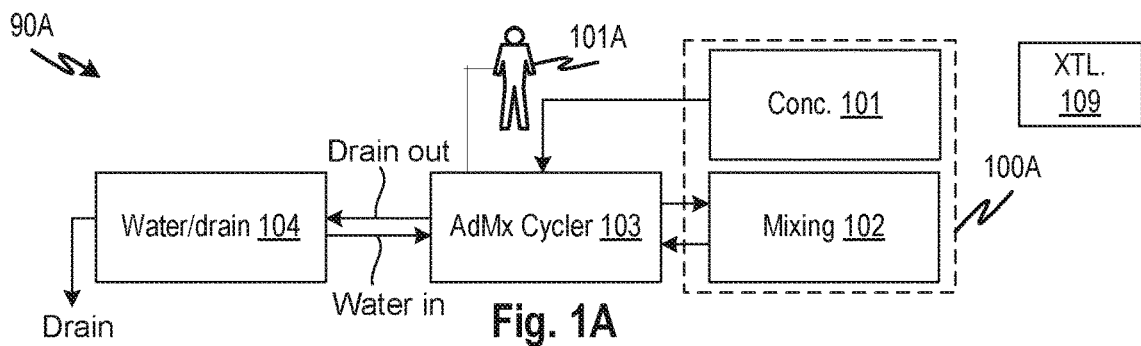
Fig. 1A
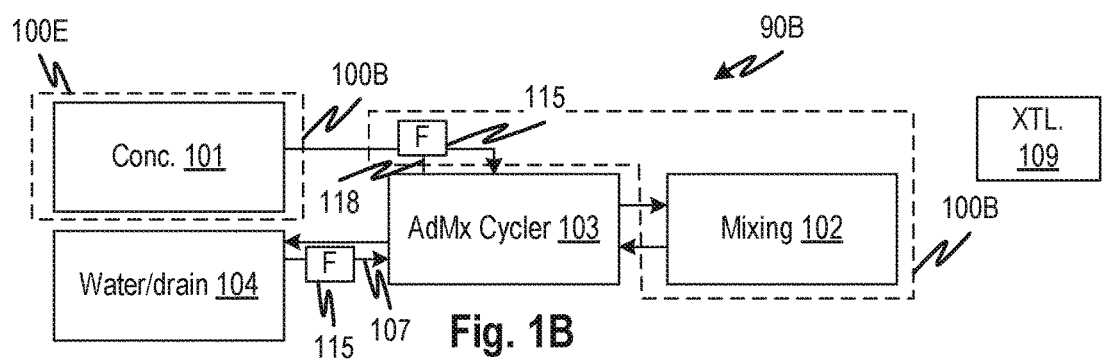
Fig. 1B
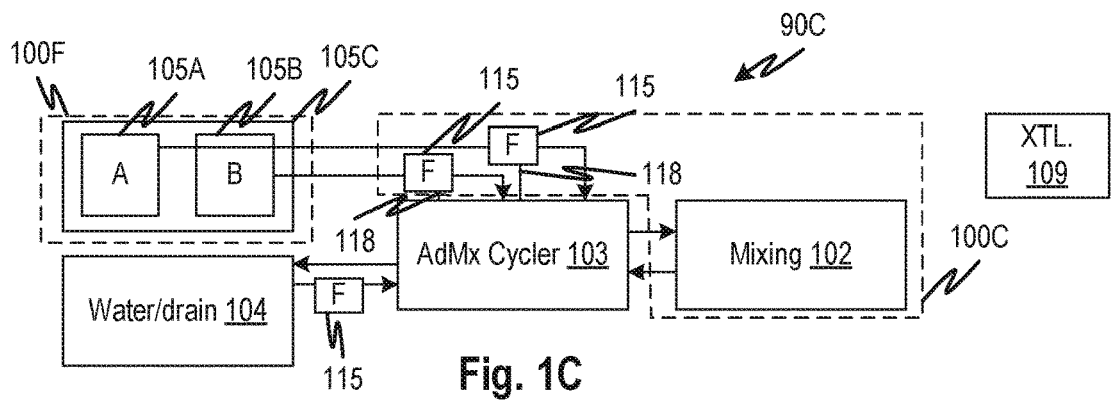
Fig. 1C
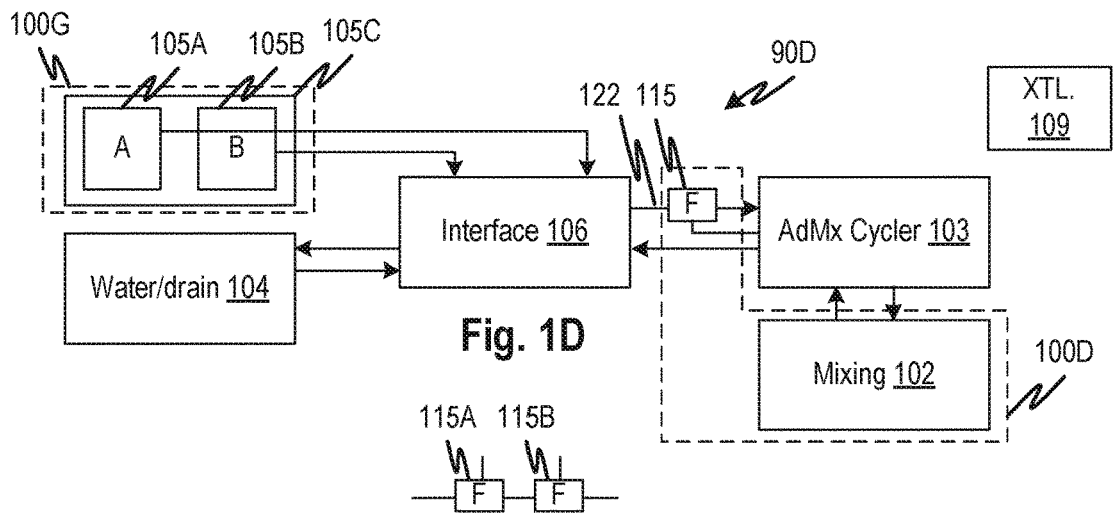
Fig. 1D
Fig. 1E

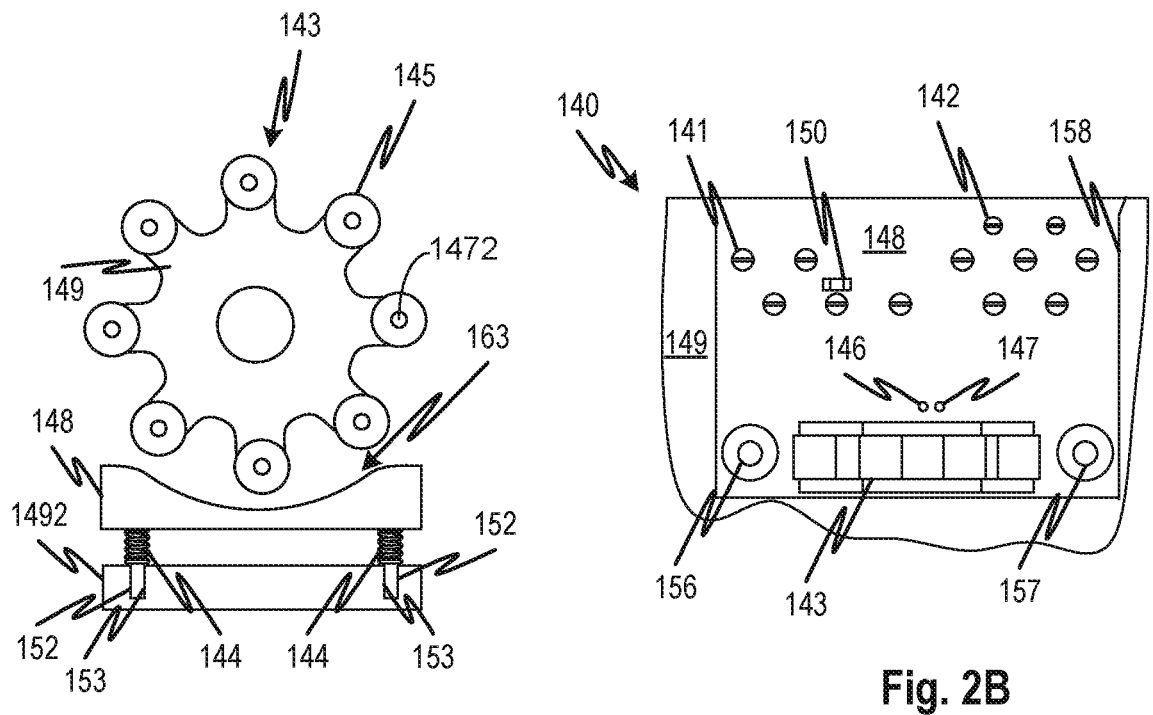
Fig. 2D
Fig. 2B
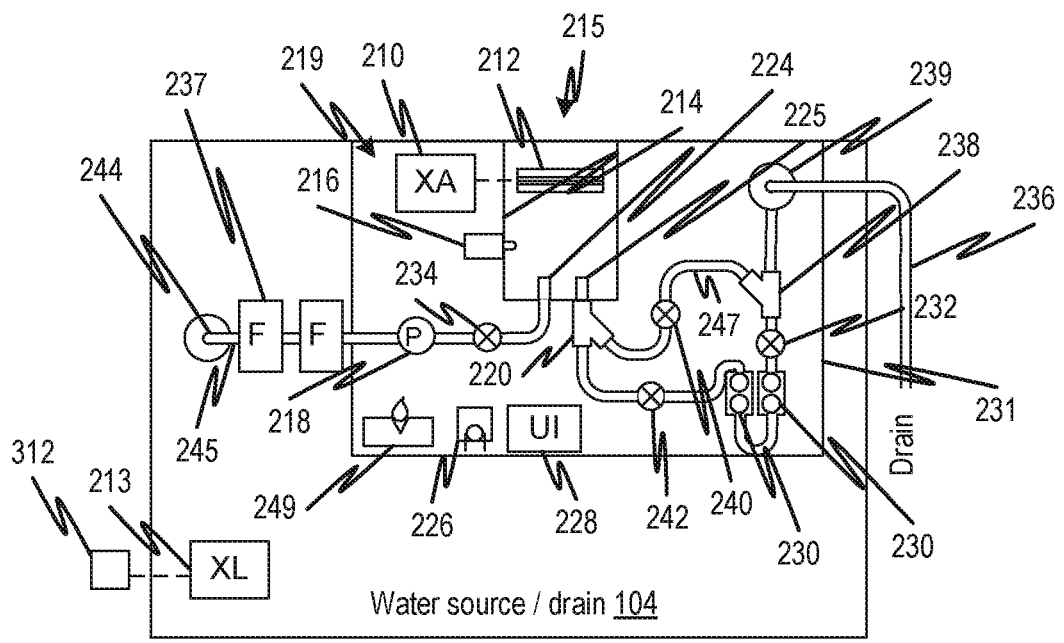
Fig. 2C

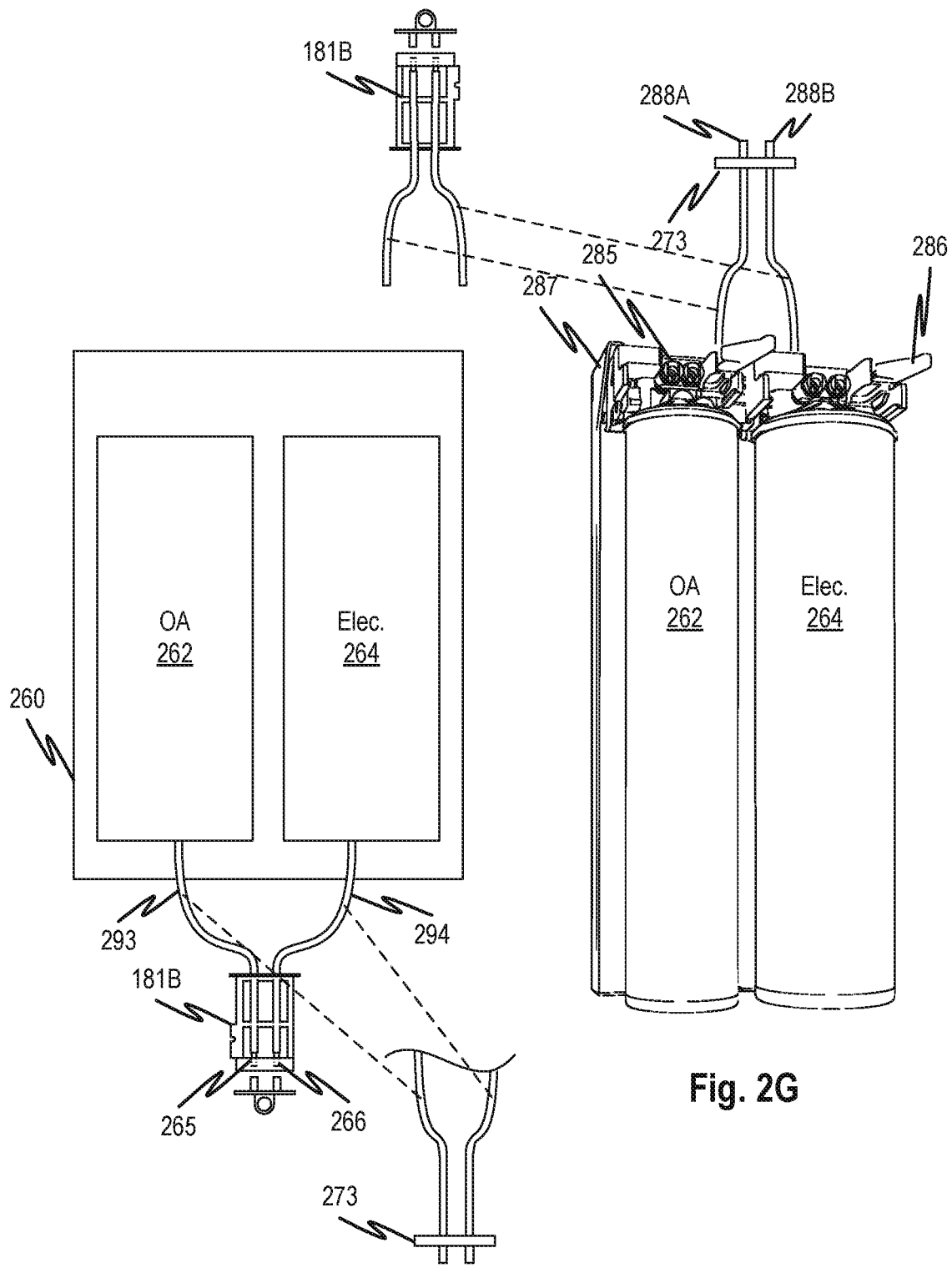

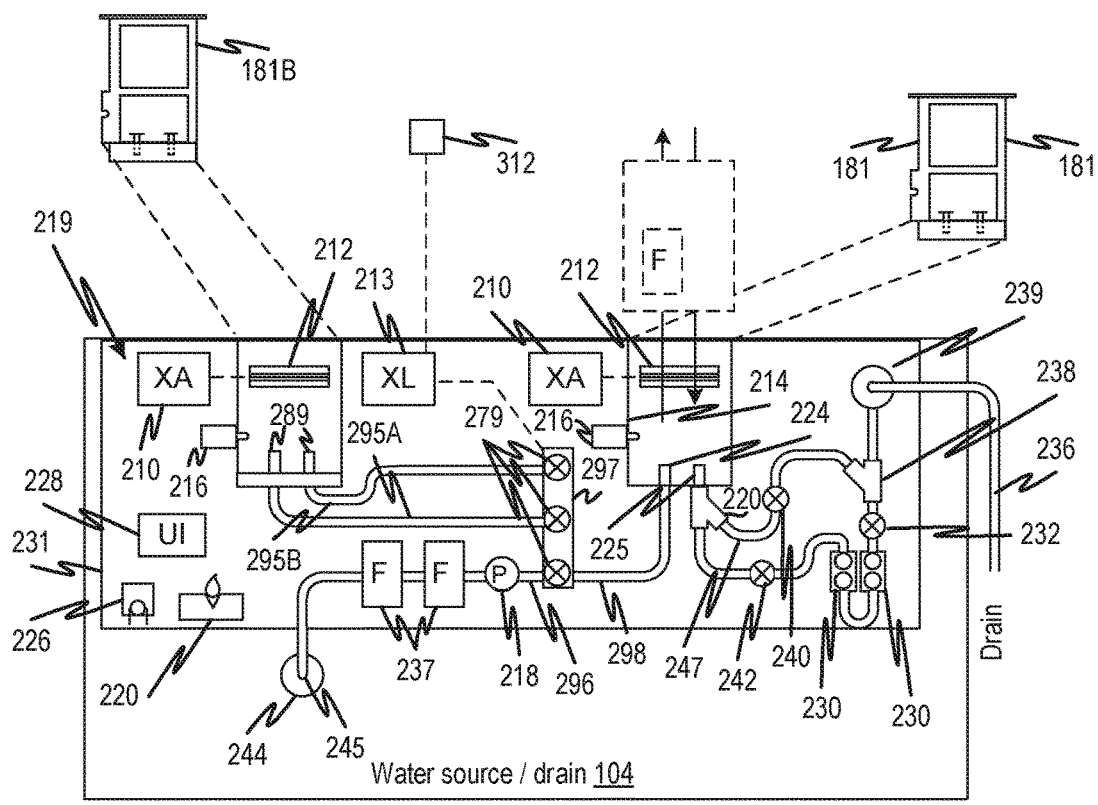
Fig. 2K
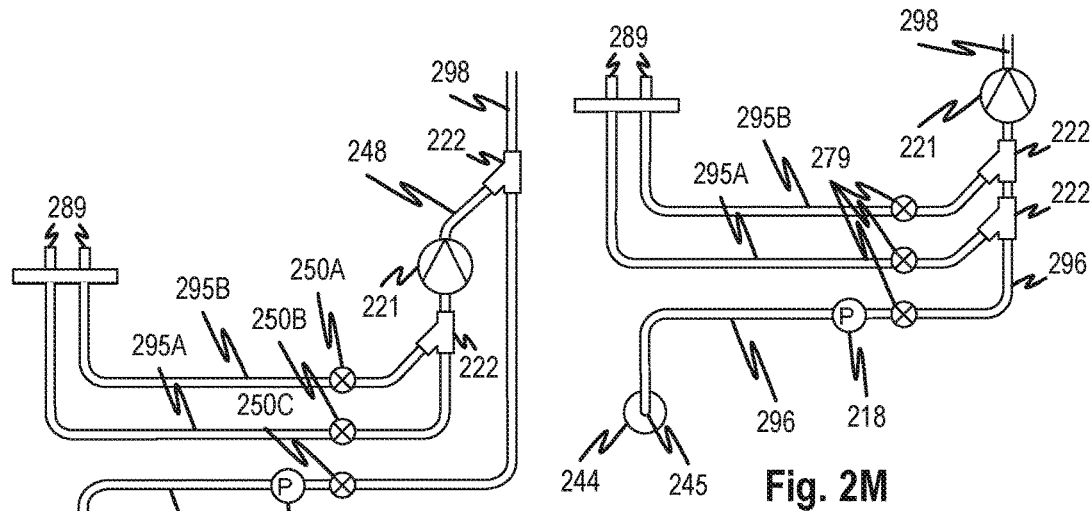
Fig. 2L
Fig. 2M
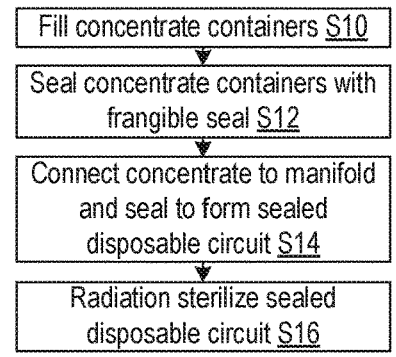
Fig. 3

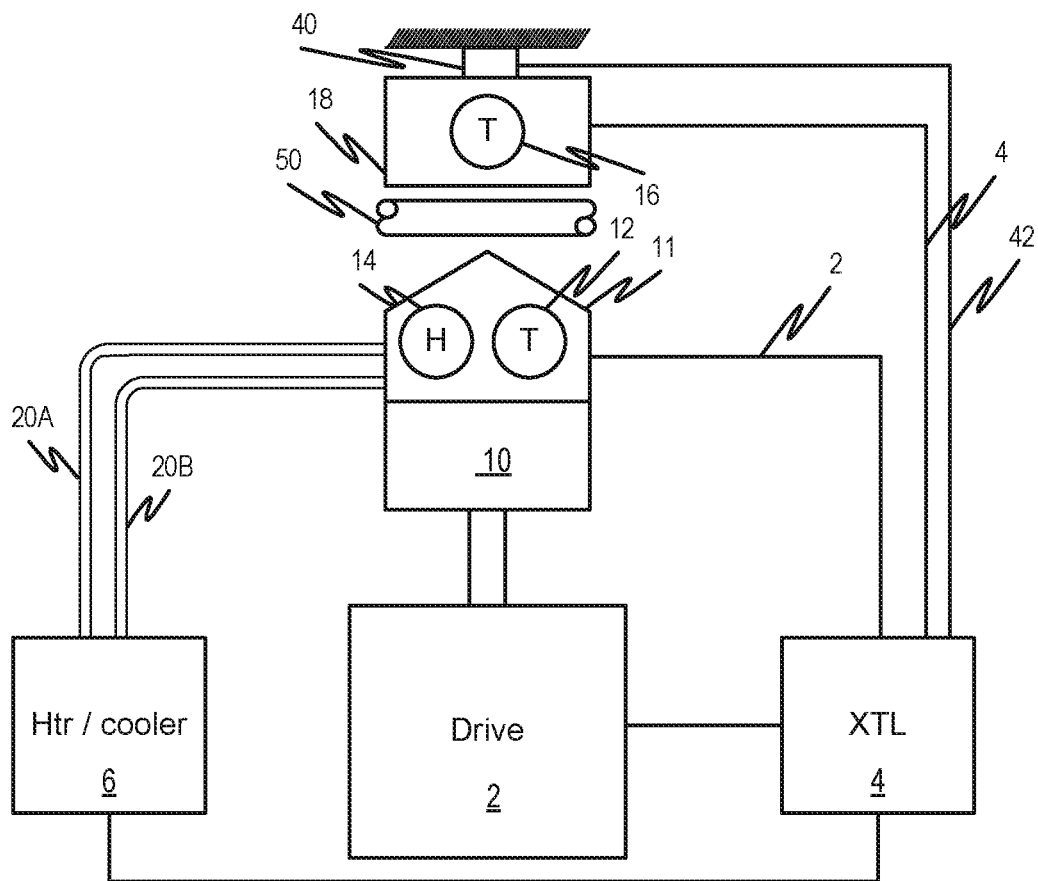
Fig. 6A
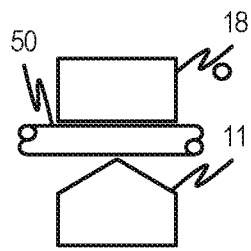 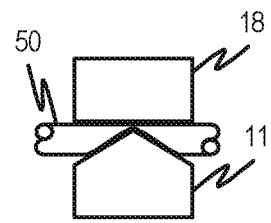 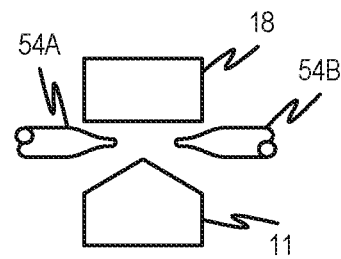
Fig. 6B      Fig. 6C      Fig. 6D

| | | | | |
|---|---|---|---|---|
| 1.0 | Add initial water | | | |
| 2.0 | Add Concentrate #1 | | | |
| 3.0 | Mix | | | |
| 4.0 | Measure conductivity | | | |
| | 4.1 | If good, go to oper. 5.0 | | |
| | 4.2 | If not good, recompute as follows: | | |
| | | 4.2.1 | Assume water was correct; estimate "actual" Concentrate #1 in batch based on difference between actual and target condo - use this estimate going forward. | |
| | | 4.2.2 | Recompute amount of Concentrate #2 required based on assumed "correct" water and estimated Concentrate #1 | |
| 5.0 | Add Concentrate #2 | | | |
| 6.0 | Mix | | | |
| 7.0 | Measure conductivity | | | |
| | 7.1 | If good, go to oper. 8.0 | | |
| | 7.2 | If not good, and oper. 4.0 was not good, then terminate batch. | | |
| | 7.3 | If not good, but oper. 4.0 was OK, then recompute as follows: | | |
| | | 7.3.1 | If conductivity indicates insufficient second concentrate, compute amount of Concentrate #2 needed to bring conductivity reading to target and add that amount; go to oper. 7.3.2.1 | |
| | | 7.3.2 | If conductivity indicates too much of second concentrate was added, compute the amount of Concentrate #1 and water (in target proportion) to bring conductivity reading to target; add Concentrate #1 and water | |
| | | | 7.3.2.1 | Mix |
| | | | 7.3.2.2 | Measure conductivity |
| | | | | 7.3.2.2.1 If conductivity good, go to oper. 8.0 |
| | | | | 7.3.2.2.2 If conductivity not good, then terminate batch. |
| 8.0 | Add balance of water | | | |
| 9.0 | Mix | | | |
| 10.0 | Measure conductivity | | | |
| | 10.1 | If good, go to oper. 11.0 | | |
| | | 10.1.1 | If low, compute amount of both concentrates (in target final proportion) needed to bring actual coductivity reading up to target; add concentrates | |
| | | 10.1.2 | If high, compute amount of water needed to bring actual conductivity reading down to target; add water | |
| | | | 10.1.2.1 | Mix |
| | | | 10.1.2.2 | Measure conductivity |
| | | | | 10.1.2.2.1 If good, go to oper. 11.0 |
| | | | | 10.1.2.2.2 If not good, terminate batch. |
| 11.0 | Test filter; if test fails, terminate batch | | | |
| 12.0 | If final conductivity, filter, and temperature all pass, release batch | | | |

Fig. 15E

S502  
Use pump 762, fluid circuit 701E, and fluid source module 723 to pump water to drain to prime then close valves 751 (all valves closed except identified as open-for all following operations) (OPTIONAL)

S503   
Pump sample of each concentrate to drain or sufficient to generate pressure drop across filter to identify concentrate and/or to detect and correct misconnection or identify concentrates (OPTIONAL)

S504   
Open valves to flow water through manifold to drain to rinse and optionally control end of rinse according to conductivity detected in drain S505   
Pump prime-sufficient electrolyte concentrate into mixing container 732 with pump 788 and by opening batch outlet line 750, fluid line 745, and electrolyte concentrate line 790 by means of respective valves 751 which primes the lines and header 758 leading to electrolyte concentrate line 742 (e.g. 12 ml) (primes GVS filter) Need 1.5 psi low pressure drop through the filter to prime it (30 ml/min)

S506   
Pump sufficient electrolyte concentrate for a cycle or treatment into electrolyte concentrate container 780 with pump 788 and by opening line electrolyte concentrate line 742, fluid line 745, and electrolyte concentrate line 790, which also primes electrolyte concentrate line 742 (day's worth or a cycle's worth)

S510   
Pump sufficient osmotic agent concentrate into mixing container 732 with pump 788 and by opening batch outline line 750, fluid line 745, and osmotic agent concentrate line 789 by means of respective valves 751 to prime the lines and header 758 leading to osmotic agent concentrate line 744

S514   
Pump sufficient osmotic agent concentrate for a cycle or treatment into osmotic agent concentrate container 781 with pump 788 and by opening osmotic agent concentrate line 742, fluid line 745, and osmotic agent concentrate line 789, which also primes osmotic agent concentrate line 744

S520   
Open respective valves 751 to pump water through lines 792, 728, 745, manifold 758, line 750 to prime with water S522   
Open respective valves 751 and recirculate fluid in mixing container 732 through lines 750, 746, 763, and manifolds 758 and 760 sufficient to break in pump segment of pump tube 763

S528   
If last fill is going to be used, then prime to drain to prime last fill line 740

S530   
Pump predefined quantity of water from water source 766 to mixing bag 732 and circulate through inflow and outflow lines 746 and 750 for a time sufficient to break in pump tube segment and mix contents S532   
Test filter 733 on fluid intake line 728 to confirm all fluids flowing into fluid circuit were sterile/pyrogen-free and if not, perform error recovery operation by instructing to replace fluid circuit 701E

Detection of negative pressure created by pump

Direct detection of power applied to pump
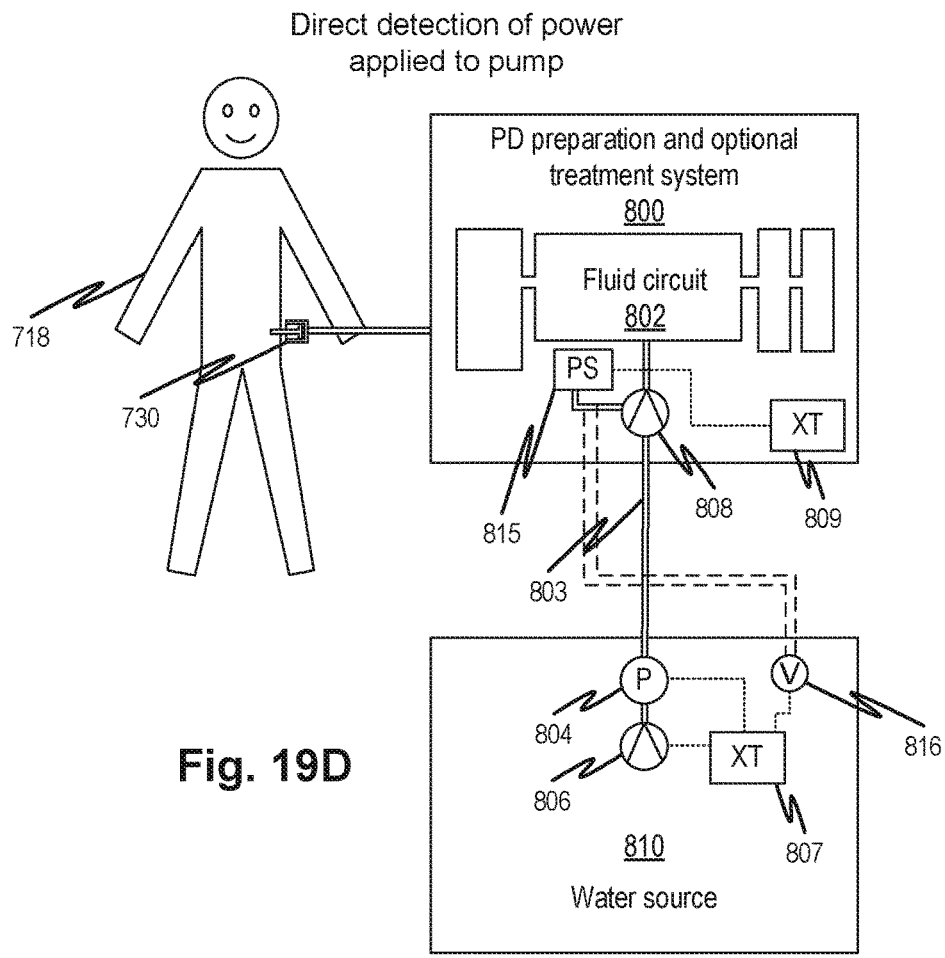
Fig. 19D
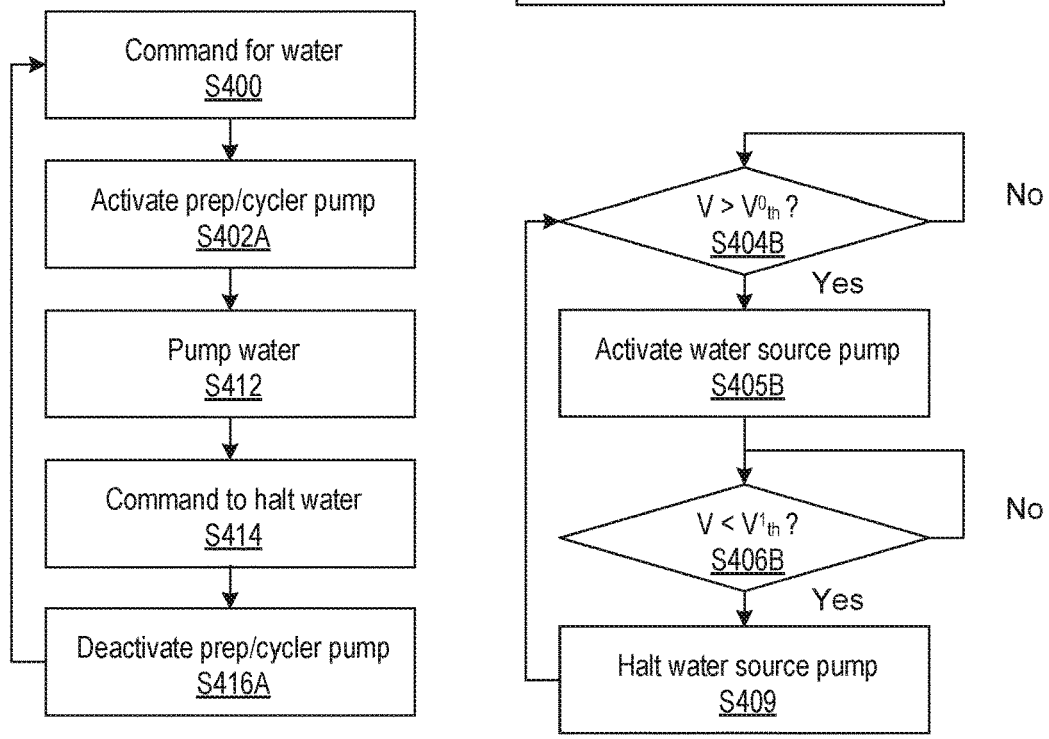
Fig. 19E
Fig. 19F

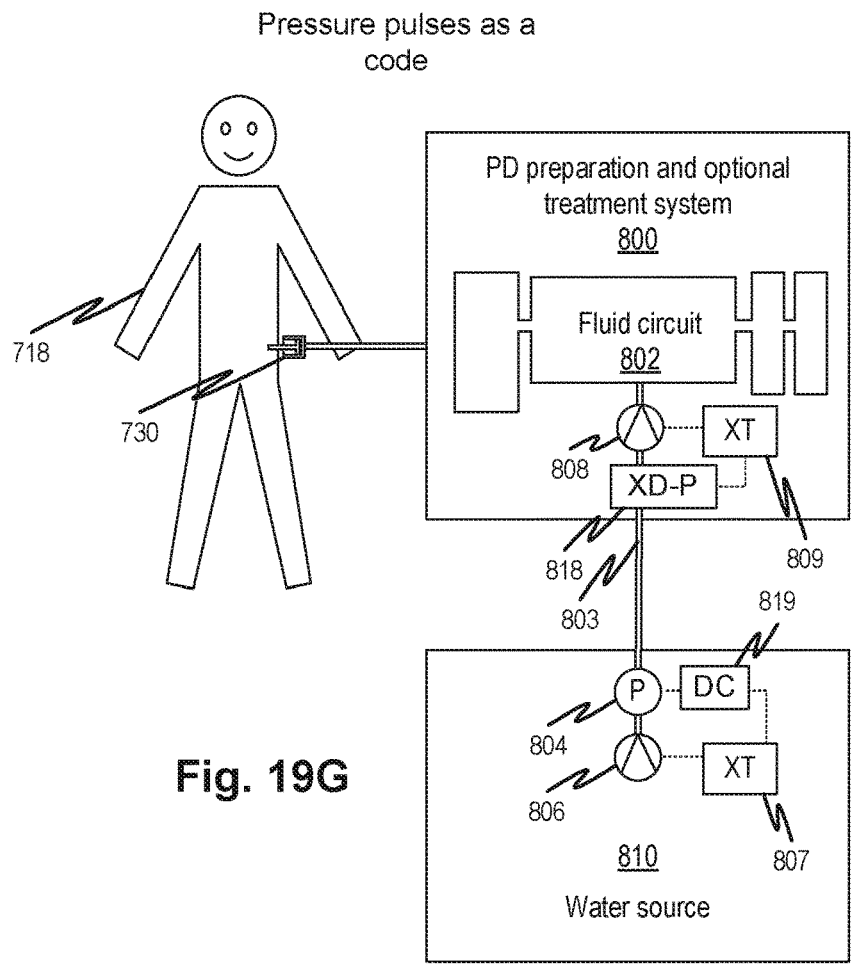
Fig. 19G
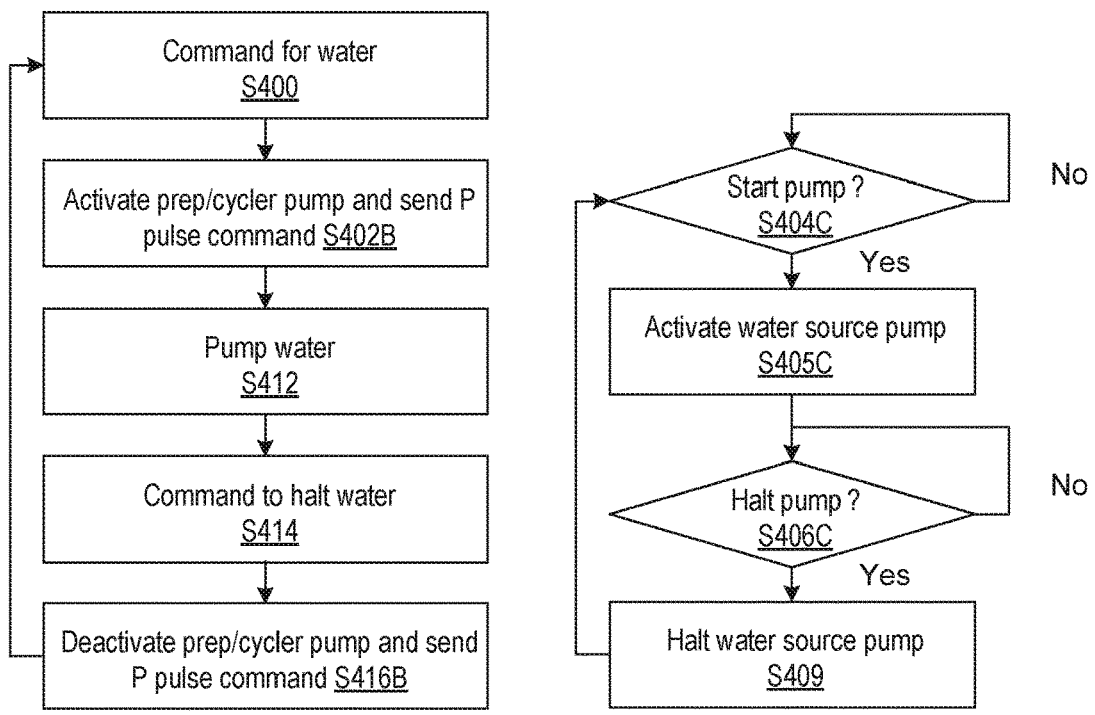
Fig. 19H
Fig. 19J

FLUID PREPARATION AND TREATMENT DEVICES METHODS AND SYSTEMS

CROSS-REFERENCE TO RELATED APPLICATIONS

This application claims the benefit of U.S. Provisional Application 62/636,404, filed Feb. 28, 2018 and of U.S. Provisional Application 62/676,098, filed on May 24, 2018, all of which are hereby incorporated by reference in their entireties.

BACKGROUND

The disclosed subject matter relates generally to the treatment of end stage renal failure and more specifically to devices, methods, systems, improvements, and components for performing peritoneal dialysis.

Peritoneal dialysis is a mature technology that has been in use for many years. It is one of two common forms of dialysis, the other being hemodialysis, which uses an artificial membrane to directly cleanse the blood of a renal patient. Peritoneal dialysis employs the natural membrane of the peritoneum to permit the removal of excess water and toxins from the blood.

In peritoneal dialysis, sterile peritoneal dialysis fluid is infused into a patient's peritoneal cavity using a catheter that has been inserted through the abdominal wall. The fluid remains in the peritoneal cavity for a dwell period. Osmotic exchange with the patient's blood occurs across the peritoneal membrane, removing urea and other toxins and excess water from the blood. Ions that need to be regulated are also exchanged across the membrane. The removal of excess water results in a higher volume of fluid being removed from the patient than is infused. The net excess is called ultrafiltrate, and the process of removal is called ultrafiltration. After the dwell time, the dialysis fluid is removed from the body cavity through the catheter.

Peritoneal dialysis requires the maintenance of strict sterility because of the high risk of peritoneal infection.

In one form of peritoneal dialysis, which is sometimes referred to as cycler-assisted peritoneal dialysis, an automated cycler is used to infuse and drain dialysis fluid. This form of treatment can be done automatically at night while the patient sleeps. One of the safety mechanisms for such a treatment is the monitoring by the cycler of the quantity of ultrafiltrate. The cycler performs this monitoring function by measuring the amount of fluid infused and the amount removed to compute the net fluid removal.

The treatment sequence usually begins with an initial drain cycle to empty the peritoneal cavity of spent dialysis fluid, except on so-called "dry days" when the patient begins automated treatment without the peritoneal cavity filled with dialysis fluid. The cycler then performs a series of fill, dwell, and drain cycles, typically finishing with a fill cycle.

The fill cycle presents a risk of over-filling or over-pressurizing the peritoneal cavity, which has a low tolerance for excess pressure. In traditional peritoneal dialysis, a dialysis fluid container is elevated to certain level above the patient's abdomen so that the fill pressure is determined by the height difference. Automated systems sometimes employ pumps that cannot generate a pressure beyond a certain level, but this system is not foolproof since a fluid column height can arise due to a patient-cycler level difference and cause an overpressure. A reverse height difference can also introduce an error in the fluid balance calculation as a result of incomplete draining.

Modern cyclers may fill by regulating fill volume during each cycle. The volume may be entered into a controller based on a prescription. The prescription, which also determines the composition of the dialysis fluid, may be based upon the patient's size, weight, and other criteria. Due to errors, prescriptions may be incorrect or imperfectly implemented resulting in a detriment to patient well-being and health.

SUMMARY

Embodiments of peritoneal dialysis systems, devices, and methods are described herein. The features, in some cases, relate to automated peritoneal dialysis and in particular to systems, methods, and devices that prepare peritoneal dialysis fluid in a safe and automated way at a point of care. Other features relate to the precision, safety, and ease of use of such systems.

Objects and advantages of embodiments of the disclosed subject matter will become apparent from the following description when considered in conjunction with the accompanying drawings.

BRIEF DESCRIPTION OF THE DRAWINGS

FIGS. 1A-1D show peritoneal dialysis fluid proportioner/cyclers according to respective embodiments of the disclosed subject matter.

FIG. 1E shows a series testable filter arrangement that may be substituted for the filters employed in the embodiments of FIGS. 1A-1D.

FIG. 2B shows an actuator portion of a peritoneal dialysis fluid proportioner/cycler, according to embodiments of the disclosed subject matter.

FIG. 2C shows a connection platform between a purified water source and the peritoneal dialysis fluid proportioner/cycler, according to embodiments of the disclosed subject matter.

FIG. 2D shows a peristaltic pumping actuator that permits the use of a straight pumping tube segment in a generally planar cartridge, employed as a feature of embodiments disclosed herein.

FIGS. 2F and 2G show concentrate disposable components for use with embodiments of the disclosed subject matter.

FIGS. 2I, 2J, and 2K show respective embodiments of connection platforms between a purified water source and a separate concentrate source and the peritoneal dialysis fluid proportioner/cycler embodiments disclosed herein, according to embodiments of the disclosed subject matter.

FIGS. 2L and 2M show details of variations of the embodiments described with reference to FIG. 2K.

FIG. 3 shows a method of manufacturing a disposable circuit such as is disclosed in FIG. 2A.

FIG. 6A shows mechanical aspects and a control and sensor system for the cut-and-seal devices with actuation, temperature, and force control features, according to embodiments of the disclosed subject matter.

FIGS. 6B through 6G show various embodiments of cut-and-seal devices.

FIGS. 7A through 7D show various jaw arrangements for cut-and-seal devices according to different embodiments of the disclosed subject matter.

FIG. 15E is a flow chart in outline form for conductivity error recovery for various mixing methods described herein.

FIG. 18B-18D show a single flow chart when linked together to define a process for making a batch of dialysis fluid based on the embodiment of FIG. 18A.

FIG. 19D through 19F describe a second device and corresponding method of controlling the supply of water to a peritoneal dialysis fluid treatment device, according to embodiments of the disclosed subject matter.

FIGS. 19G through 19H and 19J describe a third device and corresponding method of controlling the supply of water to a peritoneal dialysis fluid treatment device, according to embodiments of the disclosed subject matter.

Figure 1F:
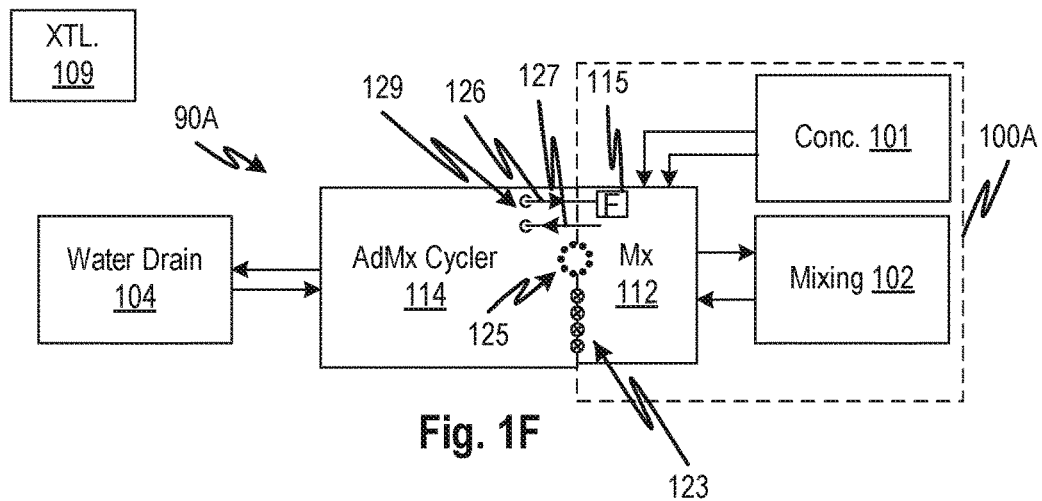
FIGS. 1F-1H show embodiments similar to those of FIGS. 1A-1D and elaborating further details thereof.

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

FIGS. 1A-1D show peritoneal dialysis fluid proportioner/cyclers according to respective embodiments of the disclosed subject matter. Referring now to FIG. 1A, medical fluid preparation and peritoneal dialysis fluid proportioner/cycler system 90A includes a purified water source 104 that provides water suitable for peritoneal dialysis to a peritoneal dialysis fluid proportioner/cycler 103 which is connected to a disposable component 100A. The purified water source 104 also provides a connection to a drain (shown in FIG. 1A only, but similar in FIGS. 1B-1D). The peritoneal dialysis fluid proportioner/cycler 103 meters concentrate from one or more concentrate containers 101 (one container is shown but multiple containers may be present) and adds them to, and dilutes them with purified water in a mixing container 102. The concentrate containers 101 and mixing container 102 form parts of a single disposable which may also contain a switchable fluid circuit (not shown) that forms part of the disposable component 100A. Mixed dialysis fluid (or other medicament) is pumped by the peritoneal dialysis fluid proportioner/cycler 103 through a connected line to a patient 101A, for example for peritoneal dialysis. The configuration of FIG. 1A allows the sterile concentrate and the fluid circuit and containers used for preparation, as well as short term storage, to be provided as a single sealed sterile disposable with a small predefined number of connections to external devices. These may include connections to the purified water source 104 and connections to the external medicament consumer. The small number of connections minimizes the risk of contamination. By diluting and mixing concentrate at the point of use, the volume of fluid that has to be stored at a peritoneal dialysis treatment location is also minimized. In a peritoneal dialysis embodiment, the disposable component 100A may be configured with sufficient concentrate to perform multiple fill/drain cycles of a single peritoneal dialysis treatment. For example, the disposable component 100A may have sufficient concentrate for multiple fill cycles of a daily automated peritoneal dialysis treatment (APD).

Referring now to FIG. 1B, a medical preparation and peritoneal dialysis fluid proportioner/cycler system 90B is similar to the medical fluid preparation and peritoneal dialysis fluid proportioner/cycler system 90A except that the disposable component 100B that has a fluid circuit for proportioning and diluting as well as delivering the product medicament does not contain the concentrate. This allows the size of the disposable component 100B, which is handled frequently, for example, daily, to be reduced in mass and easier for a patient and/or user to handle and store. It also can make the disposable component 100B more economical by reducing waste and providing packaging and manufacturing economies. To provide the concentrate, a separate disposable component 100E is provided which contains one or more concentrate containers 101. The disposable component 100E may have a large capacity and may be changed on a schedule that is much less frequent than the frequency of the replacement of the disposable component 100B. For example, the disposable component 100B may be replaced each time a daily peritoneal dialysis treatment is performed. It may be called a "daily disposable component." For example, the disposable component 100E may be replaced once every month so it may be called a "monthly disposable" or it may be replaced every week and called a "weekly disposable". The precise capacity and the time the disposable generally lasts is not a limiting feature of the disclosed subject matter. What is relevant is that the disposable component 100E (and others disclosed below) have sufficient capacity for multiple treatments where each treatment includes multiple fill/drain cycles of a peritoneal dialysis treatment.

The disposable component 100B may also have, as part of the fluid circuit included therein, a sterilizing filter 115 of a type that has an air-line 118 to permit the pressure testing of a membrane thereof. The latter type of filter test may be performed automatically by a controller of the peritoneal dialysis fluid proportioner/cycler 103 on a schedule that is more frequent than the replacement schedule for the disposable component 100E. In embodiments, the sterilizing filter 115 may be integrated, and therefore, replaced with, the disposable component 100B. This allows the sterilizing filter 115 to be sealed and sterilized with the disposable component 100B and mixing container 102 as a single unit along with the switchable fluid circuit (not shown). Note details of a suitable configuration for a switchable fluid circuit may be found in International Patent Application Publication WO2013141896 to Burbank, et al.

A function provided by the sterilizing filter 115 is to provide safety given that a new sterile disposable component 100B is attached to the concentrate 101 for each peritoneal dialysis treatment. A similar filter may be employed in all the embodiments for the line indicated at 107 conveying the purified water to the peritoneal dialysis fluid proportioner/cycler 103. Since a new connection is required each time the disposable component 100B is replaced, there is a risk of contamination from the new connection. The sterilizing filter 115 (and others) can be provided as a sterile barrier to protect the sterile interior of the disposable component 100B, thereby ensuring that any contamination resulting from the newly-made connection does not enter the disposable component 100B interior. In addition, the automatic testing of the filter provides assurance that the sterilizing filter 115 integrity has provided the expected sterile fluid. Thus, the testability functions as a guarantee of the filter's sterilizing function. Testing of sterilizing filters using pressurized air testing can be done in various ways, for example, a bubble point test can be performed. Alternatively, a pressure decay test can be done where fluid is pumped across the membrane and the pressure drop measured and compared with a pressure drop representative of an intact filter or pressure is increased on one side, pumping stopped, and the rate of decay of pressure compared to a predefined curve representative of an intact filter. In other embodiments, the filter is housed in an air-tight container and the container is pressurized to a level that is below the expected bubble point, but high enough to guarantee that the membrane is sterilizing grade. The filter has air vents so this pressurizes the membrane. The rate of (air) pressure decay is then measured and if the decay rate is greater than a predefined threshold rate, the filter is indicated to have failed. Other means of testing filter integrity may be used, for example, concentrates can include a large-molecule excipient whose presence can be detected using automatic chip-based analyte detection (e.g., attachment of fluid samples to selective fluorophore after flowing through the filter and optical detection after concentration). A feature of the embodiments that use a filter to provide the guarantee, as mentioned, is that the filter forms part of a sterilized unit that is otherwise hermetically sealed or protected by one or more additional sterilizing filters. Thus, in embodiments, the entire sealed and sterilized circuit may have sterilizing filters (1) at all openings to its interior or at least (2) at all openings to which fluid is admitted from the external environment.

Referring now to FIG. 1C, a medical preparation and peritoneal dialysis fluid proportioner/cycler system 90C is similar to the medical fluid preparation and peritoneal dialysis fluid proportioner/cycler system 90B in that the disposable component 100C that has a fluid circuit for proportioning and diluting as well as delivering the product medicament does not contain the concentrate. As in peritoneal dialysis fluid proportioner/cycler system 90B, a separate disposable component 100F is provided which contains one or more concentrate containers 101, in this example, a first concentrate container 105A and a second concentrate container 105B are shown. These may be in the form of canisters held by a single packaging wrapper 105C or they may be replaced separately when they expire or are exhausted. As in the peritoneal dialysis fluid proportioner/cycler system 90B, the disposable component 100C may have a large capacity and may be changed on a schedule that is much less frequent than the frequency of the replacement of the disposable component 100B. For example, the first concentrate container 105A and/or second concentrate container 105B may be sized to be replaced on a monthly basis.

In the medical fluid preparation and peritoneal dialysis fluid proportioner/cycler system 90C, the disposable component 100C may also have, as part of the fluid circuit included therein, two sterilizing filters (collectively indicated as the sterilizing filter 115), each of the type that has an air-line 118 to permit the pressure-testing of a membrane thereof. Each of the concentrates from first concentrate container 105A and second concentrate container 105B may thereby be sterile-filtered and the filter tested for each separately. As in the peritoneal dialysis fluid proportioner/cycler system 90B, this configuration allows the sterilizing filters 115 to be sealed and sterilized with the disposable component 100C and mixing container 102 as a single unit along with the switchable fluid circuit (not shown). As in any of the embodiments a sterilizing filter may be used in the water line as indicated at 107.

Referring now to FIG. 1D, a medical preparation and peritoneal dialysis fluid proportioner/cycler system 90D is similar to the medical fluid preparation and peritoneal dialysis fluid proportioner/cycler system 90C in that the disposable component 100C that has a fluid circuit for proportioning and diluting as well as delivering the product medicament does not contain the concentrate. As in peritoneal dialysis fluid proportioner/cycler system 90C, a separate disposable component 100G is provided which contains a first concentrate container 105A and a second concentrate container 105B. As in any of the embodiments, the number of concentrates may be greater or fewer. The concentrates may be held in the canisters which may have a single packaging wrapper 105C or they may be replaced separately when they expire. As in the peritoneal dialysis fluid proportioner/cycler system 90C, the disposable component 100G may have a large capacity such that it can be replaced on a schedule that is much less frequent than the frequency of the replacement of the disposable component 100D. For example, the first concentrate container 105A and/or second concentrate container 105B may be sized to be replaced on a monthly basis. In the medical fluid preparation and peritoneal dialysis fluid proportioner/cycler system 90D, the disposable component 100D may also have, as part of the fluid circuit included therein, the sterilizing filter 115, also of the type that has an air-line 118 to permit the pressure testing of a membrane thereof. To sterile-filter each of the concentrates from first concentrate container 105A and second concentrate container 105B, a connection platform allows the peritoneal dialysis fluid proportioner/cycler 103 to draw purified water, first concentrate container 105A or second concentrate container 105B selectively by closing a valve on all but one of these at a time by the connection platform 106 under control of the peritoneal dialysis fluid proportioner/cycler 103. As in the peritoneal dialysis fluid proportioner/cycler system 90B, this configuration allows the sterilizing filter 115 to be sealed and sterilized with the disposable component 100D and mixing container 102 as a single unit along with the switchable fluid circuit (not shown). The switching fluid circuit of the connection platform 106 may be part of a disposable that is replaced with the first concentrate container 105A and second concentrate container 105B.

In the present and any of the embodiments, the long-term concentrate containers (e.g., monthly disposable) may be replaced on separate schedules so they need not be packaged as a single disposable. This may provide further economy when one concentrate is used at a lower rate by some patients than others, thus allowing the concentrate to be consumed fully before replacing.

It should be evident that there is the potential for the reduction of waste of concentrate by structuring the batch preparation components to permit the changing of concentrates independently of each other and at intervals that cover multiple peritoneal dialysis treatment sessions. Each concentrate container can be used until exhaustion. For embodiments, exhaustion may be defined to be a condition where insufficient concentrate remains in a single container to permit the preparation of a full batch of peritoneal dialysis fluid, a full batch, in embodiments, being a quantity of concentrate component sufficient for a single fill cycle. In other embodiments, a concentrate container may be exhausted when there is insufficient concentrate to make a predefined number of batches or enough to make sufficient dialysate for a full treatment. If two concentrates are mixed to form a batch, each component concentrate may be changed out when the prescription's required contribution of that concentrate to make a single batch exceeds the remaining volume in the particular container. The residual volume threshold associated with this insufficiency is a fixed volume, so that its percentage of the total volume available from a full container is smaller for a large container than for a smaller container. Thus, in embodiments where the concentrate container is replaced only when the threshold is reached, which container holds large total volume, for example, enough for multiple fill cycles, or better, enough for multiple peritoneal dialysis treatments each including multiple fill cycles, the total waste is much smaller than a disposable component containing concentrate for a single peritoneal dialysis treatment. An example of the latter is discussed below with reference to FIGS. 8A and 8B. In addition, since each concentrate container can be replaced separately, the fixed residual thresholds of the multiple concentrate containers are independent of each other because each container can be replaced independently of the other. In contrast, in the embodiments of FIGS. 8A and 8B, if one container reaches the minimum volume before the other, the contents of neither concentrate container can be used further.

In embodiments, the concentrate containers are sized to permit a single peritoneal dialysis treatment. For convenience and convention, a single peritoneal dialysis treatment would be considered a single day's worth of peritoneal dialysis treatment, for example, a series of nocturnal PD cycles ending with a fill. So, a single day's peritoneal dialysis treatment is equal to a sufficient quantity of fluid to perform multiple fill and drain cycles. Embodiments in which the concentrate containers are sized for a single day's peritoneal dialysis treatment differ from those described with reference to the embodiments of FIGS. 8A and 8B in that the concentrates can be changed independently thereby achieving a potential savings of a first concentrate that is used at a rate such that a residual volume of the first concentrate can be used more fully as described above. More specifically, if the concentrate containers are sized such that batches of at least predefined prescriptions require more of a first concentrate component than of a second concentrate component and such that at least one batch, or at least one day's worth of batches can be completed while leaving sufficient residual concentrate of the second component to make at least one additional batch, or one additional day's worth of batches, after replacing the first concentrate component, then a savings of the second concentrate may be enjoyed. In embodiments, the total concentrate of the most heavily used container of a multiple-component concentrate system is at least sufficient for:

Multiple batches, a batch being sufficient for a single peritoneal cycle (fill volume of a peritoneum of a predefined class of patient (e.g., child, adult, adult of a certain size, etc.);

Same as 1, but where the multiple batches are sufficient for a single peritoneal dialysis treatment of multiple fill-drain cycles;

Same as 2, but the most heavily used concentrate container is sufficient for making enough dialysis fluid for multiple peritoneal dialysis treatments;

Same as 2, but the most heavily used concentrate container is sufficient for making enough dialysis fluid for multiple days' worth of peritoneal dialysis treatments if a single day's worth is not identical to a single peritoneal dialysis treatment's worth;

A full week's worth of peritoneal dialysis treatments; or

A full month's worth of peritoneal dialysis treatments or some other interval on the order of a month or multiple months.

Figure 1G:
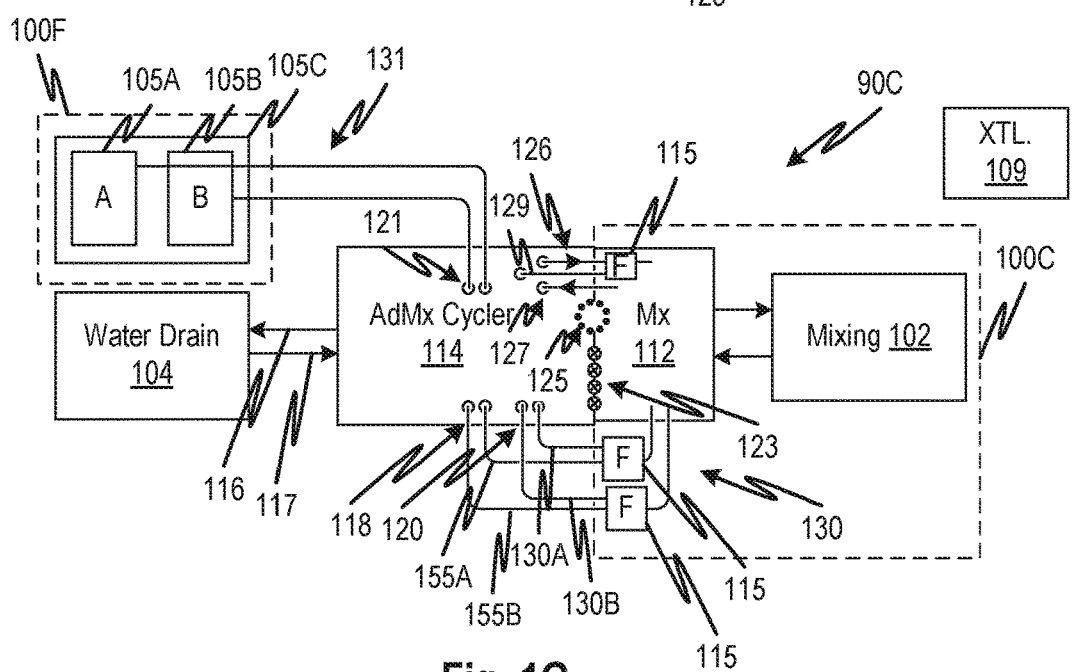
Figure 1H:
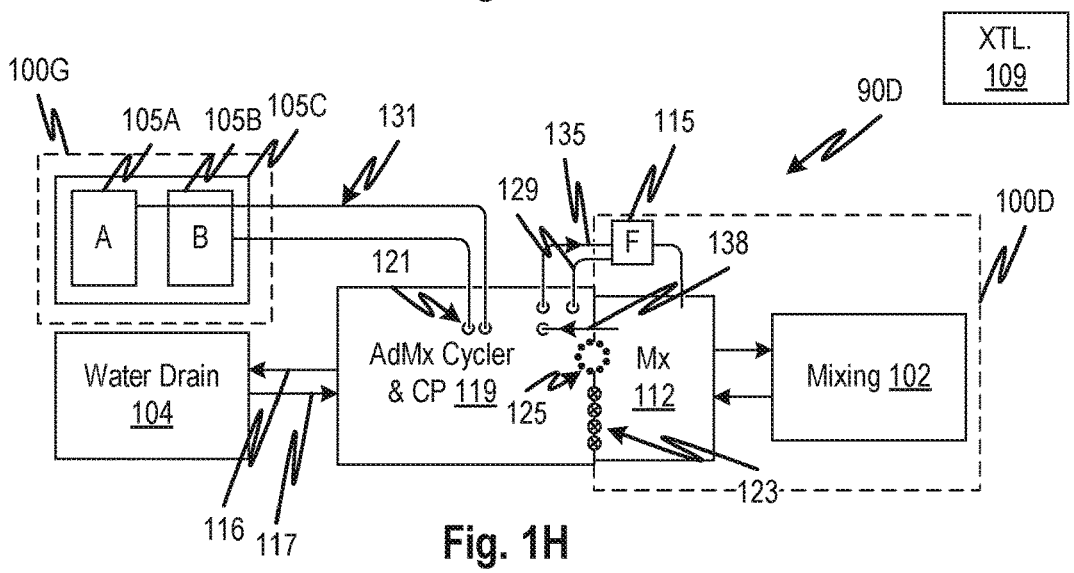

FIGS. 1F-1H show embodiments similar to those of FIGS. 1A-1D and elaborating further details thereof. Referring now to FIG. 1F, a fluid circuit is indicated at 112. The fluid circuit 112 engages with the peritoneal dialysis fluid proportioner/cycler 114 by means of valve actuators 123 and one or more pumping actuators 125 which engage the fluid circuit elements of the fluid circuit 112 without wetting the actuator components. For example, a type of valve actuator such as a linear-motor driven pinch clamp may close and open tubing for flow therethrough and peristaltic pump rollers may engage pumping tube segments. The configuration is not limited to such examples, and many are known in the art, any of which may be used in the present embodiment. The fluid circuit 112 has water suitable for peritoneal dialysis and drain lines 126, 127. The water suitable for peritoneal dialysis flows through a line with a sterilizing filter 115 according to any of the disclosed embodiments including a testable filter and two sterilizing filters in series. The only connections that need to be made for supplying fluid or draining fluid are connections indicated at 129. The water suitable for peritoneal dialysis and drain lines 126, 127 may be formed as part of the fluid circuit 112. In embodiments, the fluid circuit 112, concentrate container(s) 101, and mixing container 102 may be pre-connected to form a complete disposable fluid circuit 100A including concentrate.

Referring now to FIG. 1G, further details of the peritoneal dialysis fluid proportioner/cycler system 90C are shown. The separate disposable component 100F contains concentrate containers 105A and 105B and connects to the peritoneal dialysis fluid proportioner/cycler 114 by connectors 121, which may include a double connector as described in embodiments described herein or other types. The peritoneal dialysis fluid proportioner/cycler 114 has pumping actuators 125 and valve actuators 123 that engage the fluid circuit 112. Here the peritoneal dialysis fluid proportioner/cycler 114 provides a pass-through connection for the concentrate while the sterilizing filters 115 on the concentrate lines 130 form part of the disposable component 100C, which includes the fluid circuit 112 and mixing container 102. That is, the peritoneal dialysis fluid proportioner/cycler 114 connects the concentrate lines 131 respectively to the concentrate lines 155A and 155B of the fluid circuit 112. Here also, connectors for air-lines 130A and 130B are provided to the peritoneal dialysis fluid proportioner/cycler 114 where an air pump (not shown) can generate a positive pressure and a pressure sensor can measure the positive pressure. A filter integrity test may be done after flowing fluid into the fluid circuit. During set-up, the disposable component 100C may be connected by connecting water suitable for peritoneal dialysis and drain lines 116, 117, concentrate lines 155A and 155B and air-lines 130A and 130B, while the connectors 121 can remain in place through the entire long-term disposable cycle, that is, until the separate disposable component 100F is expired. Since the latter is replaced much less frequently, the connectors 121 can remain in place for a relatively long period, and frequent changes can be limited to changing connectors 122, 120, and connectors for water suitable for peritoneal dialysis and drain lines 116, 117 as well as the air-lines 130A and 130B. In embodiments, for convenience, all of these connections can be provided in the form of ganged connectors to make and unmake multiple connections at once. The concentrate containers 105A and 105B may connect to a connection platform (not shown as a unit but may include the connectors and a support for the concentrate containers 105A and 105B) and a holder for the by the peritoneal dialysis fluid proportioner/cycler 114. See further connection platform embodiments for details.

Referring to FIG. 1H, a simplified arrangement becomes possible if the disposable component 100G is connected to the peritoneal dialysis fluid proportioner/cycler 114 by connectors 121, but all concentrates and water flow into the fluid circuit 112 via the fluid line 135 and all of these fluids are filtered by sterilizing filter 115. To provide this, a connection platform with its own controller (not shown separately) may be provided and connected to a peritoneal dialysis fluid proportioner/cycler, the combination being illustrated at 119. The connection platform portion of the combined peritoneal dialysis fluid proportioner/cycler and connection platform 119 may be as described with reference to FIGS. 2K through 2M, for example. The connection platform portion of the combined peritoneal dialysis fluid proportioner/cycler and connection platform 119 selects one of the fluids at a given time by closing off the others and opening a fluid path to the selected one of water, concentrate A, and concentrate B. As indicated, here and in any embodiments, further or fewer concentrates may be used. A drain line 135 is present. A communications interface may be provided to allow commands to be sent from the fluid circuit 112 to the peritoneal dialysis fluid proportioner/cycler and connection platform 119.

Figure 2A:
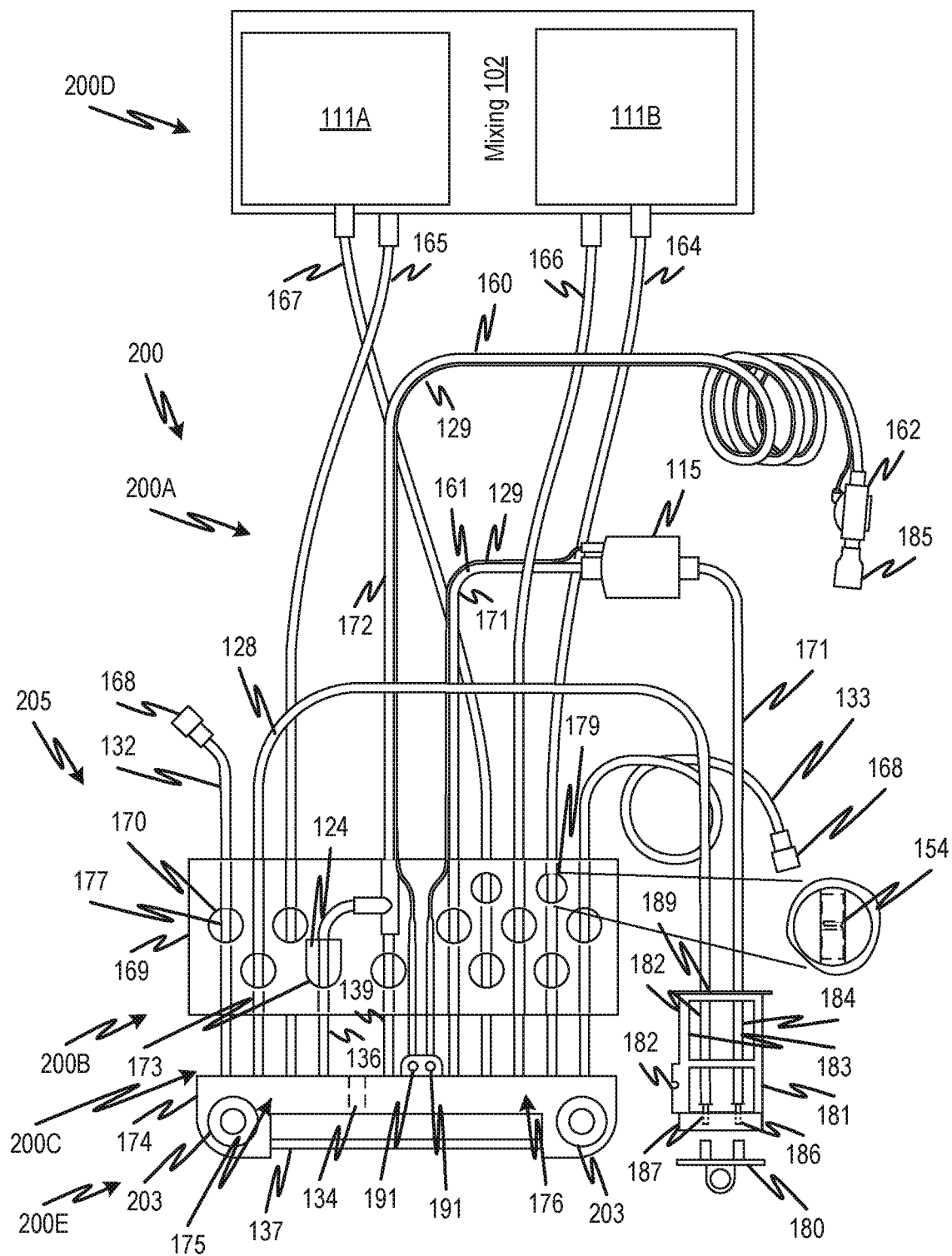
FIG. 2A shows a disposable fluid circuit for use with peritoneal dialysis fluid proportioner/cyclers of certain embodiments disclosed herein.

FIG. 2A shows a disposable fluid circuit 200 with fluid lines and components 200A and a cartridge portion 205 containing a fluid flow director portion 200B and a manifold portion 200E. The disposable fluid circuit 200 is used as a replaceable disposable component with a peritoneal dialysis fluid proportioner/cycler according to embodiments disclosed herein. The present disposable fluid circuit 200 may be used with the peritoneal dialysis fluid proportioner/cycler system 90A, for example. Two concentrate containers 111A and 111B and a mixing container 102 are connected as a pre-connected unit with other parts of the fluid circuit. The two concentrate containers 111A and 111B and mixing container 102 may be provided as a welded double panel sheet with welded seams that define the respective chambers. The mixing container 102 has two lines, an inflow line 165 and an outflow line 166. A first concentrate container 111A container has 167, which may be pre-connected and a second concentrate container 111B line 164, which may be pre-connected. The present embodiment is for a peritoneal dialysis fluid proportioner/cycler and has a pre-connected fill-drain line 160 with a dialysis fluid line 172 attached to an air-line 129. The latter may be formed as a single unit by co-extrusion. The air-line 129 attaches to a pressure-sensing pod 162 located at a distal end of the pre-connected fill-drain line 160. A connector 185 at the distal end of the pre-connected fill-drain line 160 is sealed. Another double line 161 has an air-line 129 and a fluid line 171. The fluid line 171 receives fluid from peritoneal dialysis fluid proportioner/cycler 114 and the air-line is used for testing the membrane of the filter. The two air-lines 129 connect to respective ports 191 that automatically connect in the actuator portion 140 of any of the suitable peritoneal dialysis fluid proportioner/cycler embodiments. The actuator portion 140 may be is described with reference to FIG. 2B. Sample ports are provided at 168 at the ends of sample fluid lines 132 and 133 for extracting fluid from respective chambers 175 and 176 of a manifold 174. The two chambers 175 and 176 are separated by a barrier 134 and connected by a pumping tube segment 137. Pressure pods 178 are installed in each of the two chambers 175 and 176 to measure pressure on the suction and pressure sides of the pumping tube segment 137. The dialysis fluid line 172 has two branches 136 and 139. A waste line 128 and the fluid line 171 connect via a double connector 181. Lines 132, 128, 165, and branch 136 connect to chamber 175. Lines 133, 164, 166, 167, 171 and branch 139 connect to chamber 176.

The double connector 181 supports lines 171 and 128 and provides a pair of connectors 186 and 187 to permit connection of lines 171 and 128 to water inlet and fluid drain line ports on the peritoneal dialysis fluid proportioner/cycler 114. The connectors 186 and 187 are sealed by a cap 180. A recess 5251 (See FIGS. 5A, 5B) to engage a détente pin (not shown, but may be a spring-biased pin in the opening that receives the double connector 181) provides tactile confirmation of full engagement of the double connector 181. The double connector 181 has a window 183 that provides access to a cut and seal actuator (not shown in this drawing but indicated at 210 in FIGS. 2I through 2K). When the segments 182 and 184 of lines 171 and 128 are cut, the double connector can remain in place sealing the water inlet and fluid drain line ports until it is removed immediately prior to connecting a fresh double connector 181. This provides a barrier to prevent contaminants from entering the water inlet and fluid drain line ports, which in turn protects the sterile fluid path used by the peritoneal dialysis fluid proportioner/cycler or connection platform.

The first concentrate container 111A and concentrate container 111B are both sealed by a frangible seal 154 in each of the lines 164 and 167. The seal is fractured automatically by an actuator after the manifold cartridge 205 is loaded into a receiver that engages it with the interface shown in FIG. 1B. Holes 170 are provided in a cartridge support 169 that holds the lines in predefined positions. Holes 170 provide access to pinch actuators that selectively close and open the lines 177. Certain lines such as lines 177 engage with valve actuators so that they function as valve segments. Holes 179 provide access to actuators that fracture the frangible seals 154. Note that the cartridge support 169 is bridged to the manifold 174 by a battery of tubes indicated collectively at 200C. Even though the polymer of the tubes is flexible, their lengths, number, are such that the overall structure including the cartridge support 169 and the manifold 174 is sufficiently stiff may be readily inserted in a receiving slot.

FIG. 2B shows an actuator portion 140 of a peritoneal dialysis fluid proportioner/cycler, according to embodiments of the disclosed subject matter. Referring to FIG. 2B, a receiving slot 158 receives the cartridge portion 205 and aligns it with the various actuators and sensors now identified. The various actuators and sensors include pinch clamp actuators 141 that selectively press against selected tubes to provide a valve function. The actuators and sensors further include frangible seal actuators 142 that fracture frangible seals 154 in the concentrate lines that contain them. The frangible seal actuators 142 may be activated simultaneously to open the lines between the pump and the concentrate containers once the pump (e.g., eight-roller peristaltic pump 143—note that the number of rollers can be any number) is engaged with the pumping tube segment 137. The actuators and sensors further include an air sensor 150, for example an optical air sensor, that wraps partly around the tube segment of branch 136 in the upper portion of the hole indicated at 124. Ports 146 and 147 connect a vacuum or pressure pump to the respective ports 191.

FIG. 2C shows connection platform 219 that serves as an interface between a purified water source and the peritoneal dialysis fluid proportioner/cycler, according to embodiments of the disclosed subject matter. Connection platform 219 is an embodiment that may provide for connection to water and drain lines 116 and 117 of embodiments of FIGS. 1G and 1H as well as connectors for the concentrate containers 105A and 105B for interfacing with the peritoneal dialysis fluid proportioner/cycler 114. The connection platform 219 permits the purified water source 104 to be connected to different devices, such as peritoneal dialysis treatment devices. Shown here is a configuration adapted for peritoneal dialysis medicament preparation, and optionally peritoneal dialysis treatment also.

Water from the purified water source 104 is received in water line 245 via connection 244 and flows through ultra-filters 237. Pressure of the water suitable for peritoneal dialysis supply is monitored by a pressure sensor 218. A valve 234 selectively controls the flow of water suitable for peritoneal dialysis to a double connector 215. The purified water source terminates at a purified water connector 224 of the double connector 215. The double connector 215 also has a drain terminal connector 225 which splits at a junction 220 into a path that flows to a pair of conductivity sensors 230 and then merges at junction 238 to proceed to a drain 236 and a path that flows directly to the drain 236. The selected path is controlled by valves 232, 240, and 242 which are controlled by a controller 210. The double connector 181 previously described is received in a slot 214 where connections are made to the purified water connector 224 and drain terminal connector 225. A détente mechanism 216 provides tactile and audible feedback to the operator when a home (fully connected) position of the double connector 181 is realized by inserting into the receiving slot 214. The receiving slot 214A has a cutting and sealing actuator 212 driven by a controller 210 that cuts the tubes through the window of double connector 181. A connector 239 serves as an adapter to permit connection to various types of drains. The connection platform 219 is also provided with sensors including a moisture sensor 249 located to detect leaking fluid in the connection platform 219, a tilt sensor 226 to indicate the proper orientation of the connection platform 219, and a user interface to interact with the controller 210. The connection platform 219 may be received in a receiving slot 231 and may be formed as a unitary replaceable component. If sterility or leakage problems arise, the connection platform 219 can be replaced easily.

FIG. 2D shows a peristaltic pumping actuator 143 that permits the use of a straight pumping tube segment in a generally planar cartridge, employed as a feature of embodiments disclosed herein. The rollers 145 are attached to a rotor that has recesses to permit clearance for the bulge of an adjacent pumping tube segment positioned between a race 148 and the rollers 145. The rollers 145 are unsprung, unlike other peristaltic pump rollers, and rotate on fixed bearings 1472. Instead, the race 148 is sprung by springs 144 which urge the race against a pumping tube segment pinched by the rollers 145. This is a particular embodiment of a pump and at least some of the embodiments are not limited based on whether the rollers or race are sprung. Either the rotor 149 can be moved toward the race 148 to engage a pumping tube segment, or the race 148 can be moved toward the rotor 149. A sufficient gap at 1492 during loading allows a cartridge, such as cartridge portion 200B with a pumping tube segment to be slid in with no interference. The race 148 is constrained to tilt (in the plane of the drawing) and translate up and down in the plane of the drawing by pins 152 received in guides 153.

Figure 2E:
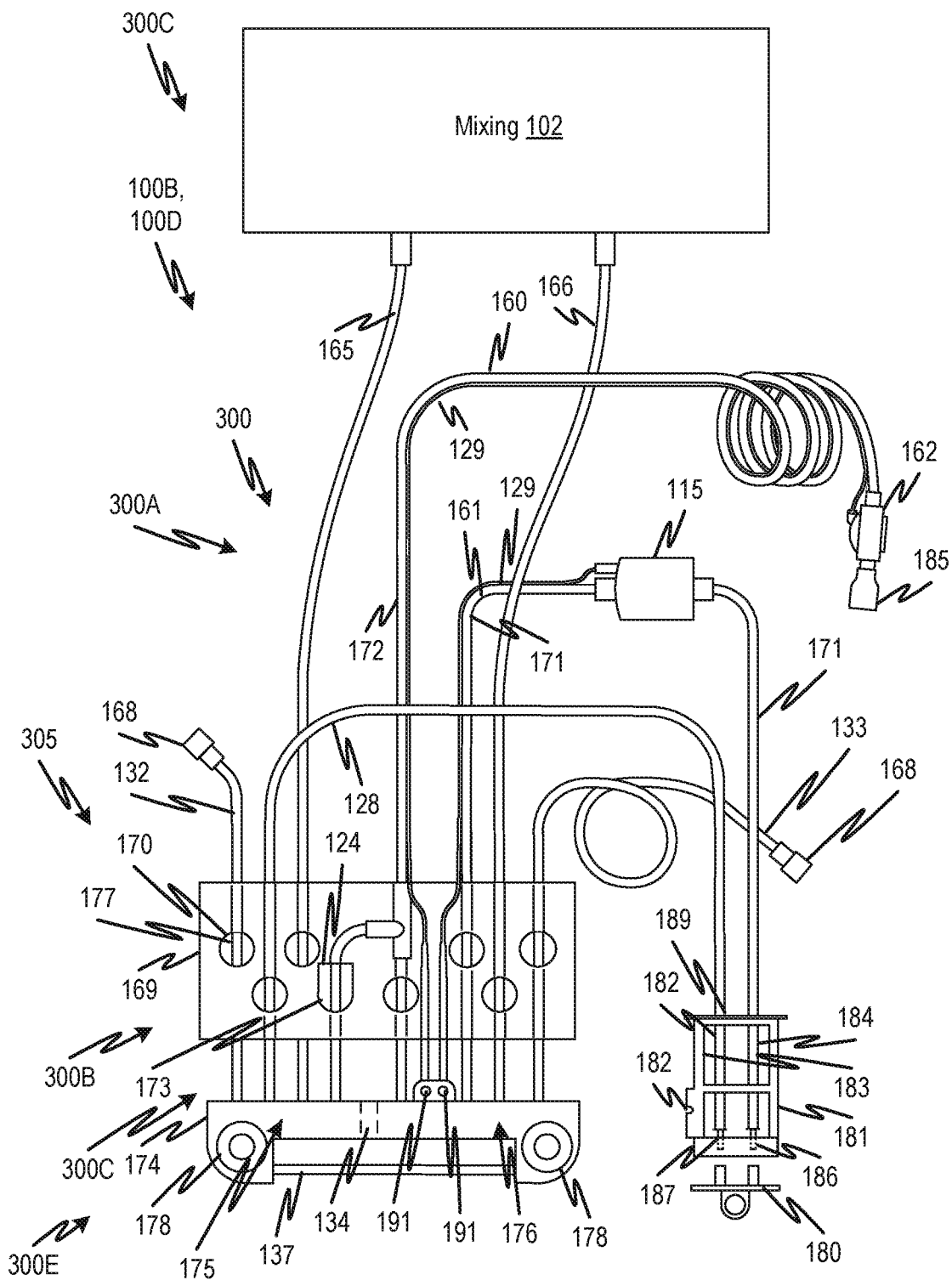
FIG. 2E shows a disposable fluid circuit for a peritoneal dialysis fluid proportioner/cycler according to embodiment of the disclosed subject matter in which concentrates are extracted from a disposable component that is separate from the cycler/preparation fluid circuit.

FIG. 2E shows a disposable fluid circuit for a peritoneal dialysis fluid proportioner/cycler according to an embodiment of the disclosed subject matter in which concentrates are extracted from a disposable component that is separate from the cycler/preparation fluid circuit. A disposable fluid circuit 300 has fluid lines and components 300A and a cartridge portion 305 containing a fluid flow director portion 300B and a manifold portion 300E. The disposable fluid circuit 300 is for use with peritoneal dialysis fluid proportioner/cyclers of certain embodiments disclosed herein. The present disposable is an embodiment that may be used with the peritoneal dialysis fluid proportioner/cycler system 90B or 90D, for example, where two concentrate containers 105A and 105B (not shown in this drawing but shown in FIGS. 1B and 1H—again, only as examples so other features of the peritoneal dialysis fluid proportioner/cycler are not limiting of the disposable fluid circuit 300) are provided as a separate unit from disposable fluid circuit 300, which has a mixing container 102 and no concentrate containers. The mixing container 102 may be provided as a welded double panel sheet with welded seams that define the chambers. The mixing container 102 may have two lines, an inflow line 165 and an outflow line 166. In alternative embodiments, the mixing container 102 may have only a single line for both inflow and outflow.

The present embodiment is for a peritoneal dialysis fluid proportioner/cycler and has a pre-connected fill-drain line 160 with a dialysis fluid line 172 attached to an air-line 129. The latter may be formed as a single unit by co-extrusion. In alternative embodiments, the fill-drain line may be separate and connectable with a separate connector. In the present embodiment, the air-line 129 attaches to a pressure-sensing pod 162 located at a distal end of the pre-connected fill-drain line 160. A connector 185 at the distal end of the pre-connected fill-drain line 160 is sealed. Another double line 161 has an air-line 129 and a fluid line 171. The fluid line 171 receives fluid from peritoneal dialysis fluid proportioner/cycler 114 and the air-line is used for testing the membrane of the filter. The two air-lines 129 connect to respective ports 191 that automatically connect in an actuator portion 140 as described with reference to FIG. 2B. Sample ports are provided at 168 at the ends of sample fluid lines 132 and 133 for extracting fluid from respective chambers 175 and 176 of a manifold 174. The two chambers 175 and 176 are separated by a barrier 134 and connected by a pumping tube segment 137. Pressure pods 178 are installed in each of the two chambers 175 and 176 to measure pressure on the suction and pressure sides of the pumping tube segment 137. The dialysis fluid line 172 has two branches 136 and 137. A waste line 128 and the fluid line 171 connect via a double connector 181. Lines 132, 128, 165, and branch 136 connect to chamber 175. Lines 133, 164, 166, 167, 171 and branch 139 connect to chamber 176.

The double connector 181 supports lines 171 and 128 and provides a pair of connectors 186 and 187 to permit connection of lines 171 and 128 to water inlet and fluid drain line ports on the peritoneal dialysis fluid proportioner/cycler 114. The connectors 186 and 187 are sealed by a cap 180. A recess to engage a détente pin provides tactile confirmation of full engagement of the double connector 181. The double connector 181 has a window 183 that provides access to a cut and seal actuator (not shown in this drawing). When the segments 182 and 184 of lines 171 and 128 are cut, the double connector can remain in place sealing the water inlet and fluid drain line ports on the peritoneal dialysis fluid proportioner/cycler 114 until it is removed immediately prior to connecting a fresh double connector 181. This provides a barrier to prevent contaminants from entering the connection platform 219 fluid path, which in turn protects the sterile fluid path used by the peritoneal dialysis fluid proportioner/cycler 114. The connection platform 219 selects the fluid to be delivered to the fluid line 171. Holes 170 are provided in the cartridge support 169 that holds the lines in predefined positions. Holes 170 provide access to pinch actuators that selectively close and open the lines 177. Note that the cartridge support 169 is bridged to the manifold 174 by a battery of tubes indicated collectively at 300C. Even though the polymer of the tubes is flexible, the cartridge support 169 and the manifold 174 may be readily inserted in a receiving slot.

FIGS. 2F and 2G show concentrate disposable components for use with embodiments of the disclosed subject matter. Referring to FIG. 2F, a concentrate package 206, for example a cardboard box, contains a pair of concentrate containers 262 and 264. Each of the concentrate containers 262 and 264 may be connected to a respective port 265, 266 of a double connector 181B, the double connector 181B may be as the one described above (FIGS. 2A, 2E) or below (e.g., 5A-5E) or another type of connector or pair of connectors. For example, a simple two-port connector 273 may be used. Separate connectors may also be used to permit the containers to be replaced independently of each other. In embodiments, the double port may be connected to a receiving device 287 as shown in FIG. 2G so that each concentrate 262 or 264 can be installed in the receiving device 287 independently of the other while the double connector 181B remains connected to the receiving device 287. The receiving device 287 has fluid connectors 285 for connecting to corresponding connectors on the concentrate containers 262 and 264 such that once a respective one of the containers 262 or 264 is installed, fluid can be drawn through the ports 288A and 288B of the two-port connector 273. The latter may be connected to the connection platform 219, for example as shown in FIG. 2I.

Figure 2H:
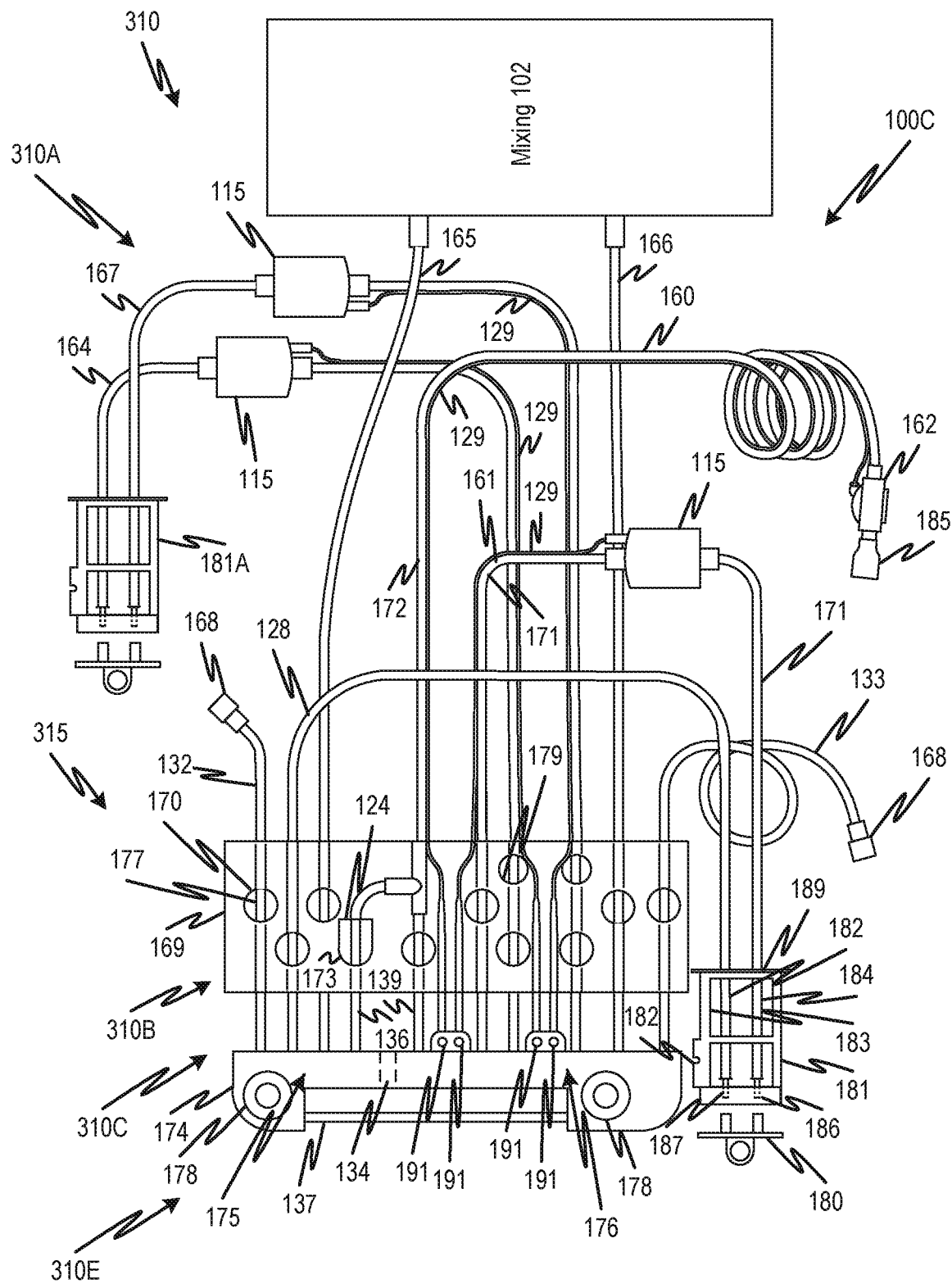
FIG. 2H shows a disposable fluid circuit for a peritoneal dialysis fluid proportioner/cycler according to embodiments of the disclosed subject matter in which concentrates are extracted from a disposable component that is separate from the cycler/preparation fluid circuit through respective filtered lines.
Figure 2I:
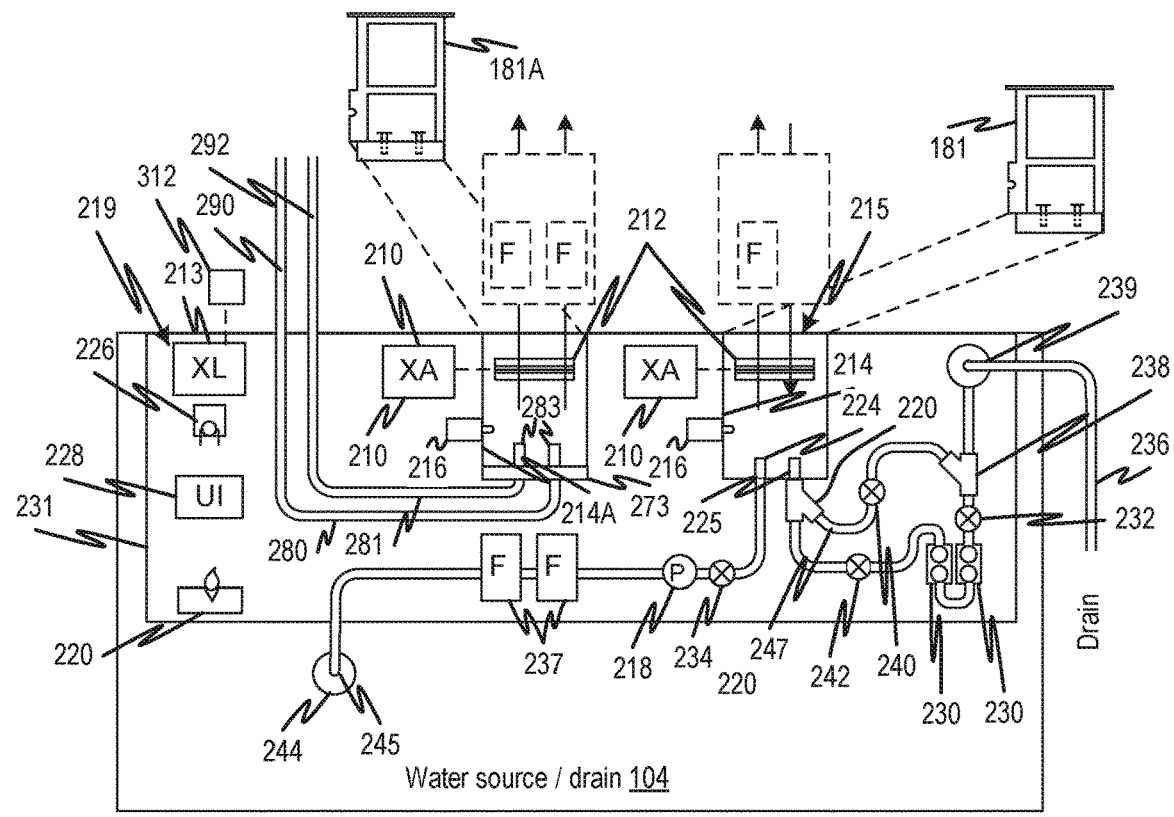

FIG. 2H shows a disposable fluid circuit 310 for a peritoneal dialysis fluid proportioner/cycler according to embodiments of the disclosed subject matter in which concentrates are extracted from a disposable component that is separate from the cycler/preparation fluid circuit through respective filtered lines. The disposable fluid circuit 310 has fluid lines and components 310A and a cartridge portion 315 containing a fluid flow director portion 310B and a manifold portion 310E. The disposable fluid circuit 310 is for use with peritoneal dialysis fluid proportioner/cyclers of certain embodiments disclosed herein. The present disposable is an embodiment that may be used with the peritoneal dialysis fluid proportioner/cycler system 90C where two concentrate containers 105A and 105B are provided as a separate disposable from one shown in 100C with a mixing container 102, only. The mixing container 102 may be provided as a welded double panel sheet with welded seams that define a chamber. The mixing container 102 has two lines, an inflow line 165 and an outflow line 166. The present embodiment is for a peritoneal dialysis fluid proportioner/cycler and has a pre-connected fill-drain line 160 with a dialysis fluid line 172 attached to an air-line 129. The fill-drain line 160 with a dialysis fluid line 172 attached to an air-line 129 may be formed as a single unit by co-extrusion of both lines. The air-line 129 attaches to a pressure-sensing pod 162 located at a distal end of the pre-connected fill-drain line 160. A connector 185 at the distal end of the pre-connected fill-drain line 160 is sealed. Another double line 161 has an air-line 129 and a fluid line 171. The fluid line 171 receives fluid from peritoneal dialysis fluid proportioner/cycler 114 and the air-line is used for testing the membrane of the filter. The two air-lines 129 connect to respective ports 191 that automatically connect in an actuator portion such as 140 as described with reference to FIG. 2B (see 146 and 147 of FIG. 2B). Sample ports are provided at 168 at the ends of sample fluid lines 132 and 133 for extracting fluid from respective chambers 175 and 176 of a manifold 174. The two chambers 175 and 176 are separated by a barrier 134 and connected by a pumping tube segment 137. Pressure pods 178 are installed in each of the two chambers 175 and 176 to measure pressure on the suction and pressure sides of the pumping tube segment 137. The dialysis fluid line 172 has two branches 136 and 139. A waste line 128 and the fluid line 171 connect via a double connector 181. Lines 132, 128, 165, and branch 136 connect to chamber 175. Lines 133, 164, 166, 167, 171 and branch 139 connect to chamber 176. The fluid line 171 connects to a water source.

Figure 2J:
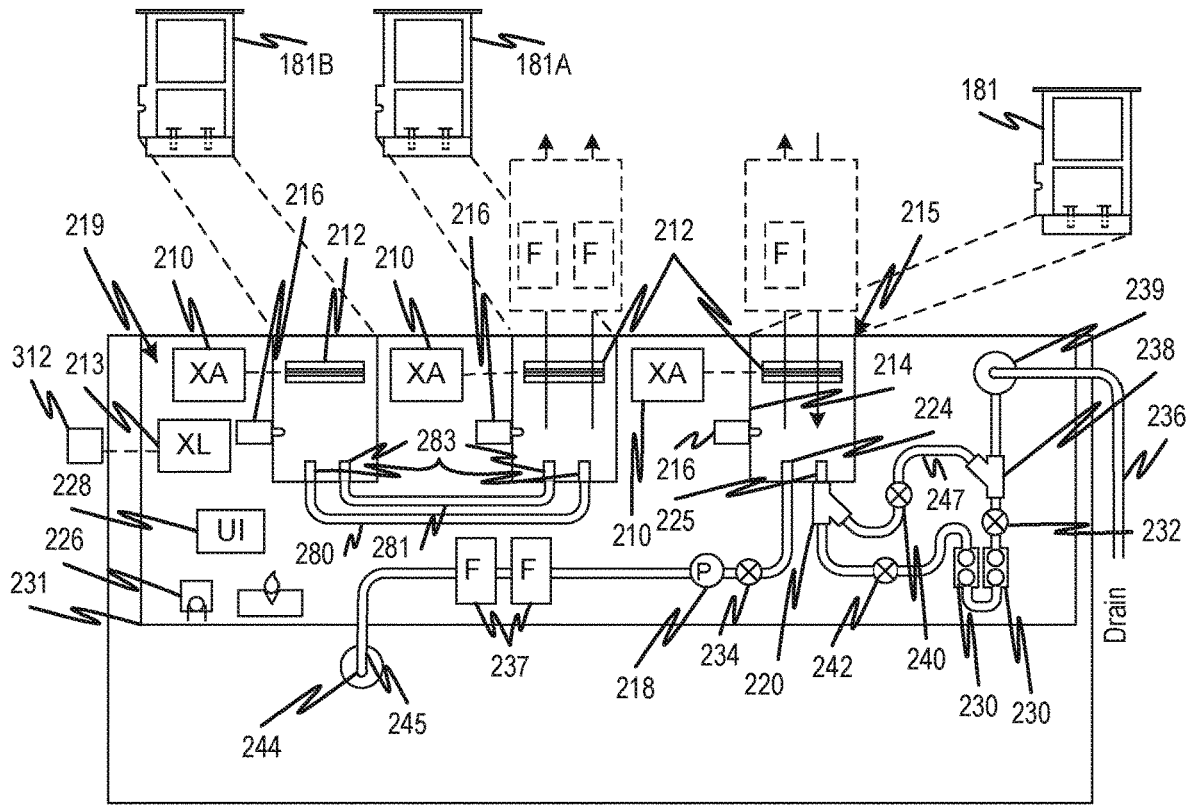

The double connector 181 supports lines 171 and 128 and provides a pair of connectors 186 and 187 to permit connection of lines 171 and 128 to water inlet and fluid drain line ports on the peritoneal dialysis fluid proportioner/cycler 114. The connectors 186 and 187 are sealed by a cap 180. A recess to engage a détente pin provides tactile confirmation of full engagement of the double connector 181. The double connector 181 has a window 183 that provides access to a cut and seal actuator (not shown in this drawing). When the segments 182 and 184 of lines 171 and 128 are cut, the double connector can remain in place sealing the water inlet and fluid drain line ports on the peritoneal dialysis fluid proportioner/cycler 114 until it is removed immediately prior to connecting a fresh double connector 181. This provides a barrier to prevent contaminants from entering the connection platform fluid path, which in turn protects the sterile fluid path used by the peritoneal dialysis fluid proportioner/cycler 114. The connection platform 219 selects the fluid to be delivered to the fluid line 171. Holes 170 are provided in a cartridge support 169 (which may be vacuum-formed) that holds the lines in predefined positions. Holes 170 provide access to pinch actuators that selectively close and open the lines 177. Note that the cartridge support 169 is bridged to the manifold 174 by a battery of tubes indicated collectively at 310C. Even though the polymer of the tubes is flexible, the cartridge support 169 and the manifold 174 may be readily inserted in a receiving slot. Two concentrates are received through lines 164 and 167, respectively. Each of the lines is filtered by a filter 115 as described with reference to FIG. 1G. Respective holes 170 are provided to control the flow of concentrate through each of the lines 164 and 167. FIGS. 2I and 2J show examples of connection platforms 219 for connecting to a double connector 181A to permit concentrate to be drawn through the lines 164 and 167.

Note that the actuators and sensors of the embodiments of FIGS. 2I, 2J, 2K, 2L, and 2M may be controlled by a single controller, for example.

FIGS. 2I, 2J, and 2K show respective embodiments of connection platforms that interface between a purified water source and a separate concentrate source and the peritoneal dialysis fluid proportioner/cycler embodiments disclosed herein, according to embodiments of the disclosed subject matter. Referring now to FIG. 2I and connection platform 219 is an embodiment of the interface providing the water supply and drain connections (116, 117, See FIGS. 1G and 1H) between the purified water source 104 and the peritoneal dialysis fluid proportioner/cycler 114. The connection platform 219 permits the purified water source 104 (FIGS. 1F-1G) to be connected to different devices, such as different peritoneal dialysis treatment devices. Shown here is a configuration adapted for peritoneal dialysis medicament preparation, and optionally peritoneal dialysis treatment also. The present configuration differs from that of FIG. 2C in that the present arrangement includes a mechanism for connecting a circuit such as disposable fluid circuit 310 of FIG. 2H which draws concentrate from a double connector 181A which fits in slot 214A to receive concentrate through ports 283. The double connector 181A also has a détente mechanism 216 to provide feedback to the operator when a home (fully connected) position of the double connector 181A is realized by inserting into the receiving slot 214A. The receiving slot 214A has a cutting and sealing actuator 212, driven by controller 210, that cuts the tubes through the window of double connector 181, 181A. The ports 283 may be supported on a replaceable double connector 273 as described in FIG. 2F so that these ports are provided by a replaceable connector as part of a concentrate package 260 as shown in FIG. 2F that includes concentrate containers 262 and 264 or is fitted to the receiving device 287 described above with reference to FIG. 2G. In alternative embodiments, the ports 283 may be part of the connection platform 219. In that case, the tubes 290 and 292 may be part of the connection platform 219 and provided with separate connectors for connecting the tubes 293 and 294 of the concentrate contains 262 and 264 (FIG. 2F) or similarly to connect the receiving device 287.

As in the FIG. 2C embodiment, water from the purified water source 104 is received in water line 245 via connection 244 and flows through ultrafilters 237. Pressure of the water suitable for peritoneal dialysis supply is monitored by a pressure sensor 218. A valve 234 selectively controls the flow of water suitable for peritoneal dialysis to a double connector 215. The purified water source terminates at a purified water connector 224 of the double connector 215. The double connector 215 also has a drain terminal connector 225, which splits at a junction 220 into a path that flows to a pair of conductivity sensors 230, and then merges at junction 238 to proceed to a drain 236 and a path that flows directly to the drain 236. The selected path 247 is controlled by valves 232, 240, and 242 which are controlled by a controller 210. The double connector 181 previously described is received in a slot 214 where connections are made to the purified water connector 224 and drain terminal connector 225. A détente mechanism 216 provides tactile and audible feedback to the operator when a home (fully connected) position of the double connector 181 is realized by inserting into the receiving slot 214. A connector 239 serves as an adapter to permit connection to various types of drains. The connection platform 219 is also provided with sensors including a moisture sensor 249 located to detect leaking fluid in the connection platform 219, a tilt sensor 226 to indicate the proper orientation of the connection platform 219, and a user interface to interact with the controller 210. The connection platform 219 may be received in a receiving slot 231 and may be formed as a unitary replaceable component. If sterility or leakage problems arise, the connection platform 219 can be replaced easily.

Note that the configuration of FIG. 2I provides a simple and clean connection between the large concentrate containers and the disposable. However, there is no reason a direct connection could not be provided. That is, the long-term concentrate disposable may be provided with its own connector to connect to a double connector 181A or similar connector or pair of connectors. In another variation, shown in FIG. 2J, the connection platform 219 provides a receiving connector for the concentrate connector 181B, which may be attached to the receiving device 287 of the concentrate containers as shown in FIGS. 2F and 2G. In the connection platform 219 of FIG. 2J, a pair of lines 280 and 281 connect the double connectors 181A and 181B so that concentrate can be drawn by the peritoneal dialysis fluid proportioner/cycler 114 according to any of the various embodiments. Effectively, the connection platform 219 in this case functions as a pass-through. The connection with double 181B can be made on a low frequency basis according to the size of the concentrate containers, and the connection with double connector 181A can be made on a per-peritoneal dialysis treatment basis (or other schedule) each time the mixing container 102 and associated fluid circuit (e.g. 310) is replaced. FIG. 2K shows another mechanism for connecting and controlling flow of concentrate to the peritoneal dialysis fluid proportioner/cycler 114. Here connectors 289 connect to a manifold 297 with controllable valves 279 which open and close under the control of a controller 213 to permit only a selected one of the water suitable for peritoneal dialysis from a water line 296, the first concentrate from a first concentrate line 295A, and the second concentrate from a second concentrate line 295B. Each of these may be drawn through common fluid line 298 through connector 224. Thus, the pumping actuator 125 of the peritoneal dialysis fluid proportioner/cycler 114 (FIGS. 1F and 1G) is able to draw each of the fluids. The controller of the peritoneal dialysis fluid proportioner/cycler 114 can be made to control the valves 279 by communicating with the controller 213 through a user interface 312. The function of the controller 213 and user interface 312 (optional) may be the same except as otherwise indicated across FIGS. 2I, 2J, and 2K. Note that a single controller of the peritoneal dialysis fluid proportioner/cycler 103 (410, 109) or an independent controller common to both (e.g. as indicated by 109 in FIGS. 1A to 1H) may be employed for controlling the described functions of the peritoneal dialysis fluid proportioner/cycler systems 90A through 90D.

FIGS. 2L and 2M show modifications of the connection platform of FIG. 2K to provide for water and concentrate to be supplied through the common fluid line 298. Referring to FIG. 2L, instead of a single manifold as in manifold 297, a pair of junctions 222 is used, one to join the first concentrate line 295A and the second concentrate line 295B. The concentrates are pumped respectively, according to the selection of valves 250A and 250B which are controlled automatically by a controller of the peritoneal dialysis fluid proportioner/cycler 103 or through a separate controller 109 or through an interface by a dedicated controller 213 of the connection platform 219 (or variations as illustrated in FIGS. 2L and 2M). If the fluid circuit 100B, 110D is used which has a testable type of filter such as the filter 115 (e.g., FIGS. 1B, 1C) having an air side and a fluid side separated by a membrane, then the fluid may advantageously be pumped by a pump 221 in a push configuration with respect to the filter (arranged downstream of the pump 221 as is filter 115) rather than relying solely on a suction force provided by the pumping actuator through pumping tube segment 137. A particular concentrate is selected by valves 250A and 250B. A control valve 250C is also operated by the controller to control flow in the water line 296. In any of the embodiments, water may be advantageously pumped by a push pump 246 if water is supplied through a filtration plant 223. For example, water may be filtered through reverse osmosis, deionization, activated carbon, and other types of filters in filter plant 223 to generate water suitable for peritoneal dialysis from potable water. The pumps 221, and 246 may be controlled as indicated above with respect to the valves 250A and 250B to operate in tandem with the pumping actuators of the peritoneal dialysis fluid proportioner/cycler (e.g., 103). Thus, the present variant of the connection platform of FIG. 2K, functions to select one of multiple fluids among water and one or more concentrates thereby allowing all fluids to pass into the fluid circuit through a single inlet line (as in the fluid circuit of FIG. 2E, for example). This allows a single filter to be used for sterilization. The embodiment of FIG. 2M, another variant of the connection platform 219 of FIG. 2K, may be employed advantageously where a push pump such as push pump 246 (as in FIG. 2L) is not required to draw water, for example, if instead of using the cycler to prepare dialysis fluid, a premixed dialysis fluid is connected to one of the inlets instead with suitable programming of the controller to permit flow only from one of the premixed containers at a time. Here, control valves 279 select the fluid to be drawn each time and the pump 221 draws the selected fluid, pushing it through the filter. Note that in the embodiment of FIG. 2L, the pressure sensor 218 may be used for feedback control of the push pump 246.

FIG. 3 shows a method of manufacturing a disposable circuit such as is disclosed in FIG. 2A. First, the concentrate containers are filled at S10. The concentrate containers are then sealed with frangible elements that form a hermetic seal at S12. This isolates the contents of the concentrate containers from the outside environment and causes them to be protected from intrusion of contaminants. Then at S14, the concentrate containers are connected to a remainder of the fluid circuit, for example the disposable fluid circuit 200. The remaining portions of the fluid circuit are sealed by ensuring that end caps are placed on any line terminations that are not interconnected within the circuit. For example, caps are present on connector 185, sample ports 168, and connectors 186 and 187. Finally, optionally at S16, the entire circuit assembly with the concentrates, may be radiation sterilized or sterilized by other means.

Figure 4A:
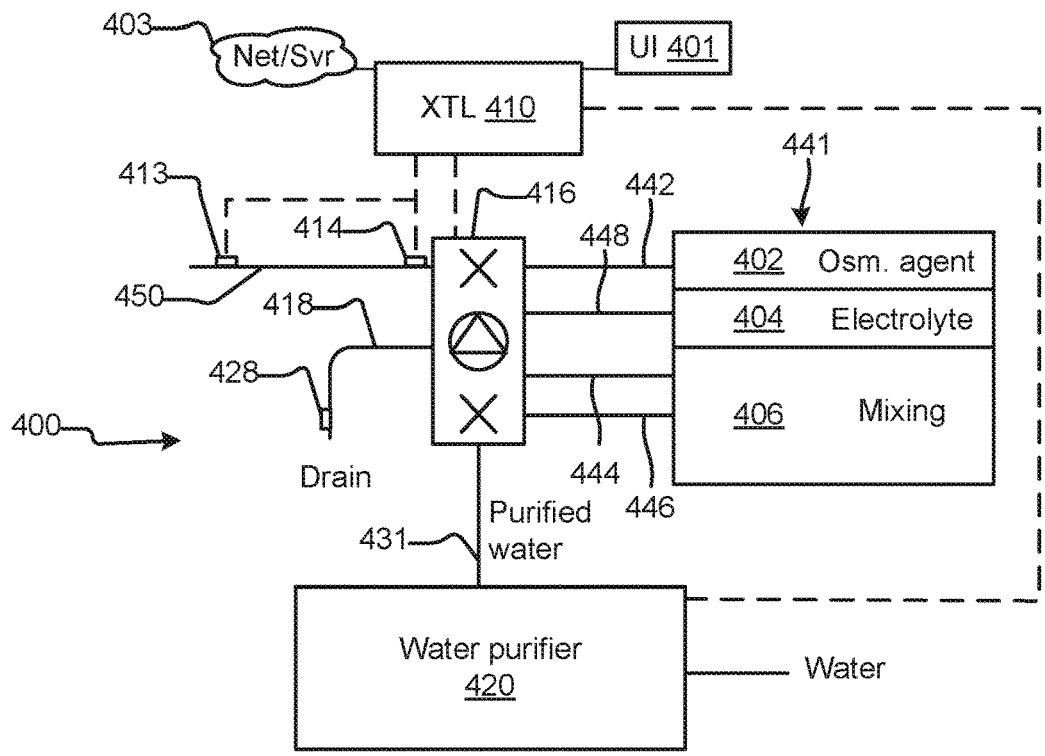
FIG. 4A shows a peritoneal dialysis fluid proportioner/cycler according to embodiments of the disclosed subject matter.

FIG. 4A shows a peritoneal dialysis fluid proportioner/cycler according to embodiments of the disclosed subject matter. The present FIGS. 4A through 4K are generalizations of the various embodiments disclosed above for purposes of explaining the operational use thereof for preparing peritoneal dialysis fluid and for treating a patient using the structures described above. Referring now to FIG. 4A, a peritoneal dialysis fluid proportioner/cycler 400 may correspond to any of the foregoing embodiments described for generating dialysis fluid by mixing concentrates and water. For example, note embodiments 90A-90D. Here, the peritoneal dialysis fluid proportioner/cycler 400 generates custom peritoneal dialysis fluid according to a prescription stored in a controller 410 (corresponding to controllers described above). The prescription may be entered in the controller via a user interface 401, via a remote terminal and/or server 403, or by other means such as a smart card or bar code reader (not shown). The controller applies control signals to a fluid conveyer and valve network 416 and a water purifier 420 and receives signals from distal and proximal pressure sensors 413 and 414, respectively, on a fill/drain line 450 which may be in accord with foregoing embodiments.

The fluid circuit with pump and valve network 416 is a fluid circuit element with one or more sensors, actuators, and/or pumps which is effective to convey fluid between selected lines 442, 444, 446, 448, 450 and 418 responsively to control signals from the controller 410. Example embodiments are described herein, but many details are known from the prior art for making such a device so they are not elaborated here.

A multiple-container unit 441 includes a pre-filled, pre-sterilized osmotic agent concentrate container for osmotic agent concentrate 402 and another electrolyte concentrate container 404 for electrolyte concentrate. The multiple-container unit 441 also contains the mixing container 406 (which is empty) which is large enough to hold a sufficient volume of dialysis fluid for the completion of at least one fill cycle of an automated peritoneal dialysis treatment. The containers 402, 404, and 406 may be flexible bag-type containers that collapse when fluid is drawn from them and therefore, do not require any means to vent air into them when drained.

Osmotic agent concentrate container 402, electrolyte concentrate container 404, and mixing container 406 are all connected by respective lines 442, 448, 444, and 446 to the fluid circuit with pump and valve network 416. The fill/drain line (or multiple lines) 450 and a drain line 418 for spent fluid (and other fluids) with a conductivity sensor 428 may also be connected to the fluid circuit with pump and valve network 416. The fluid circuit with pump and valve network 416 also has a purified water line 431 for receiving water. The water purifier 420 may be a purifier or any source of sterile and purified water including a pre-sterilized container of water or multiple containers. In a preferred configuration, water purifier 420 may be configured as described in WO2007/118235 (PCT/US2007/066251) and US20150005699, which are hereby incorporated by reference in their entireties. For example, the water purifier 420 may include the flow circuit components of FIG. 22A of WO2007/118235 including the water purification stages and conform generally to the mechanical packaging design shown in FIG. 24 of WO2007/118235.

It should be evident that 416 is a generalization of the peritoneal dialysis fluid proportioner/cycler 114 as well as elements of a fluid circuit such as fluid circuit 112 and connection platform 219. It should also be evident that 402 and 404 represent concentrate containers according to any of the disclosed embodiments including the concentrate containers 101 and 102, 262 and 264, 105A and 105B. The mixing container 406 corresponds to any of the mixing container embodiments (102) described above. Other elements will be evident from their description with the understanding that the figures represent generalizations thereof for purposes of describing the function. It should also be understood that the number and type of concentrates may differ from the present figure which is disclosed as an example, only. It should also be evident that the examples of concentrates discussed herein are glucose and electrolyte concentrates but they could be one or other multiples or other concentrates in other embodiments. Also, the osmotic agent concentrate or glucose concentrate is presumed here to include an electrolyte concentrate marker to permit the concentration of osmotic agent to be inferred from a measurement of conductivity of diluted agent with a priori knowledge (stored in a memory used by the controller) of the ratio of osmotic agent concentrate to electrolyte concentrate in the osmotic agent concentrate. See US20150005699. In alternative embodiments, the osmotic agent is not provided with an electrolyte marker and the peritoneal dialysis fluid proportioner/cycler 400 may rely on volumetric proportioning for the transfer of osmotic agent. Note also that the order of concentrate addition may be reversed, with electrolyte being added first.

Figure 4B:
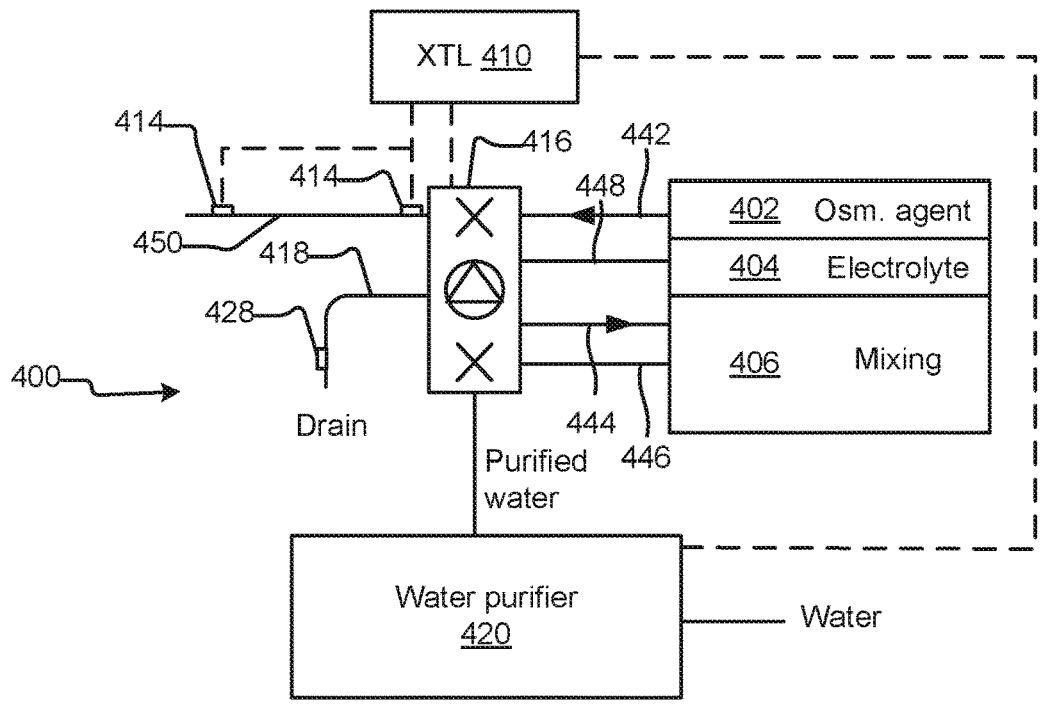
FIG. 4B shows the peritoneal dialysis fluid proportioner/cycler of FIG. 4A in a first phase of fluid preparation in which osmotic agent concentrate is added to a mixing container, according to embodiments of the disclosed subject matter.

FIG. 4B shows a preliminary stage of fluid preparation prior to peritoneal dialysis treatment according to an embodiment of the disclosed subject matter. The controller 410 reads a prescription and generates a command, responsive to a peritoneal dialysis treatment preparation initiation command, to flow osmotic agent concentrate from osmotic agent concentrate container 402 to the mixing container 406. The command is applied to the fluid circuit with pump and valve network 416 to connect the osmotic agent concentrate line 442 to the batch fill line 444 and also to convey the osmotic agent concentrate into the mixing container 406. This may be done by one or more valve actuators and one or more pumps that form the fluid circuit with pump and valve network 416. The fluid circuit with pump and valve network 416 may be configured to meter the quantity of osmotic agent concentrate precisely according to a predicted amount of dilution by electrolyte concentrate and water to produce the desired prescription fluid. The metering may be performed by a positive displacement pump internal to the fluid circuit with pump and valve network 416 or other means such as a measurement of the weight of the osmotic agent concentrate container 402 or the mixing container or a volumetric flow measurement device.

In an alternative embodiment, part of the water (less than the total used for dilution as discussed below with reference to FIG. 4C) is added to the mixing container first, before the osmotic agent concentrate and electrolyte concentrates (if needed) are pumped into the mixing container.

Figure 4C:
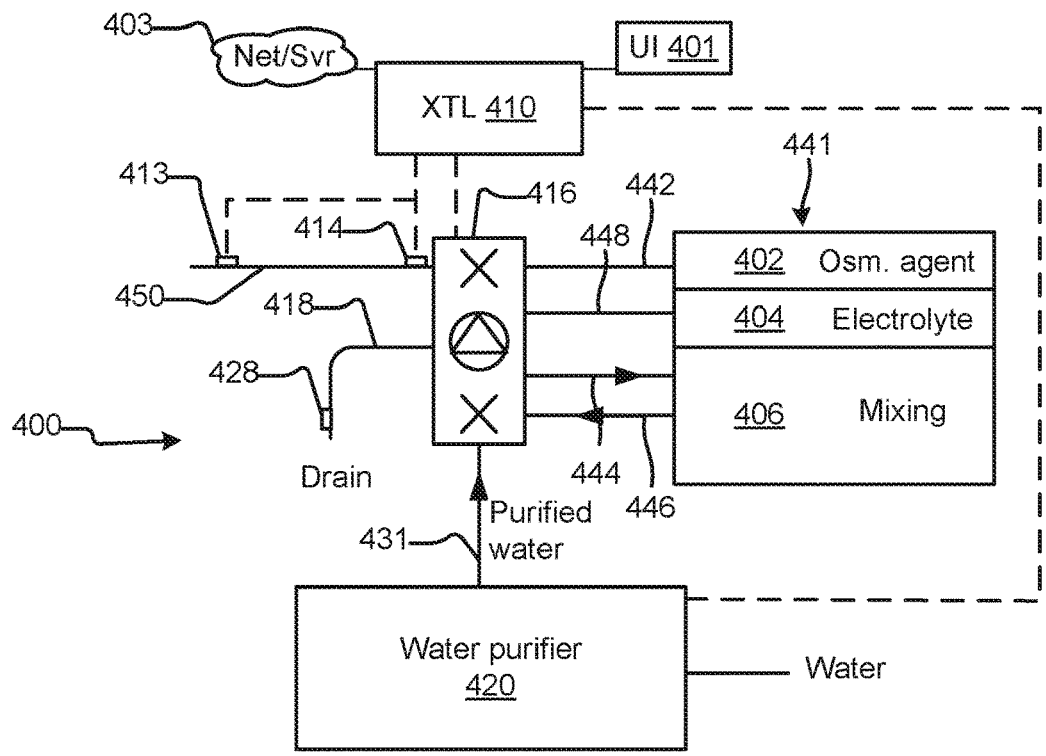
FIG. 4C shows the peritoneal dialysis fluid proportioner/cycler of FIG. 4A in a second phase of fluid preparation in which a dialysis fluid precursor is obtained by diluting and mixing the contents of the mixing container, according to embodiments of the disclosed subject matter.

Referring now to FIG. 4C, a dilution stage is performed using the peritoneal dialysis fluid proportioner/cycler 400. The controller 410, in response to the prescription, generates a command to flow purified water from the water purifier 420 to the mixing container 406. The command is applied to the fluid circuit with pump and valve network 416 to connect the purified water line 431 to the mixing container 406 to add a measured quantity of water to dilute the osmotic agent concentrate in the mixing container 406. The controller 410 may control the fluid circuit with pump and valve network 416 to ensure the correct amount of water is conveyed. Alternatively, the water purifier may incorporate a flow measurement device or metering pump or other suitable mechanism to convey the correct amount of water. The controller 410 may be connected to the water purifier 420 to effectuate the dilution result. The fluid circuit with pump and valve network 416 may also be configured to circulate diluted osmotic agent concentrate solution through lines 444 and 446 either simultaneously with the dilution or after the diluting water has been transferred to the mixing container 406 according to alternative embodiments. The circulation mixes the contents of the mixing container 406.

The relative amounts of water, osmotic agent concentrate, and electrolyte concentrate may be realized based on the ratiometric proportioning properties of the pump. Since a single pump tube is used to convey all the liquids into the mixing container, most sources of offset from predicted pumping rate (based on shaft rotations, for example) to actual pumping rate affect all the fluids roughly equally.

Figure 4D:
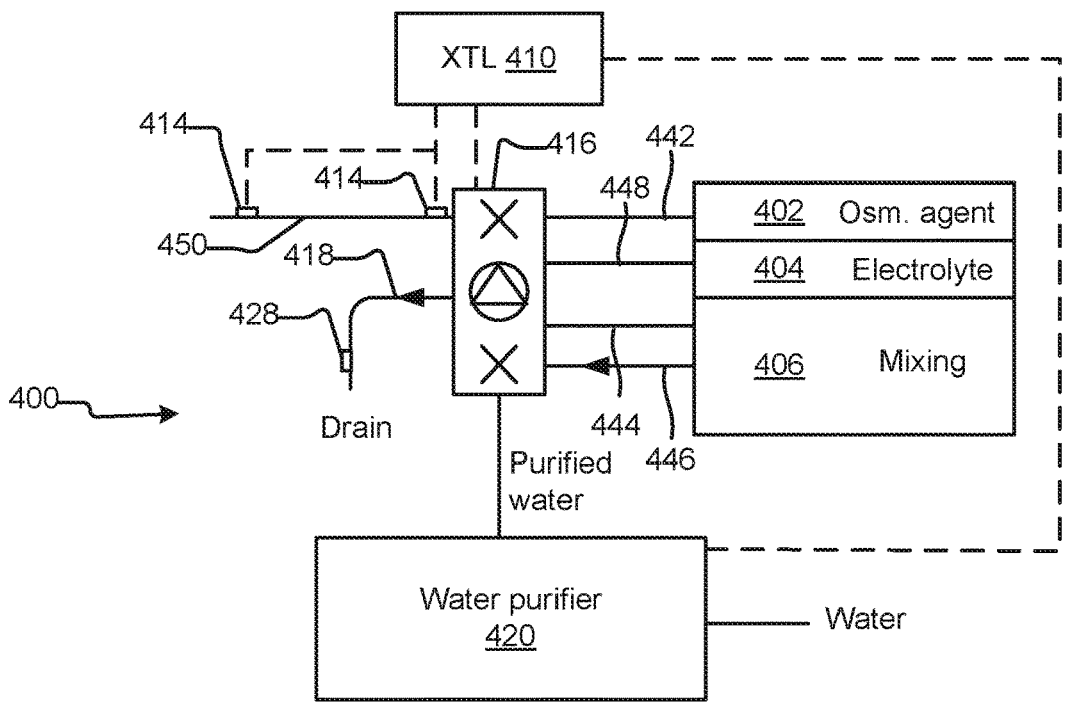
FIG. 4D shows the peritoneal dialysis fluid proportioner/cycler of FIG. 4A in a third phase of fluid preparation in which the peritoneal dialysis fluid precursor properties are verified, according to embodiments of the disclosed subject matter.

Referring now to FIG. 4D, the diluted osmotic agent concentrate solution in the mixing container 406 is tested to ensure that the correct concentration of osmotic agent is achieved. In an embodiment, the osmotic agent concentrate 402 has an amount of electrolyte concentrate to generate a conductivity signal using the conductivity sensor 428 when fluid from the mixing container 406 is conveyed by the fluid circuit with pump and valve network 416 to the drain line 418 past the conductivity sensor. The amount of electrolyte concentrate pre-mixed with the osmotic agent concentrate may be the lowest ratio of electrolyte concentrate to osmotic agent concentrate that a predetermined prescription may require. The fluid circuit with pump and valve network 416 may perform the function using one or more valve actuators and one or more pumps that form the fluid circuit with pump and valve network 416. The fluid circuit with pump and valve network 416 may be configured to meter the quantity of water precisely or the function may be provided by the water purifier 420. The controller 410 may add additional water or osmotic agent concentrate and test the conductivity again if the measured concentration of osmotic agent and/or electrolytes, if applicable, is incorrect. In addition to using a combined osmotic agent and electrolyte concentrate in osmotic agent concentrate container 402, in an alternative embodiment, the osmotic agent concentrate container 402 holds osmotic agent concentrate with no electrolytes and osmotic agent concentration is optionally measured directly by other means such as specific gravity (hydrometer), refractive index (refractometer), polarization, infrared absorption or other spectrographic technique.

Figure 4E:
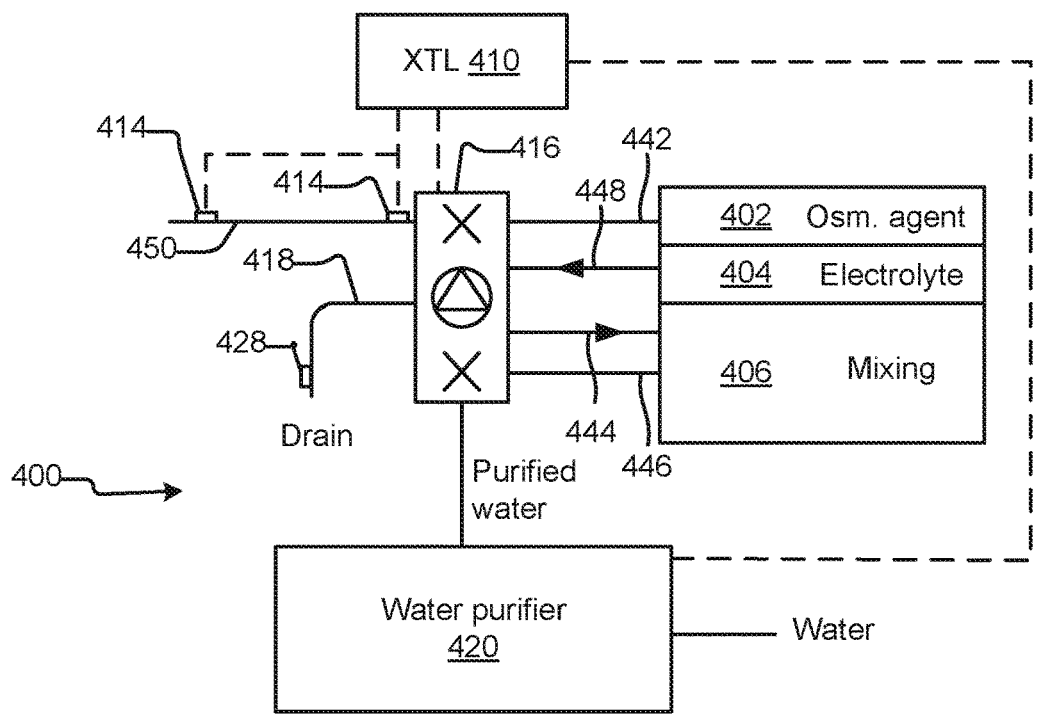
FIG. 4E shows the peritoneal dialysis fluid proportioner/cycler of FIG. 4A in a fourth phase of fluid preparation in which dialysis fluid precursor is further prepared by addition of electrolyte concentrate to the mixing container, according to embodiments of the disclosed subject matter.

FIG. 4E shows an electrolyte concentrate addition stage of fluid preparation prior to peritoneal dialysis treatment according to an embodiment of the disclosed subject matter. The controller 410 reads a prescription and generates a command to flow electrolyte concentrate from container 404 to the mixing container 406. The command is applied to the fluid circuit with pump and valve network 416 to connect the electrolyte concentrate line 448 to the mixing container 406 fill line 444 and also to convey the electrolyte concentrate into the mixing container 406. This may be done by one or more valve actuators and one or more pumps that form the fluid circuit with pump and valve network 416. The fluid circuit with pump and valve network 416 may be configured to meter the quantity of electrolyte concentrate precisely according to a predicted amount of dilution by osmotic agent concentrate and water that has been previously determined to be in the mixing container 406, to achieve the prescription. The metering may be performed by a positive displacement pump internal to the fluid circuit with pump and valve network 416 or other means such as a measurement of the weight of the electrolyte concentrate container 404 or the mixing container 406 or a volumetric flow measurement device.

Figure 4F:
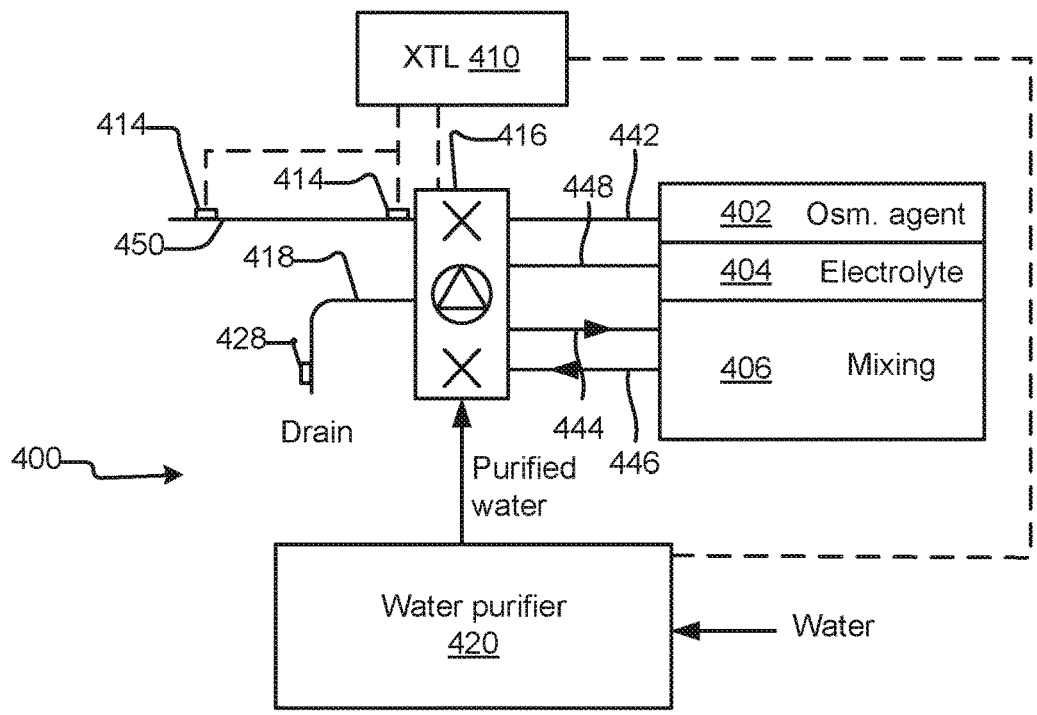
FIG. 4F shows the peritoneal dialysis fluid proportioner/cycler of FIG. 4A in a fifth phase of fluid preparation in which end-use dialysis fluid is prepared by adjustment of the dilution of the mixing container contents, according to embodiments of the disclosed subject matter.
Figure 4G:
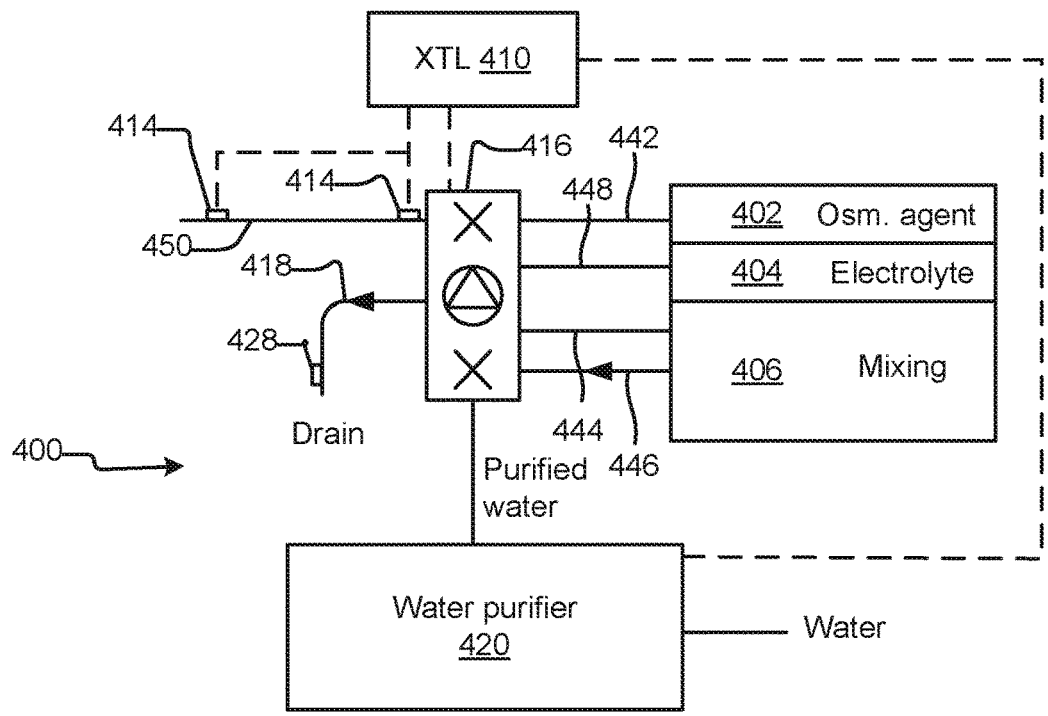
FIG. 4G shows the peritoneal dialysis fluid proportioner/cycler of FIG. 4A in a sixth phase of fluid preparation in which dialysis fluid in the mixing container is verified, according to embodiments of the disclosed subject matter.

Referring now to FIG. 4F, the electrolyte concentrate may be mixed using the batch fill and drain lines 446 and 444 in a closed loop. If necessary, depending on how much dilution was performed during the osmotic agent concentrate dilution process, further dilution may be performed as described above. The final formulation may be achieved by the process illustrated in FIG. 4F. Then, as illustrated in FIG. 4G, the final electrolyte concentration of the mixture in mixing container 406 may be determined with a conductivity sensor 428 by flowing a sample therethrough.

Although gravimetric and tracer/conductance sensing were described as devices for ensuring proper proportioning and dilution rates for achieving target prescriptions, it should be clear that any embodiments of a peritoneal dialysis fluid proportioner/cycler disclosed herein may employ ratiometric proportioning as well, particularly where positive displacement pumping is employed. Ratiometric proportioning takes advantage of the volumetric repeatability and predictability of certain pumps. For example, a particular pump can deliver a highly repeatable volume of fluid for a given number of pumping cycles (pump rotations for a peristaltic pump or cycles for a diaphragm pump, for example). If all dialysis fluid components (water, osmotic agent concentrate, and electrolyte concentrate, for example) are delivered to the mixing container using the same pump, including, for example, the pumping tube segment of a peristaltic pump, then the volume ratios of the components will, after adjustment for potential flow path and/or viscosity differences as described below, be fully determined by the number of pump cycles used to convey each component.

Ratiometric proportioning may supplement or substitute for measurement of the fluid conductance or density or other measurements. To convert the number of pump cycles to actual displaced mass or volume, a calibration may be performed and/or flow path (including fluid properties) compensation parameters may be employed. The flow path compensation parameters may be respective to each particular fluid flow path and/or fluid type, or may be identical for all fluid paths and fluid types. To provide enhanced accuracy, one or more pump calibration and/or flow path compensation parameters may be generated through a calibration procedure. Typically, flow path compensation factors will be established and stored in non-volatile memory. Typically, one or more flow path calibration procedures will be performed when the peritoneal dialysis fluid proportioner/cycler is used by a patient. The calibration procedure may be performed after each new fluid set is installed, or before each batch preparation cycle, or even multiple times during the preparation of a single batch. A disposable fluid set may be installed every day. The calibration procedure may be done using water. The calibration may sequentially pump fluid through one or more of the stages provided in Table 1.

TABLE 1

Example stages for sequentially pumping fluid during calibration

| From | To |
|---|---|
| Water source | Drain |
| Mixing container | Drain |
| Osmotic agent concentrate container | Drain |
| Electrolyte concentrate container | Drain |
| Patient access | Drain |
| Osmotic agent concentrate container | Mixing container |
| Electrolyte concentrate container | Mixing container |
| Water source | Mixing container |

In the calibration procedure, fluid is pumped between any or all of the paths identified above. A separate calibration coefficient may be generated for each of the paths. The calibration coefficient may be stored in a memory or non-volatile data store, for example, as a parameter representing the number of ml/per pump rotation (or diaphragm pump cycle), or as a proportionality ratio relative to a particular reference flow path. The actual fluid quantity transported during the calibration step may be measured by any suitable device (flow sensor) including volume or mass measurement devices or direct flow rate measurement with integration, for example, using laser Doppler velocimetry, thermal transit time, magnetohydrodynamics, propeller hydrometer, positive displacement flow measurement, differential pressure through a resistance such as a venturi, nozzle, orifice plate, or other flow obstruction, variable area or rotameter, pitot or impact tube, vortex shedding frequency counting, ultrasonic, or other device. A particularly advantageous device for flow calibration is to measure the transit time of a fluid property perturbation between spaced fluid property sensors as described below. Any of the disclosed embodiments may employ a flow sensor in which at least the portion of which that carries fluid is disposable so that the flow rate (or total displaced fluid quantity) can be input to a controller while allowing the use of a disposable fluid circuit. Examples include an ultrasonic soft tube flowmeter made by Strain Measurement Devices SMD that non-invasively measure flow in soft tubing by means of slotted transducers in which a length of tubing can be inserted during fluid circuit installation. For cartridge embodiments, the PD cycler can employ a moving transducer stage that engages an exposed tube length of the cartridge after passive insertion of the cartridge.

The pumping system may also be sufficiently repeatable in a way that allows precise ratios to be established without calibration, depending on the predefined tolerances. If the manufacturing tolerances, including materials, are sufficiently controlled, a desired level of control over ratios may be achieved without in situ (point of care) calibration. A particularly sensitive component in terms of guaranteeing repeatability is the pumping tube segment of a peristaltic pump. In a first embodiment, the peristaltic pump tube segment is made from a material whose mechanical and material tolerances are controlled within predefined limits. The lengths of the tubing circuit elements and mechanical parameters are also controlled within respective predefined limits. A calibration may then be done outside the peritoneal dialysis treatment context, e.g., in the laboratory, to calculate precise values to convert pump cycles to fluid quantity transferred for a single lot of replaceable fluid circuits. The calibration may be done for multiple lots. The calibration may also be done for each fluid circuit. The calibration may also be done by the peritoneal dialysis fluid proportioner/cycler for each fluid circuit. The calibration may also be done for each batch of peritoneal dialysis fluid prepared by the fluid circuit.

Figure 4H:
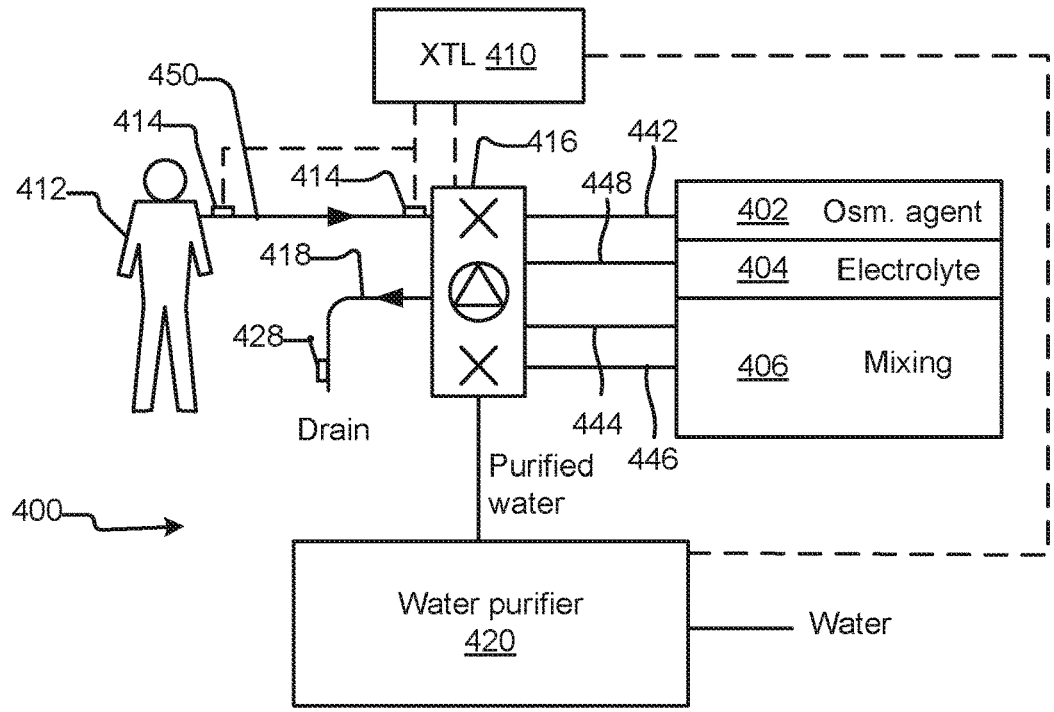
FIG. 4H and FIG. 4K show the peritoneal dialysis fluid proportioner/cycler of FIG. 4A in various peritoneal dialysis treatment modes, according to embodiments of the disclosed subject matter.
Figure 4K:
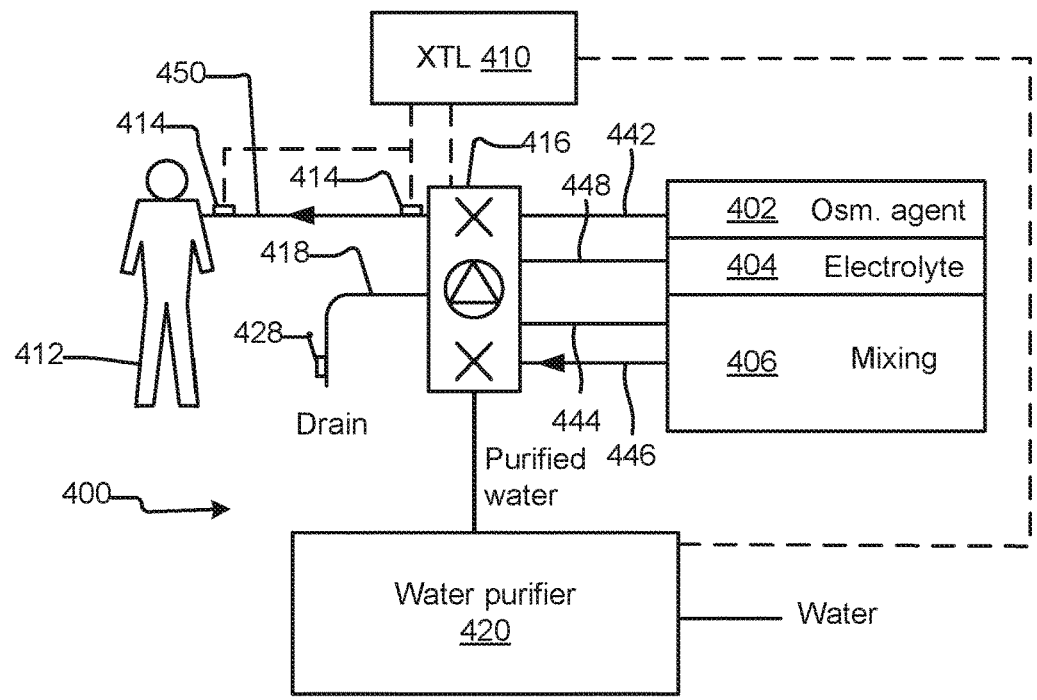

Referring to FIG. 4H, subsequent to the preparation of the contents of the mixing container 406 as described above, the fluid circuit with pump and valve network 416 may be configured to drain the patient 411 depending on the patient's prior status. Spent dialysis fluid may be withdrawn by the fluid circuit with pump and valve network 416 and conveyed through the drain line 418. Then, the contents of the mixing container 406 may be conveyed as illustrated in FIG. 4K to the patient. Here the controller 410 has configured the fluid circuit with pump and valve network 416 to flow fluid to a patient 412.

Figures 5A, 5B:
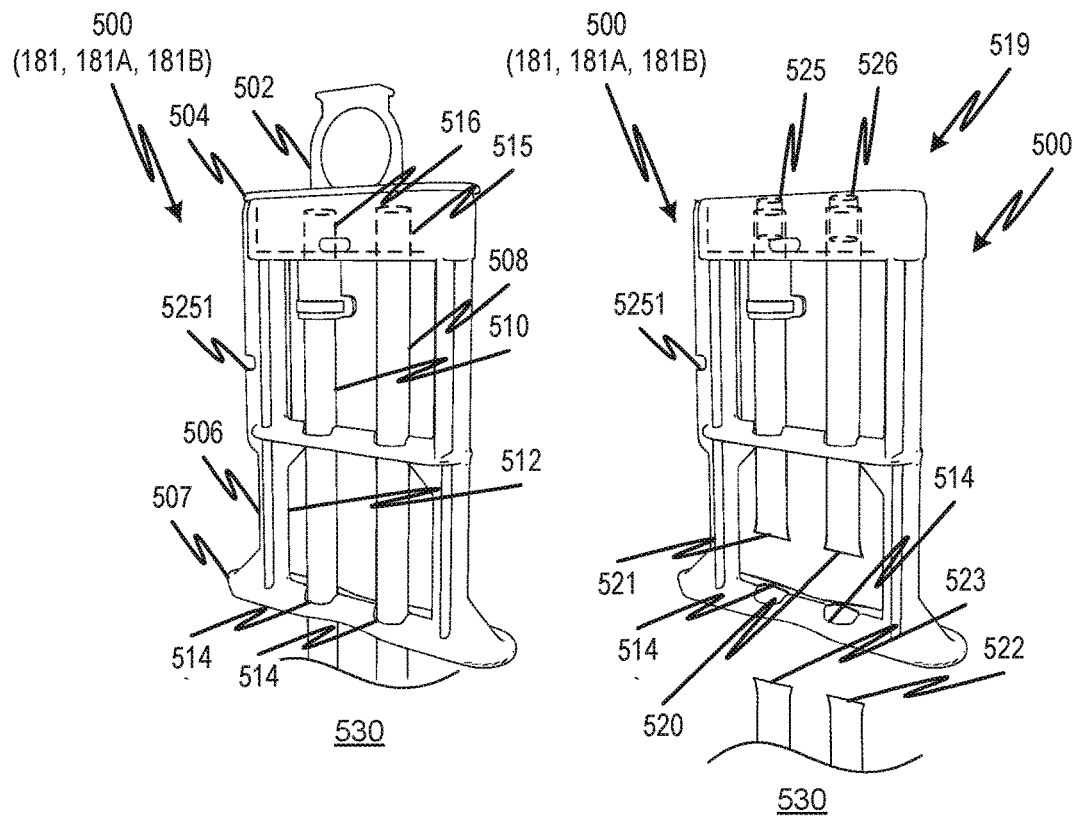
FIGS. 5A-5D illustrate the structure and use of a multi-function connector according to embodiments of the disclosed subject matter.

Referring now to FIG. 5A, the double connector of 181, 181A, 181B is shown in detail as the connector embodiment 500. A single monolithic member has a shape with at least one window, where two windows are shown one of which is indicated as window 512. The body 506 has a ridge 507 that overhangs the frame 506 to permit the frame 506 overall to be grasped easily by a user, for pushing or pulling, to connect ports 515, 516 to ports of a device (e.g., 219) to which lines 508 and 510 of a fluid circuit 530 are to be connected. A releasable port cover 502 (see also cap 180) seals ports 525 and 526 to prevent contamination thereof. The window 512 provides access to cut and seal elements that seal and cut the lines 508, 510 when the double connector 500 is to be replaced. Lines 508 and 510 pass through holes 514 in the frame 506. FIG. 5B shows the double connector 500 after cutting and sealing, the sealed ends of one end of cut tubes forming stubs indicated at 520 and 521 and the opposing ends at 522, 523. The ends 522, 523 remain attached to a fluid circuit 530 which is to be replaced. The stubs 520, 521 remain attached to a resulting stub connector 519 which can remain attached to a connected device, after use, so as to act as a cover and seal against environmental contamination of a connected device, such as connection platform 219 connectors 224 and 225. Here, the protected ports of the connected device are indicated at 525 and 526. Although two channels are shown, it should be evident that the configuration may be modified to provide connections for any number of channels including one or more than two.

Figure 5C:
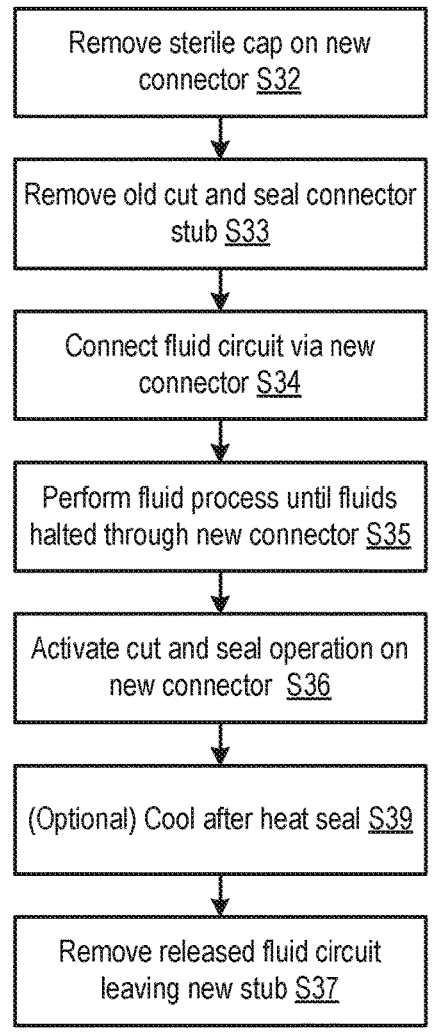
Figure 5D:
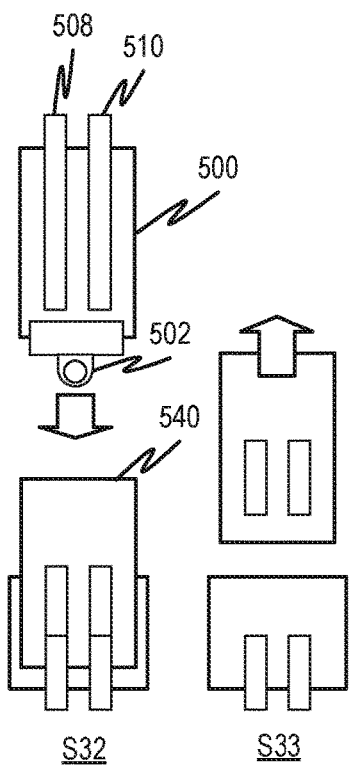
Figure 5D:
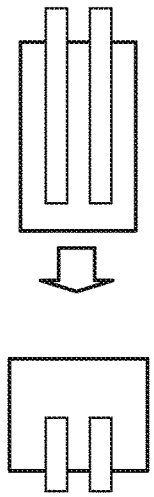
Figure 5D:
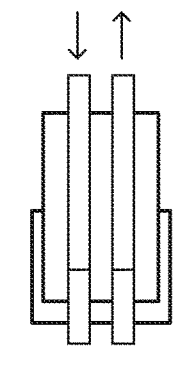
Figure 5D:
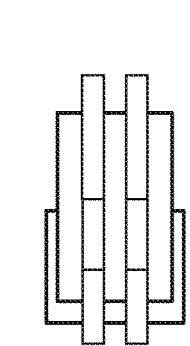
Figure 5D:
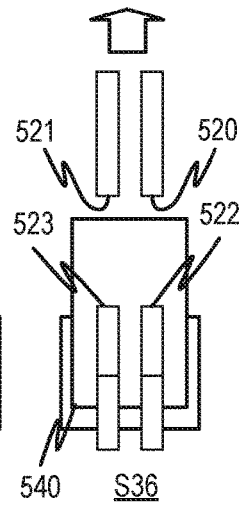

Referring to FIGS. 5C and 5D, the use of a connector 500 (which may be a double connector) including a cut and seal operation in which a portion 540 of a connector (e.g., double connector 181) is left in place to act as a sterile barrier begins with the removal of a sterile barrier-type cap from the end of the connector S32. For example, the sterile barrier may take the form of the double releasable port cover 502. Next, as S33, the sterile barrier formed by a previous connector which was cut and sealed (see FIGS. 6A-7D and elsewhere in the present disclosure) is removed, and a new replacement connector of the same form as the connector 500 is attached S34. Then the circuit connected by means of the new connector is used until it is expired S35. A cut and seal operation is initiated at S36, resulting in the separation of the fluid circuit (cut and sealed forming the stubs 520, 521 and ends 522, 523) and a new portion 640 of the new connector to be left in place to act as a sterile barrier. The cut and seal operation may include cooling the cut ends of the tube to speed the operation so that a delay for sufficient passive cooling is not required. The latter may also permit the cutting heads to act as a mechanism for gripping the stubs 520 and 521 to prevent them being removed before cooling. See, for example, the embodiment of FIGS. 6E and 6F which have a broad flat interface for gripping the ends of the cut tube 666.

Figure 5E:
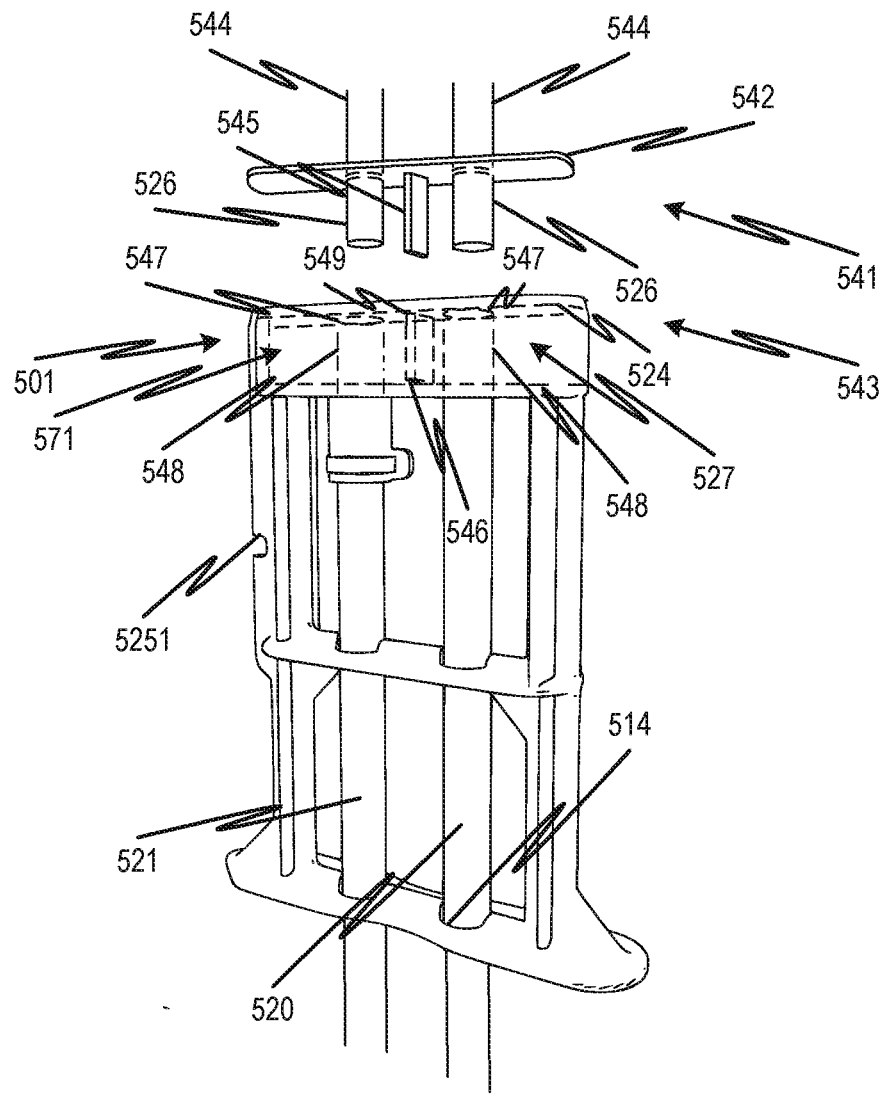
FIG. 5E shows features for a variation of a double connector 500 that protects against contamination.

FIG. 5E shows features for a variation of a double connector 501 that protects against contamination. A male connector portion 541 mates with a female connector portion 543. Ports 526 (male) pass through openings 547 of female ports 548. A pin 545 is provided on the male connector portion 541 that is received within a recess 546. The female ports 548 open in a wall 524 as does an access 549 of the recess 546. Lines 544 connect to the male connector portion 541. The remainder of the double connector 501 is as described with reference to connector 500 shown in FIGS. 5C and 5D. The pin 545 may be sized to prevent the ports 526 from contacting a flat surface inadvertently and thereby prevent contact contamination. The pin 545 may also be shaped asymmetrically to prevent incorrect orientation of the connectors. In variations, the double connector 501 may be modified such that it has a greater or lesser number of tubes 508, 510, and connectors 547. Also, the number of pins 545 and recesses 546 may differ from what is shown. For example, two pins and recesses may be provided at the edges 527 with or without the illustrated pin and recess. Note that in variations of the embodiments, the male and female connectors may be swapped or mixed on a given side of the male connector portion 541 and the female connector portion 543. One or more pins 545 may be provided on either side or mixed, as may openings 547.

Figures 7A, 7B, 7C:
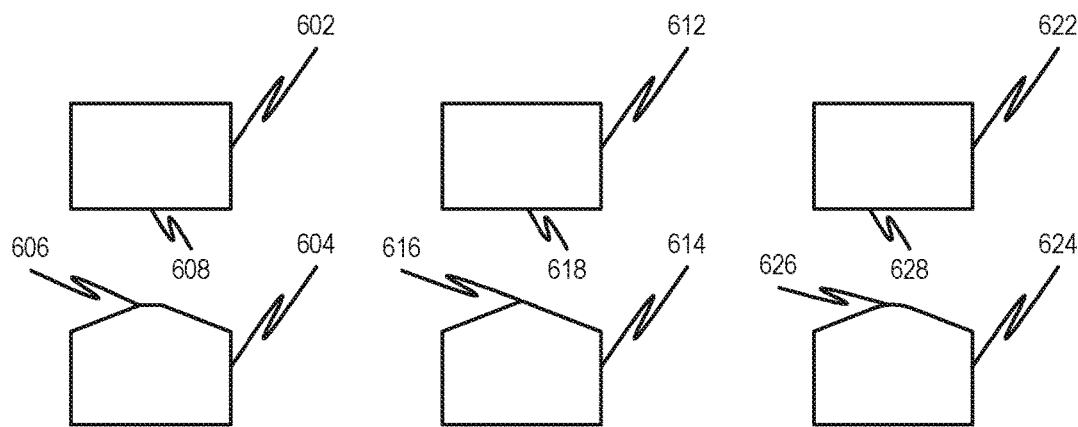
Figures 6E, 6F, 7D:
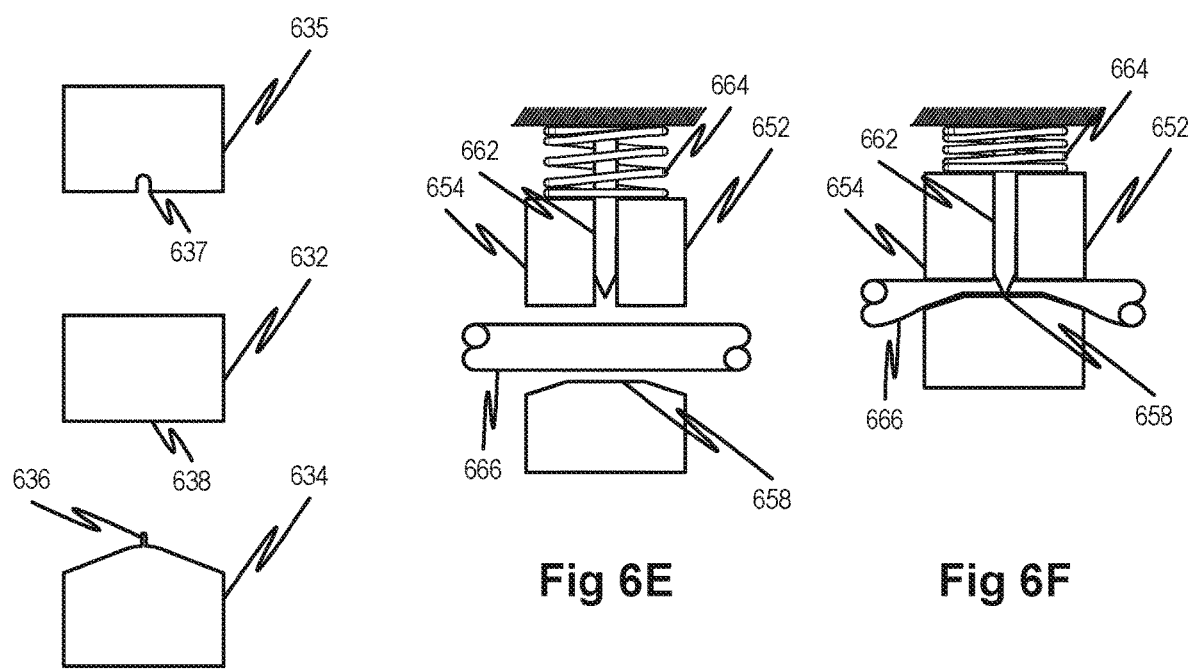

FIG. 6A shows mechanical aspects and a control and sensor system for the cut-and-seal devices with actuation, temperature, and force control features, according to embodiments of the disclosed subject matter. FIGS. 6B through 6D show a sealing and cutting operation provided by the embodiment of FIG. 6A. A pair of jaws 11 and 18 close on opposite sides of a tube 50 to cut and seal the tube 50 such that the tube 50 is divided into two parts with ends 54A and 54B sealed. The jaw 11 receives heating or cooling through a conveyance 20A or multiple conveyances 20B which may be electrical conductors for resistive heating element 14 or a combination of heating and cooling heat transfer fluids such as molten salt and refrigerant. The source of heat/cool or current supply is provided by a source 6. Either jaw 11 or 18 may be heated to achieve the described effect in alternative embodiments. A drive 2 under control of a controller 4 moves at least one of the jaws 11 and 18 toward the other or together. Temperature sensors 16 and 12 may be provided to regulate the temperature and provide feedback control for a cutting and sealing operation. The controller 4 may receive the temperature signals and control the drive 2. A force sensor 40 may indicate to the controller the magnitude of force applied through the tube 50 for feedback control of a cutting operation or for error detection (out of bounds force, for example). The cutting heads can have various shapes as shown in FIGS. 7A-7D. FIG. 7A illustrates opposing jaw shapes with jaw 604 having a flattened tip 606 and jaw 602 having a flat surface. FIG. 7B illustrates opposing jaw shapes with jaw 614 having a sharp tip 616 and jaw 602 having a flat surface. FIG. 7C illustrates opposing jaw shapes with jaw 624 having a rounded tip 626 and jaw 622 having a flat surface. In FIG. 7D, a sharp ridge 636 is provided on jaw 634 and a recess 637 on jaw 635. An alternative jaw 632 that may be used with the jaw 634 has a flat surface 638.

Figure 6G:
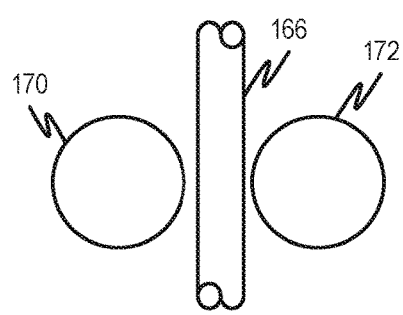

FIGS. 6E and 6F show a cut and seal arrangement in which the cutting and sealing portions move partially independently. A cutting knife 662 cuts a tube 666 when a jaw 658 pushes up against it. The jaw 658 or the jaw 654 (or both) may be heated to melt the tube 666 such that tube is cut and sealed in a single operation. A spring 664 ensures that a predefined amount of force is maintained for heating the tube 666 during the closing of the jaws. FIG. 6G shows a configuration in which the jaws are rounded elements 670 and 672 which may cut and seal the tube 666 where either or both jaws may be heated. Cooling in the above embodiments may be provided to cool the jaws and the tubing cut ends for safety or speed of completion. The arrangements of FIGS. 6A through 6F are details that may apply to the cutting and sealing actuator 212.

Figure 8A:
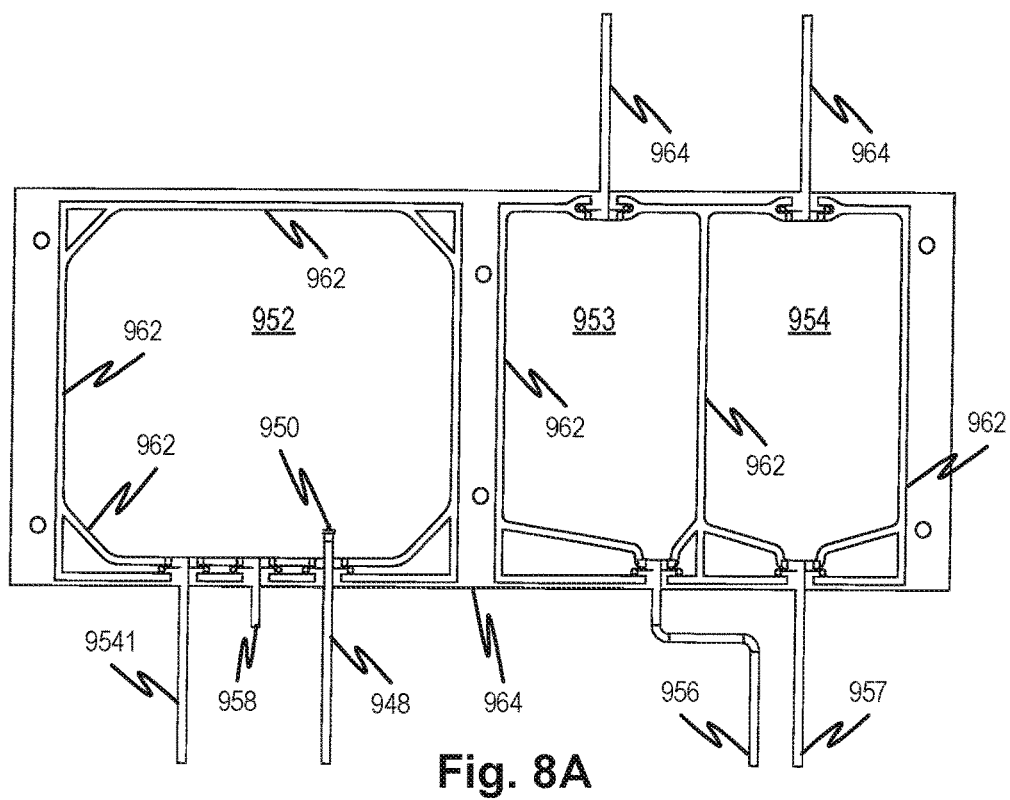
FIGS. 8A and 8B show details of chamber portions of fluid circuits according to embodiments of the disclosed subject matter.
Figure 8B:
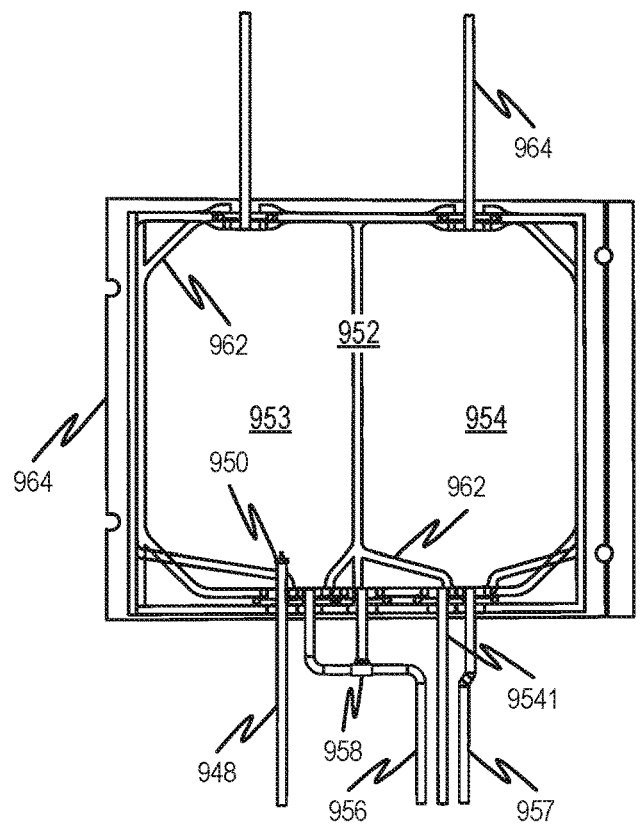

Referring to FIGS. 8A and 8B, a multiple chamber portion 200D (e.g., FIG. 2A) of disposable fluid circuit 200 is shown in greater detail. Features of the present embodiment may be applied to other fluid circuit portions as well, including the single mixing container 300C (FIG. 2E). Concentrate containers 953 and 954 and mixing container 952 are formed from a single pair of sheets by welding seals 962, shown as a pair of lines all around the depicted structure. Concentrate fill tubes 964, concentrate outlet tubes 956 and 957, mixing container inlet 948 and outlet line 9541, as well as a mixing container sample tube 958 are all welded as the seals 962 are closed by solvent bonding, thermal welding, polymer fill-bonding, ultrasonic welding, or other means. The entire structure may then be folded as shown in FIG. 8B to form a compact structure before or after a predefined quantity of concentrate is conveyed through the concentrate fill tubes 964 and the latter sealed.

A nozzle 950 may terminate the mixing container inlet 948 tube which extends into the chamber. This causes the extended part of the tube to whip around to inject incoming fluid around the mixing container 952 to agitate the contents and promote effective mixing of the contents. The mixing container sample tube 958 may be terminated by a septum to permit the insertion of a hypodermic needle. The length of the extended part may be at least 3 diameters into the container. The length may be five, 7.5, 10, or 15 diameters. The length may be between 3 diameters and 25 diameters. The length may be at least 5 diameters. Here, the term diameter refers to the tube outer diameter. Note that another alternative is for the inlet line to have a nozzle but no extended part, that is, the nozzle may be located at the wall of the mixing container and be aimed toward the center of the mixing container.

Figure 8C:
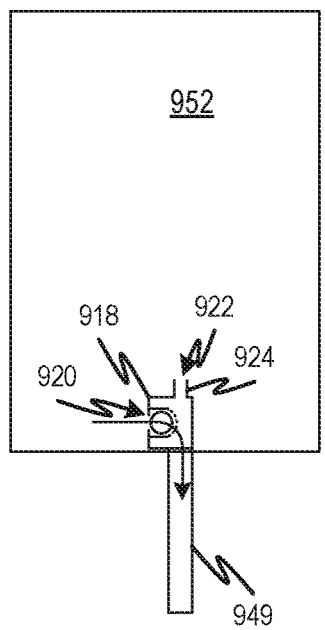
FIGS. 8C through 8G show various features to promote mixing of fluids in a mixing container according to embodiments of the disclosed subject matter.
Figure 8D:
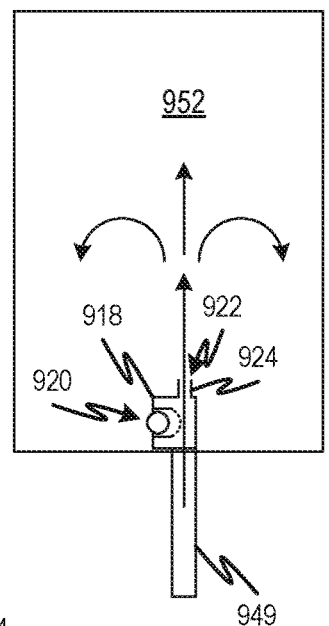
Figure 8G:
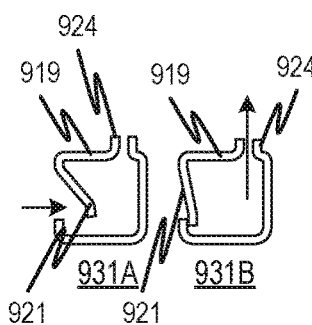
Figure 8E:
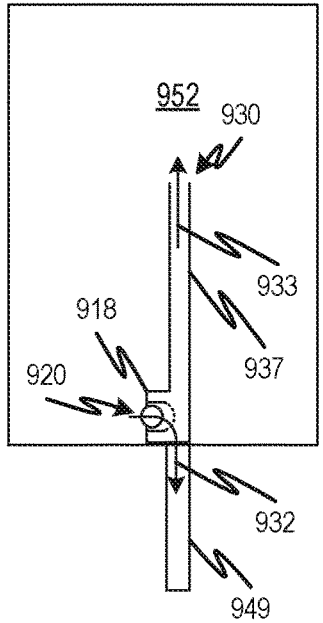
Figure 8F:
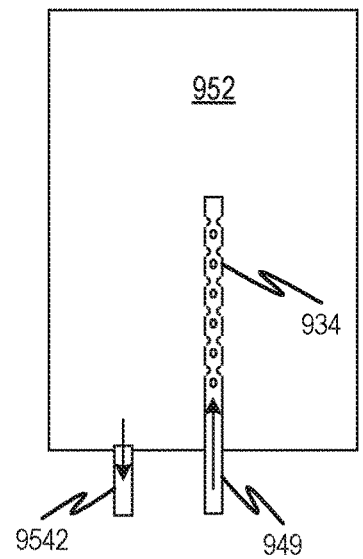

FIGS. 8C through 8F show various features to promote mixing of fluids in a mixing container according to embodiments of the disclosed subject matter. A mixing container 952 uses a single mixing container inlet and outlet line 949 that functions as a mixing container 952 inlet and outlet line 949. FIG. 8C shows a fluid outgoing from the mixing container 952 and FIG. 8D shows fluid incoming into the mixing container 952. A two-way header 924 has a check valve 918 that allows outgoing fluid to be drawn through an opening 920 into the mixing container 952 inlet and outlet line 949 but blocks flow out of the opening 920. When fluid is pumped into the mixing container 952, the check valve 918 closes and all of the flow is forced through a nozzle 924 so that it emerges at high velocity from a nozzle opening 922 as illustrated in FIG. 8D. As result, mixing is promoted and a substantial convective flow or jet is generated to transport the incoming flow to locations remote from the opening 920, thereby promoting mixing. A similar effect is obtained in the embodiment of FIG. 8E in which incoming flow is released from a tube 937 inside the mixing container 952 from an opening 930 remote from the opening 920. In this embodiment, also, a check valve 918 causes the incoming and outgoing flows to take different paths. Note that a check valve, although not shown, may be incorporated in the flow path of the tube 937 or the nozzle 924 to block flow through opening 922 or 930 when fluid is pumped out of the mixing container 952 to enhance the separation effect between the ingoing and outgoing flows. FIG. 8F shows an embodiment in which the container inlet and outlet line 949 attaches to a header tube 934 that is similar in structure to a peritoneal catheter in that it has openings distributed along a portion of its length such that ingoing flows are distributed. Such a header tube 934 may be used as a single container inlet and outlet line as for 949 or, in combination with a dedicated outlet line 9542, as an inlet line. In the foregoing embodiments, instead of a check valve, a flexible member such as a reed or flap valve as indicated in FIG. 8G, which creates greater resistance for flow in one direction than another, may be employed. So flow does not necessarily need to be halted altogether in a selected direction to achieve substantially the above effect. In FIG. 8G, a single part that may be formed, for example, by 3D printing, assembled from parts, or molded directly has a flap 921 that bends in response to both suction and pressure resulting from pumping fluid from and to the mixing container 952, causing flow out of the mixing container to be drawn through the inlet covered by the flap 921 and to be projected by the nozzle 924 when fluid is pumped into the mixing container as described with reference to FIGS. 8C and 8D. Here the flap 921 need not fully close or open but may, in embodiments, merely create a differential resistance to ingoing and outgoing flows such that fluid pumped into the mixing container is projected away from the location where it is drawn in, thereby facilitating the mixing process.

Figure 4L:
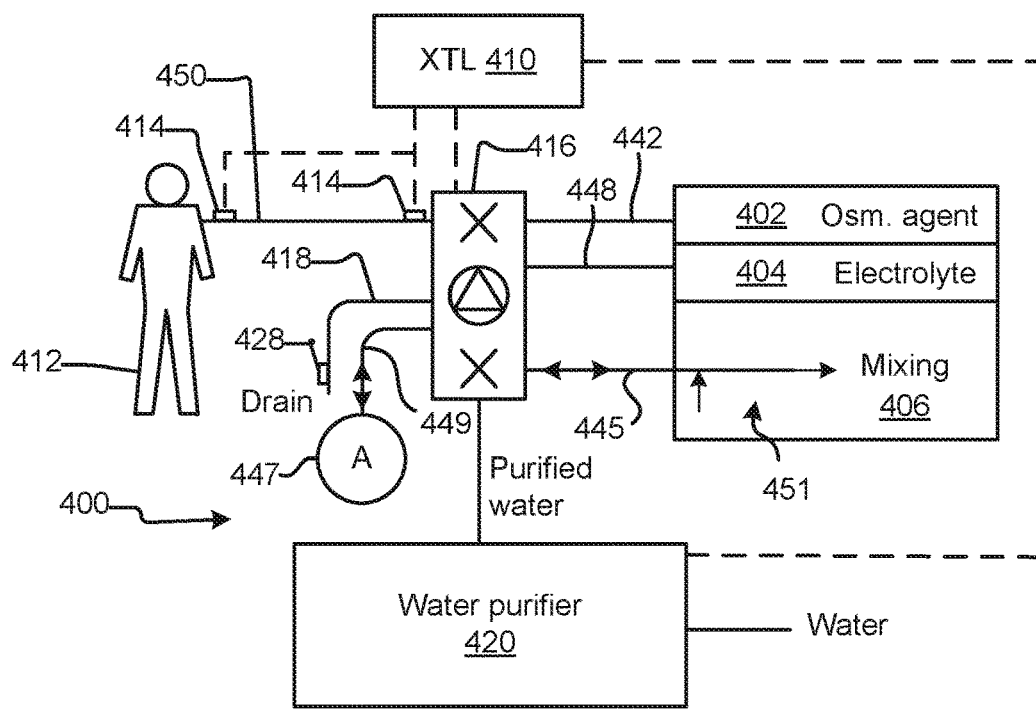
FIG. 4L shows a peritoneal dialysis fluid proportioner/cycler similar to that of FIG. 4A in which a single mixing container line connects a valve network to the mixing container.

FIG. 4L illustrates schematically a variation of the peritoneal dialysis fluid proportioner/cycler 400 of FIG. 4A with the addition of an accumulator 447 connected by an accumulator line 449 to allow a pump such as a peristaltic pump according to any of the disclosed embodiments, to provide mixing with a single mixing container line 445 connecting the mixing container 406. The controller 410 pumps fluid from the mixing container 406 to the accumulator 447 back and forth multiple times to mix the contents of the mixing container 406. This is in contrast to the disclosed embodiments in which two lines connect the mixing container 406 to the fluid circuit with pump and valve network 416. As indicated, use of a pump that has the ability to accumulate fluid, such as a diaphragm pump, may allow fluid to be pumped into and out of the mixing container 406 without a separate accumulator 447, by pumping fluid into the mixing container 406 from the diaphragm pump internal volume. Reference numeral 451 points to the arrows indicating spaced ingoing and outgoing flows to/from the mixing container that may be provided by the foregoing embodiments of devices for separating (at least partially) the ingoing and outgoing flows.

Figure 9A:
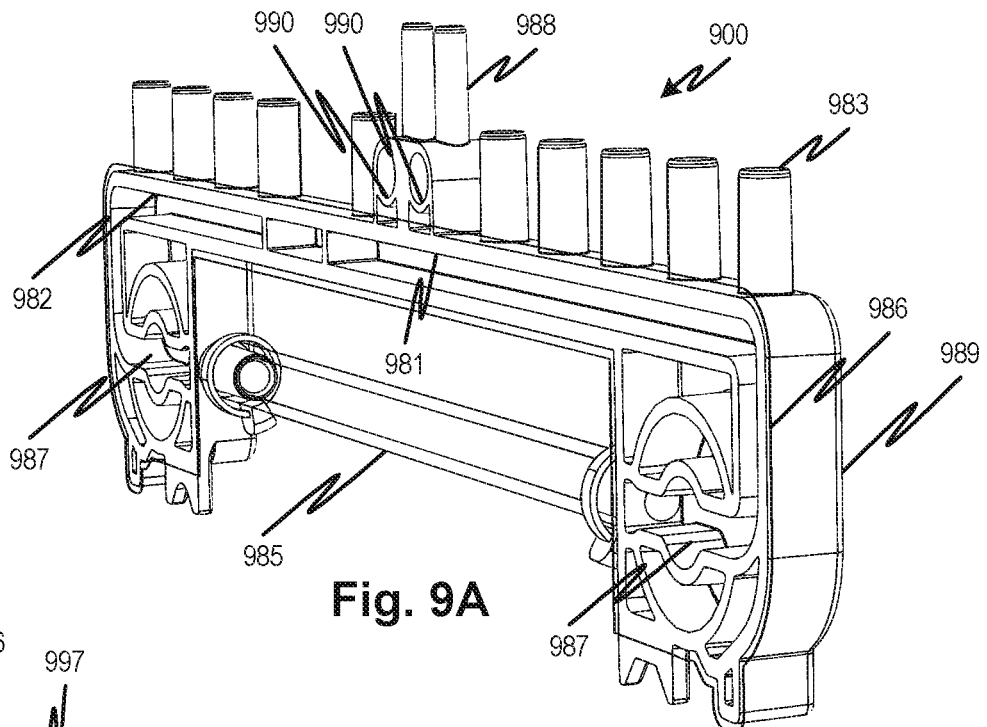
FIG. 9A shows a manifold according to embodiments of the disclosed subject matter.

Referring to FIG. 9A, a manifold 900, which functions as manifold 174 (e.g., FIG. 2A), has two chambers 982 and 981 defined by the shape of a rigid housing 989 that is sealed by a welded or bonded film 986. Rigid housing 989 may be formed by casting and an internal volume sealed by the bonded film. The film has regions 987 overlying the housing for pressure detection. Pressure transducers (not shown) contact the regions 987 and detect a force applied by pressure within the chambers 982 and 981 at either end of a pumping tube segment 985 which connects the two chambers 982 and 981. Respective ones of ports 983, for the various fluids described herein according to the different embodiments, convey fluid to respective ones of the chambers 982 and 981. Tubes may be friction fitted or bonded to the ports 983. The ports 988 have air-lines attached to them and these are respectively fluidly coupled to air ports 990 which sealingly engage pressure transducers (See 146 and 147 of FIG. 2B). In other embodiments, the rigid housing 989 is replaced with a fully enclosed housing (not shown) with pod type pressure sensors embedded in them and there is no film required for sealing the structure closed.

Figure 9B:
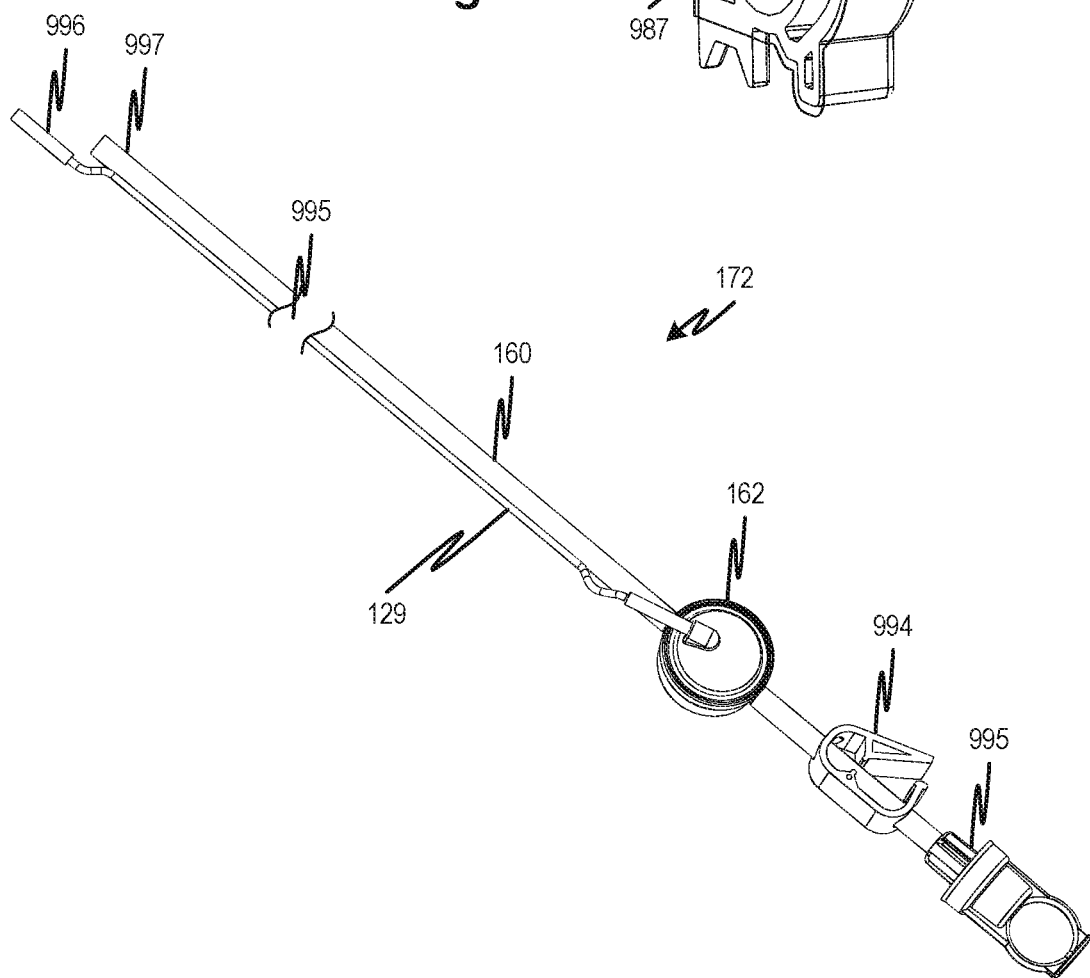
FIG. 9B shows a peritoneal dialysis fill/drain line according to embodiments of the disclosed subject matter.

Referring to FIG. 9B, a dialysis fluid line 172 has a pre-connected fill-drain line 160 and an air-line 129 as well as a pressure-sensing pod 162 which has an internal diaphragm which is displaced responsively to pressure changes in the pre-connected fill-drain line 160 near the patient connector 995. Movement of the internal diaphragm compresses or expands an air volume in the air-line 129 which is conveyed to a connector 181. The patient connector 995 connects to a peritoneal catheter. The proximal end 997 of the pre-connected fill-drain line 160 is attached or bonded to a respective one of the ports 983.

Figure 10A:
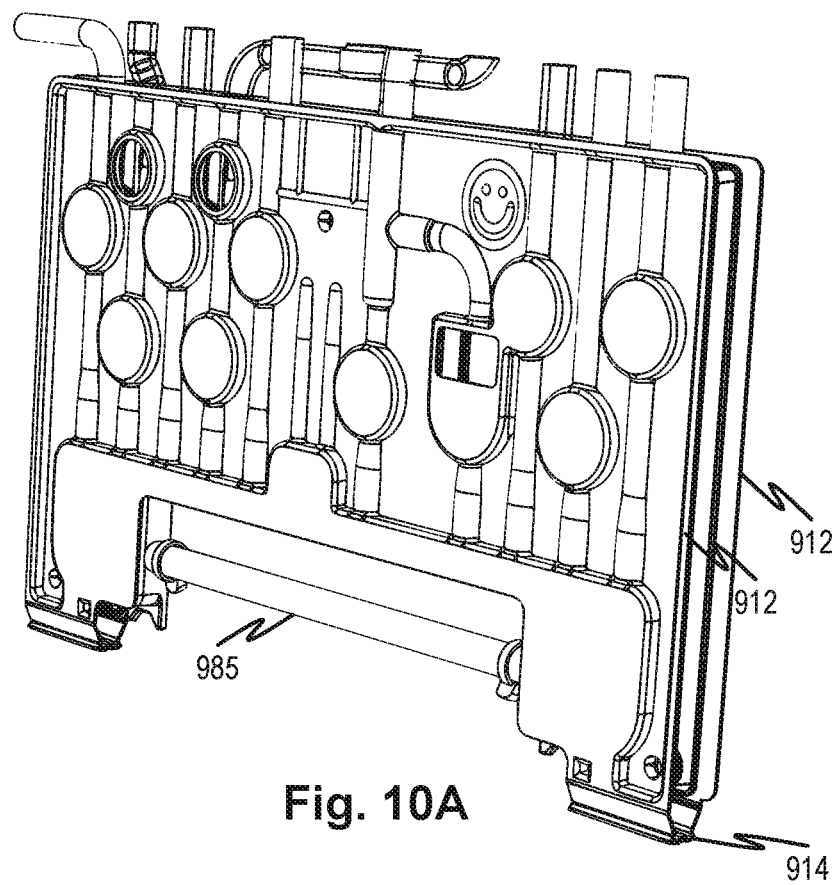
FIGS. 10A and 10B show the structure of a valve network portion of a fluid circuit according to embodiments of the disclosed subject matter.
Figure 10B:
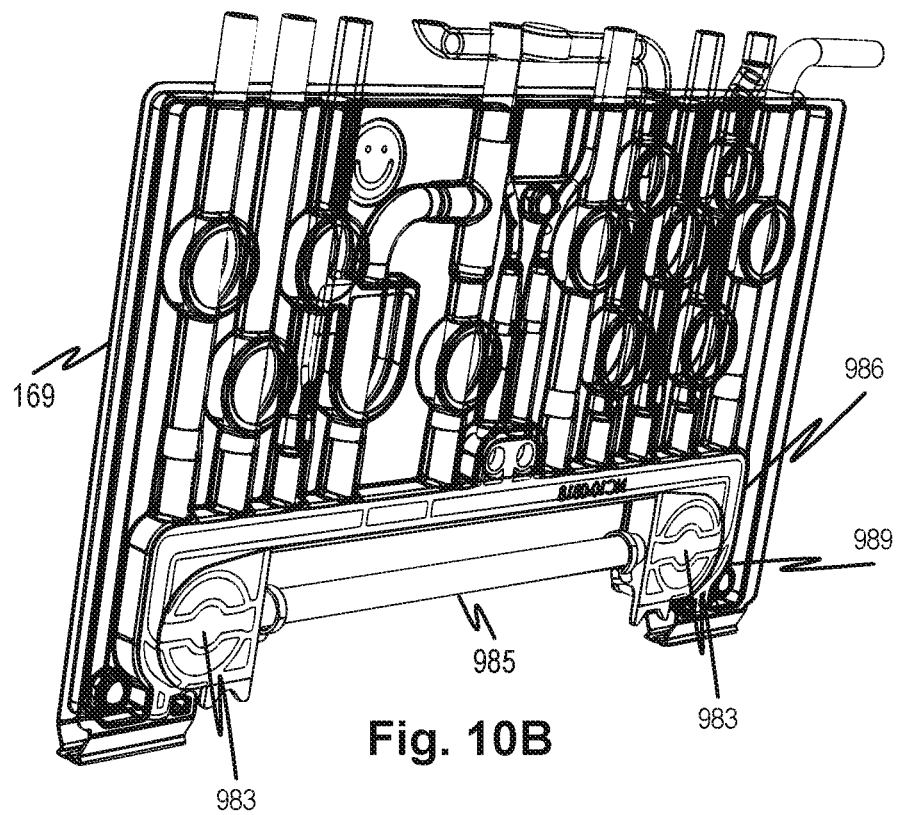
Figure 11:
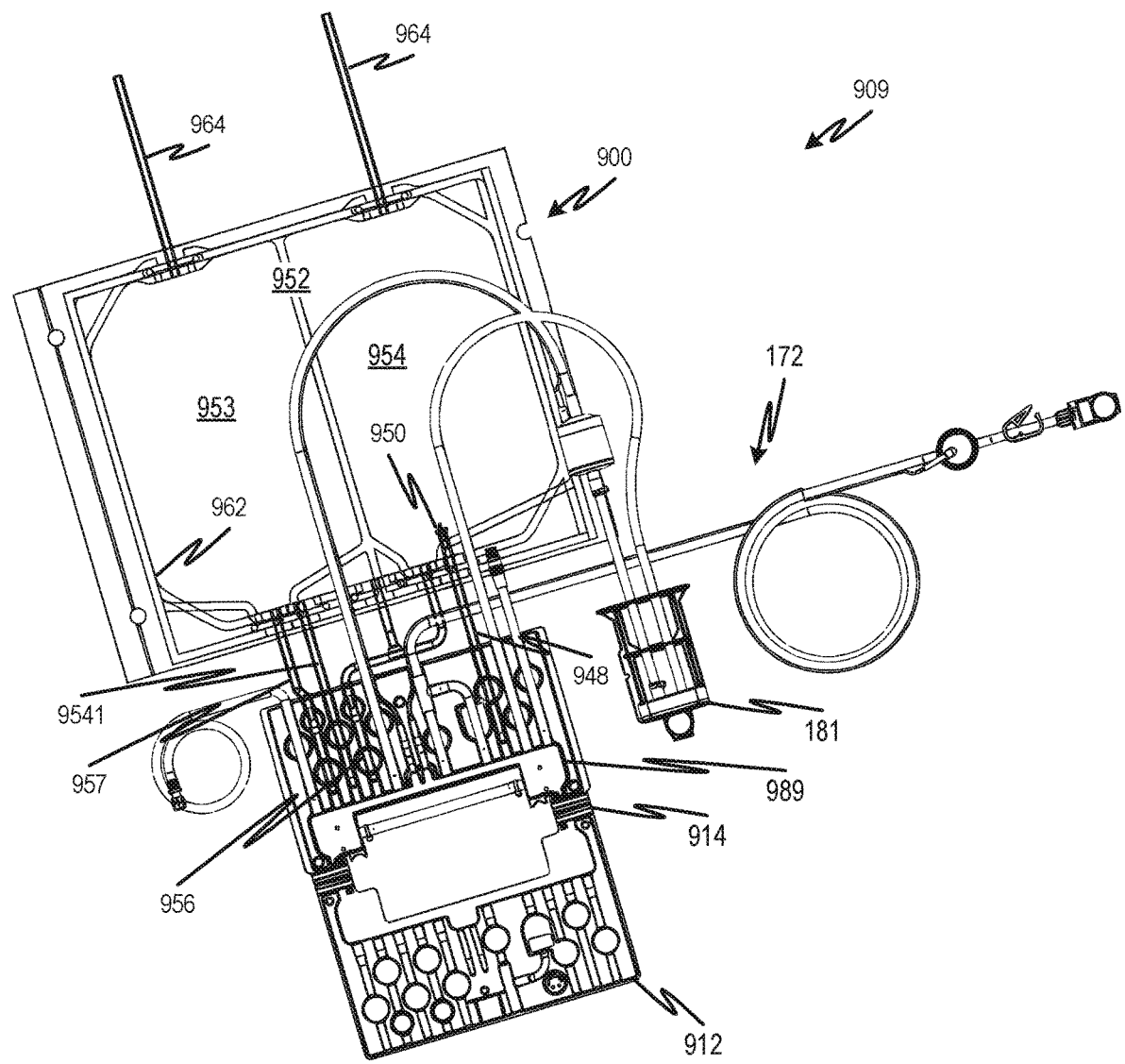
FIG. 11 shows a fluid circuit for peritoneal dialysis according to embodiments of the disclosed subject matter.

Referring now to FIGS. 10A and 10B, a cartridge portion 910 of the fluid circuits according to the various embodiments provides the manifold and the pumping and pressure sensing portions previously described. The cartridge support 169 may be made from a single panel 912 that is folded at a pair of creases indicated at 914. The panel 912 portions contain recesses for all the tubes held between them precisely controlling their positions. A compartment is defined by the shapes of the panels to hold the rigid housing 989. FIG. 2A shows an alternative embodiment in which the manifold 174 is connected by a battery of tubes indicated collectively at 200C so the double panel structure is not directly attached to the manifold 174. FIG. 11 shows the single vacuum formed panel 912 before it is closed about the pair of creases 914. FIG. 11 otherwise shows a complete fluid circuit 909 including how the features of 8A through 10B are assembled in a completed fluid circuit 909.

In any and all of the foregoing disposable fluid circuits, the components may be integrally-attached, meaning the components may be permanently bonded or otherwise locked together as delivered for use except for removable caps on inlets and outlets. In embodiments, only a single cap may be required to connect one or more concentrate inlets and a single cap may be required to connect a peritoneal dialysis catheter to the integrally-attached fill/drain line. This helps to ensure that a fluid circuit as-delivered will have less of a chance of being contaminated as a result of having only a small number of connections.

Generally, in systems that process or treat fluids and return processed or treated fluids to a patient, it is necessary to eliminate air from the fluid circuit prior to and/or during use to avoid introduction of air into the individual undergoing treatment. This may be accomplished by "priming" the fluid circuit which refers to circulating a fluid in the fluid circuit so that the fluid circuit is filled prior to treating a patient.

In the disclosed embodiments, preparing a complete batch for a PD treatment cycle, which is hereinafter referred to as the "main" batch, may take a certain minimum amount of time depending on the number of components that need to be mixed, the amount of fluid required for treatment of a patient, the need for proportioning error recovery, etc. For example, preparing a full batch of peritoneal dialysis fluid may take a significant fraction of an hour. Generally, the full batch will also be used for priming the fluid circuit when the new fluid circuit is loaded. Since the fluid circuit generally should be primed before being connected to the patient, the patient would have to start preparation of a full batch and then wait until the full batch is prepared before connecting and then either getting in bed or attending to some other activity such as relaxing. Thus, a patient desiring to connect to the cycler may be required to perform initial activities including attachment of a new fluid circuit to the cycler and then wait for a full treatment batch to be fully prepared before connecting to the fluid circuit. In a situation where the patient is tired and wishes to connect quickly in order to go to sleep or perform some other activity, this delay may be inconvenient. In particular, this delay may cause lost sleep and impact patient health.

In embodiments, a priming batch which is considerably smaller in volume than the treatment batch is first prepared and used for priming the fluid circuit so that the patient does not have to wait for the full batch to be prepared before the patient connects to the fluid circuit. The smaller volume of the priming batch may be just sufficient to prime the fluid circuit. In alternative embodiments, the smaller batch has a different composition which may be faster to generate than the composition of the batch used for treatment. For example, in embodiments in which multiple concentrate components are diluted by combining with water to form a treatment batch, a subset of the multiple concentrates and water is used to form the priming batch. In embodiments, the subset may include only water. In further embodiments, the priming fluid may be a blood-normal fluid, or formed from a concentrate that is different from the composition of the treatment fluid. For example, the single component may be a saline fluid or concentrate. Since the priming fluid is used solely for priming, there is minimal advantage to including an osmotic agent concentrate as does regular PD fluid.

The disposable fluid circuit that includes a small priming batch or concentrate container may be pre-attached and sealed to the disposable. After priming, the priming fluid may be flushed from the fluid circuit to the drain along with the spent dialysis fluid during initial treatment stage so that the composition of the dialysis fluid supplied to the patient is not altered by the differing composition of the priming fluid. Thus, the method of priming may include, following priming the fluid circuit, including the fill-drain line, pumping spent dialysis fluid from the patient immediately to the drain and flushing any portions of the fluid circuit containing residual priming fluid with the first treatment batch of fluid prior to filling the patient with a fresh batch. In this way, the quantities and proportions of fluid for the treatment do not have to account for any impact of the composition of the priming fluid. This can be the case irrespective of the type of fluid used, be it saline, pure electrolyte concentrate, purified water, or some other fluid.

In further embodiments, the disposable fluid circuit is provided with a container of priming fluid. The latter may be filled with a single or multi-component concentrate which is further diluted in preparation for priming or it may be provided fully diluted and ready for use. The priming fluid container may be pre-attached as described with reference to the concentrates described in the disclosed embodiments. Note that a single component concentrate container may be provided for priming-only because the weight and volume-saving benefits of the embodiment may be less important for the small volume of priming fluid than for treatment.

Accordingly, embodiments allow for quick priming and patient connection. In some embodiments, the quick priming may be provided as a user-selectable option, and if the user does not select the option, the system simply starts by preparing the treatment batch and using it for priming the fluid circuit.

In embodiments, the priming batch is mixed in the same disposable unit as used for the treatment batch. For example, with reference to FIG. 1A, the dialysis fluid preparation/cycler unit 103 may generate the priming batch by metering concentrate from concentrate containers 101 and adding them to, and diluting them with purified water in, the mixing container 102. However, in alternative embodiments, the priming batch may be stored separately from the treatment batch. In embodiments, the priming batch is formed from a subcombination of multiple components used for preparing a treatment batch. For example, the priming fluid may be formed from only the electrolyte concentrate component and water without mixing the osmotic agent concentrate. In this way time may be saved by only diluting and mixing a single component. In such embodiments, the composition of the single component used to make the priming batch may be selected such that when mixed with the second component it forms a dialysis fluid that is suitable for treatment and when mixed with water alone, it forms a desired blood-normal fluid.

Figure 12:
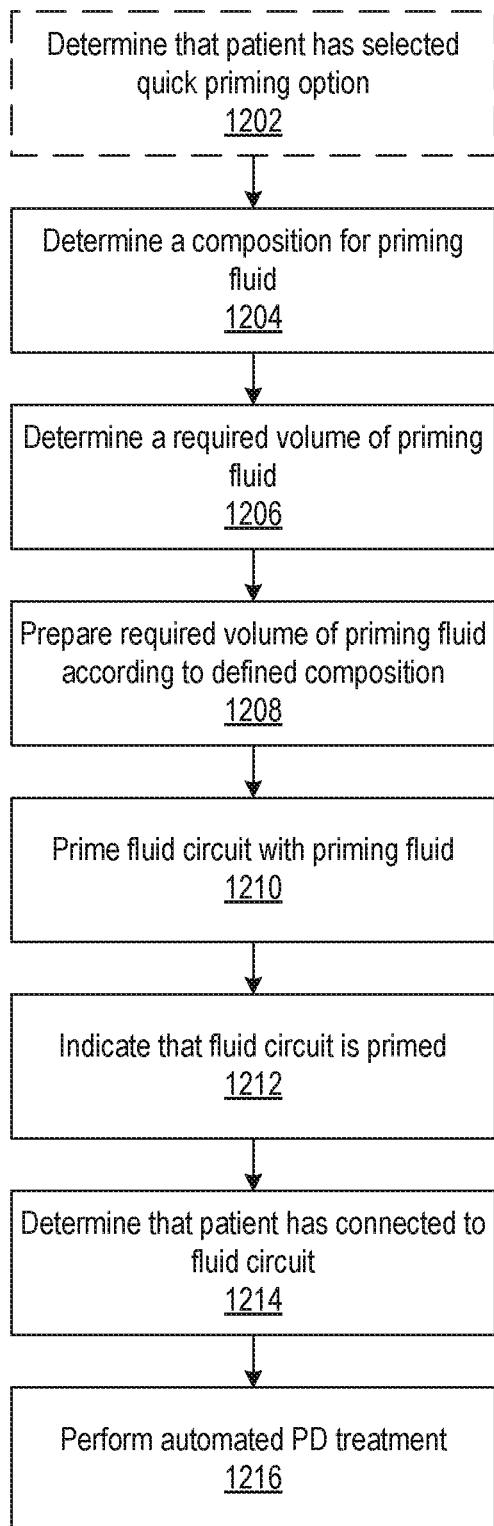
FIG. 12 shows a method of priming a fluid circuit according to embodiments of the disclosed subject matter.

FIG. 12 shows a method of priming a fluid circuit according to embodiments of the disclosed subject matter. At optional step 1202, a controller determines that the patient has selected an option for quick priming, for example, by activating a soft or hard key on a user interface in communication with the controller. Alternatively, quick priming may be performed by default and without receiving any explicit indication from the patient. If the patient chooses not to do quick priming, the method of FIG. 12 is not executed. In embodiments, the controller may request an indication of whether the patient is full or dry, meaning whether the patient's peritoneum is already full and therefore to be drained initially, or empty (dry) in which case the peritoneum is not to be emptied. If empty, the quick prime operation is skipped and a full batch of treatment fluid is made. The purpose of quick prime is to allow the drain cycle to be initiated quickly, so the patient doesn't have to wait for the cycler to prepare a full batch of treatment fluid. For example, this may be done at a time the patient is going to bed.

At 1204, the controller determines a composition for the priming fluid. For example, the composition may be based on a prescription or other data stored on a memory device connected with the controller. In embodiments, the composition may be configured by a physician or other healthcare professional via the user interface or over a network communication with a server or a central control system at a medical facility. In embodiments, the composition may be the same as used for the treatment of the patient, another composition as discussed elsewhere, or it may be water or saline solution.

At 1206, the controller determines a required volume of priming fluid. The determination may be a predefined volume stored in a non-volatile data store connected with the controller. In embodiments, the required volume may be configured by a physician or other healthcare professional via the user interface or over a network communication with a server or a central control system at a medical facility. In embodiments, the required volume may be based on physical properties of the fluid circuit such as the length and diameter of fluid lines.

At 1208, the controller operates a dialysis fluid preparation/cycler unit and corresponding connections/valves/pumps to prepare the required volume of the priming fluid according to the composition. For example, with reference to FIG. 1A, the dialysis fluid preparation/cycler unit 103 may generate the priming batch by metering concentrate from concentrate containers 101 and adding these to, and diluting them with purified water, in the mixing container 102 according to methods described elsewhere in the present disclosure or other methods such as described in US 2015-0005699A1, a copy of which is attached hereto as an appendix.

At 1210, the controller primes the fluid circuit with the priming fluid. The priming may be performed by pumping fluid as in the preparation phases described above to generate a batch of smaller size, and then pumping the resulting mixed batch through the fill/drain line (e.g., 450, FIG. 4A) until some reaches a point near the end of the fill/drain line. In embodiments in which water is used alone, water may be pumped into the mixing container and then into the fill/drain line, thereby filling the flow switching mechanism. The described flow diverters may also permit the water to flow from the mixing container to the drain thereafter, in preparation for making the first batch of a sequence for treatment.

At 1212, the controller indicates to the patient that the fluid circuit is primed and ready to be connected. The indication may be performed by generating a visual and/or audible alarm and corresponding text on the user interface. At this time, the patient may connect to the fluid circuit. Alternatively, the patient may indicate when fluid has reached the end of the fill/drain line by inputting a command through the user interface, the result of which would be to ready the system to begin treatment after the patient indicates s/he has made a connection to the peritoneal access.

At 1214, the controller may confirm that the patient has connected the patient access to the fluid circuit, for example by receiving an indication/confirmation via the user interface and/or by receiving sensor inputs (proximity sensors, switches, etc.) that indicate a physical connection of the fluid circuit to a catheter. The distal pressure sensor may be used by the system to confirm connection by having the controller detect and respond to pressure signals from patient respiration or pulse. At this time, the patient may place the system in a treatment mode at 1216 and allow automated treatment to proceed without attending to the system any longer. For example, the patient may go to sleep to receive a nocturnal treatment.

Figure 13A:
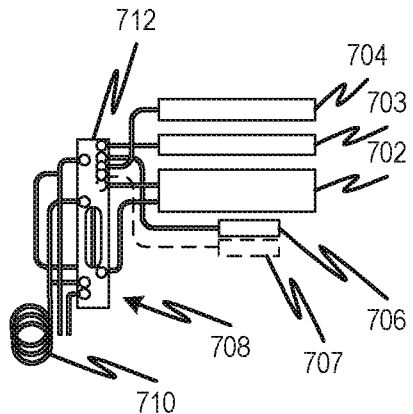
FIGS. 13A and 13B show embodiments of a fluid circuit with sources of concentrate where different compositions are provided for priming.
Figure 13B:
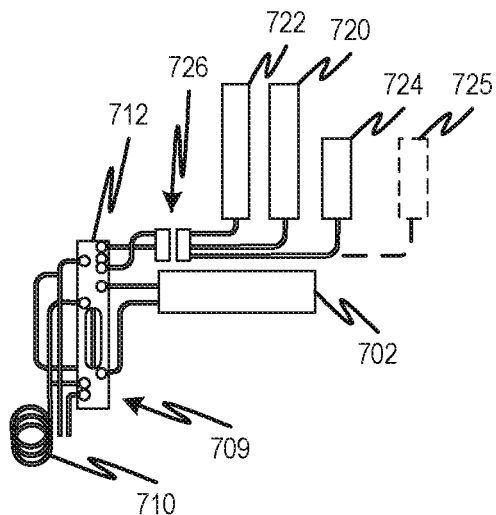

Referring to FIG. 13A, a fluid circuit has an attached priming fluid container 706. The fluid circuit includes a flow switching circuit 708 with a manifold and a pre-attached fill/drain line 710. Concentrate containers 703 and 704 are diluted as described to form a treatment batch which fills a mixing container 702. A priming concentrate may be provided in container 706 or, alternatively, a container of fully diluted priming fluid 707 is attached. The latter may be used as described above. FIG. 13B shows a fluid circuit that may be used to provide a priming batch by mixing a special composition from larger containers 724 of concentrate or fully diluted container 725 alternatively. The configuration may employ a multiple connector 726 as described elsewhere for connection to the long-term concentrate containers 720 and 722 for treatment batch preparation. In yet other embodiments, the fluid circuit may have a pre-attached priming fluid container (concentrate or diluted) and the multi-use container 724 or 725 may be omitted.

In alternative embodiments, quick priming may be done with priming fluid that remains in the mixing container after a normal priming process is used to prime the fluid circuit. The normal fluid circuit priming process begins with pumping water into and through the fluid circuit including circulating fluid into and out of the mixing container, at least partly in order to break-in the pumping tube segment, ultimately leaving a volume of, for example, four hundred ml. in the mixing container. The sterilizing filter protecting the water inlet according to any of the foregoing embodiments may then be tested to confirm its integrity after the priming operation. If the filter integrity is confirmed by the testing, this indicates the fluid in the mixing container which has passed through the sterilizing filter, the mixing container and fluid circuit being sterile as initially provided, must also be sterile, at least with a high certainty. That is, the only means by which contaminants can enter the mixing container, which is pre-sterilized, is through at least one filter (see foregoing embodiments), which essentially guarantees the contents are sterile. The quick prime operation may be performed using a portion of the contents of the mixing container. Other limitations of the quick priming as discussed above may be as indicated except for the use of concentrate.

Note that the quick prime procedure is contraindicated if the patient begins a treatment without a full peritoneal cavity. The term "full" in this context does not specify a particular volume, except that it should be sufficient for the treatment following the quick prime to begin with an initial drain cycle.

In any of the claimed embodiments identifying an element, it is understood that the identification of an element does not preclude the claims covering embodiments having multiple ones of the elements. For example, in any of the claimed embodiments identifying a concentrate line or concentrate container, it is understood that the identification of a single concentrate line or container does not preclude the claim covering multiple concentrate lines or concentrate containers. Further embodiments are contemplated in which multiple ones of the claimed elements may be provided to form additional embodiments, for example, the concentrate lines or containers. The same applies to method claims where additional steps may be provided to form new embodiments, where the additional steps repeat an operation performed by a recited step and act upon another material or article in equivalent fashion, for example, an additional concentrate.

Figure 15A:
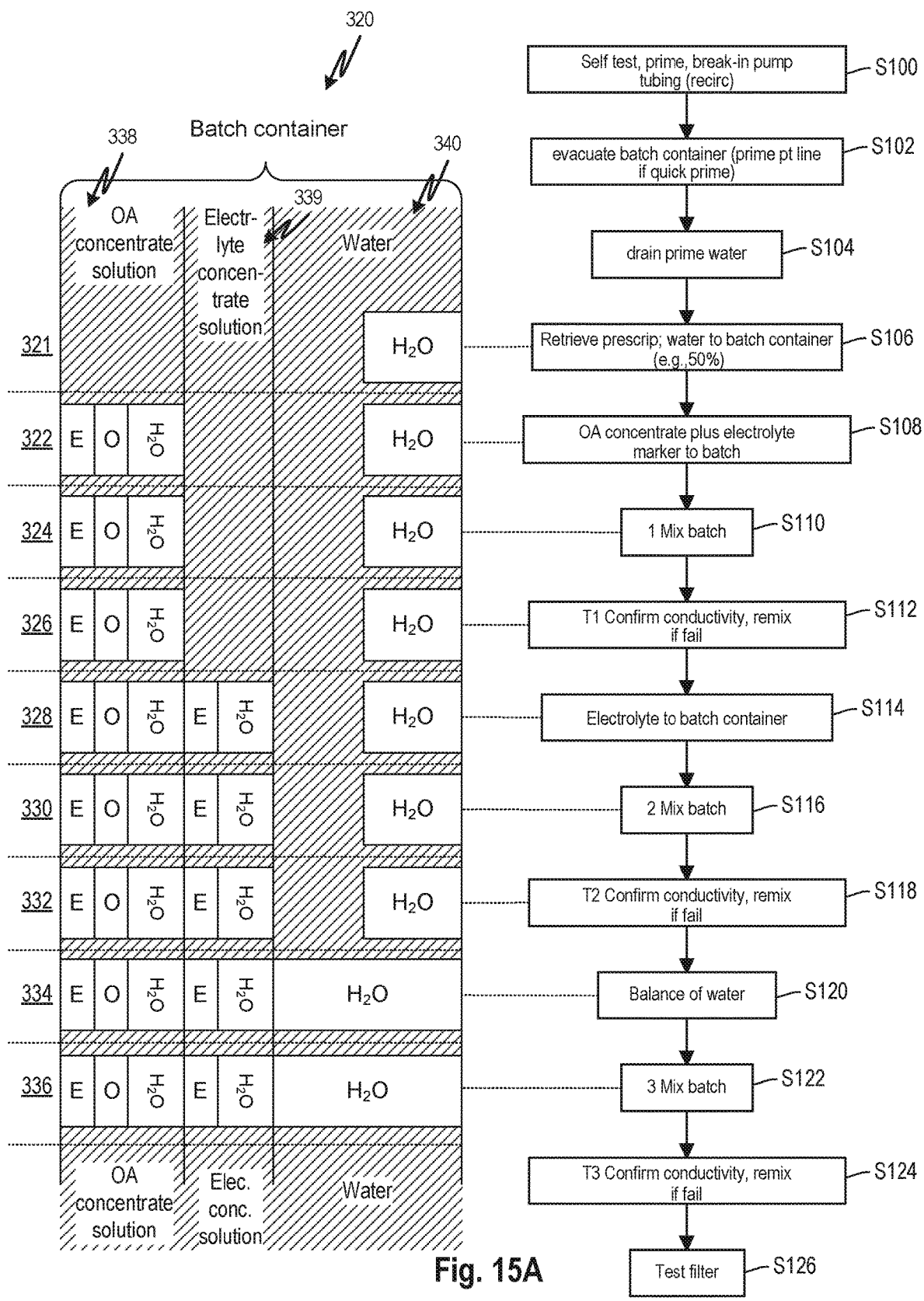
FIGS. 15A and 15B illustrate a mixing method according to embodiments of the disclosed subject matter.
Figure 15B:
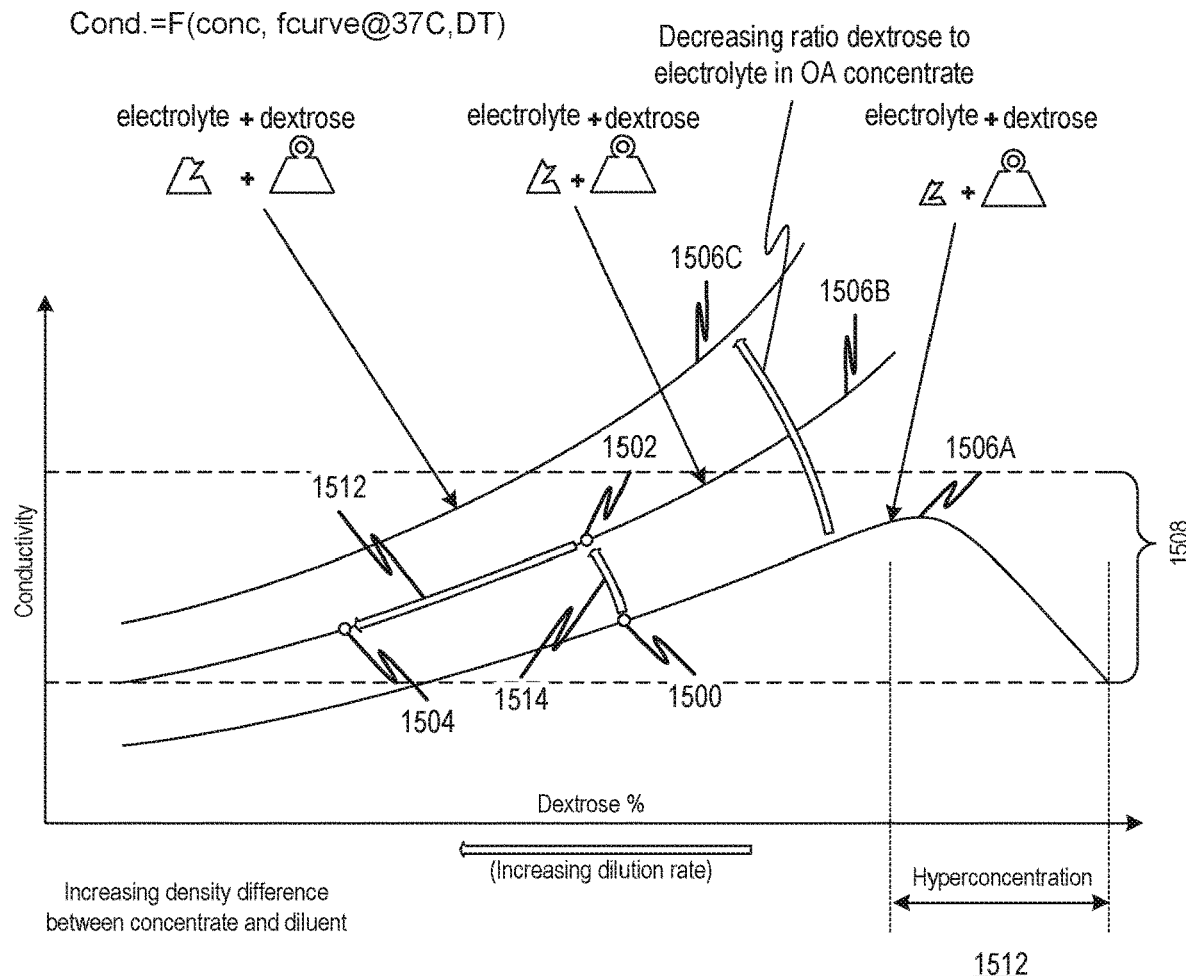
Figure 15C:
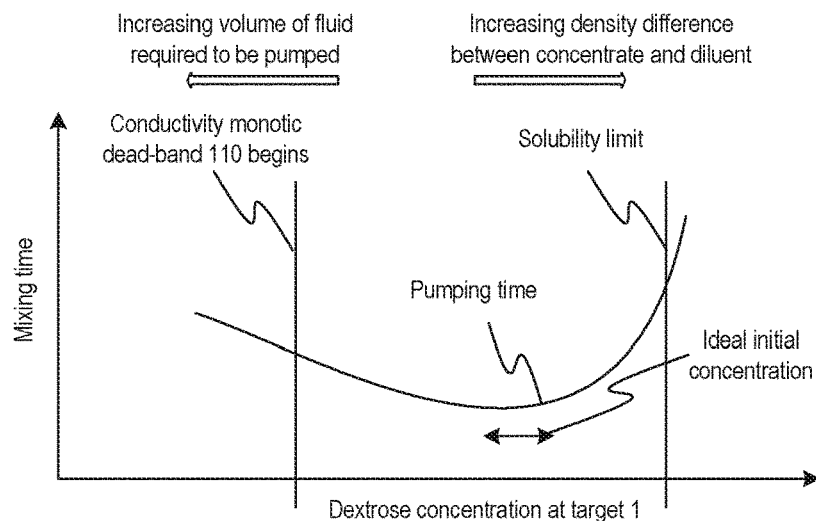
FIG. 15C illustrates an optimization point for a mixing method according to embodiments of the disclosed subject matter.

Referring now to FIGS. 15A-15C, method and system embodiments for proportioning concentrates and water are described. FIG. 15A shows a flow chart of the proportioning procedure next to a schematic diagram of the mixing container contents 320. The diagram at each stage of processing has rows 321 through 336, each of which shows a figurative representation of components of electrolyte, osmotic agent, and the water contained by the container after addition of a fluid. In this example, the osmotic agent concentrate contains both osmotic agent with water so its addition to the mixing container adds osmotic agent, electrolyte, and the water contained in the osmotic agent concentrate. See row 322 column 338. Row 321 shows the mixing container contains water alone after addition of water. Row 322 shows the components of electrolyte and osmotic agent plus the water contained by the osmotic agent concentrate all of which are combined to form the osmotic agent concentrate plus electrolyte marker added at S108.

The rows 322 through 336 are aligned with the process stages S106 through S122 and each row shows a composition that exists, or is achieved by, the corresponding process stage. Columns 338, 339, and 340 show the concentrates and water components. The concentrates are further broken down in the columns to indicate the constituents thereof. Again, the osmotic agent concentrate 338 has constituents water, osmotic agent, and electrolyte used as a marker. These constituents are indicated by "E," "0," and "H2O." The electrolyte concentrate 339 has constituents electrolyte and water indicated by "E" and "H2O."

In an initial operation S100 the fluid circuit, including the manifold, if one is present (the method is not exclusive to the mechanical features of the foregoing embodiments as will be evident from the presentation), is primed with water and the water is circulated through the mixing container to break-in the pump tube segment. The sterilizing filter, through which water is drawn, may be tested at this point to ensure its integrity. At S102, if a quick prime is to be performed, the batch contents may be used for this purpose. Either way, the remaining batch contents are emptied to the drain S104. The controller stores final target quantities of water, osmotic agent concentrate, and electrolyte concentrate ultimately to be transferred to the mixing container, mixed, and tested. Initially the mixing container is empty. At S106, an initial quantity of water is transferred to the mixing container. Prior to S106, the mixing container is essentially empty, although there may be a small residual trace from the priming operation. The resulting batch contents are indicated in alignment with the S106 process in row 321. The quantity of water may be optimized to minimize mixing time. In embodiments, the water quantity may be 50% of the target water requirement. At S108 osmotic agent concentrate is transferred to the mixing container as required by the target composition. The transferred osmotic agent concentrate illustrated at 322 indicates the that entire target quantity of concentrate is transferred. Also illustrated at 322 is that a quantity of water and a quantity of electrolyte concentrate are also transferred as part of the osmotic agent concentrate 338.

Note that the target quantities of the electrolyte, the osmotic agent, and water can be stored as the quantities of electrolyte concentrate and osmotic agent concentrate or the quantities of the undissolved species. The quantities can be converted between each and can be stored as volume or mass or other suitable measure.

In the present embodiment, the volume of osmotic agent concentrate includes electrolyte as a marker, which contributes to the amount of electrolyte of the target stored by the controller. If a final dialysis fluid requires no more than the quantity of electrolyte appearing in the osmotic agent concentrate to function as a marker, then the quantity of electrolyte concentrate transferred in this initial step is sufficient to form the final dialysis fluid. Next, the mixing container contents are mixed by pumping at S110. At S112, the batch content conductivity is tested to determine if the concentration is as expected. The controller may store a number indicating a number N of conductivity retests that can be performed in the event the conductivity test result is outside of an expected range. To retest, the controller mixes the contents of the mixing container again. In embodiments, this latter mixing may be for a shorter predefined interval than a predefined interval of operation S110. The testing and mixing may be iterated the N number (N being a predefined number) of times and if the final test fails, the preparation is halted and a recovery operation invoked, for example, halting pumping and outputting a display to restart preparation with a new disposable fluid circuit. Through S108 to S112, the contents of the mixing container remain the same as indicated at 324 and 326.

If the final dialysate calls for a higher ratio of electrolyte concentrate to osmotic agent concentrate than is in the osmotic agent concentrate, then at S114, a corresponding quantity of electrolyte concentrate is added to the mixing container. Otherwise operations S114, S116, and S118 are skipped. Proceeding with S114, the mixing container contents are mixed at S116 and a conductivity check is performed at S118 with M iterations where M may be any number including equal to N. The balance of the required water for achieving the target is added at S120. At that point the final composition indicated at 334 and 336 is obtained. Then, as above, the mixing container contents are mixed at S122 and a conductivity check is performed at S124 with L iterations where L may be any number including equal to N or M. In a final operation S126 the one or more filters used to protect against touch contamination (depending on the configuration of the fluid circuit) is tested to confirm its integrity during the fluid proportioning.

The reason only a fraction of the water is added initially at S106, even if the ratio of electrolyte to osmotic agent in the osmotic agent concentrate is correct for the target dialysis fluid, is that mixing initially with part of the water and then again with the remainder of the water may reduce the total mixing time compared to adding all of the water at once at S106.

In the foregoing methods, there were described three steps of mixing and testing. Within any of these operations, a titration process may be used to adjust the quantity of water or concentrate added to the mixing container or for adjusting the accounting of the total volume of water to be added in a final dilution operation. At S112, for example, in embodiments, the amount of osmotic agent concentrate may be increased if the conductivity measurement indicates the quantity falls below a minimum mass of osmotic agent (the solute) for the target dialysis fluid. Since ratiometric proportioning is relied upon, such a correction would assume that the amount of water transferred is validly quantified and the osmotic agent concentrate quantity is inaccurate. If testing indicates that the quantity of osmotic agent concentrate is consistently less accurately or precisely metered by the pumping than the water, then this correction would be valid for such systems. In further embodiments, the controller may be programmed so as to make an adjustment in the concentrate only after a predefined number of mixing/testing reattempts. This will ensure against any concentration bias resulting from incomplete mixing. When a dialysis fluid is being made, whose ratio of electrolyte to osmotic agent is identical to that in the osmotic agent concentrate containing electrolyte concentrate as a marker, the testing of the batch contents at S112 is sufficient to indicate the concentrations of both the osmotic agent concentrate and electrolyte concentrate because the ratio of electrolyte concentrate to osmotic agent concentrate is fixed in the osmotic agent concentrate. Many dialysis fluids are characterized by standard ratios of osmotic agent concentrate to electrolyte concentrate. If the highest osmotic agent/electrolyte ratio of such a fixed set is equal to the proportion of electrolyte concentrate used as a marker in the osmotic agent concentrate, then this ability to confirm the final dialysis fluid quality by a conductivity test will be available. A controller may be programmed to control the proportioning process such that a final batch is cleared only after confirmation of the final conductivity. For standard dialysis fluids having lower ratios of osmotic agent to electrolyte, the system may rely on ratiometric proportioning.

Figure 15D:
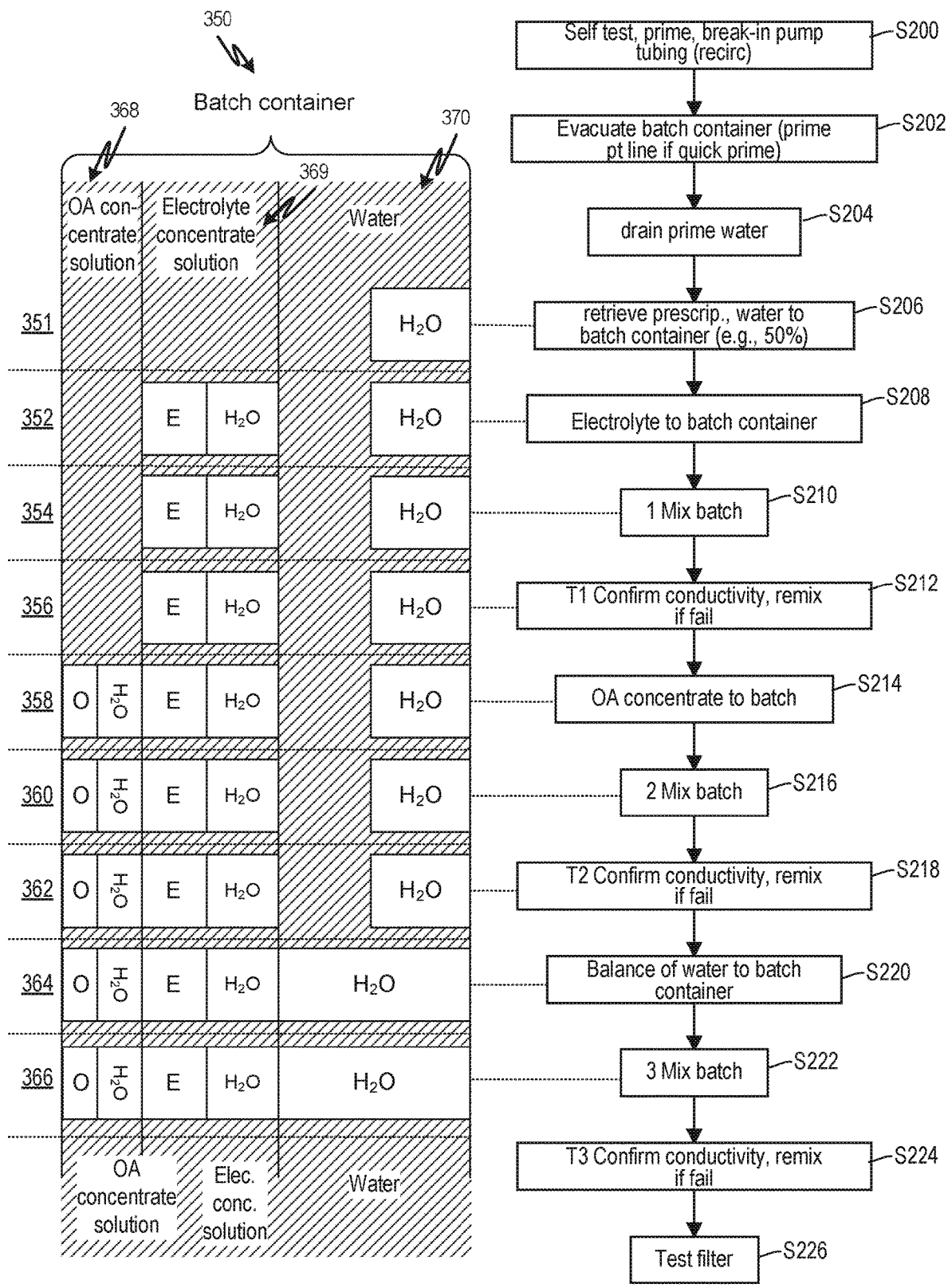
FIG. 15D illustrates a mixing method different from that of FIG. 15A according to further embodiments of the disclosed subject matter.

FIG. 15D shows a flow chart of another proportioning procedure next to a corresponding schematic diagram of the mixing container contents 320. As in FIG. 15A, the diagram at each stage of processing has rows 351 through 366, each showing a figurative representation of components of electrolyte concentrate, osmotic agent concentrate with no electrolyte marker, and water. As discussed with reference to FIG. 15A, the concentrates contribute some water in addition to the respective electrolyte and osmotic agent components they contribute. Also, the rows 351 through 366 are aligned with the process stages S206 through S222, with each row showing a composition that exists at the corresponding stage. Columns 368, 369, and 370 show the concentrates and water components. The concentrates are further broken down in the columns to indicate the constituents thereof. The osmotic agent concentrate 368 has as constituents osmotic agent and water only. No marker is used. The electrolyte concentrate 339 has as constituents electrolyte and water. The constituents are indicated by "E," "O," and "H2O" as in FIG. 15A.

In an initial operation S200, the fluid circuit including the manifold, if present, is primed with water and the water is circulated through the mixing container to break-in the pump tube segment. The sterilizing filter through which water is drawn may be tested at this point to ensure sterility. At S202, if a quick prime is to be performed, the batch contents may be used for this purpose. Either way, remaining batch contents are emptied to the drain S204. The controller stores final target quantities of water, osmotic agent concentrate and electrolyte concentrate ultimately to be transferred to the mixing container, mixed, and tested. Initially the mixing container is empty. At S206, an initial quantity of water is transferred to the mixing container. Prior to S206, the mixing container is essentially empty although there may be a small residual trace from the priming operation. The resulting batch contents are indicated in alignment with the S206 process in row 351. The quantity of water may be optimized to minimize mixing time. In embodiments, the water quantity may be 50% of the target water requirement.

At S208 electrolyte concentrate is transferred to the mixing container as required by the target composition. This may be the full quantity of electrolyte concentrate required in the target composition. The transferred electrolyte concentrate illustrated at 352 indicates the quantity of electrolyte solute that is transferred. Also illustrated at 352 is that a quantity of water is also transferred as part of the electrolyte concentrate 369.

Next, the mixing container contents are mixed by pumping at S210. At S212, the batch content conductivity is tested to determine if the concentration is as expected. The controller may store a number indicating a number N of conductivity retests that can be performed in the event the conductivity test result is outside of an expected range. To retest, the controller mixes the contents of the mixing container again. In embodiments, this latter mixing may be for a shorter predefined interval than a predefined interval of operation S210. The testing and mixing may be iterated the N number of times and if the final test fails, the preparation is halted and a recovery operation invoked, for example, halting pumping and outputting a display to restart preparation with a new disposable fluid circuit. Through S208 to S212, the contents of the mixing container remain the same as indicated at 354 and 356.

Proceeding with S214, the osmotic agent is added to the mixing container and the mixing container contents are mixed at S216. Then a conductivity check is performed at S218 with M iterations where M may be any number including equal to N. The quantity of osmotic agent concentrate added can be verified at S218 because the combined effect of dilution by the water constituent and the osmotic agent constituent is to lower the conductivity a measurable amount which depends on how much water and osmotic agent concentrate is added. This decrement in conductivity may be stored as a predefined quantity by the controller and compared to measured levels just as the other conductivity measurements are.

The balance of the required water for achieving the target mixture is added at S220. At that point the final composition indicated at 364 and 366 is obtained. Then, as above, the mixing container contents are mixed at S222 and a conductivity check is performed at S224 with L iterations where L may be any number including equal to N or M. In a final operation S226 the one or more filters used to protect against touch contamination (depending on the configuration of the fluid circuit) is tested to confirm its integrity during the fluid proportioning.

The reason only a fraction of the water is added initially at S206 is that mixing initially with part of the water and then again with the remainder of the water may reduce the total mixing time compared to adding all of the water at once at S206. In embodiments, however, mixing all the water at once is a possible alternative embodiment.

In all of the foregoing conductivity measurement operations, the conductivity and the temperature of the fluid may be converted directly to concentration of the electrolytes in water, or for a fluid that contains both electrolytes and an osmotic agent, to concentration of either the electrolytes or the osmotic agent, or both. A similar result may be achieved by correcting a measured conductivity to account for a difference between a reference temperature and the temperature of the fluid to obtain the conductivity at the reference temperature. A table of concentrations of the various admixtures vs conductivity at the reference temperature can then be stored in the controller to determine the concentration for purposes of making corrections in the dialysis fluid composition. In embodiments of disclosed proportioning systems, the reference temperature may be a human body temperature and the proportioning process may include controlling the temperature of the dialysis fluid to be at the body temperature (e.g., 37C) such that the actual temperature at the time of conductivity measurement is close to the reference temperature. This makes any errors in the corrected conductivity measurement very small because the actual and reference temperatures will be close due to the control of the dialysis fluid temperatures.

In a method embodiment, the constituents are warmed to the delivery temperature in advance of combining them. In alternative embodiments, the constituents are warmed after combining but prior to testing. In embodiments, the conductivity is used without compensation for comparison to reference values. In embodiments, the estimated temperature at which concentration or target conductivity is taken is an estimated room temperature. This would be relevant where the combining is done before warming the product to a temperature for administration to the patient. Warming to body temperature may be done at a later time. In embodiments, the conductivity levels and associated temperature compensation coefficients for each of the expected concentration targets are taken at 37 C.

FIG. 15B shows, approximately, the relationship between conductivity and concentration of dextrose during the proportioning procedure described above with reference to FIG. 15A. Curves 1506A, 1506B, and 1506C represent dilution curves for each of three kinds of dialysis fluid having final concentrations of osmotic agent in the finally diluted dialysis fluid. The fully diluted concentrate of each curve may represent, for example, 4.25% dextrose in curve 1506A, 2.5% dextrose in curve 1506B, and 1.5% dextrose in curve 1506C, respectively. The other constituents may be the same in all three, i.e., the clinically accepted components of what is carried in the electrolyte concentrate including sodium, magnesium, calcium chloride, etc. In other words, at all points to the right of the final diluted dialysis fluid (diluted to usable concentration) are over-concentrated solutions for 4.25%, 2.5%, and 1.5% dialysis fluid. By selecting the ratio of dextrose (osmotic agent concentrate, more generally) to electrolyte concentrates to be in the proportions of a final dialysis fluid characterized as a 4.25% osmotic agent (dextrose) dialysis fluid, a usable dialysis fluid can be formed without the addition of electrolyte concentrate and other dialysis fluids can be formed by adding respective amounts of electrolyte.

Presenting the dilution curves as shown in FIG. 15B highlights what has been pointed out above, namely, that the steps of mixing constituents in stages has implications for mixing efficiency and also, as discussed now, for proper measurement of conductivity. The ability to make unambiguous conductivity measurements varies for different points in the dilution vs. conductivity space. For example, curve 1506A illustrates the dilution curve for a concentrate with lowest percentage of electrolyte to osmotic agent and it can be seen that certain conductivity values indicate two different dilution levels. Also indicated at 1508 is a range for efficient mixing. The indications are all figurative and the precise ranges would be determined by experiment.

In the proportioning procedure of FIG. 15A outlined above, the measurement zones are restricted to a range where conductivity is single-valued and optimized mixing efficiency regions 1508. Referring also to FIG. 15A, water S106 is combined with electrolyte concentrate and osmotic agent concentrate S108 and mixed in the mixing container and the conductivity measured at S112. This corresponds to point 1500 where the composition corresponds to 4.25% dextrose that is partially diluted. Next, assume that the target dialysis fluid is 2.5% dextrose dialysis fluid. The addition of electrolyte concentrate S114 brings the composition of the mixing container to point 1502 which is on curve 1506B which corresponds to an overconcentrated 2.5% dextrose dialysis fluid. The final dilution at S120 brings the composition to the point 1504 which is that for ready to use 2.5% dextrose dialysis fluid. The measurement points 1500, 1502, and 1504 are all in desirable regions of the dilution/conductivity space. In the graph the osmotic agent concentrate is identified as dextrose but could be other kinds of osmotic agent concentrate.

In all of the foregoing embodiments, the final product can be obtained by ratiometrically balanced proportioning, relying purely on the repeatability of volumes delivered by the pumping. In such embodiments, the concentration need not be detected and proportioning can be done independently of any concentration measurements. In further embodiments, the final composition can be verified through a single concentration sampling and measurement.

Referring now to FIG. 15C, a graph shows mixing time versus dextrose concentration (note that other osmotic agent concentrates may be similarly represented) with a curve indicating total pumping time required to transfer the required full water and concentrate quantities and to mix the contents to a point that ensures complete mixing. The latter may be determined experimentally by periodically sampling the contents of a mixing container at times during mixing and identifying the time required for full transfer and complete mixing ("pumping time") as the point where the concentration reads a constant value. The ratio of water and the osmotic agent (e.g., dextrose) concentrate in the initial combination at 1500 in FIG. 15B may affect the total time required to create the admixture including time to pump water and concentrate and time to mix the container contents. Requiring the point 1500 to lie in the range of ratios of water and osmotic agent concentrate where the concentration measurement is monotonic and requiring the point to be remote from the solubility limit of the osmotic agent, a minimum pumping time may be identified. Accordingly, an optimum initial ratio of ratio of masses of osmotic agent concentrate and water may be found and used to define the combination identified with the point 1500 in FIG. 15B. In embodiments of the disclosed subject matter, for example the method of FIG. 15D, the point 1500 may be determined responsively to these conditions.

Note that in any of the embodiments, the use of peristaltic pumps can be replaced by metering pumps that employ any of a variety of pumping mechanisms that may provide sufficient absolute accuracy to satisfy a prescribed treatment (i.e., a ratio of the commanded quantity transferred to the actual is bounded by a predefined range that further falls within the permitted proportions of the admixture or final product dialysate constituents). This is compared to a pumping mechanism that relies on ratiometric accuracy in that the ratio of components is accurate even if the ratio of commanded-to-actual rates (or volumes) is not as accurate as the prescribed requirement.

Figure 16A:
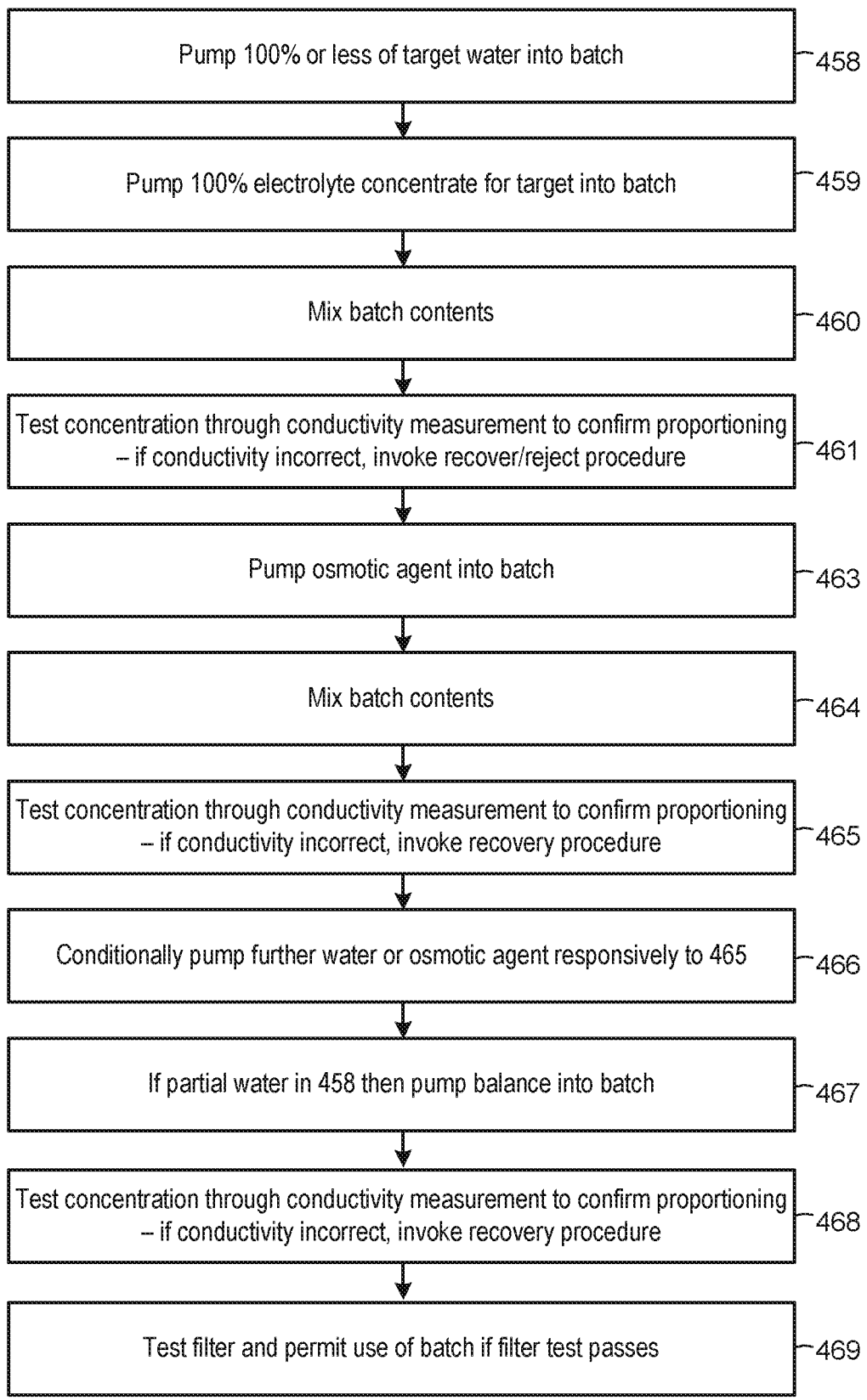
FIGS. 16A through 16C are flow diagrams describing a method for mixing a medicament in which electrolyte concentrate is added first to a mixing container according to embodiments of the disclosed subject matter.

Referring to FIG. 16A, in another method embodiment for creating a batch of dialysis fluid, electrolyte concentrate is pumped into the mixing container before osmotic agent concentrate is added. This allows the testing and adjustment of the electrolyte concentrate concentration to be performed on the mixed batch prior to the addition of osmotic agent concentrate. Because the tolerance of the dialysis fluid prescription to variation in the electrolyte concentrate concentration is much tighter, for example +/−2.5%, than the concentration of osmotic agent concentrate (+/−5%), the addition, confirmation, and adjustment of electrolyte concentrate alone allows the proportioning to be more tightly controlled. In embodiments, additional water or concentrate may be added to ensure the concentration is within the electrolyte concentrate limits. In embodiments, the dose of osmotic agent concentrate is controlled solely by volumetric control. In embodiments, the quantity of osmotic agent concentrate added during proportioning is checked with a conductivity measurement but the quantity is not titrated to adjust it based on conductivity measurements.

The method begins with the pumping of all, or a fraction of the required water for the batch into the mixing container 458. In a variation, a quantity of water equal to a predefined fraction required for the final batch is pumped into the mixing container. For example, 50% of the target quantity of water may be added. As noted elsewhere, the quantity may be selected to minimize overall pumping time or at least responsively to overall mixing time. Next, 100% of the required dose of electrolyte concentrate is pumped into the mixing container 459. The mixing container contents are then mixed at 460 and a sample of the mixing container is withdrawn and tested at 461 by pumping a sample through one or more conductivity sensors, for example as described in the above embodiments. At 463, the osmotic agent concentrate dose is pumped into the mixing container and the batch contents are mixed 464. Mixing here, and in all method embodiments, may be done by any of the mechanisms identified above or by any suitable method. Magnetohydrodynamic mixing (excitation circuits may be provided, for mixing and/or for warming, in a support for the mixing container) may be employed here to reduce the count of roller strikes on the fluid circuit that would otherwise occur if pump mixing were used. A sample may be pumped from the mixing container and tested at 465 by pumping a sample through one or more conductivity sensors, for example as described in the above embodiments. If additional water is required, depending on the amount originally added at 458, then the final balance of water is pumped into the mixing container at 467 and the final diluted concentration check as at 465 is done at 468.

At 469 a pressure test of one or more sterilizing filters depending on the embodiment (e.g., 115 of any FIG. 1A-1D, 2A, 2E or 2H) may be performed and a result of the test may be made a condition for the release of the batch for a treatment. That is, in the method, all fluids added to the batch that are not otherwise preconnected to the mixing container (as done in some but not all disclosed embodiments) may have an inline sterilizing filter preconnected between the outside source and the mixing container. That is, the sterilizing filter is preconnected such that its sterilizing filter membrane defines a barrier to the interior of the mixing container such that any touch contamination resulting from the making of a connection to the mixing container is blocked by the filter membrane when a fluid transfer occurs through the made connection. When the sterilizing filter or filters is/are pressure tested—that is, one or more sterilizing filters relied upon to define the sterile barrier are pressure tested—the controller makes a determination as to whether they have passed the pressure test and then either prevents or permits the batch to be used. In a method, the controller generates a message indicating the outcome of the pressure test or tests. The controller may generate the message to be output on a display along with an indication that the batch is not permitted to be used. The controller may further prevent the transition to a treatment mode in which the batch is used. The controller may, in an alternative embodiment, transition to a mode for preparation of a new batch. The controller, in the latter case, may output an instruction to replace a failed disposable with a new one and to initiate preparation of a new batch.

At 461, 465, and 468, the conductivity of the mixing container is detected and compared to an expected value in order to ensure the proportioning process is proceeding correctly. If a comparison to an expected value stored in a controller fails to pass, a recovery procedure may be performed as described with reference to FIGS. 15A and 15D, that is, the batch may be mixed (for any time, or for an interval shorter or equal to a mixing time of 460) and the batch contents sampled and tested again. Thus, one form of recovery is to recover from an invalid test rather than a bad mixture. If, after some predefined number of remix/test attempts, the conductivity differs from the stored expected value by more than a predefined amount or percentage, the proportioning process may stop, and the controller may output a message to restart the proportioning process. In addition to stopping the proportioning process, the controller may prevent access to the batch by clamping a line or take some other safety precaution to prevent misuse of the failed batch contents.

An additional recovery process may be implemented by the controller to adjust the conductivity of the batch in a way that corrects for a mixing error. When a conductivity test fails, i.e., the measured conductivity is outside a predefined range with respect to a stored expected value, the controller may adjust the proportions of the batch by adding water or one or both concentrates in an amount that is in response to the magnitude of the error. As an initial operation, the controller may compare the magnitude of the error in combination with the stage of proportioning in order to determine if an adjustment is permitted. In embodiments, the controller stores a respective error magnitude range of conductivity for each test (461, 465, and 468). The stored error magnitude, which may be different for negative and positive errors, may be compared with a detected error at 461, 465, or 468 and the controller may proceed with an adjustment process if the error magnitude is below the stored error magnitude or terminate proportioning if not. The error magnitude may be advantageously based on the last remix/test cycle for the particular operation 461, 465, or 468.

The recovery procedure may also employ a scale that measures the weight of the disposable unit. The disposable unit includes a mixing container and one or more concentrate containers depending on the embodiment. Only water is added and it is added to the mixing container. After obtaining a baseline weight after the disposable unit is rested on a scale, thereafter the quantity of water added to the mixing container can be detected by weight. No change in the total weight of the disposable unit occurs when concentrate is transferred to the mixing container. Using the conductivity plus the weight of the disposable unit, at each operation 461, 465, or 468, the controller can determine precisely the amount of added water or concentrate needed to achieve the target ratios.

In embodiments without a scale, or in which a scale is not used for proportioning control, the controller may perform operations as follows to recover by changing the mixing container contents to correct for an erroneous reading. Referring to FIG. 15E, a flow chart is shown in outline form. It repeats elements of other mixing methods presented here but is not a separate embodiment in that it can be added (with substitution, as necessary) as a conductivity error recovery method to any of the methods presented herein.

Referring to FIG. 15E, at 1.0 an initial water dose is added to the mixing container. At 2.0 a first concentrate is added, which can be, for example, osmotic agent concentrate or electrolyte concentrate according to any of the embodiments. At 3.0 the batch contents are mixed and at 4.0, the conductivity is measured. At 4.1 the controller determines if the conductivity measurement matches, within a predefined tolerance, the expected value and if so, operation proceeds to 5.0. Otherwise, at 4.2, an error recovery method 4.2.1 calculates an actual first concentrate in the batch by assuming that the correct quantity of water was pumped into the container. This may be obtained because the relationship between concentration and conductivity is stored. This relationship can be stored as a lookup table, a power function fitted formula, or some other way to allow a new quantity of concentrate to be calculated from the given water quantity and the calculated concentration of the first concentrate. The new quantity of concentrate (e.g., volume, but the units of the computation are not essential) is used to calculate a new target quantity of the second concentrate at 4.2.2.

At 5.0 the second concentrate is added, mixed 6.0, and the batch contents conductivity measured 7.0. If the conductivity value matches the expected conductivity based on the reset volume transfer of concentrate from 4.2.2 if this operation was performed previously, then control proceeds to 8.0. If the conductivity is erroneous and was previously erroneous for the first concentrate, then at 7.2 then the proportioning process is terminated and a recovery process initiated. The batch is a failed batch at this point. Control reaches 7.3 if the conductivity measurement at 4.0 was in range and the conductivity measurement at 7.0 was not in range. At 7.3.1 if the conductivity indicates deficiency of the second concentrate was added to the batch container at 5.0, then an additional amount to be added is calculated based on the magnitude of the conductivity measurement and thereafter added to the mixing container. Control proceeds to 7.3.2.1. At 7.3.1 if the conductivity indicates a surfeit of the second concentrate was added to the mixing container at 5.0, then an additional amount the first concentrate and water to be added are calculated based on the magnitude of the conductivity measurement and thereafter added to the mixing container. At 7.3.2.1 the batch contents are mixed and conductivity measured again at 7.3.2.2. If the measurement is within expected range, then at 7.3.2.2.1 control proceeds to 8.0; otherwise the proportioning is terminated at 7.3.2.2.2.

If no hard termination of the proportioning has occurred, then at 8.0 the balance of the water is added, at 9.0 the mixing container contents are mixed, and at 10.0 the conductivity of the batch fluid is measured. If the measurement is good, at 10.1, then control proceeds to 11.0. If the conductivity measurement is within the expected range, then control proceeds to 11.0, otherwise control proceeds to 10.1.1 or 10.1.2 based on whether the conductivity measurement indicated under-dilution or over-dilution at 8.0. If over-dilution is indicated by the conductivity measurement (i.e., measured conductivity is lower than the expected threshold) then at 10.1.1 both concentrates are added in the prescribed ratio as described in the present disclosure. If under-dilution is indicated at 10.1.2, water is added as described in the present disclosure. In both cases, the water deficit or surfeit can be estimated from the conductivity measurement based on the prescribed quantities of the concentrate constituents with any adjustments stored due to preceding recovery operations. In this final adjustment stage it is possible to add water or concentrates in increments and test repeatedly to titrate the batch contents to a final target level of conductivity. At 10.1.2.1 the batch contents are mixed and conductivity measured again at 10.1.2.2. If the measurement is within the expected range, then at 10.1.2.2.1 control proceeds to 11.0; otherwise, the proportioning is terminated at 10.1.2.2.2.

At 11.0, the filter or filters that ensure sterility of all fluids is/are tested and if the test fails, the batch is terminated as discussed above. Otherwise the batch is released at 12.0.

Note that in all the relevant operations in FIG. 15E, a magnitude of the error between the expected value of conductivity and the measured value is compared to a permitted range and if outside that range, control may proceed to a hard termination of the proportioning, as in 7.2, for example and as described elsewhere.

Figure 17A:
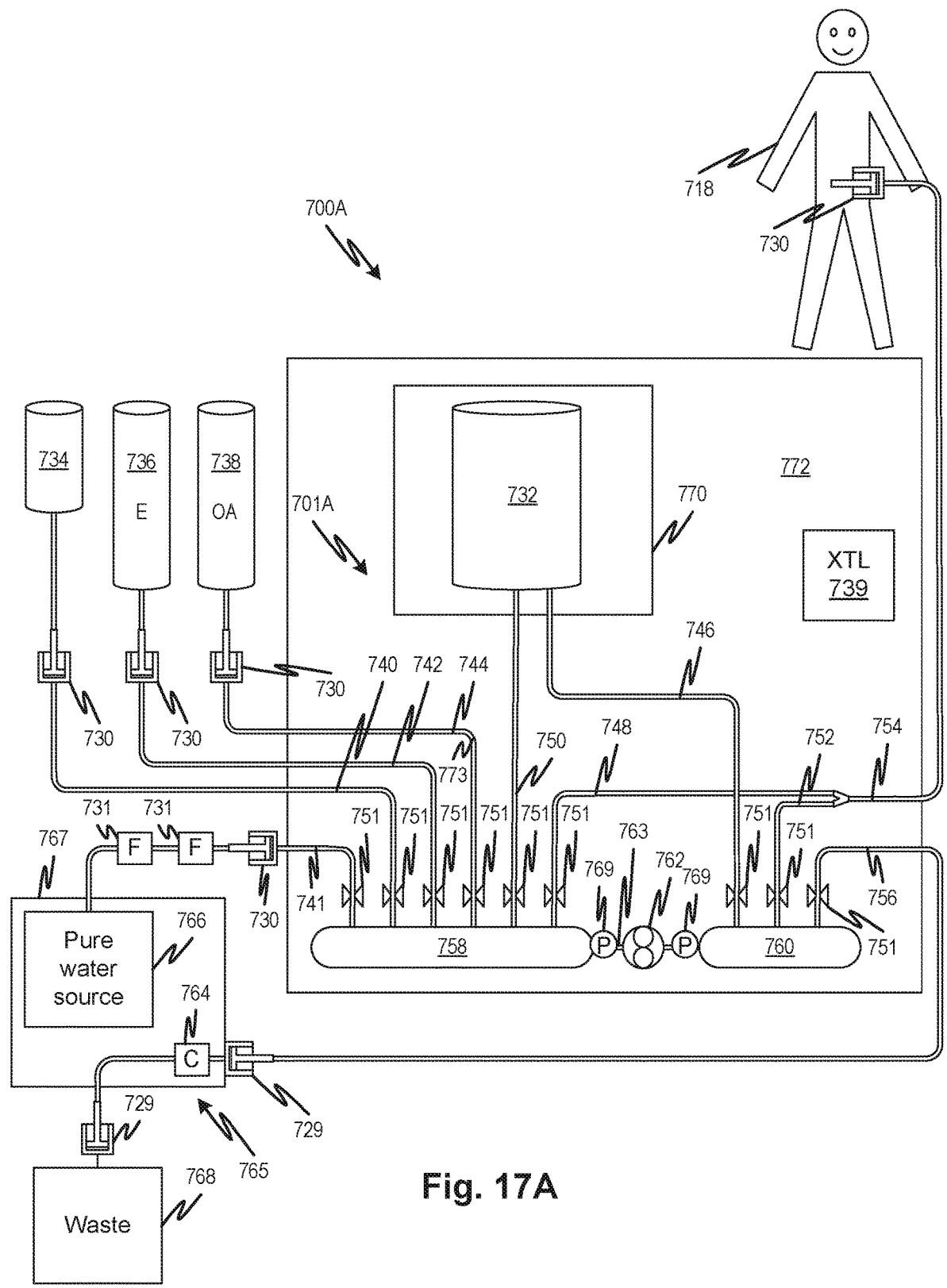
FIGS. 17A through 17D show embodiments of proportioning/treatment systems in which long-term, multi-treatment containers of concentrate are used to form a ready-to-use peritoneal dialysis fluid according to embodiments of the disclosed subject matter.

FIG. 17A shows a proportioning and treatment system for peritoneal dialysis 700A. Two multi-treatment containers 736 and 738 contain electrolyte concentrates and osmotic agent concentrates, respectively. They are connected by aseptic connectors 730 to a fluid circuit 701A by respective osmotic agent concentrate 744 and electrolyte concentrate 742 lines. Non-aseptic connectors may also be used. In embodiments, where the connectors are non-aseptic, the osmotic agent concentrate 744 and electrolyte concentrate 742 lines may contain sterilizing filters. Due to the cost and number of filters required this is not a preferred way to ensure sterility. A last fill container 734 may also be connected to the fluid circuit 701A via last fill line 740. The last fill container 734 may contain a specific medicament for the last fill cycle of a multi-cycle treatment. The fluid circuit 701A contains first 758 and second 760 manifolds connected by a pumping tube 763. The manifolds 758 and 760 define selectable fluid paths connecting various sources of fluids to fluid consumers using clamps 751 under control of a controller 739. The details of the flow switching may be as discussed above with respect to similar embodiments. A purified water source 766 supplies purified water to the manifold 758 through redundant sterilizing filters 731. The filters 731 may be replaced by a single testable filter that is automatically tested to confirm that a batch is sterile as described in method embodiments in the present disclosure. Manifold 760 is connected by a drain line 756 to a drain line circuit 765 through a non-aseptic connector 729. The drain line circuit has a conductivity sensor 764 in its path to permit the measurement of conductivity of samples of fluid conveyed through the manifold 760 under control of the controller 739. The mixing container 732 is connected by inlet and outlet lines 746 and 750 to the manifolds 758 and 760, respectively, to allow fluid to be pumped into the mixing container 732, to be drawn from the mixing container 732, and to permit mixing via recirculation of the contents of the mixing container 732. A pump 762 pumps fluid between the manifolds 758 and 760. Pressure sensors 769 are positioned on either side of the pump 762 to detect pump inlet and outlet pressures in pump tube 763. Signals corresponding to the pressures are applied to the controller 739 and used for pump pressure compensation and/or pump calibration as discussed elsewhere and in US Patent Publication 2015-0005699, hereby incorporated by reference in its entirety herein. A waste container 768 may be attachable to the drain line circuit 765 by a non-aseptic connector 729. A heater 770 contacts the mixing container 732. In embodiments, the heater 770 forms a bed on which the mixing container 732 rests. A patient line 754 is connected by a Y-connector to separate lines 748 and 752 to permit the filling and draining of a patient 718 through the patient line 754, which is connected to a catheter (not shown) by means of another aseptic connector 730.

The fluid circuit 701A connects to proportioning/cycler machine 772 by a mechanism that aligns clamps 751 with respective clamping portions of lines 741, 740, 742, 744, 750, 746, 752, and 756. Various such mechanisms are known in the art such as supports that hold tubing portions at predefined positions in cassettes and cartridges and compact fluid circuits that can be easily laid over a set of actuators and sensors. The manifolds and clamps can be replaced by a variety of different types of flow selector devices known in the art, so the current system is not limited to using flow selectors based on clamping of tubing. If the pump 762 is a peristaltic pump, a pumping tube segment of line 763 may be aligned by the connection of the fluid circuit 701A. The purified water source 766 may be housed in an enclosure 767 together with the drain line circuit 765 or portions of either. The waste container 768 may be housed in the same enclosure, or not, as illustrated. The concentrate containers 736 and 738 may contain sufficient concentrate for multiple fill/drain cycles, multiple days' worth of treatments, each consisting of multiple fill/drain cycles, a week's worth of treatments, a month's worth of treatments, or some other schedule. The concentrate containers 736 and 738 may be independently replaceable by use of the aseptic connectors. The benefits of independent replacement are discussed elsewhere in the present disclosure. The contents of the last fill medicament container 734 may be fully diluted or may consist of, or include, a concentrate that requires further dilution. The manifolds 758 and 760 may have a minimum volume to reduce waste when changing over fluids. In embodiments, the maximum hydraulic diameters of the manifolds 758 and 760 are each no more than 5 times the diameter of the largest line connecting to them. In further embodiments, they are no more than 3 times the diameter of the largest line and in still further embodiments, no more than twice.

Figure 16B:
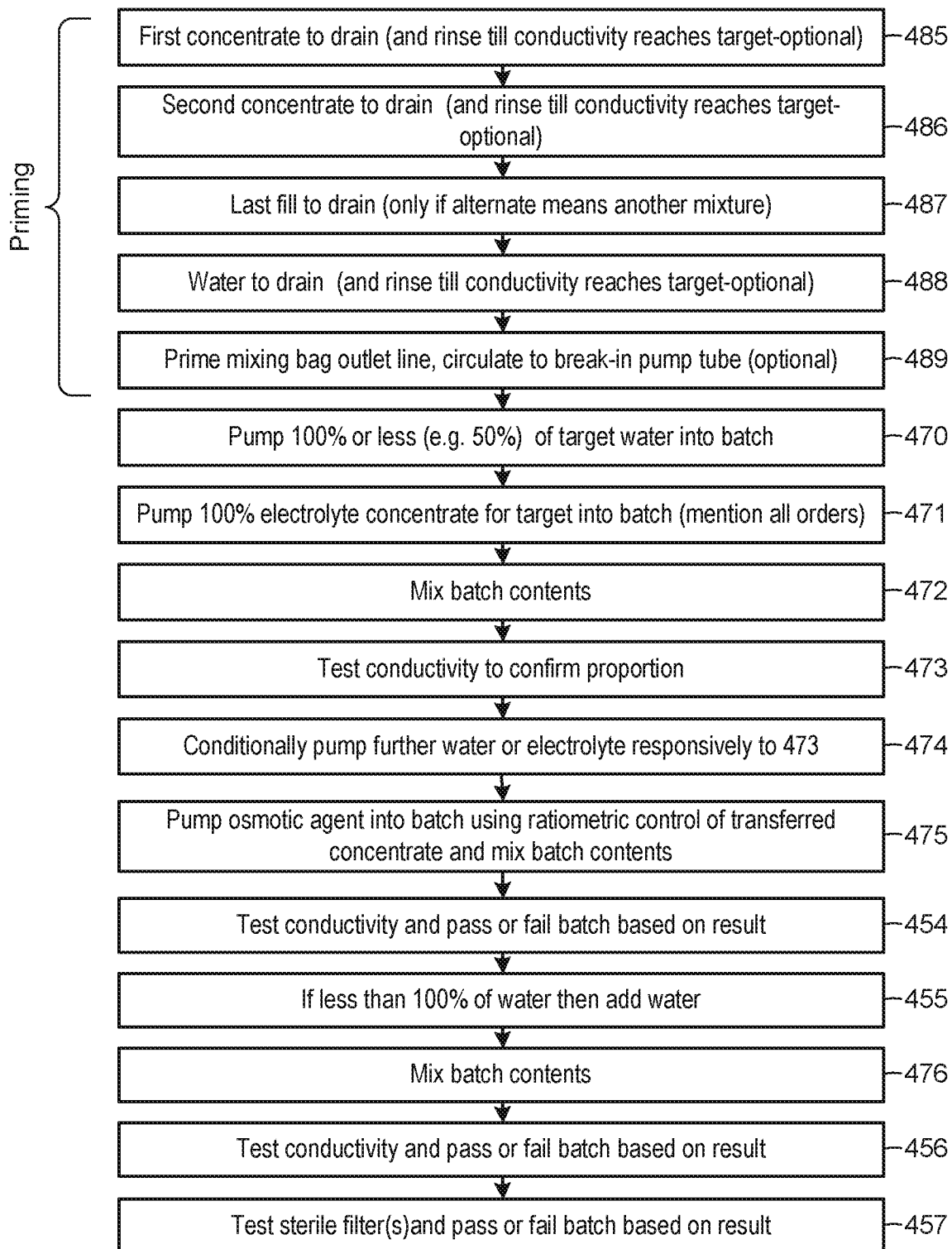

Referring to FIGS. 16B and 17A, in a method for creating a batch of dialysis fluid, a set of priming operations is first performed. The operations 485, 486, 487, 488 and 489 collectively form an overall operation sequence that fills osmotic agent concentrate, electrolyte concentrate and last fill lines 740, 742, and 744 with the respective fluids and fills the mixing container 732 inlet 746 and outlet 750 lines as well as the manifold 758, pumping tube 763, manifold 760, and water line 741 with purified water. The operations can be in any order but in particular embodiments, the water is primed through the manifold last.

At 485, a first concentrate 736 or 738 is conveyed to the waste container 768 (which can be a sewage drain rather than a container) by closing the valves 751 for all of the lines except for the valves 751 that permit flow through the respective concentrate line 742 or 744 and the valve 751 that permits flow through the drain line 756. The pump 762 is operated to establish a flow until a predefined condition is met. The predefined condition may be detected by the controller 739. The predefined condition may be a detected volume of concentrate determined by the controller 739, a number of cycles (e.g., rotations) of a pump actuator, or a detected conductivity or rate of change thereof, indicated by the conductivity sensor 764. The condition may be selected to ensure that the respective concentrate line 742 or 744 is filled. The condition may be further selected to ensure that the respective concentrate line 742 or 744 is purged of any air. The absence of any air in the respective concentrate line 742 or 744 may be established by an air detector, for example one that is located at the conductivity sensor 764 or located elsewhere along the path. The condition may include a combination of a threshold level of (or no) detected air combined with a predefined threshold of conductivity.

At 486, a second concentrate 736 or 738 (other than the first concentrate) is conveyed to the waste container 768 (which can be a sewage drain rather than a container) by closing the valves 751 for all of the lines except for the valves 751 that permit flow through the respective concentrate line 742 or 744 and the valve 751 that permits flow through the drain line 756. The pump 762 is operated to establish a flow until a predefined condition is met. The predefined condition may be detected by the controller 739. The predefined condition may be a detected volume of concentrate determined by the controller 739, a number of cycles (e.g., rotations) of a pump actuator, or a detected conductivity or rate of change thereof indicated by the conductivity sensor 764. The condition may be selected to ensure that the respective concentrate line 742 or 744 is filled. The condition may be further selected to ensure that the respective concentrate line 742 or 744 is purged of any air. The absence of any air in the respective concentrate line 742 or 744 may be established by an air detector, for example one that is located at the conductivity sensor 764 or located elsewhere along the path. The condition may include a combination of a threshold level of (or no) detected air combined with a predefined threshold of conductivity.

At 487, a last fill (either a concentrate or a ready for use medicament) is conveyed to the waste container 768 (which can be a sewage drain rather than a container) by closing the valves 751 for all of the lines except for the valves 751 that permit flow through the last fill line 740, and the valve 751 permits flow through the drain line 756. The pump 762 is operated to establish a flow until a predefined condition is met. The predefined condition may be detected by the controller 739. The predefined condition may be a detected volume of fluid determined by the controller 739, a number of cycles (e.g., rotations) of a pump actuator, or a detected conductivity or rate of change thereof indicated by the conductivity sensor 764. The condition may be selected to ensure that the last fill line 740 is filled. The condition may be further selected to ensure that the last fill line 740 is purged of any air. The absence of any air in the last fill line 740 may be established by an air detector, for example one that is located at the conductivity sensor 764 or located elsewhere along the path. The condition may include a combination of a threshold level of (or no) detected air combined with a predefined threshold of conductivity.

At 488, purified water is conveyed to the waste container 768 (or sewage drain) by closing the valves 751 for all of the lines except for the valves 751 that permit flow through the water line 741 and the valve 751 that permits flow through the drain line 756. The pump 762 is operated to establish a flow until a predefined condition is met. The predefined condition may be detected by the controller 739. The predefined condition may be a detected volume of water determined by the controller 739, a number of cycles (e.g., rotations) of a pump actuator, or a detected conductivity or rate of change thereof indicated by the conductivity sensor 764. The condition may be selected to ensure that the water line 741 is filled. The condition may be further selected to ensure that the water line 741 is purged of any air. The absence of any air in the water line 741 may be established by an air detector, for example one that is located at the conductivity sensor 764 or located elsewhere along the path. The condition may include a combination of a threshold level of (or no) detected air combined with a predefined threshold of conductivity.

At 489, an optional step is performed of recirculating the water through the mixing container 732. In embodiments, this may be done before or in the middle of the operation at 488 as well as after. The valves 751 opening inlet line 746 and the valve opening water line 741 are opened while all other valves 751 are closed so that when the pump 762 is operated, water is pumped into the mixing container 732. Then the water line 741 valve 751 is closed and the outlet line 750 valve 751 is opened so that when the pump 762 runs, water can be continuously recirculated in the mixing container 732. The controller implements this flow configuration for a predetermined number of pump cycles or a predefined time (which may depend on the flow rate). This operation breaks in the pump tube 763 for a peristaltic pump, thereby making the relationship between pump cycle rate (e.g., RPM) and flow rate more consistent. This operation is beneficial when a new fluid circuit 701A is installed. After the pump tube 763 break-in is completed, the inlet line 746 may be closed by the respective valve 751 and the drain line 756 opened by the respective valve, after which the pump 762 operates to drain the mixing container. Whether the pump break-in is completed after, before, or during priming of the manifold and drain line with water, the operation serves to prime the inlet 746 and outlet 750 lines and further prime the drain line 756 and manifolds 758 and 760.

Note that instead of a conductivity detector at 764, other types of sensors may be used to detect the filling of the respective concentrate line. For example, a flow sensor may be responsive to the density or viscosity of fluid flowing in the drain line 756. Another alternative is a temperature sensor for cases where the temperature of the fluid reaching the sensor is different from the fluid being displaced.

In the embodiment of FIG. 16A, electrolyte concentrate is pumped into the mixing container before osmotic agent concentrate is added. However, in alternative embodiments, osmotic agent concentrate (which may contain electrolytes that function as a marker) is added to the mixing container before the remaining electrolyte concentrate. The method begins with the pumping of 100% or less of the required water for the treatment batch into the mixing container 732. By closing all valves 751 except those closing water line 741 and inlet line 750, a predefined volume of water is pumped by the pump 762 from the purified water source 766 through sterilizing filters 731 (or a single testable filter if present), through the optionally aseptic connector 730, through water line 741, manifold 758, through pumping tube 763, into manifold 760, through mixing container inlet line 746, and into the mixing container 732. The volume displaced may be controlled by the controller by controlling the number of cycles of the pump 762 to a predefined number of cycles (e.g., rotations of a peristaltic pump). The embodiment of FIG. 16B can be modified in a similar manner, however, the osmotic agent concentrate pumped into the mixing container first, may contain electrolyte concentrate in sufficient quantity to serve as a marker in order to test the admixture at 473.

For purposes of accounting for the precise quantities of fluids that are pumped into the mixing container 732, the controller's operations to the pump 762 are such that displacement of residual volumes of fluids remaining in respective parts of the fluid circuit are accounted for. In operation 470, the total quantity entering the mixing container is equal to the quantity displaced by the pump 762 in this operation because the manifolds 758 and 760 and the inlet line 746 were previously primed. So, no additional accounting is reflected in the control of the pump in that case. The pump is operated to displace a target volume of water and the controller can be programmed to do calculations based on the batch volume being equal to the displaced volume during operation 470. For convenience in discussing the further operations where displacement of a fluid also displaces another remaining in the fluid circuit 701A, the following identifiers will be used:

MIMO, for the combined volume of the manifold 758, pump tube 763, and manifold 760;

MOTI, for the volume of the inlet line 746 between the mixing container 732 and the manifold 760;

SOMI, for the volume of the outlet line 750 between the mixing container 732 and the manifold 758.

At 471, electrolyte concentrate from electrolyte concentrate container 736 is pumped to the mixing container 732 by opening respective valves 751 for the electrolyte concentrate line 742 and the inlet line 746 and closing other valves 751 to form a direct path that includes MOTI and MIMO. The electrolyte concentrate is pumped by the pump 762 from the electrolyte concentrate container 736, through the manifold 758 by opening only the clamp 751 that closes the electrolyte concentrate line 742. The pump draws the electrolyte concentrate from manifold 758 through the pump tube 763 and into manifold 760 through the inlet line 746 into the mixing container 732. A volume equal to 100% of the required dose of electrolyte concentrate is pumped toward the mixing container 471 but a predetermined fraction equal to MOTI and MIMO remains behind. In addition, through the pumping of electrolyte concentrate, a volume of water equal to MOTI and MIMO is added to the mixing container 732. The controller uses a predetermined conductivity threshold for a mixed diluted electrolyte concentrate based on the added volume MOTI plus MIMO of water. This conductivity threshold allows the testing at 473 and adjustment at 474 of the electrolyte concentrate concentration to be performed on the mixed batch prior to the addition of osmotic agent concentrate with the concomitant tolerance benefits discussed above.

The mixing container contents are then mixed at 472 by closing all valves 751 except those closing the inlet 746 and outlet 750 lines to the mixing container 732 such that fluid is circulated into and out of the mixing container 732. As a result, the fraction of electrolyte concentrate equal to MOTI and MIMO is integrated into the batch contents and the water left in SOMI is integrated in as well. For concentration measurement purposes the total pumped volume of concentrate conveyed at 471 is mixed with the total pumped volume of water conveyed at 470 with the additional dilution of a SOMI volume to determine the expected concentration. A sample of the mixing container is withdrawn and tested at 473 by pumping a sample through one or more conductivity sensors, for example as described in the above embodiments. This is done by closing all the valves 751 except for those controlling the outlet line 750 and the drain line 756 and operating the pump 762 to convey a predetermined volume of fluid from the mixing container 732 to the conductivity sensor 764. The controller 739 may account for the drained volume in making adjustments to its internal model of the batch contents at 474 including total volume and proportions of constituents. The concentration of electrolyte concentrate can be determined by the controller 739 by the conductivity measurement permitting the controller to add more water or electrolyte concentrate to change the concentration to fit a target. Alternatively, the internal model of composition of the mixing container stored by the controller 739 may be adjusted responsively to the measurement and accounted for later to change the amount of osmotic agent concentrate and/or water added to the mixing container 732 in later operations to generate the target prescription fluid. At 474, if the batch contents are adjusted immediately and responsively to the results of the concentration test, then water or additional electrolyte concentrate may be pumped into the mixing container 732 using the valve 751 settings identified above, depending on whether the concentration measurement indicated over-dilution or under-dilution. If less than 100% of the water dose is used in 470 (as in the embodiment variation identified above), then additional water may be added up to the requirement per prescription. Again, such a water balance may be added after 475 and 454 at 455.

At 475, osmotic agent concentrate from osmotic agent concentrate container 738 is pumped to the mixing container 732 by opening respective valves 751 for opening the osmotic agent concentrate line 744 and the inlet line 746 and closing other valves 751 to form a direct path that includes MOTI and MIMO. The osmotic agent concentrate is pumped by the pump 762 from the osmotic agent concentrate container 738, through the manifold 758 by opening only the clamp 751 that control the osmotic agent concentrate line 744 and the inlet line 746. The pump draws the osmotic agent concentrate from manifold 758 through the pump tube 763 and into manifold 760 through the inlet line 746 into the mixing container 732. A volume equal to 100% of the required dose of osmotic agent concentrate is pumped toward the mixing container 471 but a predetermined fraction equal to MOTI and MIMO remains behind. The required dose may be determined, in part, by the results of the conductivity test at 473 as indicated above. The volume transferred may also account for the volume of diluted electrolyte concentrate of the prior batch contents which remains in MOTI and MIMO before the osmotic agent concentrate is pumped. Finally, the residual volume is transferred to the mixing container 732 in the final dilution at 455, if present, such that the volume of osmotic agent concentrate transferred to the mixing container 732 is in part compensated to account for that additional volume. The batch contents are mixed using the valve settings identified in the discussion of operation 472. This mixes-in the residual MOTI and MIMO volumes of osmotic agent concentrate remaining behind after pumping the osmotic agent concentrate, as well as the SOMI volume of the mixture, before addition of osmotic agent concentrate.

At 454, the batch contents may be sampled as discussed in relation to the operation 473 by setting appropriate valves 751 and operating the pump 762. The conductivity determined from the sample indicates to the controller whether the batch is good and can be used for a treatment cycle or whether it is bad and should be drained and remade or some other recovery cycle implemented. The addition of osmotic agent concentrate and associated water has a measurable effect on the conductivity. The addition of osmotic agent concentrate, depending on the specific type (dextrose, for example), tends to lower the conductivity. However the concentrate impacts the conductivity, it can be predetermined and stored by the controller so that the conductivity measurement at 454 can be used to determine if the conductivity corresponds to the internal model or is outside a predefined range thereabout. As stated, the controller will enable the batch to be used for a treatment or regenerated or it will prevent usage by preventing the advance of the control system to treatment mode, generate an error signal, drain and generate a new batch, or any combination thereof, based on the conductivity result.

At 455, if less than 100% of the required water for a complete batch was added to the mixing container 732 at 470, then the remaining complement of water is added at 455 using the settings described above with regard to operation 470. The total amount of water displaced is ultimately added to the batch, even though a fraction remains behind initially in MOTI and MIMO. This is because of the additional mixing operation at 476, where the MOTI and MIMO portions are mixed into the batch. The SOMI volume of the previous mixture attained at the end of 475 is also mixed in.

At 475, an osmotic agent concentrate volume is transferred to the mixing container 732. A dose is pumped into the mixing container 732 and the batch contents are mixed. At 454 the conductivity of the batch contents is measured and if it is within limits, control moves on to 455, and if not, the proportioning is terminated. At 455, if less than 100% of the water was added at 470, then the final volume of water is added to the mixing container 732. At 476, the batch contents are mixed and the MOTI and MIMO volumes of water are mixed in as well as the prior mixture from SOMI to form the final mixed batch. At 456, the conductivity is tested using the procedure described above in reference to 473. At 457, any sterilizing filters responsible for ensuring sterility of fluids may be tested or redundant filters may be used. If the filter(s) integrity is/are confirmed, then the batch will be released; otherwise, the batch is not released. The possible responses to an out-of-range reading of conductivity may be as described with reference to operation 454.

Figure 16C:
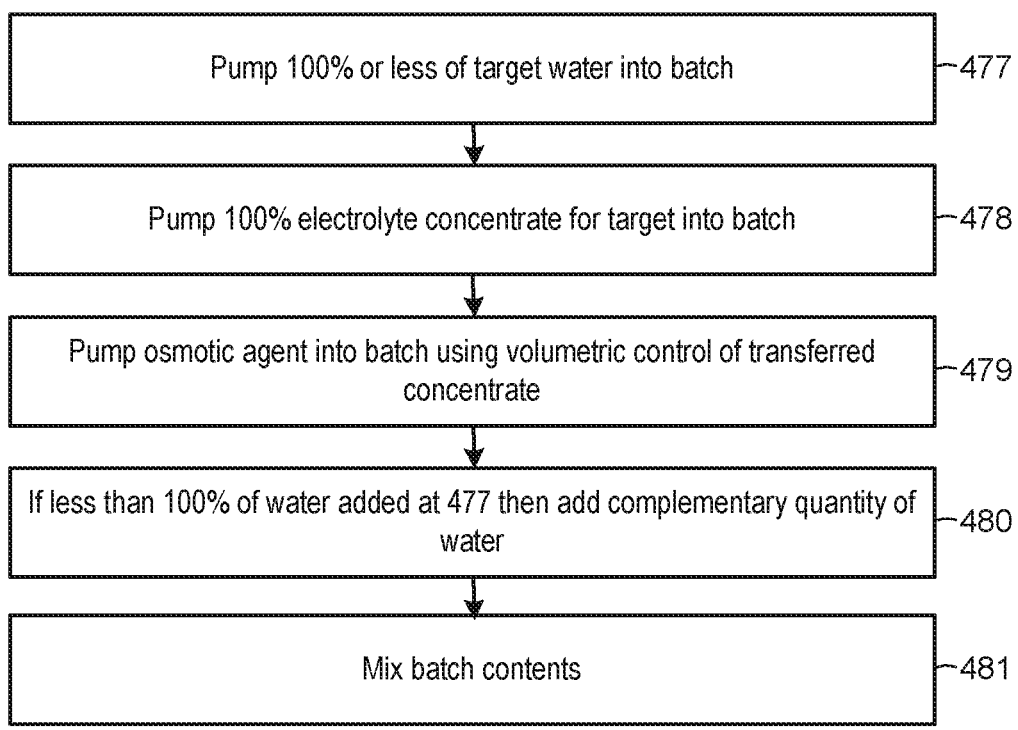

Referring to FIG. 16C, in a further embodiment, suitable for a pumping system and/or method that provides a high degree of volumetric accuracy, water and osmotic agent concentrate and electrolyte concentrates are transferred to the mixing container and mixed 477-481 in a single set of operations relying on volumetric control. At 477 100% or a fraction of a target water volume is pumped into the mixing container. At 478, 100% of a target volume of electrolyte is transferred to the mixing container. At 479, a volume of osmotic agent is pumped into the mixing container. At 480, if less than 100% of the water was transferred at 477, then a complementary quantity of water is added to bring the total to 100%. At 480 the conductivity of the mixing container contents can be measured and if necessary additional water added. Conductivity is measured after mixing. At 481 the mixing container contents are mixed. The operations may be followed by a pressure test of a sterilizing filter as discussed with reference with the other embodiments.

Figure 17B:
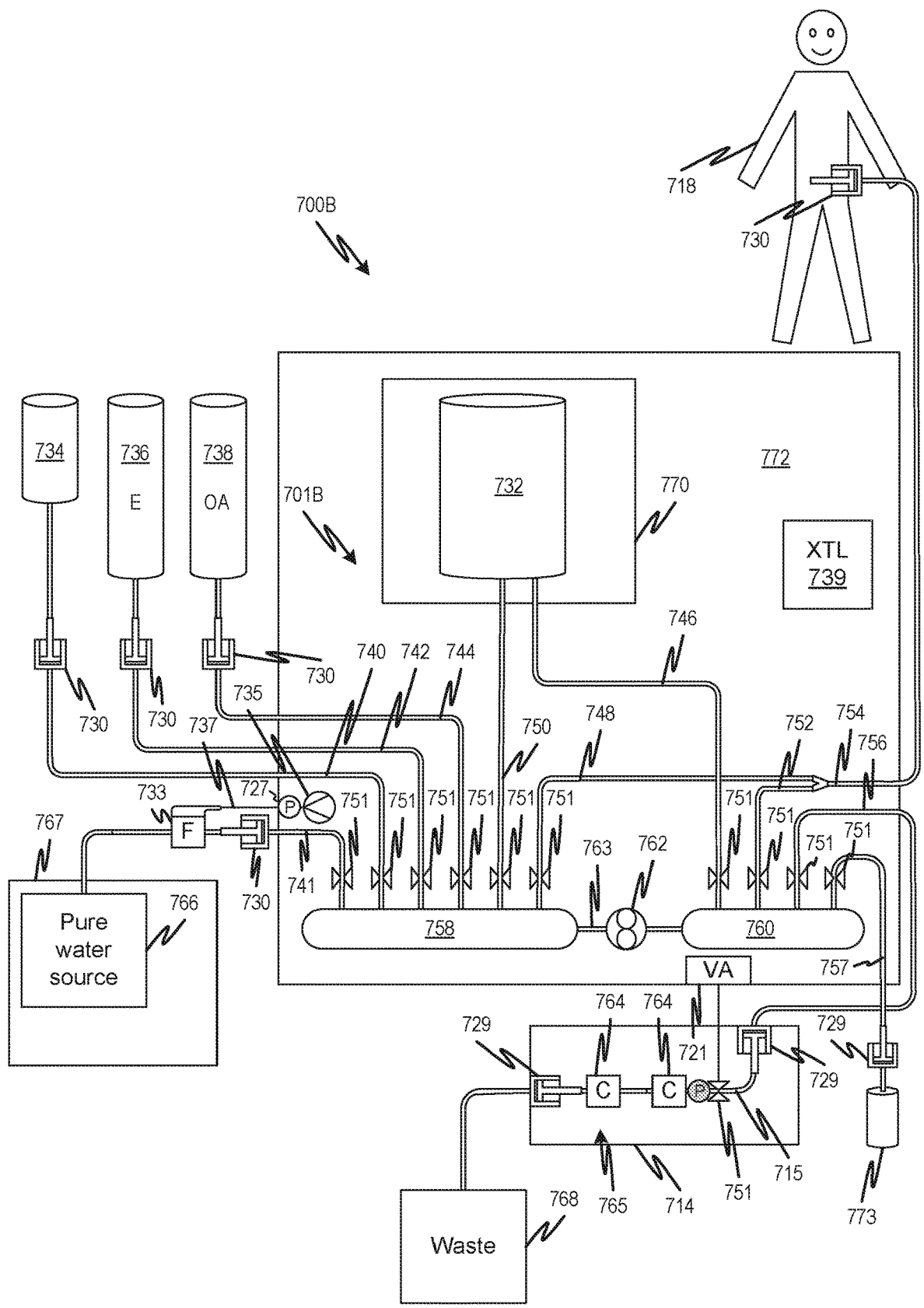

FIG. 17B shows a proportioning and treatment system for peritoneal dialysis 700B. Two multi-treatment containers 736 and 738 contain electrolyte concentrates and osmotic agent concentrates, respectively. They are connected by aseptic connectors 730 to a fluid circuit 701B by respective osmotic agent concentrate 744 and electrolyte concentrate 742 lines. Non-aseptic connectors may also be used. In embodiments where the connectors are non-aseptic, the osmotic agent concentrate 744 and electrolyte concentrate 742 lines contain sterilizing filters. Due to the cost and number of filters required this is not a preferred way to ensure sterility. A last fill container 734 may also be connected to the fluid circuit 701B via last fill line 740. The last fill container 734 may contain a specific medicament for the last fill cycle of a multi-cycle treatment. The fluid circuit 701B contains first 758 and second 760 manifolds connected by a pumping tube 763. The manifolds 758 and 760 define selectable fluid paths connecting various sources of fluids to fluid consumers using clamps 751 under control of a controller 739. The details of the flow switching may be as discussed above with respect to similar embodiments. A purified water source 766 supplies purified water to the manifold 758 through redundant sterilizing filters 731. The filter 733 is a single testable filter that is automatically tested by pumping air by means of an air pump through an air line 737 and measuring pressure, detecting whether the filter's bubble point has been exceeded, and if not, confirming the integrity of a filter membrane of the filter 733. Alternative filter integrity tests may also be provided such as a pressure decay test. The test of the filter 733 is used by the controller 739 to confirm that a batch is sterile as described in method embodiments in the present disclosure. Manifold 760 is connected by a drain line 756 to a conductivity sensor module 714 through a non-aseptic connector 729. The conductivity sensor module 714 is a replaceable component interconnectable between outlet manifold 760 and a waste container 768 (or a waste outlet such as a drain). The conductivity sensor module 714 has a pair of conductivity sensors 764 in a drain channel 715. The conductivity sensors 764 provide independent indications of conductivity that can be compared to indicate a bad sensor and/or to provide a mechanism for flow sensing based on a time of flight of a conductivity perturbation in the flow through the drain channel 715. The conductivity module 714 engages with the proportioning/cycler machine 772 which houses a valve actuator 721. The latter is not replaced when the conductivity module 714 is replaced. The conductivity module 714 can be a low cost component by employing plastic conductivity cells, a tube with connectors and a pinching portion defining a valve 751 by separating the valve actuator 721 (the one shown that controls flow through the drain channel 715) from the tube pinching portion and selecting a low cost arrangement for the conductivity cells 764, the tubing forming the drain channel 715, the connectors 729 and a housing or support indicated at 714.

A mixing container 732 is connected by inlet and outlet lines 746 and 750 to the manifolds 758 and 760, respectively to allow fluid to be pumped into the mixing container 732, to be drawn from the mixing container 732, and to permit mixing via recirculation of the contents of the mixing container 732. A pump 762 pumps fluid between the manifolds 758 and 760. A waste container 768 may be attachable to the drain line circuit 765 by a non-aseptic connector 729. A heater 770 contacts the mixing container 732. In embodiments, the heater 770 forms a bed on which the mixing container 732 rests. A patient line 754 is connected by a Y-connector to separate lines 748 and 752 to permit the filling and draining of a patient 718 through the patient line 754, which is connected to a catheter (not shown) by means of another aseptic connector 730.

In all embodiments, 17A through 17D and others, a sampling arrangement, now described, may be provided. Although not shown in FIG. 17A, a sample line may be provided stemming from header 760. Referring to the embodiment of FIG. 17D presently, the sample line 774 is connected to a sample container 773 through a non-aseptic connector 729. A valve 751 controlling flow through the sample line 757 is controlled to sample fluid from the header 760 automatically by the controller 739. In embodiments, a temperature of draining dialysis fluid is monitored for a condition indicating an infection or some other condition for which a sample may be automatically drawn and stored during draining according to the condition. See US Patent Publication US20150005699, incorporated by reference elsewhere herein and International Patent Publication WO2018045102, for details of how parameter monitoring of the spent dialysis fluid may be used to detect a condition.

In traditional peritoneal dialysis systems, all of the patient effluent is collected in a large sample bag which may contain, for example, 10 or more liters of fluid. In the present embodiments, small samples (less than the total amount of effluent, are routed to a small volume sample collection container. Thus, an aliquot from each patient drain cycle may be generated automatically in a small container (e.g., ~200 ml, for example, but it could be less or more). The collection container may be a bag. At the end of a treatment, the system controller may output instructions for removing, sealing, and delivering the collected sample. For example, the container may be delivered to the patient's dialysis center which would analyze it to assess the adequacy of therapy.

According to a method, the following control scheme may be implemented by the proportioner/cycler controller 739. The controller 739 first initiates a drain cycle of a predefined number of drain cycles of an entire treatment. A command indicating the aliquot volume or mass may be generated and used to control the pump 762 of the proportioner/cycler. A command may also be generated to indicate an initial volume or mass to pass to waste container or drain 768 before beginning a diversion of the drain flow while metering the size of the cumulating sample and then switching valves 751 to a configuration where the spent peritoneal dialysis fluid is sent to waste container or drain 768. The sequence may be implemented using valves 751 and pump 762. The process of switching between patient line 754 to waste container or drain 768 and patient line to sample container 773 may include halting the pump while the relevant valves 751 are activated and deactivated to define the correct flow path. The volume that is drained before the aliquot is transferred to the sample container 773 may be determined by how long it takes to clear any residual fluid (fresh peritoneal dialysis fluid, for example) in MIMO. In embodiments, the sample container 773 may be changed at each drain cycle in order to collect samples representative of multiple cycles of a single treatment. The controller may also permit sampling to be done in a manner that acquires multiple fractions throughout the drain cycle to be stored in the sample container 773 by repeatedly, over multiple instances, diverting to drain and diverting to the sample container 773. This may allow for the sample to better represent the composition of the entire drain volume which may change through the drain cycle. These fractional samples can also be stored in separate sample containers 773. Parameters of collection, which may be set by the patient, nurse, or physician accessing the controller 739 locally or remotely, include:

- The volume of the sample;
- Spacing of samples (for example 1 spacing would be a sample for each drain cycle and 2 spacing would refer to every other drain cycle);
- For spaced samples, the first drain cycle to start sampling;
- The volume to be discarded before beginning the diversion to the sample container 773;
- The days on which to take one or more samples and according to a predefined cluster of the listed parameters;
- A permitted number of reschedulings of samplings;
- A schedule of samplings by date, day of week, day of month, or number of times per time interval;
- The number of samples per drain cycle;
- The number of samples per treatment; and
- The flow rate of draining.

The controller 739 may store a specific schedule for the taking of samples, for example a particular day of the week. The controller 739 may output a reminder for the benefit of an operator or patient to let that person know of an imminent scheduled sample so that the user can prepare. For example, the system may let the patient know that today is a day to take a sample. The notification can be attended, or followed, by an input control that accepts input indicating whether the patient desires to override, comply, or reschedule. The controller 739 may reschedule automatically in the event the patient or other user fails to acquire samples or overrides. The controller 739 may store a guided instruction script for helping the user to set up and store samples after acquisition. The guided instruction may be stored on a web server and displayed on the proportioner/cycler through a browser so that the script can be updated centrally. The guided instruction may be prompted upon entry of a user command indicating that the user will perform a scheduled or unscheduled sampling procedure.

Figure 26A:
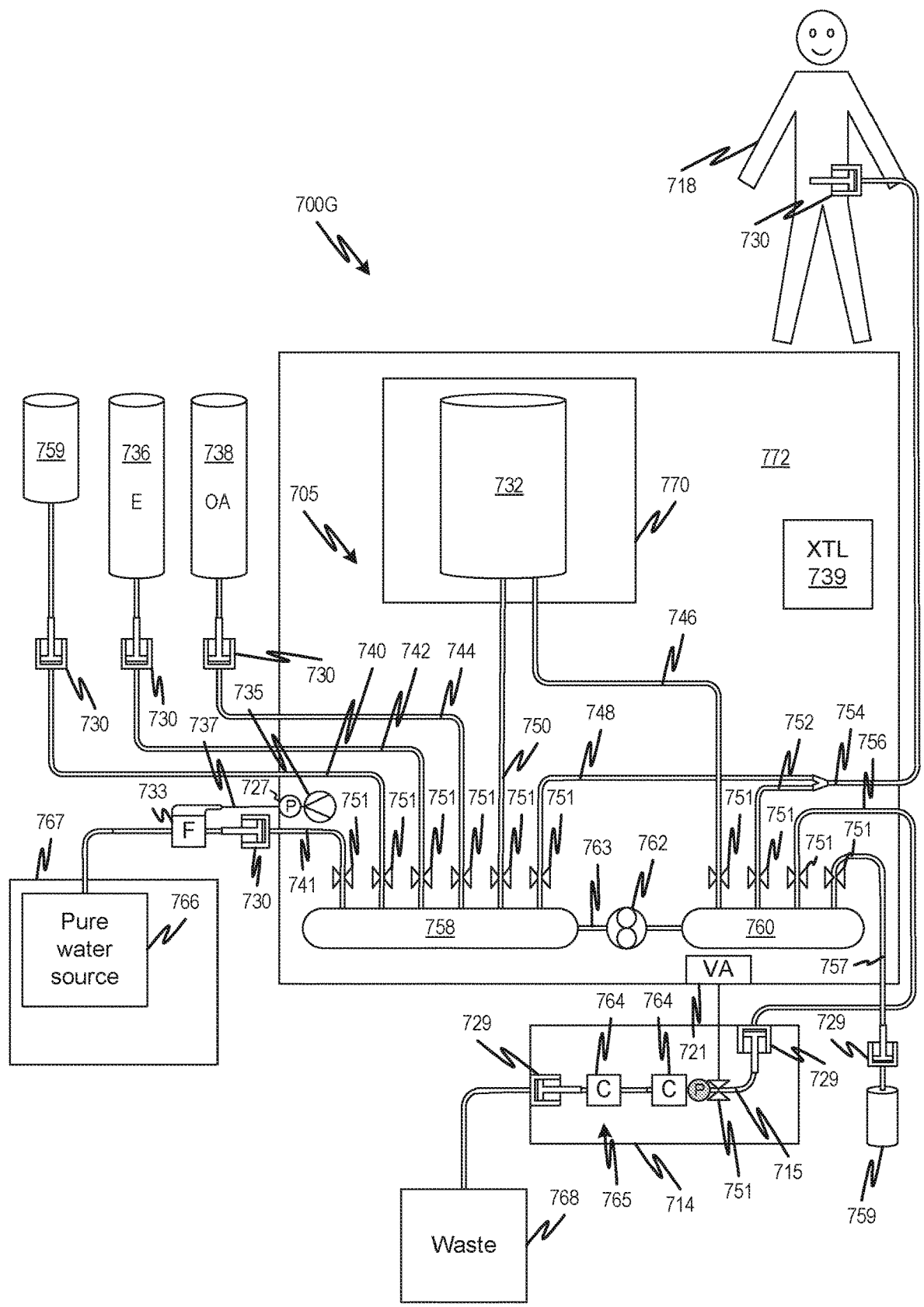
FIGS. 26A through 26C illustrate a system and method for using a proportioning system to infuse a medicament with a drug or other substance.

Referring now to FIG. 26A, an proportioning and treatment system for peritoneal dialysis 700G has a fluid circuit 705 that is identical to 701B except for the connection of a medication container 759 at port 730 or port 729. Connections at both are shown but it should be understood that it may be that only one may be connected at a given time and the ports 730 and 729 may otherwise be used for the purpose described above. Medication container 759 may contain a medication (e.g., antibiotics), an anticoagulant, or other substance to be mixed with peritoneal dialysis fluid. The substance may be mixed with the contents of the mixing container 732 in an automated way.

Figure 26B:
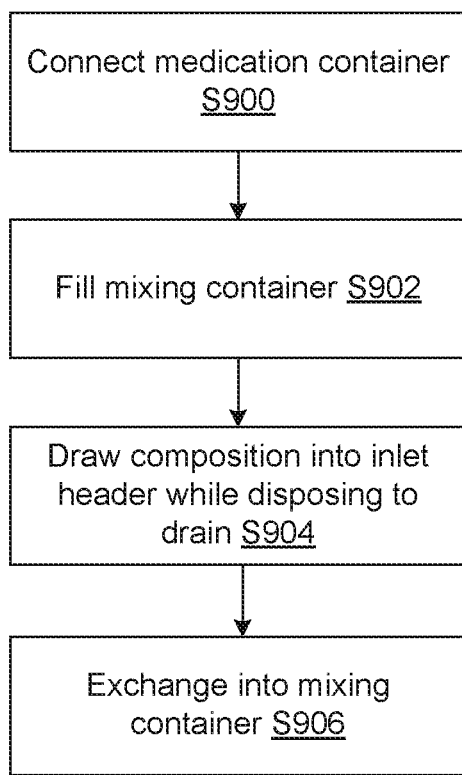

Referring to FIG. 26B, at S900 the substance container 759 is connected to the first manifold 758. Then at S902 the mixing container 732 is filled by preparing a dialysis fluid. Then at S904 the valve 751 is opened and the pump operated to draw the substance from substance container 759 into the mixing container 732. Then at S906, the pump recirculates the contents of the mixing container 732 in a recirculating mixing mode to mix the substance with the dialysis fluid.

Figure 26C:
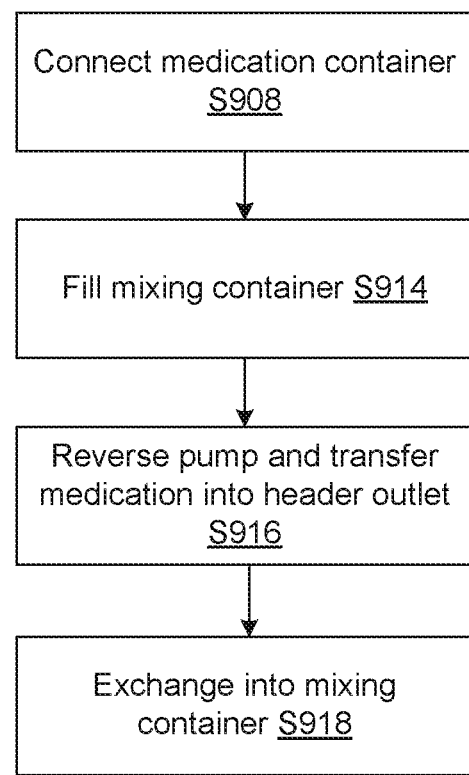

Referring to FIG. 26C, at S908 the substance container 759 is connected to the second manifold 760. Then at S914 the mixing container 732 is filled by preparing a dialysis fluid. Then at S916 the valve 751 is opened and the pump operated in reverse to draw the substance from substance container 759 into the mixing container 732. Then at S918, the pump recirculates the contents of the mixing container 732 in a recirculating mixing mode to mix the substance with the dialysis fluid.

Figure 23:
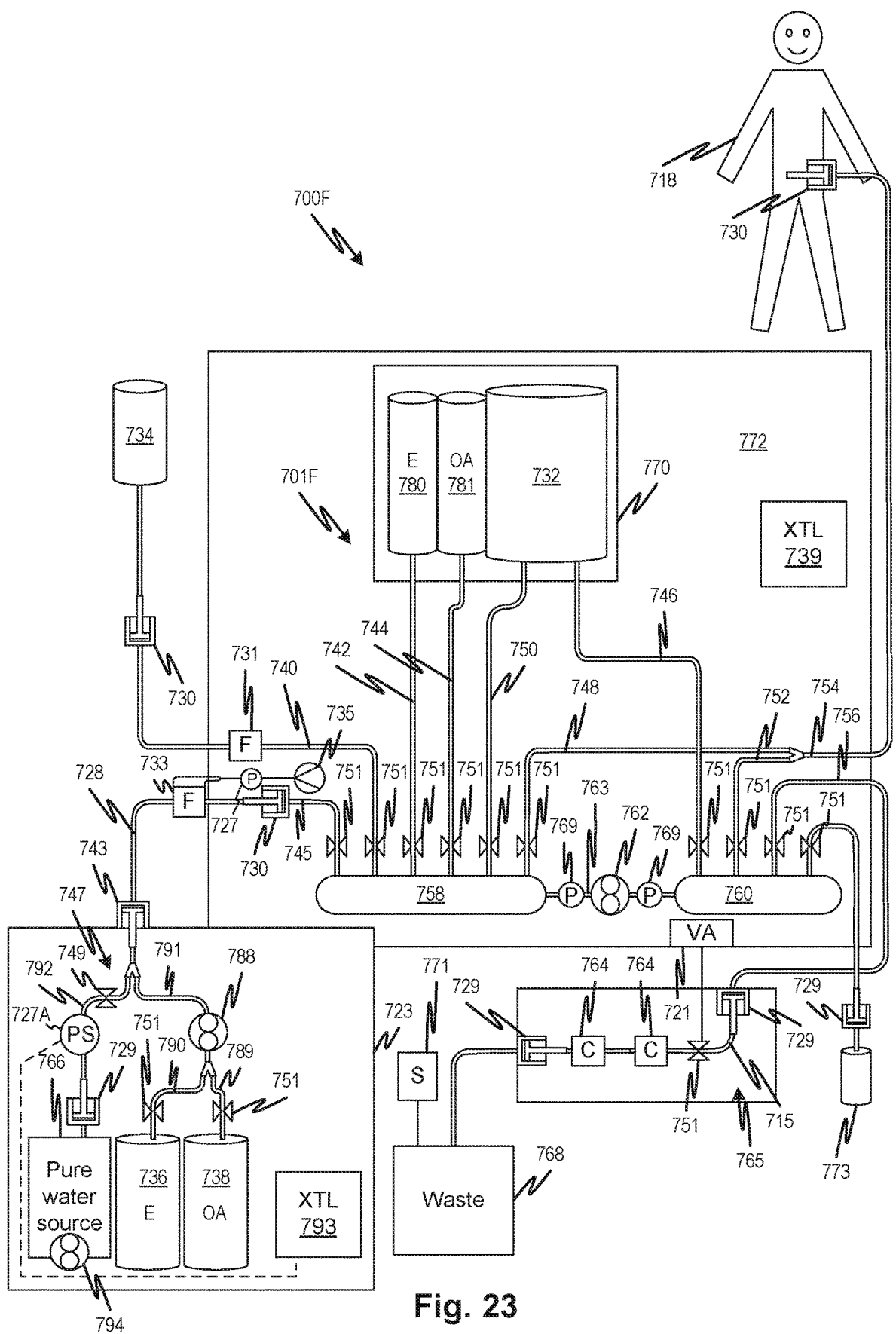
FIG. 23 shows an embodiment of a proportioning and treatment system in which sampling of spent dialysate is supplemented by a mechanism to allow for the sampling and testing of spent dialysate aliquots rather than a full treatment volume of spent dialysate.

Referring to FIG. 23, in embodiments, the drain is replaced by a container connected to a scale 771 that generates a weight indication that is stored by the controller 739. This total weight can be combined with a detected measure of the volume captured in the same container 773 to provide a cumulative total mass of collected peritoneal dialysis fluid. For example, the total mass can be taken as an average of the mass calculated from weight and the mass calculated from volumetric measurement. These data may be associated by a code with a code read from the sample container 773 such as by means of a bar code, smart chip, RFID tag, or other means. The data indicative of cumulative total mass estimate may be uploaded to a web site for a laboratory with data representing the sample container 773 code. Alternatively, a chip attached to the sample container 773 may hold the cumulative mass data so that when shipped to a laboratory, the data can be read by the workers analyzing the samples. In embodiments, the sample container 773 and the waste container 768 can be attached to the scale 771 or may be formed as a single disposable unit with the sample bag portion being detachable from the waste container 768.

The fluid circuit 701F connects to proportioning/cycler machine 772 by a mechanism that aligns clamps 751 with respective clamping portions of lines 741, 740, 742, 744, 750, 746, 752, and 756. Various such mechanisms are known in the art such as supports that hold tubing portions at predefined positions in cassettes and cartridges and compact fluid circuits that can be easily laid over a set of actuators and sensors. The manifolds and clamps can be replaced by a variety of different types of flow selector devices known in the art, so the current proportioning and treatment system is not limited to using flow selectors based on clamping of tubing. If the pump 762 is a peristaltic pump, a pumping tube segment of line 763 may be aligned by the connection of the fluid circuit 701F. The purified water source 766 may be housed in an enclosure 767 together with the drain line circuit 765 or portions of either. The waste container 768 may be housed in the same enclosure, or not, as illustrated. The concentrate containers 736 and 738 may contain sufficient concentrate for multiple fill/drain cycles, multiple days' worth of treatments, each consisting of multiple fill/drain cycles, a week's worth of treatments, a month's worth of treatments, or some other schedule. The concentrate containers 736 and 738 may be independently replaceable by use of the aseptic connectors. The benefits of independent replacement are discussed elsewhere in the present disclosure. The contents of the last fill medicament container 734 may be fully diluted or may consist of, or include, a concentrate that requires further dilution. The manifolds 758 and 760 may have a minimum volume to reduce waste when changing over fluids. In embodiments, the maximum hydraulic diameters of the manifolds 758 and 760 are each no more than 5 times the diameter of the largest line connecting to them. In further embodiments, they are no more than 3 times the diameter of the largest line and in still further embodiments, no more than twice. In other respects, the embodiment of FIG. 23 is identical to that of FIG. 18A.

Figure 17C:
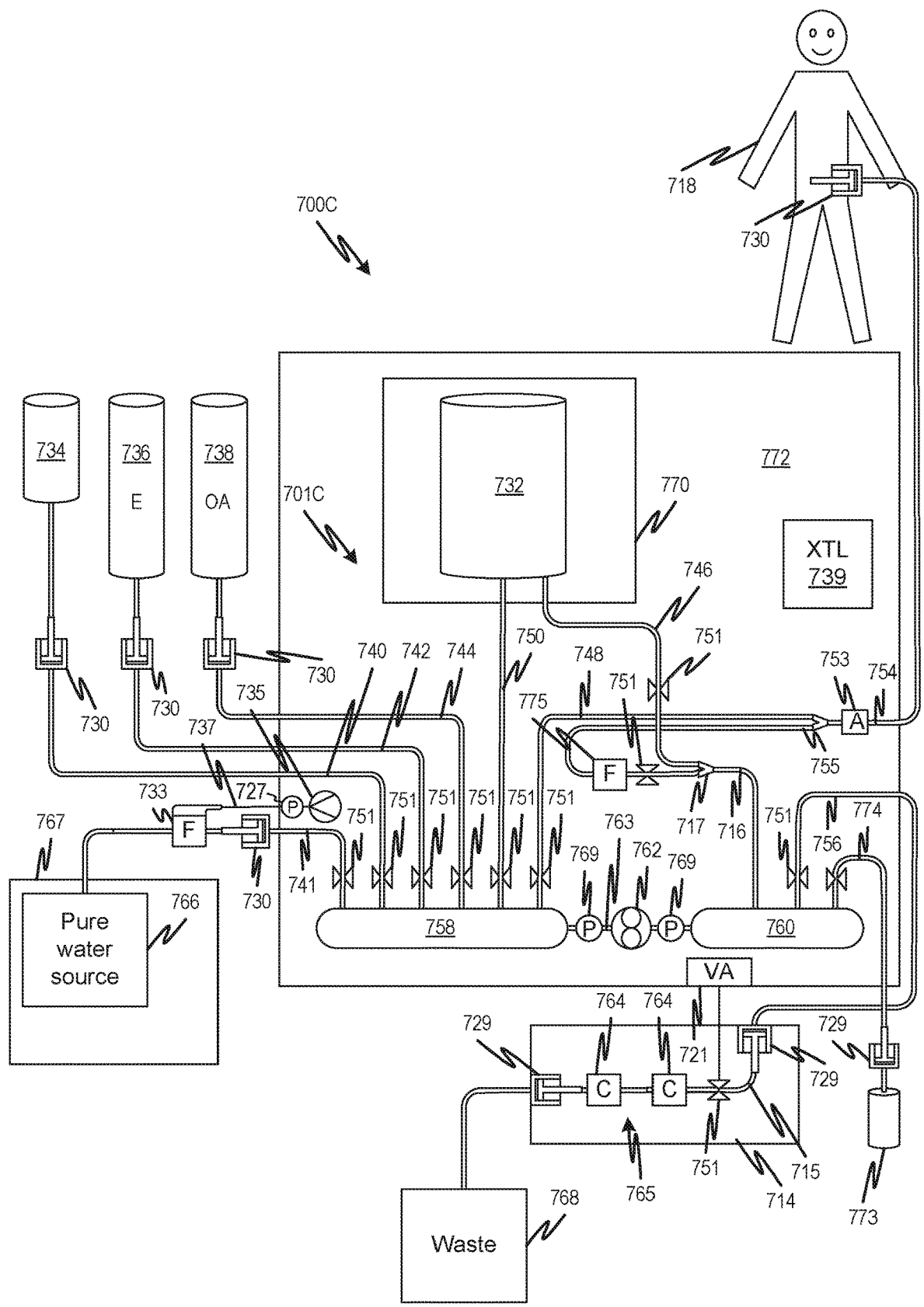
Figure 17D:
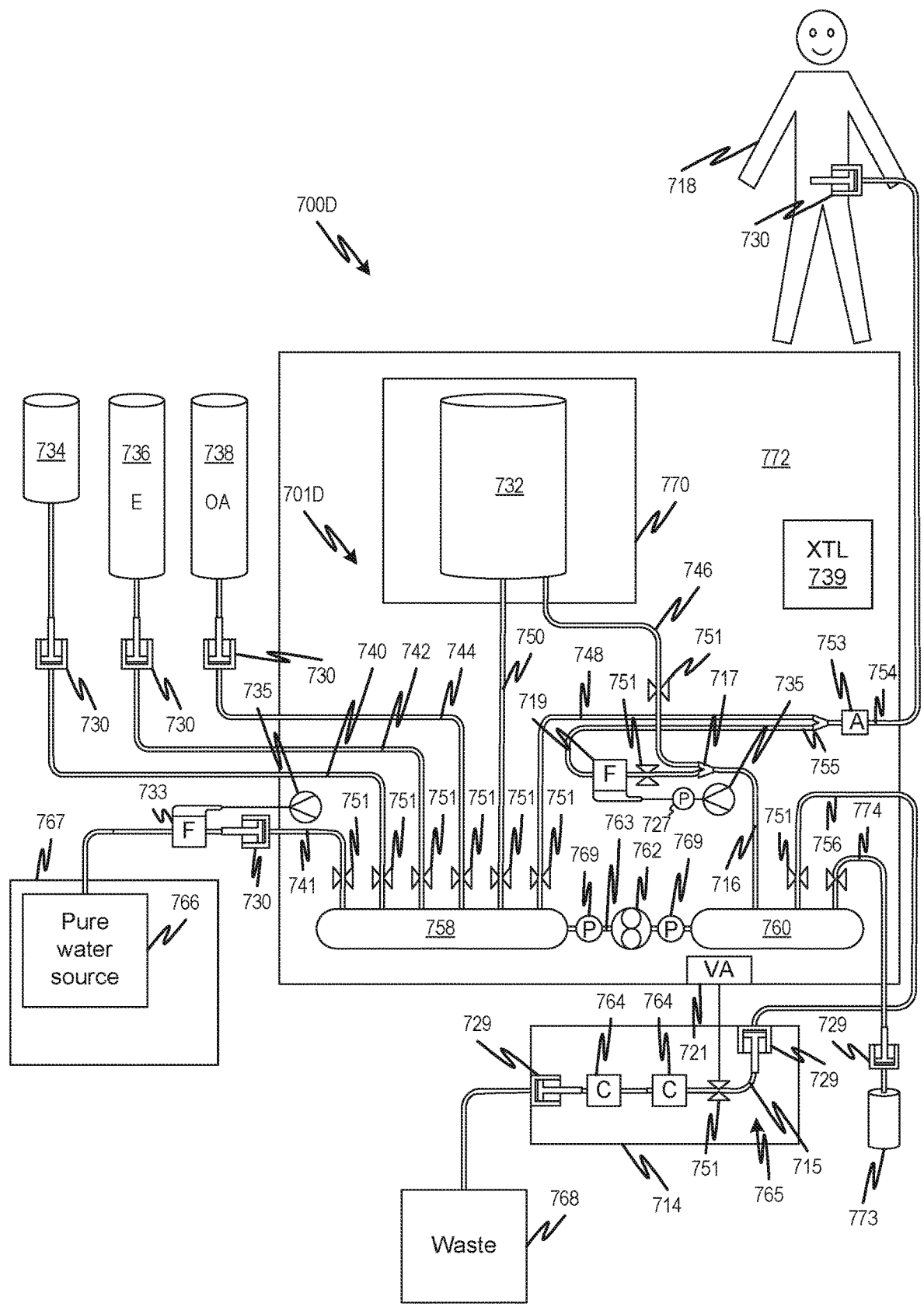

FIG. 17C shows an proportioning and treatment system for peritoneal dialysis 700C. Two multi-treatment containers 736 and 738 contain electrolyte concentrates and osmotic agent concentrates, respectively. They are connected by aseptic connectors 730 to a fluid circuit 701C by respective osmotic agent concentrate 744 and electrolyte concentrate 742 lines. Non-aseptic connectors may also be used. In embodiments, where the connectors are non-aseptic, the osmotic agent concentrate 744 and electrolyte concentrate 742 lines contain sterilizing filters. Due to the cost and number of filters required this is not a preferred way to ensure sterility. A last fill container 734 may also be connected to the fluid circuit 701C via last fill line 740. The last fill container 734 may contain a specific medicament for the last fill cycle of a multi-cycle treatment. The fluid circuit 701E contains first 758 and second 760 manifolds connected by a pumping tube 763. The manifolds 758 and 760 define selectable fluid paths connecting various sources of fluids to fluid consumers using clamps 751 under control of a controller 739. The details of the flow switching may be as discussed above with respect to similar embodiments. A purified water source 766 supplies purified water to the manifold 758 through redundant sterilizing filters as shown FIG. 17A at 731, or a testable filter may be used as shown in FIG. 17C. The filter 733 is a single testable filter that is automatically tested by pumping air by means of an air pump through an air line 737 and measuring pressure, detecting whether the filter's bubble point has been exceeded, and if not, confirming the integrity of a filter membrane of the filter 733. Alternative filter integrity tests may also be provided such as a pressure decay test. The test of the filter 733 is used by the controller 739 to confirm that a batch is sterile as described in method embodiments in the present disclosure Manifold 760 is connected by a drain line 756 to a conductivity sensor module 714 through a non-aseptic connector 729. The conductivity sensor module 714 is a replaceable component interconnectable between outlet manifold 760 and a waste container 768 (or a waste outlet such as a drain). The conductivity sensor module 714 has a pair of conductivity sensors 764 in a drain channel 715. The conductivity sensors 764 provide independent indications of conductivity that can be compared to indicate a bad sensor and/or to provide a mechanism for flow sensing based on a time of flight of a conductivity perturbation in the flow through the drain channel 715. The conductivity module 714 engages with the proportioning/cycler machine 772 which houses a valve actuator 721. The latter is not replaced when the conductivity module 714 is replaced. The conductivity module 714 can be a low-cost component by employing plastic conductivity cells, a tube with connectors and a pinching portion defining a valve 751 by separating the valve actuator 721 (the one shown that controls flow through the drain channel 715) from the tube pinching portion and employing injection-molded rigid plastic for the conductivity cells 764, tubing to define the drain channel 715, aseptic connectors 729 such as locking luer-type, and a housing or support indicated at 714.

A mixing container 732 is connected by inlet and outlet lines 746 and 750 to the manifolds 758 and 760, respectively, to allow fluid to be pumped into the mixing container 732, to be drawn from the mixing container 732, and to permit mixing via recirculation of the contents of the mixing container 732. A pump 762 pumps fluid between the manifolds 758 and 760. A waste container 768 may be attachable to the drain line circuit 756 by a non-aseptic connector 729. A heater 770 contacts the mixing container 732. In embodiments, the heater 770 forms a bed on which the mixing container 732 rests.

A patient line 754 is connected to the fluid circuit in such a manner as to ensure that fluid sent to the patient through fill line 755 is sterile filtered by sterilizing filter 719, thereby providing a sole, or additional, assurance against exposure of the patient to unsterile fluid including fluids or fluids containing pyrogens, which, as is known, may be removed by filter membranes with a suitably small pore diameter, for example, 0.2 micron.

A patient fill/drain line 754 has an air detector 753. Fluid is received through a junction from a fill line 755 and drained through drain line 748, flow being controlled in each of the fill line 755 and the drain line 748 by respective valves 751. Fluid is supplied to a batch inlet line 746 and the fill line 755 from header 760 through a common batch/fill line 716 from a respective junction 717. The selection of the two branches of the junction, namely the batch inlet line 746 and the fill line 752 is carried out by respective valves 751 that control flow through these branches. A sterile/pyrogen filter 733 filters all fluid flowing to the patient by filtering all fluid flowing through the fill line 752. This may obviate the need for any other filters on fluid entering the system such as water inlet 741 using filter 733 on the patient fill line. A common fill/inlet line 716 feeds the inlet 746 and fill 755 lines. The line 755 which conveys fluid to the patient 718 has a testable sterile filter 719. Flow through lines 746 and 755 is controlled by respective valves 751.

The controller 739 may invoke a failsafe operation if air is detected above a predefined threshold in the fill drain/line 754. Flow in inlet line 746 is controlled with the additional function that the valve 751 controlling flow in the fill line 755 is closed when fluid is directed to the mixing container 732.

The fluid circuit 701C connects to proportioning/cycler machine 772 by a mechanism that align clamps 751 with respective clamping portions of lines 741, 740, 742, 744, 750, 746, 752, 755, and 756. Various such mechanisms are known in the art such as supports that hold tubing portions at predefined positions in cassettes and cartridges and compact fluid circuits that can be easily laid over a set of actuators and sensors. The manifolds and clamps can be replaced by a variety of different types of flow selector device known in the art, so the current proportioning and treatment system is not limited to using flow selectors based on clamping of tubing. If the pump 762 is a peristaltic pump, a pumping tube segment of line 763 may be aligned by the connection of the fluid circuit 701C. The purified water source 766 may be housed in an enclosure 767 together with the drain line circuit 765 or portions of either. The waste container 768 may be housed in the same enclosure, or not, as illustrated. The concentrate containers 736 and 738 may contain sufficient concentrate for multiple fill/drain cycles, multiple days' worth of treatments, each consisting of multiple fill/drain cycles, a week's worth of treatments, a month's worth of treatments, or some other schedule. The concentrate containers 736 and 738 may be independently replaceable by use of the aseptic connectors. The benefits of independent replacement are discussed elsewhere in the present disclosure. The contents of the last fill medicament container 734 may be fully diluted or may consist of, or include, a concentrate that requires further dilution. The manifolds 758 and 760 may have a minimum volume to reduce waste when changing over fluids. In embodiments, the maximum hydraulic diameters of the manifolds 758 and 760 are each no more than 5 times the diameter of the largest line connecting to them. In further embodiments, they are no more than 3 times the diameter of the largest line and in still further embodiments, no more than twice. Pressure sensors 769 are positioned on either side of the pump 762 to detect pump inlet and outlet pressures in pump tube 763. Signals corresponding to the pressures are applied to the controller 739 and used for pump pressure compensation and/or pump calibration as discussed elsewhere and in US Patent Publication 2015-0005699, hereby incorporated by reference in its entirety herein.

FIG. 17D shows an proportioning and treatment system for peritoneal dialysis 700D with a fluid circuit 701D. The system 700D differs from 700C in that a testable sterilizing filter 719 is used for the fill line 755 to ensure against infusion of pyrogens and/or pathogens.

Note that instead of separate inlet 746 and outlet 750 lines leading into and out of the mixing container 732, the mixing container 732 may be attached by a single line. In such a case, mixing of the contents may be accomplished by flowing fluid between the mixing container 732 and an accumulator connected to one of the manifolds. A flow switch could be used to interconnect the single line of the mixing container to a selectable one of the manifolds. Also, the pump 762 may be run in either direction so that the inlet and outlet lines 746 and 750 can switch roles under control of the controller. Thus, the modifiers "inlet" and "outlet" serve to differentiate the two lines 746 and 750 but are not strictly limiting in terms of structure or function and it should be evident that the functionality of batch preparation, mixing, and treatment can be carried out with the roles of inlet and outlet switched during certain operations. For other operations, the manifolds may be modified to permit a different fluid source and destination to be selected that is not possible with the depicted configuration. Such variations are contemplated within the scope of the disclosure unless otherwise expressly limited.

Figure 18A:
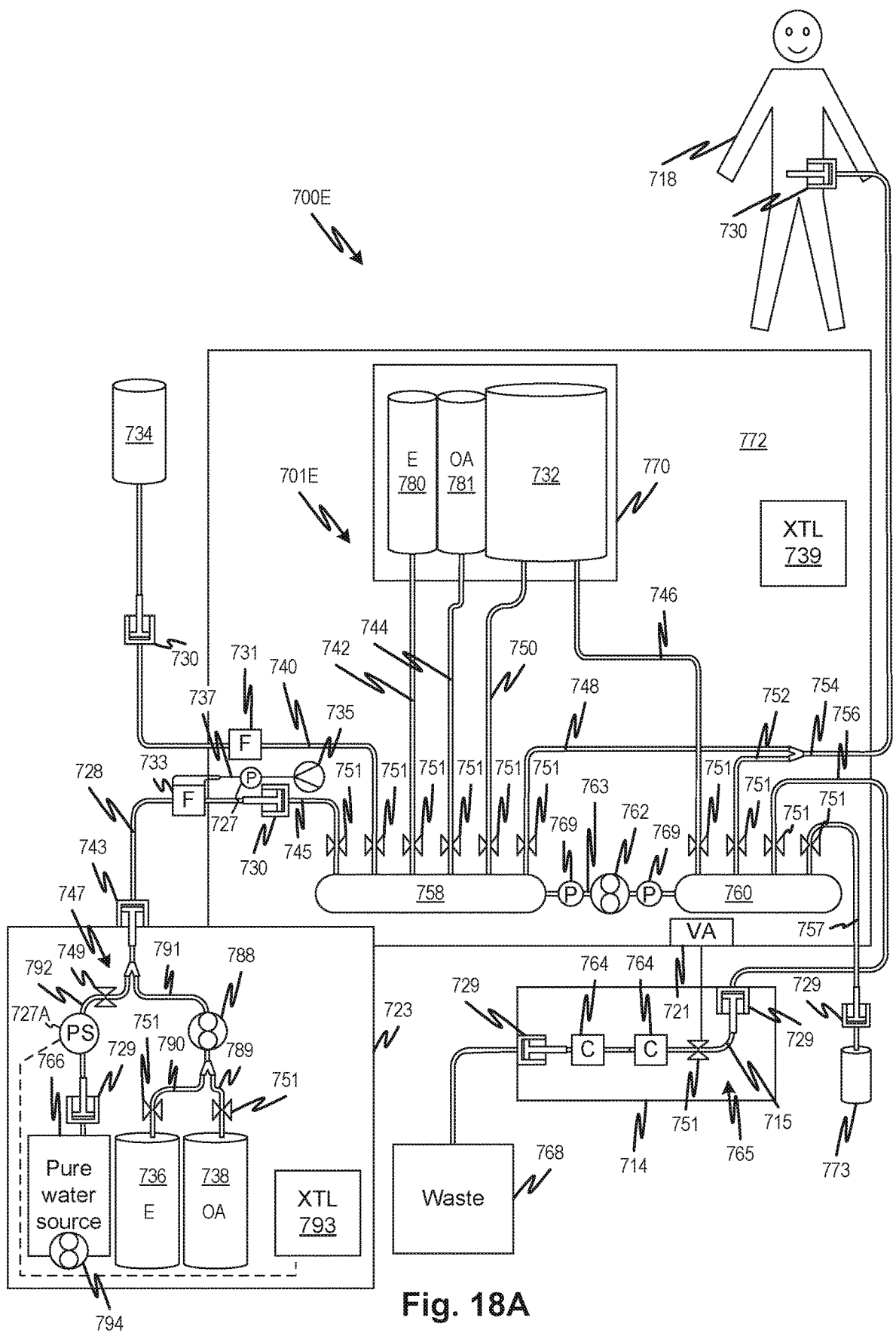
FIG. 18A shows an embodiment of a proportioning/treatment system in which long-term, multi-treatment containers of concentrate are used to fill a disposable used during a treatment to form a ready-to-use peritoneal dialysis fluid according to embodiments of the disclosed subject matter.

FIG. 18A shows a fluid circuit 701E having a disposable unit that is initially provided with empty, low-capacity concentrate containers 780 and 781 which are filled from multi-treatment concentrate containers 736 and 738 during a dialysis fluid preparation cycle. A proportioning and treatment system for peritoneal dialysis 700E has two multi-treatment concentrate containers 736 and 738 that contain electrolyte concentrates and osmotic agent concentrates, respectively. The multi-treatment concentrate containers 736 and 738 are connected through a fluid module 723 by means of a single fluid intake line 728 which has a testable filter 733 that forms part of a disposable with a fluid circuit 701E. The disposable unit is connected through the fluid intake line 728 by an aseptic connector 743 (same type as 729) to the fluid module 723. The fluid module 723 may be a permanent structure that receives multi-treatment concentrate containers 736 and 738 as a replaceable unit or as separate containers according to various embodiments. The fluid module 723 may also have a pump 788 and a purified water source 766 as well as a fluid switch circuit 747 that provides for the selective flow of water and the different concentrates into the fluid intake line 728.

The testable filter 733 may be preconnected to the fluid circuit 701E and sterilized with the remainder of the fluid circuit 701E as a unit which may be sealed in a sterile package and delivered for use. An air pump 735 and pressure sensor 727 may be provided as a permanent fixture of the proportioning/cycler machine 772.

The initially empty low-capacity concentrate containers 780 and 781 are preconnected along with the initially empty mixing container 732 to the remainder of the fluid circuit 701E. The low-capacity concentrate containers 780 and 781 may be filled, as discussed later, with osmotic agent concentrate and electrolyte concentrate from multi-treatment concentrate containers 736 and 738, respectively. A last fill container 734 may also be connected by an aseptic connector 730 to the fluid circuit 701E via last fill line 740. The last fill container 734 may contain a specific medicament for the last fill cycle of a multi-cycle treatment. The contents of the last fill medicament container 734 may be fully diluted or may consist of, or include, a concentrate that requires further dilution.

The fluid circuit 701E contains first 758 and second 760 manifolds connected by a pumping tube 763. The manifolds 758 and 760 define selectable fluid paths connecting various sources of fluids to fluid consumers using clamps 751 under control of a controller 739. The details of the flow switching may be as discussed above with respect to similar embodiments. The manifolds 758 and 760 may have a minimum volume to reduce waste when changing over fluids. In embodiments, the maximum hydraulic diameters of the manifolds 758 and 760 are each no more than 5 times the diameter of the largest line connecting to them. In further embodiments, they are no more than 3 times the diameter of the largest line and in still further embodiments, no more than twice. Pressure sensors 769 are positioned on either side of the pump 762 to detect pump inlet and outlet pressures in pump tube 763. Signals corresponding to the pressures are applied to the controller 739 and used for pump pressure compensation and/or pump calibration as discussed elsewhere and in US Patent Publication 2015-0005699, hereby incorporated by reference in its entirety herein. A waste container 768 may be attachable to the drain line circuit 765 by a non-aseptic connector 729.

The filter 733 is a single testable filter that is automatically tested by pumping air by means of an air pump 735 through an air line 737 and measuring pressure by means of pressure sensor 727, detecting whether the filter's bubble point has been exceeded, and if not, confirming the integrity of a filter membrane of the filter 733. Alternative filter integrity tests may also be provided such as a pressure decay test. The test of the filter 733 is used by the controller 739 to confirm that a batch is sterile as described in method embodiments in the present disclosure.

Manifold 760 is connected by a drain line 756 to a conductivity sensor module 714 through a non-aseptic connector 729. The conductivity sensor module 714 is a replaceable component interconnectable between the outlet manifold 760 and a waste container 768 (or a waste outlet such as a drain). The conductivity sensor module 714 has a pair of conductivity sensors 764 in a drain channel 715. The conductivity sensors 764 provide independent indications of conductivity that can be compared to indicate a bad sensor and/or to provide a mechanism for flow sensing based on a time of flight of a conductivity perturbation in the flow through the drain channel 715. The conductivity module 714 engages with the proportioning/cycler machine 772 which houses a valve actuator 721. The latter is not replaced when the conductivity module 714 is replaced. The conductivity module 714 can be a low-cost component by employing plastic conductivity cells, a tube with connectors and a pinching portion defining a valve 751 by separating the valve actuator 721 (the one shown that controls flow through the drain channel 715) from the tube pinching portion and selecting a low cost arrangement for the conductivity cells 764, the tubing forming the drain channel 715, the connectors 729, and a housing or support indicated at 714.

A mixing container 732 is connected by inlet and outlet lines 746 and 750 to the manifolds 758 and 760, respectively, to allow fluid to be pumped into the mixing container 732, to be drawn from the mixing container 732, and to permit mixing via recirculation of the contents of the mixing container 732. A pump 762 pumps fluid between the manifolds 758 and 760. A waste container 768 may be attachable to the drain line circuit 765 by a non-aseptic connector 729. A heater 770 contacts the mixing container 732. In embodiments, the heater 770 has a bed on which the mixing container 732, in the form of a plastic bag, rests. A patient line 754 is connected by a Y-connector to separate lines 748 and 752 to permit the filling and draining of a patient 718 through the patient line 754, which is connected to a catheter (not shown) by means of another aseptic connector 730. A sample line 757 is connected to a sample container 773 through a non-aseptic connector 729, or may be pre-attached. A valve 751 controlling flow through the sample line 757 is controlled to sample fluid from the header 760 automatically by the controller 739. In embodiments, a temperature of draining dialysis fluid is monitored for a condition indicating an infection or some other condition for which a sample may be automatically drawn and stored during draining according to the condition. See US 2015-0005699, incorporated by reference elsewhere herein and International patent publication WO2018045102, hereby incorporated by reference in its entirety for details of how parameter monitoring of the spent dialysis fluid may be used to detect a condition.

The fluid circuit 701E connects to proportioning/cycler machine 772 by a mechanism that align clamps 751 with respective clamping portions of lines 741, 740, 742, 744, 750, 746, 752, and 756. Various such mechanisms are known in the art such as supports that hold tubing portions at predefined positions in cassettes and cartridges and compact fluid circuits that can be easily laid over a set of actuators and sensors. The manifolds and clamps can be replaced by a variety of different types of flow selector devices known in the art, so the current proportioning and treatment system is not limited to using flow selectors based on clamping of tubing. If the pump 762 is a peristaltic pump, a pumping tube segment of line 763 may be aligned by the connection of the fluid circuit 701B.

The concentrate containers 736 and 738 may contain sufficient concentrate for multiple fill/drain cycles, multiple days' worth of treatments, each treatment consisting of multiple fill/drain cycles. For example, concentrate containers 736 and 738 may contain sufficient concentrate a week's worth of treatments, a month's worth of treatments, or some other schedule. The concentrate containers 736 and 738 may be independently replaceable by use of the aseptic connectors. The benefits of independent replacement are discussed elsewhere in the present disclosure. The pump 788 draws and pumps a concentrate selected by valves that control flow through electrolyte concentrate line 790 and osmotic agent concentrate line 789, respectively. The output of the pump 788 is pumped through a common concentrate line 791 through the connector 743 into the fluid intake line 728. When water is conveyed through the fluid intake line, it is pumped by the pump 762 with corresponding valves opened as in prior embodiments by closing the valves 751 that control flow through electrolyte concentrate line 790 and osmotic agent concentrate line 789, respectively, and by opening the valve 751 that controls the flow through a water source line 792. A pressure sensor 727 may be provided in the water source line 792 to control the flow of water as described with reference to FIGS. 19A through 19M.

Note that in all the embodiments having a water source such as 766, the latter may be provided with a pump 794 that pumps water independently of the pump of a downstream proportioning device and/or cycler such as pump 762.

Figure 18C:
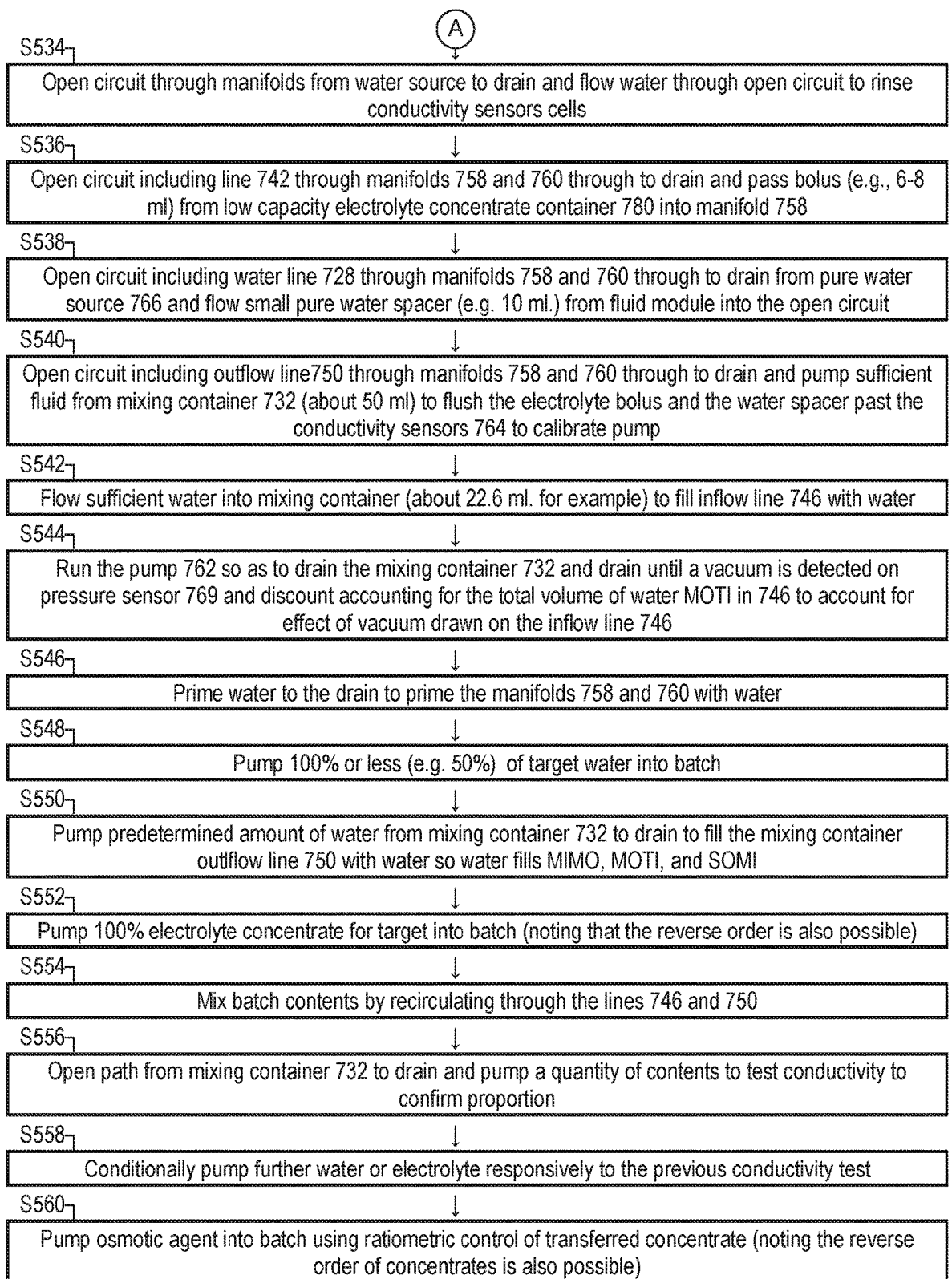
Figure 18D:
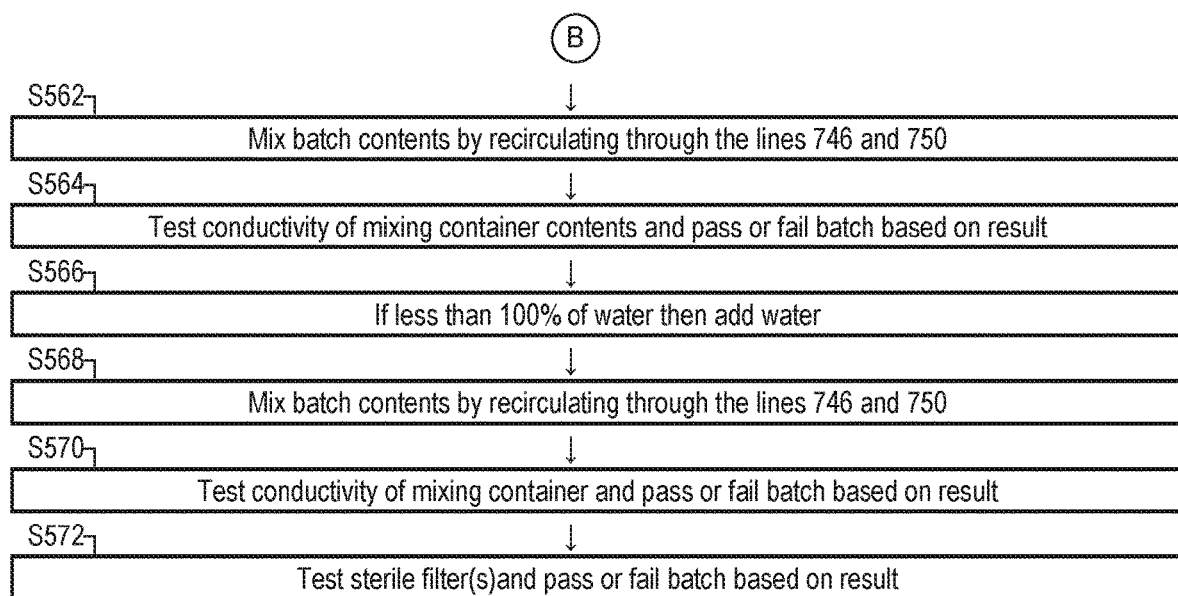

FIGS. 18B through 18D are a single flow chart illustrating a method embodiment for controlling the embodiment of FIG. 18A. The chart portion of FIG. 18B is linked at the end to the beginning of the flow chart of FIG. 18C as indicated by the letter A in a circle. The chart portion of FIG. 18C is linked at the end to the beginning of the flow chart of FIG. 18D as indicated by the letter B in a circle. At S502, the pump 762 is used to pump water from the fluid source module 723 to the drain to prime the fluid circuit manifolds 758 and 760 as well as the lines leading from the fluid source module 723 to the waste container or drain 768. The controller 739 stores a predefined value to indicate how much water to pump at this stage. For example, the controller 739 may store a predefined number of cycles of the pump 762 or a predefined volume. The controller 739 may be programmed to translate the predefined volume to a predefined number of cycles to implement a control procedure to regulate the volume transferred responsively to the predefined volume. Alternatively, the controller 739 may store a predetermined speed and interval of operation that corresponds to the predefined volume. Other alternatives are possible. In the operation S502, only the valves 751 required to open the specified path are opened and the others are closed to restrict flow to the predefined path. This is the case for all the operations described by the flow chart.

At S503, an optional operation is performed in which a sample of each concentrate is pumped to the drain to generate a pressure drop across the filter 733 and to use the pressure drop to identify the type of concentrate solution by its viscosity. For example, the osmotic agent concentrate is more viscous than the electrolyte concentrate, and therefore the pressure drop for a given flow rate will be higher. The pressure drop may be indicated by a single downstream pressure by the pressure sensor 769 since the upstream pressure may be assumed to be sufficiently identical between the two test conditions to indicate a difference. Thus, a lower pressure at sensor 769 would indicate the more viscous fluid. The controller 739 may store the identity of the type of concentrate associated with lines 789 and 790 and control the corresponding valves 751 accordingly. Alternatively, if one type of concentrate is required to be connected to a respective connector, then the controller 739 may identify a misconnection and generate an output from the controller indicating the misconnection so that corrective action can be taken.

At S504, the valves 751 are opened to define a path from the water source 766 to the waste container or drain 768. Water is pumped by the pump 794 in tandem with the pump 762 to flush the path with water. Optionally, the conductivity of the fluid passing by conductivity sensors 764 may be detected to serve as an indication that sufficient water has been flushed to prime and clear the flow path. Alternatively, another criterion may be used to stop the flow of water, such as a predetermined volume of water being flushed.

At S505, a quantity of electrolyte concentrate sufficient to prime the lines from the electrolyte concentrate container 736 through the manifold 758 and at least partly into the outflow line 750 is pumped by pump 788. This process may prime the sterilizing filter 733. The total quantity may be selected to be sufficient to ensure that the sterilizing filter 733 is primed and flushed of any air. This priming step may be performed at a preselected flow rate determined to be optimal for priming of the filter 733, for example a flow rate of about 30 ml/min.

At S506, a sufficient quantity of electrolyte concentrate for a single cycle or for a full treatment (e.g., daily treatment) including multiple fill cycles is pumped through the path 790, 791, 728, 745, 758, 742 with all valves 751 closed except those defining this path. This has the effect of priming the electrolyte concentrate line 742 as well as providing a sufficient amount of electrolyte concentrate in the osmotic agent container 781 to generate multiple batches each for respective fill cycles in sufficient number for a full treatment, for example a single day's treatment.

At S510, the pump 788 pumps sufficient osmotic agent concentrate into mixing container 732 to prime the lines and the header 760. The lines include batch outlet line 750, fluid line 745, and osmotic agent concentrate line 789, which are opened by means of respective valves 751. The volume transferred may be determined to be sufficient to prime the lines and header 760 leading to osmotic agent concentrate line 744.

At S514, a sufficient quantity of osmotic agent concentrate for a single cycle or for a full treatment (e.g., daily treatment) that includes multiple fill cycles, is pumped through the path 790, 791, 728, 745, 758, 744 with all valves 751 closed except those defining this path. This has the effect of priming the osmotic agent concentrate line 742 as well as providing a sufficient amount of osmotic agent concentrate in the osmotic agent container 781 to generate multiple batches each for a respective fill cycle and in sufficient number for a full treatment, for example a single day's treatment.

At S520, a flow channel is established by closing all valves 751 except ones required to flow from the water source 766 to outlet line 750. Water is pumped from the water source 766 using the pump 794 to prime the manifold

758 and the outlet line 750 thereby transferring a small amount of water into the mixing container 732.

At S522, a recirculating channel between in the inflow 746 and outflow 750 lines through the pump 762 is established and the mixing container 732 contents are pumped for a period of time or a number of pump rotations sufficient to break in the pumping tube segment of pump tube 763. The contents of the mixing container 732 may be mixed by this process.

At S528, if a special last fill, different from the prescriptions generated from the concentrates, is to be used, a special last fill medicament container 734 will be provided. At S528, the last fill line 740 may be primed by flowing a portion of the last fill container 734 contents to a waste container or drain 768 to prime the last fill line 740.

At 530, the pump 794 pumps a pre-determined volume of water into the mixing container 732. The pump recirculates fluid from the mixing container 732 through inflow and outflow lines 746 and 750 for a time sufficient to break in pump tube segment and mix contents. This is a closed loop path that includes the manifolds 758 and 760, the inflow and outflow lines 746 and 750 and the mixing container 732.

At S532, the controller 739 performs an integrity test of the filter 733 on fluid intake line 728. This is to confirm that all fluids that have flowed into the fluid circuit are sterile/pyrogen-free. If the integrity of the filter membrane is not confirmed, the controller 739 may perform an error recovery operation by instructing the operator to replace fluid circuit 701E. The controller 739 is programmed at least to generate a signal indicating a failed test. The controller 739 may prevent fluid in the mixing container 732 from being used by pumping the contents to the drain automatically and generating an output on the user interface indicating a failed filter, along with instructions for replacing the fluid circuit.

A S534, the controller 739 opens a circuit through manifolds 758 and 760 from the water source to drain and flows water through the open circuit to rinse the conductivity sensors 764. The conductivity may be monitored by the controller 739 to confirm that a sufficient amount of water has been transferred to rinse the conductivity cells to a predetermined threshold.

At S536, the controller 739 opens a circuit including line 742 through manifolds 758 and 760 through to drain and passes a small bolus (e.g., 6-8 ml) from electrolyte concentrate container 780 into manifold 758. This stores a marker in the line that ultimately gets pumped to the conductivity sensors 764 and is used for calibration of the pump 762.

At S538, a circuit is opened by operating valves 751 that includes water line 728 manifolds 758 and 760 and runs through to the drain from the purified water source 766 to flow a small purified water spacer (e.g. 10 ml.) from the fluid module 723 into the open circuit such that it flows into it but does not reach the conductivity sensors nor does it push the bolus formed at S536 to the conductivity sensors. Rather, the bolus and the spacer are queued in the fluid path waiting for S540 to perform a calibration operation by measuring time of flight of the bolus. That is, with a fixed volume of the channel between the conductivity sensors, the system can be calibrated to determine the flow rate from the time delay between the indications of the perturbation crossing the two conductivity sensors.

At S540, the controller 739 opens a circuit including outflow line 750 through manifolds 758 and 760 through to drain and pumps sufficient fluid from mixing container 732 (about 50 ml) to push the electrolyte concentrate bolus and the water spacer past the conductivity sensors 764 to calibrate the pump. This system is described in the US 2015-0005699 incorporated by reference. The technique is for the controller to calculate the volume flow rate of fluid by detecting the cross of a conductivity perturbation across two spaced apart conductivity sensors. With a fixed volume of the channel between the conductivity sensors, the system can be calibrated to determine the flow rate from the time delay between the indications of the perturbation crossing the two conductivity sensors.

At S542, the controller 739 flows sufficient water toward mixing container 732 (about 22.6 ml. for example) to fill inflow line 746 with water. To ensure the inflow line 746 is completely filled, an amount sufficient to transfer some water to the mixing container 732 is pumped.

At S544 the controller 739 runs the pump 762 so as to drain the mixing container 732 until a vacuum is detected on pressure sensor 769. The controller then calculates a discounted value for fluid accounting purposes accounting for the total volume of water MOTI in 746 to account for effect of vacuum drawn on the inflow line 746

At S546 the controller 739 pumps water to the drain to prime the manifolds 758 and 760 with water. All valves 751 are closed except those that define a path from the water source 766 to the drain.

At S548 the controller 739 pumps 100% or less (e.g. 50%) of a target volume of water into the mixing container 732. This is the amount of water the controller 739 determines is required for a ready-to-use PD dialysis fluid according to a current prescription stored by the controller 739.

At S550 the controller 739 pumps a predetermined amount of water from mixing container 732 to waste container or drain 768 to fill the mixing container 732 outflow line 750 with water to fill the volumes defined as MIMO, MOTI, and SOMI, that is, the inflow and outflow lines 746 and 750, the manifolds 758 and 760 and the pump tube 763.

At S552 the controller 739 pumps 100% of the electrolyte concentrate required for the target prescription into the mixing container 732 (noting that the reverse order of electrolyte and osmotic agent is also possible, so osmotic agent with electrolyte sufficient to act as a marker may be added first instead).

At S554 the controller 739 mixes the mixing container 732 contents by recirculating through the lines 746 and 750 and the manifolds 758 and 760 using the pump 762.

At S556 the controller 739 opens a path from the mixing container 732 to the drain and pumps a quantity of its contents sufficient to test conductivity to confirm the level of dilution of electrolyte. Any difference between the actual and expected conductivity measurements is compared to a threshold and if the threshold is exceeded, at S558, additional water or electrolyte concentrate may be added to provide the target ratio.

At S558 the controller 739 conditionally pumps further water or electrolyte concentrate responsively to the previous conductivity test done at S556. This process may be iterative to provide, effectively, a titration until the required ratio of electrolyte to water is achieved. In embodiments, the total measured water volume is used as ground truth by the controller 739 for purposes of adjusting the second concentrate (osmotic agent concentrate in this example) to be added.

At S560 the controller 739 pumps osmotic agent concentrate into the mixing container 732 using ratiometric control of transferred concentrate (noting the reverse order of concentrates is also possible).

At S562, the controller 739 mixes the mixing container 732 contents by recirculating through the lines 746 and 750 and the manifolds 758 and 760 using the pump 762.

At S564 the controller 739 tests conductivity of mixing container contents and passes or fails the batch based on the result by passing a sample from the mixing container 732 to the conductivity sensors 764.

At S566, the controller 739 determines and adds the complement of water depending on the initial amount provided at S548. In the example of 50% water, the 50% balance of water is added. If the quantity of water was adjusted in S558, then the balance is adjusted based on any additional quantity added to the contents of the mixing container 732.

At S568, the mixing container contents are mixed by the controller 739 by recirculating through the lines 746 and 750 and the manifolds 758 and 760 using the pump 762.

At S570, the controller 739 tests conductivity of mixing container 732 contents and passes or fails the batch based on the result. At this point, the failure of the batch may not be compensated by adjusting its constituents. If the contents do not meet the predefined expected conductivity, the contents of the mixing container 732 may be blocked from further use and a signal may be generated to indicate the failure. In embodiments, the contents of the mixing container 732 may be automatically flushed to drain in the event of a failure.

At S572, the controller 739 tests the sterilizing filter(s) and passes or fails the completed batch based on the result of the filter test. At this point, the contents of the mixing container 732 may be blocked from further use and a signal may be generated to indicate the failure. In embodiments, the contents of the mixing container 732 may be automatically flushed to drain in the event of a failure.

Figure 18E:
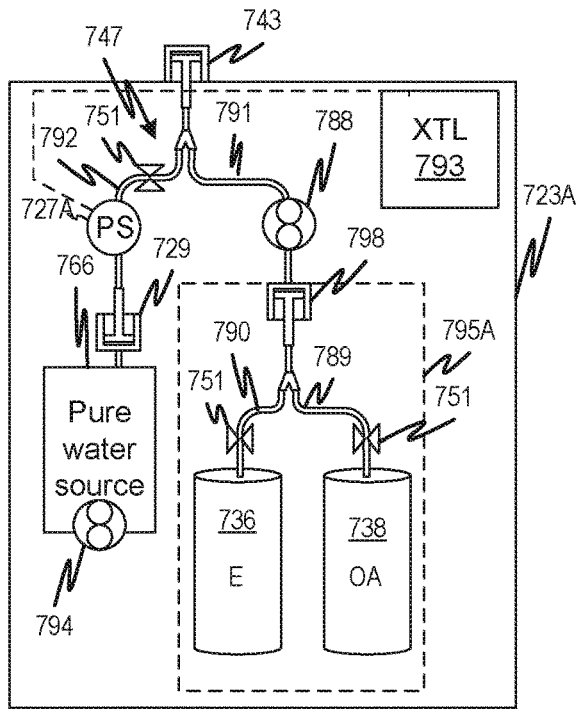
FIGS. 18E through 18H show variations of details of the embodiment of FIG. 18A for supplying concentrate or water to the fluid circuit according to embodiments of the disclosed subject matter.
Figure 18F:
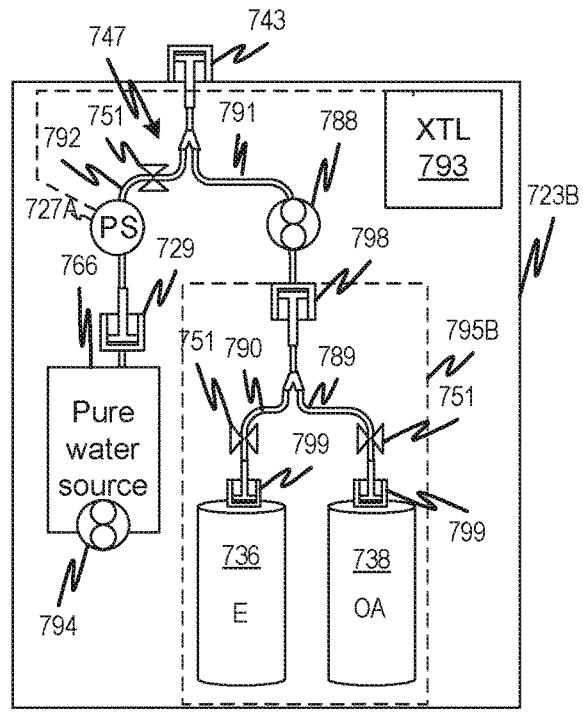
Figure 18G:
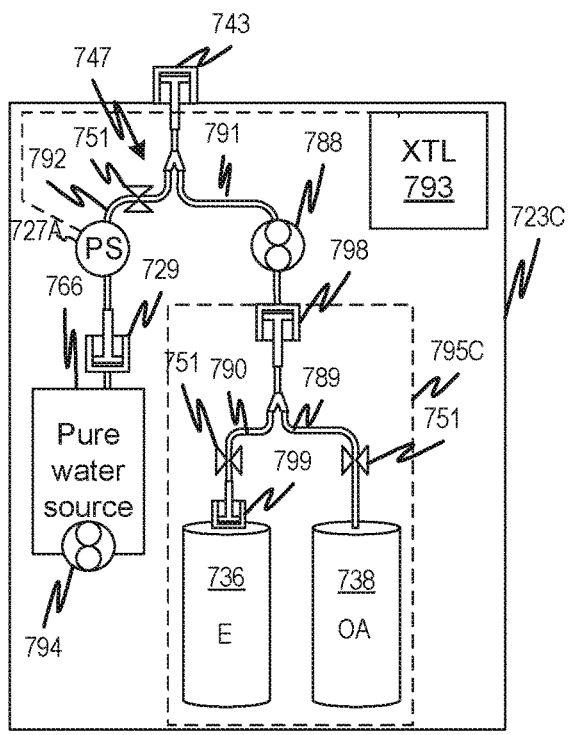
Figure 18H:
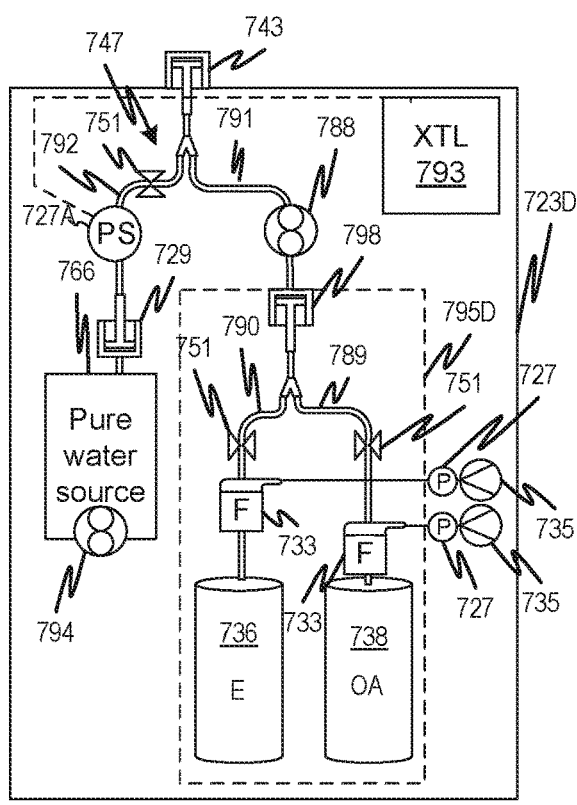

FIGS. 18E through 18H show various fluid circuit configurations for the fluid module 723 of the foregoing embodiments such as that of FIG. 18A. In the embodiment of FIG. 18E, a fluid module 723A has concentrate containers 736 and 738 which are preconnected to the respective concentrate lines 790 and 789 which are interconnected to a connector 798 for connection to the water inlet of a fluid circuit such as that of FIG. 18A. In this embodiment, the concentrate containers 736 and 738 may be mechanically attached to each other or enclosed in a common housing indicated at 795A to form a single unit that may be replaced, as a unit, when one of the concentrate containers, 736 or 738, is exhausted. FIG. 18F shows an embodiment in which the concentrate containers 736 and 738 each has its own connector 799 which allows each of the concentrate containers 736 and 738 to be replaced independently of the other. The concentrate containers 736 and 738 may be housed, or held, in a permanent fixture 795B. FIG. 18G shows a fluid module 723C where one of the concentrate containers 738 is not disconnectable from a fluid line (here, osmotic agent concentrate line 789) while the other concentrate container 736 is connected by a removable connector 799. In embodiments, which of the two concentrates is not disconnectable can be reversed so that the electrolyte concentrate container 736 is not disconnectable and the osmotic agent concentrate container 738 is disconnectable. In this embodiment, only one of the types of concentrate is ever preconnected to a line, such as line 789. The configuration of the embodiment of FIG. 18G prevents connection of a respective one of the lines 789 and 790 to the wrong type of concentrate container. FIG. 18H shows an embodiment 723D in which separate testable filters are provided for each of the concentrates 736 and 738. In this case, the fluid module may have its own air pumps 735 and pressure sensors 727.

Note that in any of the embodiments, the air pump's 735 functions may be provided by a single pump with multiple lines stemming from a common output. Each may be controlled by a respective valve under control of the controller.

Note that in any of the embodiments in which a fluid source module is provided to actively pump fluid to a consuming appliance such as proportioning and treatment systems for peritoneal dialysis 700A-700E, the fluid module may be controlled by direct electronic communication such as wired or wireless. Such direct communication may be used for closed loop control of the fluid module pump by the proportioning and treatment system for peritoneal dialysis controller, for example.

In any of the fluid module embodiments (723, 723A, 723B, 723C, 723D), the pump 794 that pumps water may be of a type that pushes water through a filtration system and may be of a high precision non-pulsatile type such as a gear pump or a screw pump. This pump, indicated in embodiments at 794, may be closed-loop controlled based on pressure by the pressure sensor 727A. In any of the fluid module embodiments, the valve of the type 751 indicated at 749 in FIG. 18A and corresponding locations in other embodiments is controlled by the controller 739.

In embodiments in which the water pump 794 is activated and deactivated in response to pressure (see for example FIG. 9A-19C and associated discussion) and is also closed-loop controlled to maintain a predefined pressure range, the control of the water pump 794 may be regulated by a control algorithm such that a pressure rise above a predefined level or above a predefined rate due to the halting of the cycler pump may be detected quickly. For example, if the pressure rises above a predefined level or rises faster than a predefined rate, the water pump controller may detect that condition and halt the water pump rather than slewing to a low flow rate in response to the close-loop control algorithm. The controller may also terminate closed-loop control of the flow rate if such a condition is detected.

Figure 19A:
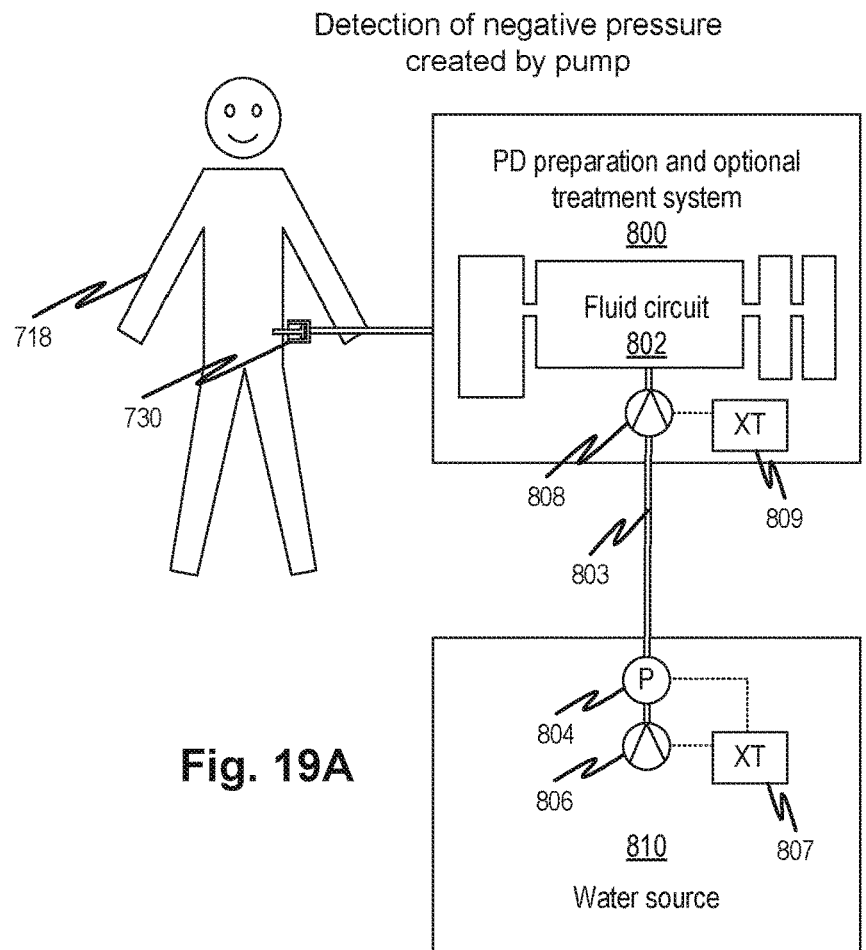
FIG. 19A through 19C describe a first device and corresponding method of controlling the supply of water to a peritoneal dialysis fluid treatment device, according to embodiments of the disclosed subject matter.
Figure 19B:
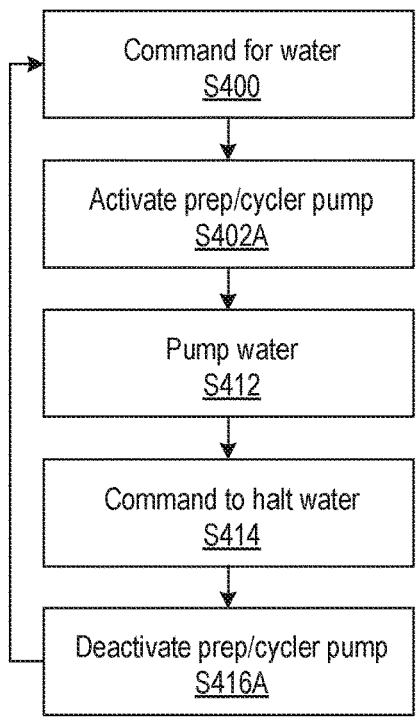
Figure 19C:
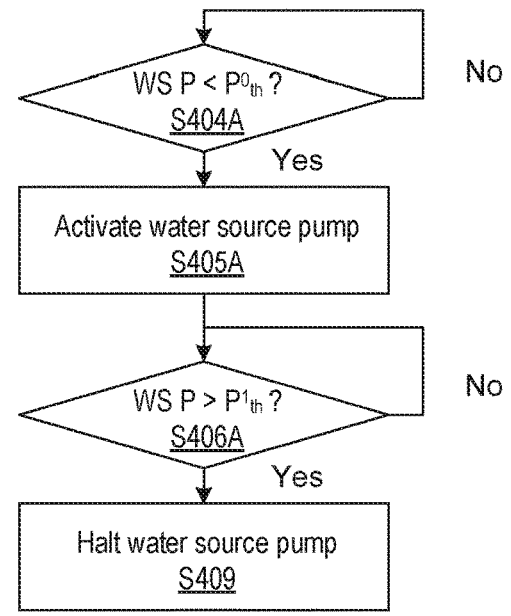

The direct control of water and/or other fluid sources by wired or wireless digital signals may be preferred. FIGS. 19A-19H and 19J-19M show embodiments for control of a fluid source, here exemplified by a water source 810, without direct data communications applying control inputs from a medical treatment device, here exemplified by a peritoneal dialysis fluid preparation device 800, which may optionally have a cycler as well. Referring to FIG. 19A, a peritoneal dialysis fluid preparation device 800 has a pump 808 and a fluid circuit 802 for mixing fluids and for performing a peritoneal dialysis treatment. The water source 810 has a pump 806 that conveys water to the peritoneal dialysis fluid preparation device 800 through a water line 803. A pressure sensor 804 detects pressure in the water line and applies a corresponding signal to a controller 807 of the water source 810. The controller 807 controls the pump 806. FIG. 19B shows a control loop executed by a controller 809 of the peritoneal dialysis fluid preparation device 800. At S400, the controller 809 receives or generates a command for water. This may be as described in the foregoing embodiments as incident to a concentrate dilution operation in the preparation of a dialysis fluid by the peritoneal dialysis fluid preparation device 800. At S402A the peritoneal dialysis fluid preparation device 800 begins operating the pump 806 to draw water through the water line 803. At S412, the peritoneal dialysis fluid preparation device 800 pump 806 draws a quantity of water until a command is received or generated at S414 to halt the pumping of water whereupon at S416A, the pump 806 is deactivated. FIG. 19C shows a control loop executed by the controller 807. At S404A, the water source 810 controller detects a pressure below a predetermined threshold indicated by the pressure sensor

804. A drop in pressure is caused by the S402A operation which causes a negative pressure in the water line 803. Note that instead of an absolute (gauge or absolute pressure in absolute terms) pressure, the controller 807 at S404A may respond to a predefined rate of change of pressure or a predefined total pressure change over a predefined interval of time. The predefined ranges may be stored in a memory of the controller 807. S404A loops continuously until the condition is met. At S405A, the controller 807 activates the water pump 806 causing water to flow into the water line and alleviating the negative pressure such that water flows freely under control of the pump 808. At S406A, control loops until the pressure indicated by the pressure sensor 804 rises above a threshold or increases a predefined total amount or at a predefined rate whereupon the water source pump 806 is halted at S409. The rise in pressure is caused by the operation S414. Thus, the water source 810 is automatically demand-controlled by the peritoneal dialysis fluid preparation device 800 controller 809 without a signal connection between the controllers 809 and the water source 810 controller 807.

Although the embodiments described with reference to FIGS. 19A through 19M described the peritoneal dialysis fluid preparation device 800 as controlling the halting of the water source 810 pump 806, it is possible in variations of these embodiments to instead cause the halting of the water source 810 pump to be controlled by providing the controller 807 with a predefined volume of water or a predefined pumping time. Water pump 806 will halt automatically after being started so that the peritoneal dialysis fluid preparation device 800 can halt operation of pump 808 independently.

Thus, in operation, the peritoneal dialysis fluid preparation device 800 controller 809 start the water source 810 pump 806 as described in the embodiments 19A through 19M, but the halting of the pump occurs automatically as a result of the expiration of the predefined volume or running time.

Note also, that in the embodiment of FIGS. 19G, 19H, and 19J the controller 809 may transmit, by means of pressure pulse signals, the duration of pumping by the water pump 806 or the amount to be pumped, by the peritoneal dialysis fluid preparation device 800 controller 809 to the water source 810 controller. This may allow the peritoneal dialysis fluid preparation device 800 controller 809 to establish the volume of fluid or the duration of pumping.

In any of the embodiments, the pressure modulator may generate pulses by modulating the peritoneal dialysis fluid preparation device 800 pump 808. For example, such pumps may be driven by motors that allow forward and reverse movement such as by means of a stepper motor drive. Other means for creating pulses are also possible such as an independent actuator such as a solenoid-driven diaphragm pump. Further variations are described elsewhere in the present application.

Note also in the embodiment of FIGS. 19A-19C, in alternative embodiments, the water source 810 may halt the flow of water after a certain quantity of water has been pumped by pump 806, instead of receiving a command at S414. In other embodiments, the pump 808 may generate a pressure spike when it is halted by the controller 809. This spike may be detected by the pressure sensor 804 and cause the controller 807 to halt the pump 806.

Referring now to FIG. 19D, as in the embodiment of FIG. 19A, the peritoneal dialysis fluid preparation device 800 has a pump 808 and a fluid circuit 802 for mixing fluids and for performing a peritoneal dialysis treatment. The water source 810 has a pump 806 that conveys water to the peritoneal dialysis fluid preparation device 800 through a water line 803. The controller 807 controls the pump 806. A power supply 815 provides power to the pump 808. In the water source, a voltage detector 816 is connected to the power supply 815 or power leads leading to the pump 808, to detect power sent to the pump 808. Thus, the voltage detector 816 applies a signal to the controller 807 indicating when the pump 808 is activated. The pressure sensor 804 may be used for flow control of the pump 806 to ensure the tandem operation of the pumps 808 and 806 are synchronized by flow such that the pump 806 does not unduly resist the pumping of pump 808. A closed loop control of pump 806, executed by controller 807, on a pressure set point may accomplish this. This closed loop control may be provided in embodiments. FIG. 19E shows a control loop executed by a controller 809 of the peritoneal dialysis fluid preparation device 800. At S400, the controller 809 receives or generates a command for water. This may be as described in the foregoing embodiments as incident to a concentrate dilution operation in the preparation of a dialysis fluid by the peritoneal dialysis fluid preparation device 800. At S402A the peritoneal dialysis fluid preparation device 800 begins operating the pump 806 to draw water through the water line 803. At S412, the peritoneal dialysis fluid preparation device 800 pump 806 draws a quantity of water until a command is received or generated at S414 to halt the pumping of water whereupon at S416A, the pump 806 is deactivated. FIG. 19F shows a control loop executed by the controller 807. At S404B, the water source 810 controller detects a voltage above a predetermined threshold indicated by the voltage detector 816. The predefined threshold may be stored in a memory of the controller 807. S404B loops continuously until the condition is met. At S405B, the controller 807 activates the water pump 806 causing water to flow into the water line and alleviating the negative pressure such that water flows freely under control of the pump 808. At S406B, control loops until the voltage indicated by the voltage detector 816 falls below a predefined threshold which may be different from the one at S404B, whereupon the water source pump 806 is halted at S409. The fall in voltage is caused by the operation S414. Thus, the water source 810 is automatically demand-controlled by the peritoneal dialysis fluid preparation device 800 controller 809 without a signal connection between the controllers 809 and the water source 810 controller 807.

Referring now to FIG. 19G, as in the embodiment of FIG. 19A, the peritoneal dialysis fluid preparation device 800 has a pump 808 and a fluid circuit 802 for mixing fluids and for performing a peritoneal dialysis treatment. The water source 810 has a pump 806 that conveys water to the peritoneal dialysis fluid preparation device 800 through a water line 803. The controller 807 controls the pump 806. A pressure modulator 818 generates pressure pulses in the water line 803 that are detected by the pressure sensor 804 of the water source 810 to apply resulting pressure pulse indications to a decoder 819 which decodes them to generate command signals that are applied to the controller 807. The controller 809 may store pressure pulse patterns that are thus decoded by the decoder 819. Using pressure pulses, various commands can be encoded and decoded to provide commands to the water source 810 from the peritoneal dialysis fluid preparation device. Such commands may include to start and stop the pump 806, or to command a speed of the pump 806, for example. The pressure sensor 804 may be used for flow control of the pump 806 to ensure the tandem operation of the pumps 808 and 806 are synchronized by flow such that the pump 806 does not unduly resist the pumping of pump 808. A closed loop control of pump 806, executed by controller 807, on a pressure set point may accomplish this. The pressure pulse signal generated by the pressure modulator may prescribe a pressure setpoint for such closed loop control. The closed loop control may be provided in embodiments. FIG. 19H shows a control loop executed by a controller 809 of the peritoneal dialysis fluid preparation device 800. At S400, the controller 809 receives or generates a command for water. This may be as described in the foregoing embodiments as incident to a concentrate dilution operation in the preparation of a dialysis fluid by the peritoneal dialysis fluid preparation device 800. At 5402B the peritoneal dialysis fluid preparation device 800 begins operating the pump 806 to draw water through the water line 803 and simultaneously, shortly or immediately before or shortly or immediately afterwards, generates a pulse command to turn on the water pump 806. At this time, further commands such as a pressure setpoint or a speed of the pump 806 may be generated using pressure pulses through the pressure modulator 818. At S412, the peritoneal dialysis fluid preparation device 800 pump 806 draws a quantity of water until a command is received or generated at S414 to halt the pumping of water whereupon at S416B, the pump 806 is deactivated and simultaneously, shortly or immediately before or shortly or immediately afterwards, generates a pulse command to turn off the water pump 806. FIG. 19J shows a control loop executed by the controller 807. At S404C, the water source 810 controller 807 detects a command from the decoder 819 to start the pump and establish operating conditions if operating conditions are included in the pulse train received by the decoder 819. S404C loops continuously until the condition is met. At S405C, the controller 807 activates the water pump 806 causing water to flow into the water line and alleviating the negative pressure such that water flows freely under control of the pump 808. The controller 807 may also set operating conditions as indicated by the received command. At S406C, control loops until a further pressure pulse signal command is received by the decoder 819 to halt the pump 806. Thereupon, the water source pump 806 is halted at S409. Thus, the water source 810 is automatically demand-controlled by the peritoneal dialysis fluid preparation device 800 controller 809 without a wired or radio-based signal connection between the controllers 809 and the water source 810 controller 807.

Figure 19K:
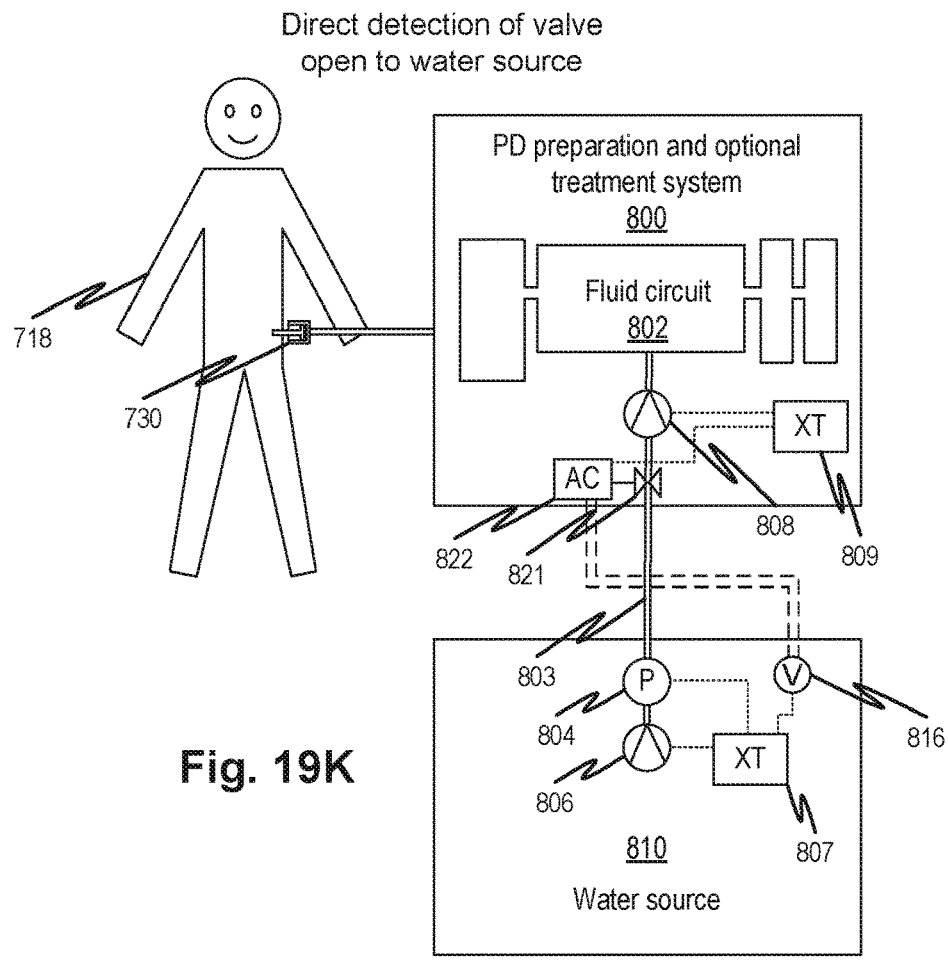
FIGS. 19K through 19M describe a fourth device and corresponding method of controlling the supply of water to a peritoneal dialysis fluid treatment device, according to embodiments of the disclosed subject matter.
Figure 19L:
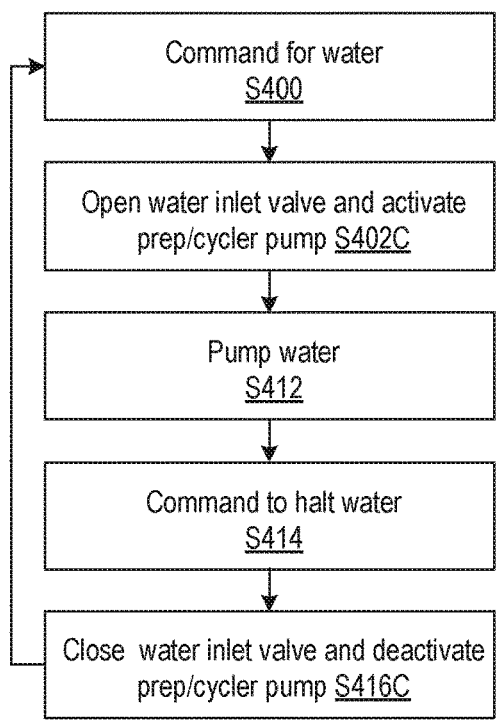
Figure 19M:
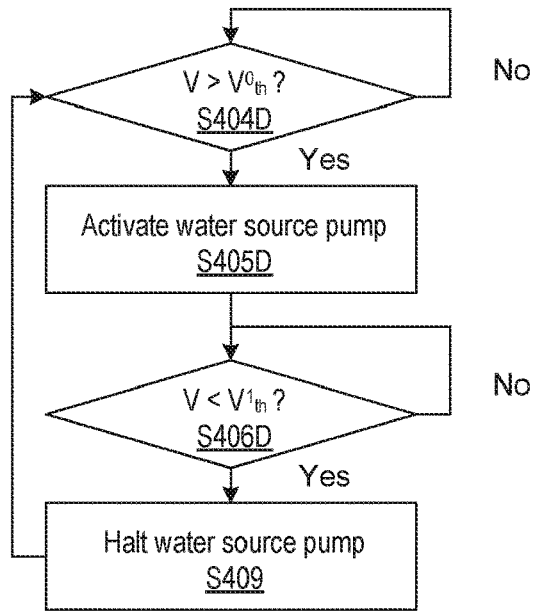

Referring now to FIG. 19K, as in the embodiment of FIG. 19A, the peritoneal dialysis fluid preparation device 800 has a pump 808 and a fluid circuit 802 for mixing fluids and for performing a peritoneal dialysis treatment. The water source 810 has a pump 806 that conveys water to the peritoneal dialysis fluid preparation device 800 through a water line 803. The controller 807 controls the pump 806. A valve actuator 822 opens and closes a valve 821 that provides for flow into the fluid circuit 802 from the water line 803. Details of such operation and embodiments are disclosed elsewhere herein. A voltage sensor 816 detects the activation of the valve actuator 822 and applies a corresponding signal to the controller 807. Both opening and closing indications may be applied and interpreted by the controller 807 using known principles and according to various valve types so details are not discussed. The pressure sensor 804 may be used for flow control of the pump 806 to ensure the tandem operation of the pumps 808 and 806 are synchronized by flow such that the pump 806 does not unduly resist the pumping of pump 808. A closed loop control of pump 806, executed by controller 807, on a pressure set point may accomplish this. This closed loop control may be provided in embodiments. FIG. 19L shows a control loop executed by a controller 809 of the peritoneal dialysis fluid preparation device 800. At S400, the controller 809 receives or generates a command for water. This may be as described in the foregoing embodiments as incident to a concentrate dilution operation in the preparation of a dialysis fluid by the peritoneal dialysis fluid preparation device 800. At S402C the peritoneal dialysis fluid preparation device 800 activates the valve actuator 822 to open the valve controlling the fluid circuit 802 access to the water line 803 and then begins operating the pump 806 to draw water through the water line 803. At S412, the peritoneal dialysis fluid preparation device 800 pump 806 draws a quantity of water until a command is received or generated at S414 to halt the pumping of water whereupon at S416C, the pump 806 is deactivated and the valve actuator 822 is activated to close (or deactivated, depending on the type of valve, for example a solenoid would be powered-down) the water inlet valve 821. FIG. 19M shows a control loop executed by the controller 807. At S404D, the water source 810 controller detects a voltage above a predetermined threshold indicated by the voltage detector 816. This is one example of the direct detection of the opening of a valve. In a linear motor actuated pinch valve, a forward applied voltage may be detected that runs the linear motor in a forward direction to close the valve 821 and a reverse applied voltage may be detected that runs the linear motor in the reverse direction to open the valve 821. For a solenoid valve, a predefined threshold voltage may be stored in a memory of the controller 807 to indicate the valve open position of the actuator 822. For other types of actuator, a suitable mechanism for direct detection of the valve status (e.g., an encoder or other mechanism) may be employed. S404D loops continuously until the condition is met. At S405D, the controller 807 activates the water pump 806 causing water to flow into the water line such that water flows freely under control of the pump 808. At S406D, control loops until the valve actuator 822 close condition is detected. Thereupon, the water source pump 806 is halted at S409. The close condition is caused by the operation in S416C. Thus, the water source 810 is automatically demand-controlled by the peritoneal dialysis fluid preparation device 800 controller 809 without a signal connection between the controllers 809 and the water source 810 controller 807.

In any of the foregoing embodiments in which pressure, voltage, or other indications are used to control the flow of a fluid, such as water, the upstream source such as fluid source may be placed in a demand mode to enable control by pressure, voltage, or other indications. This may be done by a unique user command through a connected user interface. Alternatively, the controller (e.g. 807, 739) may generate a command using a unique pattern of pressure or final control to a valve or pump power supply to indicate the demand mode. When not in the demand mode, the fluid source ability to respond to the commands for fluids is disabled.

Referring now to FIGS. 20A through 20E, any of the foregoing embodiments may be modified to employ any one of a variety of locations for a filter that removes pyrogens and infectious agents such as bacteria. Any of the filters 824 may be, or include, a single filter, for example with a membrane having pores of 0.2 micron or smaller diameter. Any of the filters 824 may be, or include, a single filter of the same type with additional apparatus and/or controls suitable for testing. For example, a pressurized line may permit the application of pressurized air below the bubble point of the membrane to one side of the filter to measure the membrane's ability to withstand the pressure and thereby indicate its integrity. This type of filter integrity test is known in the art and details are known to those skilled in the art. In other embodiments, the filters 824 may be redundant to reduce the probability of a failure to the joint probability of a failure in both filters. In each of the FIGS. 20A through 20E, a patient 842 is filled and drained through a patient fill/drain line 841 via a fluid circuit 856 which may be configured in accord with any of the embodiments disclosed herein or in the embodiments disclosed in the references referenced in the incorporation-by-reference statements. A mixing chamber 855 is connected to the fluid circuit 856 where the fluid circuit 856 prepares a batch using inflow 857 and outflow 858 lines with flow direction designated by arrows. As in the foregoing and later embodiments, a water source 850, a first long-term concentrate container 852, and a second long-term concentrate container 863 are connected to the fluid circuit 856.

Figure 20A:
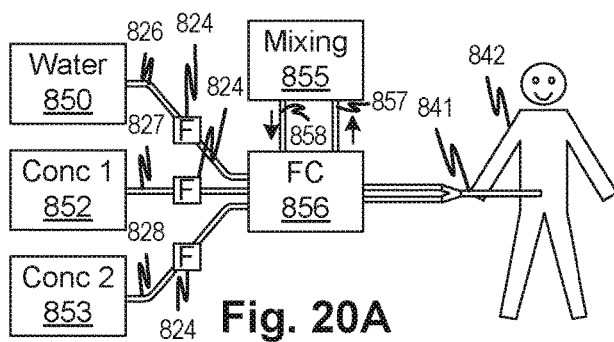
FIGS. 20A through 20E show mechanisms for providing sterile filtration in the various peritoneal proportioning/treatment systems of the various disclosed embodiments.

In the embodiment of FIG. 20A, each of the inlet lines for water 826, the first concentrate 852, and the second concentrate 853 have a filter 824 to prevent contaminants from entering the fluid circuit 856 and thereby prevent contaminants from entering the patient 842. The guarantee against contamination provided by the filters 824 is optimized if all other components are permanently (or previously, as-delivered and sterilized) connected within and to the fluid circuit 856 such that only connections to the water 850, the first concentrate 852, and the second concentrate 853 need to be made upstream of the filters 824. Thus, the filters themselves are attached to the lines 826, 827, and 828. Note that connectors are not separately shown, but may be provided for connecting between each of the respective water 850, the first concentrate 852, and the second concentrate 853 and the lines 826, 827, and 828 on the fluid-source side of the respective filter 824.

Figure 20B:
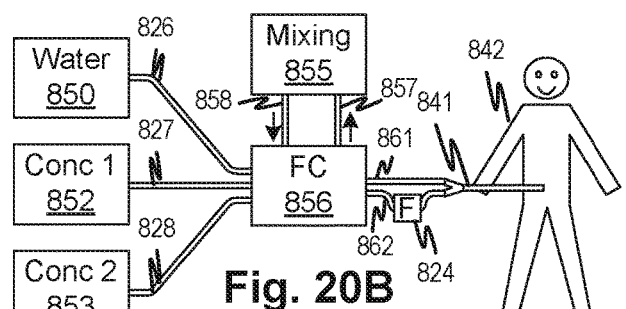

In the embodiment of FIG. 20B, a drain line 861 drains fluid from the fill/drain line 841 and a fill line 862 fills the fill/drain line. The fill line 862 has a filter 824. In this embodiment, no other filters are used. The fill/drain line 841 is permanently or previously attached to the fill line 862 prior to sterilization such that when the fill/drain line 862 is connected to the fluid circuit 856 (note that it could be previously attached and sterilized as a unit with all or parts of the fluid circuit 856), any contamination, including touch contamination, is blocked from reaching the patient 842 by the filter 824. Other elements are as described above.

Figure 20C:
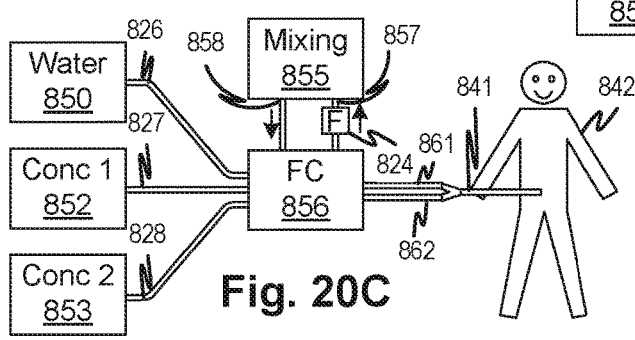

In the embodiment of FIG. 20C, a filter 824 is placed on the mixing container 855 inflow line 857. The mixing container 855 is presumed to be attached to the fluid circuit before sterilization so that a sealed unit is formed and any touch contamination is prevented from entering the mixing container 855. A filter may also be provided on the fill line 862 as in the embodiment of FIG. 20B. Alternatively, instead of a filter on the fill line 862, the fluid circuit 856 may be designed such that a dedicated channel is defined between the mixing container 855 and the fill line 862 so that unsterile fluids, or fluids not protected by sterile filtration, do not contact any part of the circuit connecting the mixing container outflow line 858 and the fill line 862. As in other embodiments, the filter 824 is connected to the downstream portion and preattached to ensure sterility of the contents of the mixing container 855.

Figure 20D:
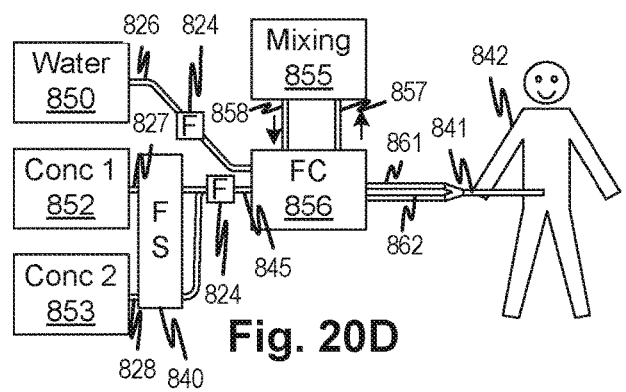

In the embodiment of FIG. 20D, the water line 826 and a common concentrate line 845 are protected by respective filters 824. The downstream side of the water line 826 and the filter 824 may be preattached to the fluid circuit 856, mixing container 855, and the patient lines including fill, drain, and fill/drain 861, 862, and 841. The downstream side of the common concentrate line 845 and the filter 824 may be preattached to the fluid circuit 856, mixing container 855, and the patient lines including fill, drain, and fill/drain 861, 862, and 841. The preattachment specifies that all these elements are sealed with each other before sterilization (or during) to ensure the delivered disposable set is sterile and protected from contamination ingress by the presence of the filters 824. In this case components upstream of the filters 824 can be replaced without risk of contamination.

Figure 20E:
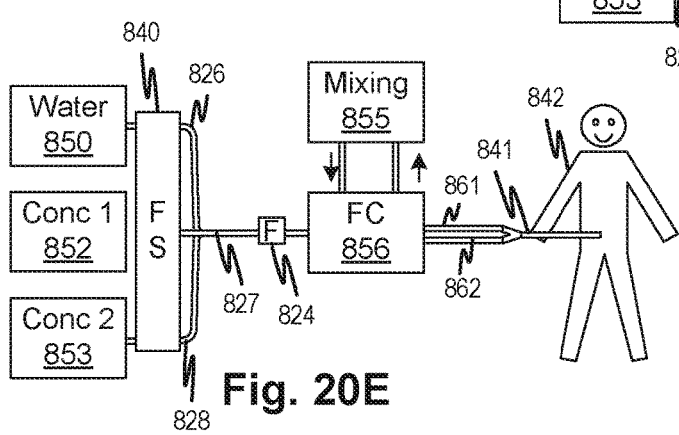

In the embodiment of FIG. 20E, which corresponds to the embodiment of FIG. 18A, the filter 824 is placed in the common fluid line 827 and preattached to the remainder of the fluid handling components which are also interattached. That is the filter 824, the portion of the common fluid line 827 downstream of the filter 824, the fluid circuit 856, mixing container, and the patient lines including fill, drain, and fill/drain 861, 862, and 841 are all interconnected to form a sealed unit prior to sterilization. This ensures the delivered disposable set is sterile and protected from contamination ingress by the presence of the filter 824. In this case components upstream of the filter 824 can be replaced without risk of contamination of the downstream circuit.

Figure 20F:
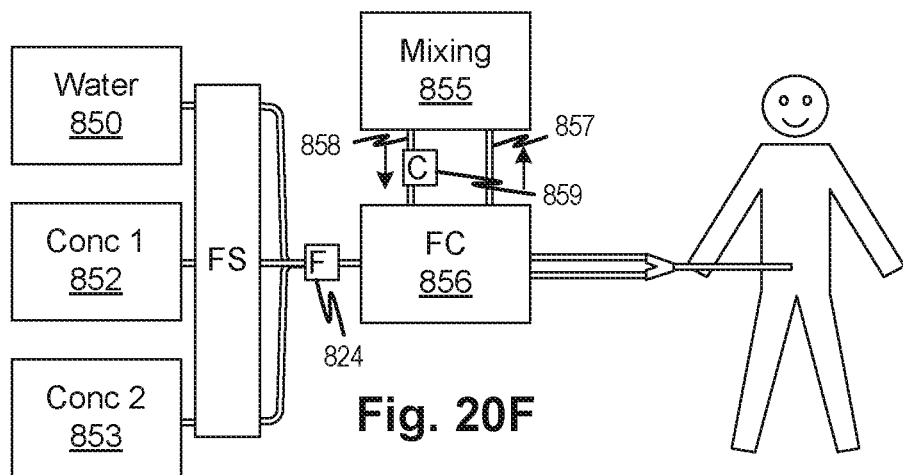
FIG. 20F shows a device for measuring conductivity with minimal loss of fluid by locating a conductivity cell in the disposable at a point where fluid exits the mixing container, according to embodiments of the disclosed subject matter.

FIG. 20F shows a generalized embodiment similar to that of FIG. 18A in which a conductivity sensor 859 is provided on the mixing container 855 outflow line 858. The configuration allows the method embodiments herein to be modified to minimize the total amount of fluid that must be drawn from the mixing container 855 toward the drain to measure conductivity of the mixing container 855 contents. The present embodiment may be modified to provide two conductivity sensors connected in series to be used for volume flow rate measurement as described herein. Note that in any of the embodiments, identified conductivity cells may be of the direct contact or capacitive type of conductivity cell.

Figure 20G:
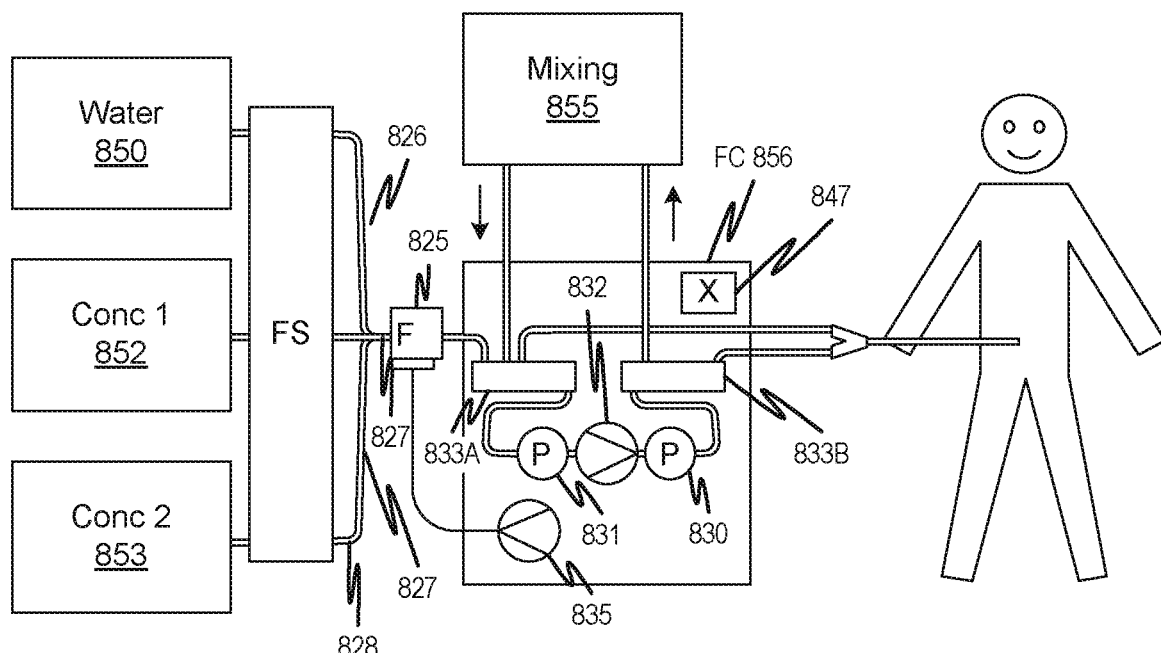
FIG. 20G shows a system and method that may be applied to any of the embodiments in which a pressure sensor used for flow control provides an additional function of pressure testing of a filter membrane by opening a particular set of valves that define a path from the fluid side of the filter to the pressure sensor.

FIG. 20G shows an embodiment similar to that of FIGS. 20E and 20F in terms of the filter placement at a common fluid inlet 827. The filter 825, in the present embodiment, permits a membrane integrity test which may be performed by pressurizing with air from an air pump 835. The pump 832 has inlet and outlet pressure sensors 831 and 830 that are used by the controller 847 for pressure compensation of a commanded rate of pump 832 as described with reference to various embodiments including the incorporated reference US Patent Publication 2015-0005699 also attached to the provisional application. The pump 832 flows fluid between manifolds 833 which may as described in the various embodiments described herein. In the present embodiment, the controller 847 is configured to open any valves necessary to open a fluid channel from the filter 825 to the pressure sensor 831 and to apply air pressure from pump 835 while monitoring the pressure signal from pressure sensor 831 for any change. A filter membrane with no compromise to its integrity will hold the pressure from the air pump 835, which may be controlled to be maintained below the bubble point of the membrane. The controller 847 may generate a signal based on whether a pressure change is indicated by the pressure sensor 831 or not. By opening a channel to a pressure sensor that provides another function, the need for an additional pressure sensor may be avoided.

Figure 21A:
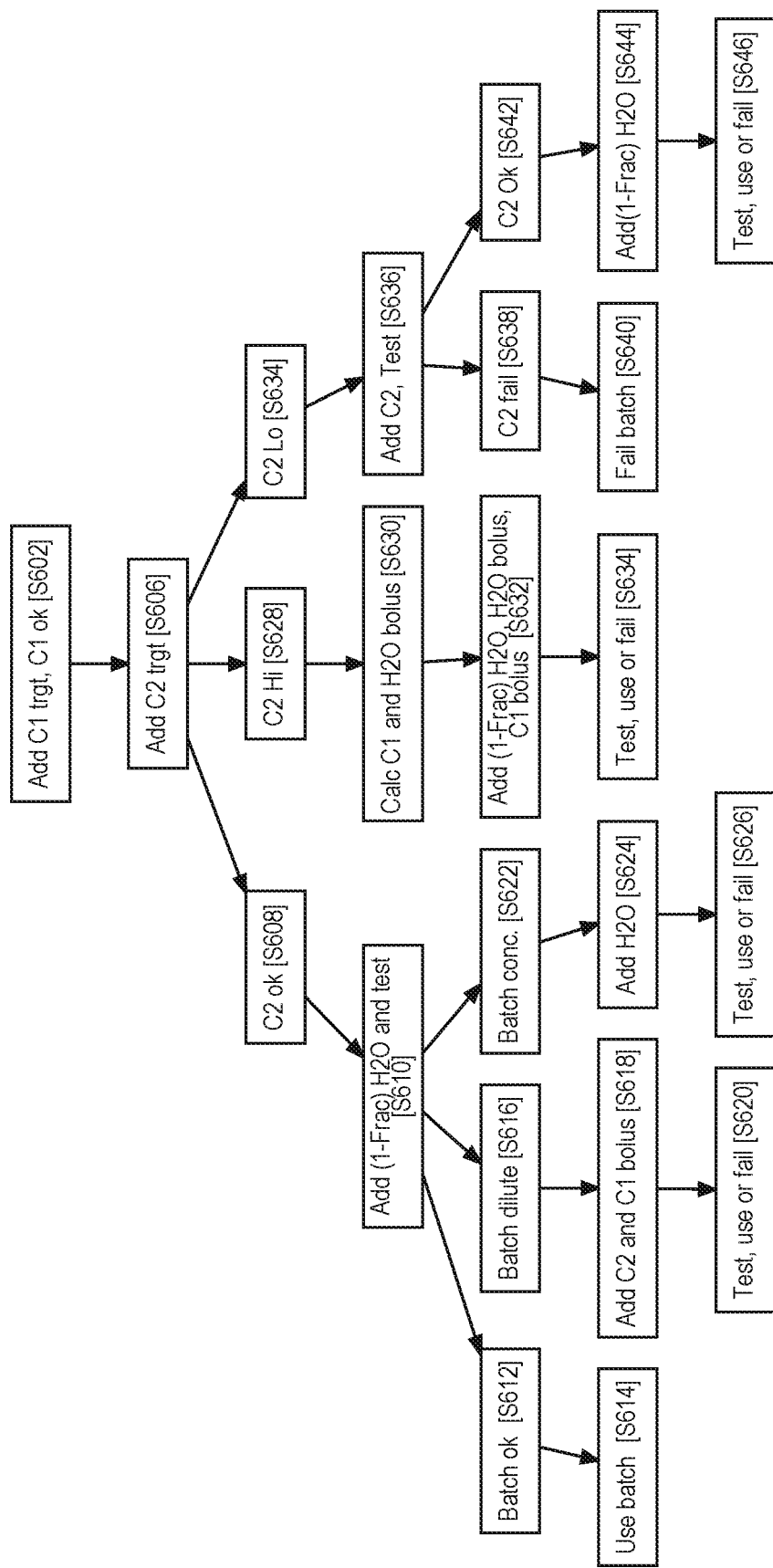
FIGS. 21A through 21C show a flow chart for making and correcting errors in water and concentrate mixtures according to embodiments of the disclosed subject matter.
Figure 21B:
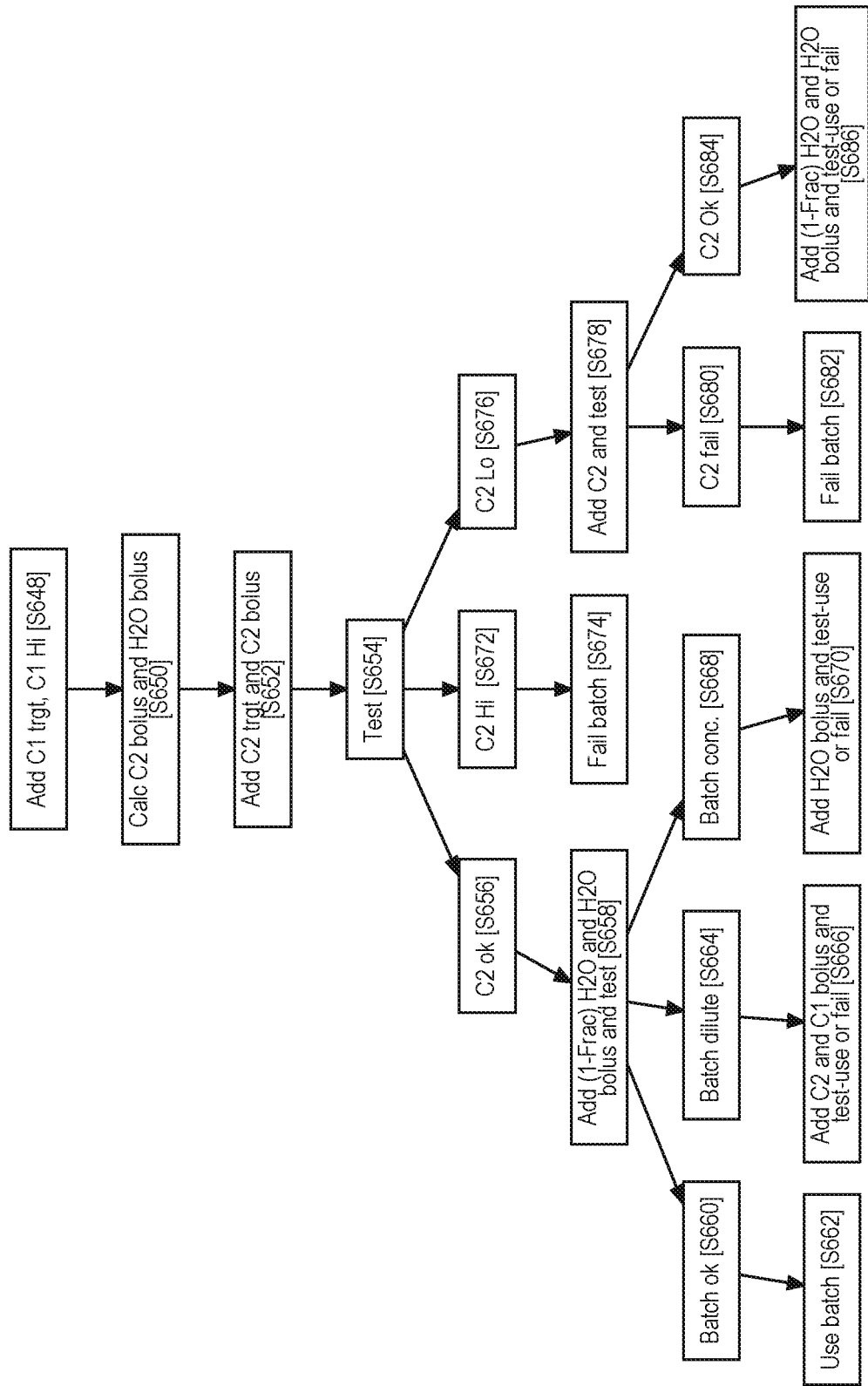
Figure 21C:
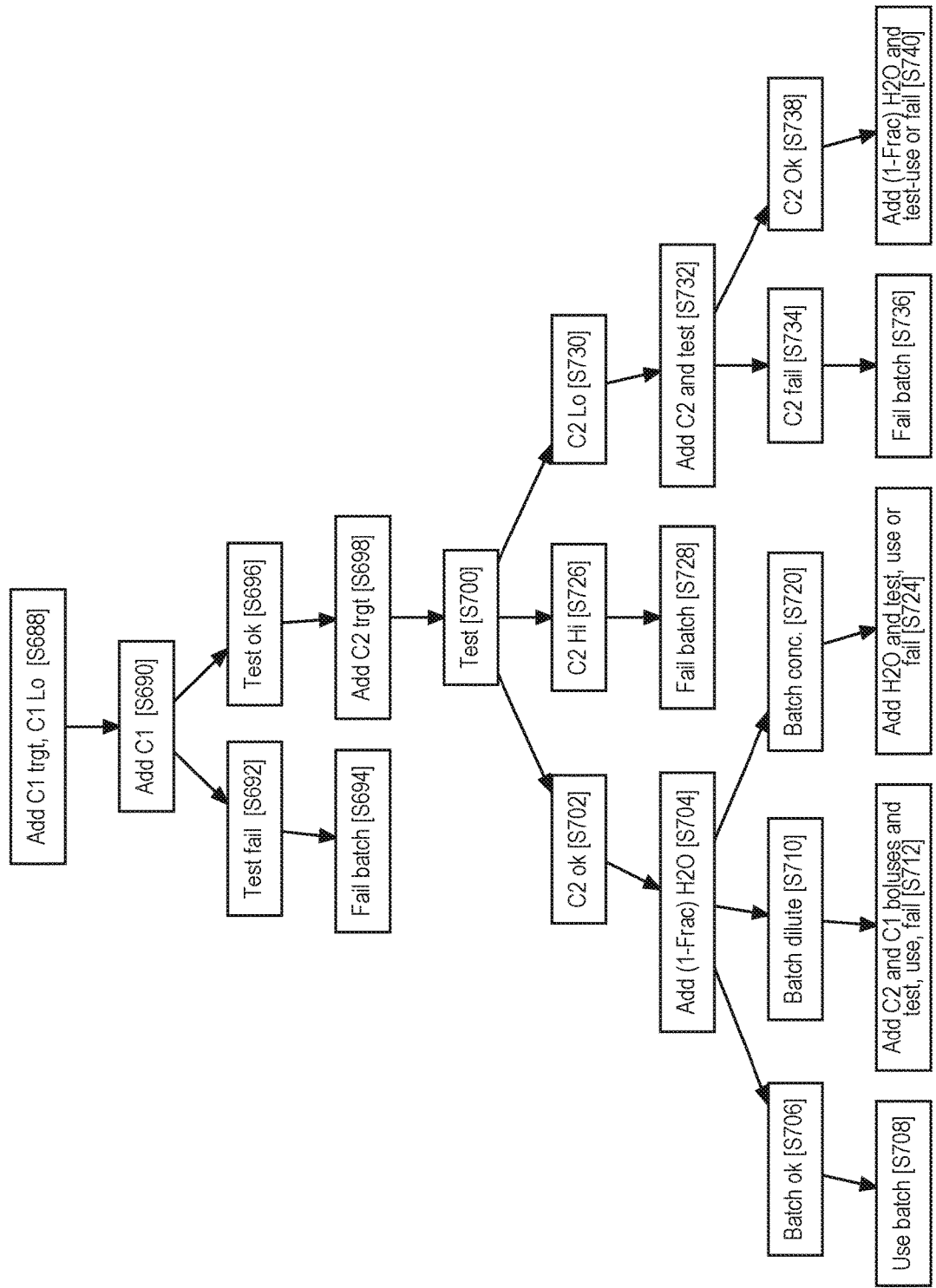

FIGS. 21A through 21C show, respectively, correction procedures for recovering from incorrect conductivity measurements in the preparation of a batch of dialysate by proportioning two concentrates and water. FIG. 21A shows the flow from, after initially adding up to 100% of the required amount of water to the mixing container (Refer to FIG. 18A, for example, noting that the method of FIGS. 21A through 21C can be used with other embodiments). Initially, before S602, a fraction (less than 100% of target quantity) of water is added to the mixing container, then at S602, a first concentrate is added, mixed, and a conductivity detected and determined to be within the expected range (C1 ok). Note that S648 (FIG. 21B) corresponds to the condition where conductivity after mixing the initial amount of water and the first concentrate is out of the expected range such that the added quantity of the first concentrate indicated to be too high and S688 (FIG. 21C) where the conductivity is out of range indicating the added quantity of the first concentrate was too low. In all three cases, water was added to the mixing chamber, the contents mixed, and the conductivity tested.

At S606, 100% of the second concentrate C2 is added to the mixing container. At S608 the mixing chamber contents, with the added second concentrate C2, is tested and conductivity found to be within the expected range. S628 corresponds to the condition where conductivity is out of the expected range and the added quantity of the second concentrate indicated to be too high and S634 corresponds to where the conductivity is out of range indicating that the added quantity of the second concentrate was too low. At S610, both the first and second concentrates were added in the correct amounts and the balance, if any, of the water is added to the mixing container and the mixing container conductivity tested to confirm its usability. At S612, the conductivity is in the expected range indicating proper dilution. If 100% of the water was previously added prior to S602, then the test can be omitted. S616 and S622 correspond to over-diluted and under-diluted conditions, respectively. If the batch is the correct dilution, then at S614 it is made available for use. At S616, if the batch is over diluted, there are two possible responses. The first response is that the batch can be indicated as failed and an output corresponding to recover operation can be output. Alternatively, additional concentrates in the same proportion as the target, can be added sequentially to the mixing container as indicated at S618, after which, at S620, the batch is tested again for conductivity and if it fails, the batch is failed or if the conductivity is in range, the batch is made available for use.

Returning to S628, the condition where conductivity is out of the expected range and the added quantity of the second concentrate indicated to be too high, at S630 an additional quantity (bolus) of each of the first concentrate and water are calculated in the target proportions to bring the proportions of these and bring the mixing container contents to the expected range of conductivity. Then, at S632, the balance, if any, of the water is added to the mixing container plus the water bolus plus the first concentrate bolus (calculated at S630) and the batch's conductivity tested S634 to confirm its usability. If the conductivity is in range, the batch is made available for use otherwise the batch is failed.

Returning to S634, the condition where conductivity is out of the expected range with the added quantity of the second concentrate indicated to be too low, at S636 an additional quantity (bolus) of the second concentrate is calculated to achieve the target proportion to bring the mixing container contents to the expected range of conductivity. The conductivity is tested again. If the conductivity is not in the expected range, then at S638, the batch is failed, otherwise S642, the balance, if any, of the water is added to the mixing container at S644 and the contents conductivity tested S646 to confirm its usability. If the conductivity is in range, the batch is made available for use otherwise the batch is failed.

Returning to S648 and FIG. 21B, which corresponds to the condition where conductivity after mixing the initial amount of water and the first concentrate is out of the expected range such that the added quantity of the first concentrate is indicated to be too high, correction begins at S650. At S650, boluses of the second concentrate and water are calculated to bring the proportions to the target and at S652, the total quantity of the first concentrate plus this bolus are added to the mixing container. The mixing container contents are then tested at S654 and if in range, meaning the second concentrate is in the correct proportion to the first, S656, the balance of the water plus the water bolus are added and the batch tested at S658. Note that the expected conductivity at S656 corresponds to a higher concentration of the second concentrate than if the first concentrate had been added in the correct amount because the water bolus is not yet added at this point. The reason for delaying the water addition is that optimally additions to the mixing container contents are scheduled to coincide with the point at which the fluid circuit is primed with the fluid corresponding to the one to be added to minimize the time spent priming between switchovers. If the batch conductivity is in the expected range S660, then the batch is released for use. If the batch is over-diluted S664, boluses of the first and second concentrate in the required proportion may be added and the batch further tested at S666 where, if it the conductivity is again out of range, the batch will be failed. In an alternative embodiment, at S664, the batch is simply failed without taking any step to correct. If the batch is under diluted S668, a bolus of water may be added and the batch further tested at S670 where, if it the conductivity is again out of range, the batch will be failed. In an alternative embodiment, at S668, the batch is simply failed without taking any step to correct.

If the quantity of second concentrate added was indicated by the conductivity measurement S654 to be too great at S672, then at S674, the batch is failed. In alternative embodiments, a correction may be performed by adding proportionate boluses of water and the first concentrate. In the present embodiment, errors in the first and second concentrate additions both occurred indicating the potential for a system problem, so the system may fail the batch and provide instructions for testing the system or replacing the fluid circuit, which may be the source of the problem. The controller may perform this as part of a batch fail recovery process. If the quantity of second concentrate added was indicated by the conductivity measurement S654 to be too low at S676, then at S678, the batch proportions may be recovered by adding a bolus of the second concentrate at S678 and testing again. If the conductivity of the mixing container is again out of range, the batch is failed at S682; otherwise, at 686, the balance, if any, of the water is added to the mixing container and the contents conductivity tested to confirm its usability and made available for use, unless the batch failed based on the outcome of the conductivity test.

Returning to S688 and FIG. 21C, where the first concentrate added was found to be too low, at S690, since the system is already primed with the first concentrate, an additional amount can be calculated from the conductivity and added. No additional bolus of water is required. The mixing container contents are sampled at S690 and if the conductivity is out of range at S692, then the batch is failed. If the conductivity is in the range S696, the second concentrate target amount is added S698 and tested S700. If the mixing container contents conductivity shows that the correct amount of the second concentrate was added S702, then the balance, if any, of the water S704 is added to the mixing container and the batch contents' conductivity is tested to confirm its usability, and is made available for use if within range S706. If the mixing container contents conductivity is not in range, and the batch is found to be too dilute S710, then boluses of the first and second concentrates are calculated and added S712 and the batch is tested and used or failed based on the result. If the batch is found at S704 to be overly concentrated, then the conductivity measurement is used to calculate a water bolus S724, which is added, and the contents are tested and used or failed depending on the result.

If at S700, the second concentrate amount added to the mixing container was found to be too high S726, then the batch is failed at S728. Again, this would be caused by two concentrate measurement failures. If at S700, the second concentrate amount added to the mixing container was found to be too low S730, then additional second concentrate is added at S734, the batch is tested, and if the conductivity is out of range, the batch is failed S736. If at S732, the conductivity is in range, then the balance, if any, of the water S740 is added to the mixing container and the contents conductivity is tested to confirm its usability and is made available for use if within range.

In alternative embodiments, instead of the procedure being based on the premise that the volume of concentrate is incorrect, the error may be presumed to be the concentration (or "strength") of the concentrate. The embodiment of FIG. 25 describes an example of a procedure based on this presumption.

Figure 22A:
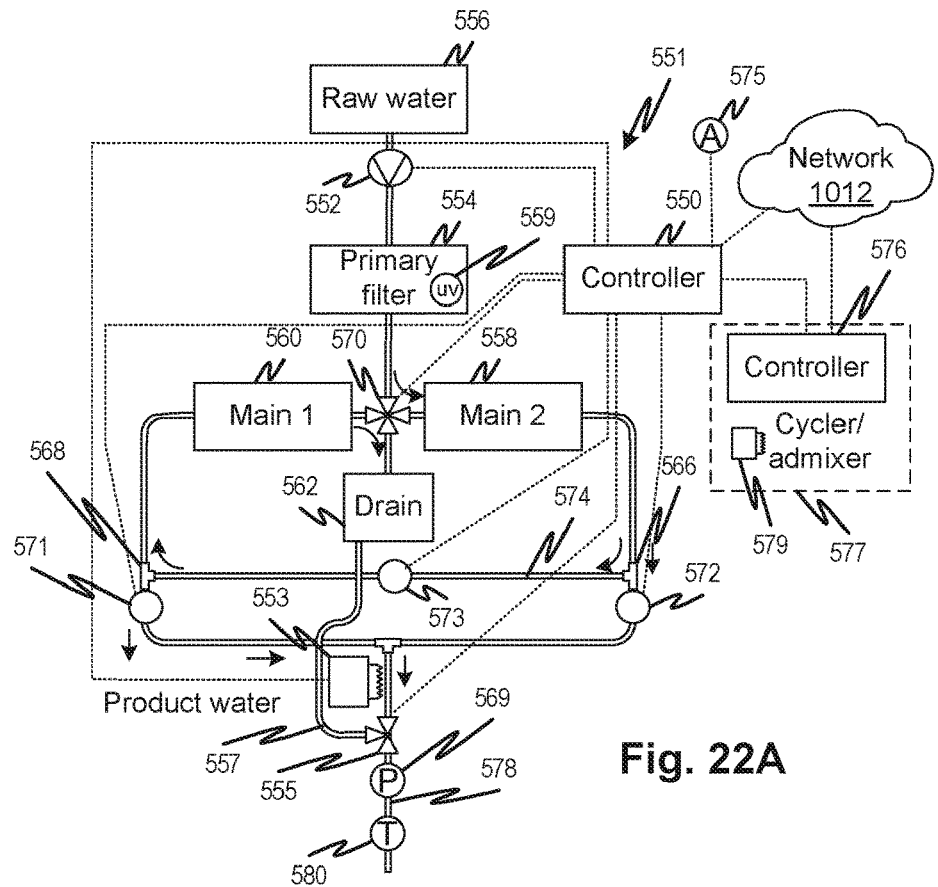
FIGS. 22A and 22B show a water filtration system with flushing and priming modes controlled by a controller which is commanded by a cycler controller according to embodiments of the disclosed subject matter with FIGS. 22A and 22B showing production with flushable filters.
Figure 22B:
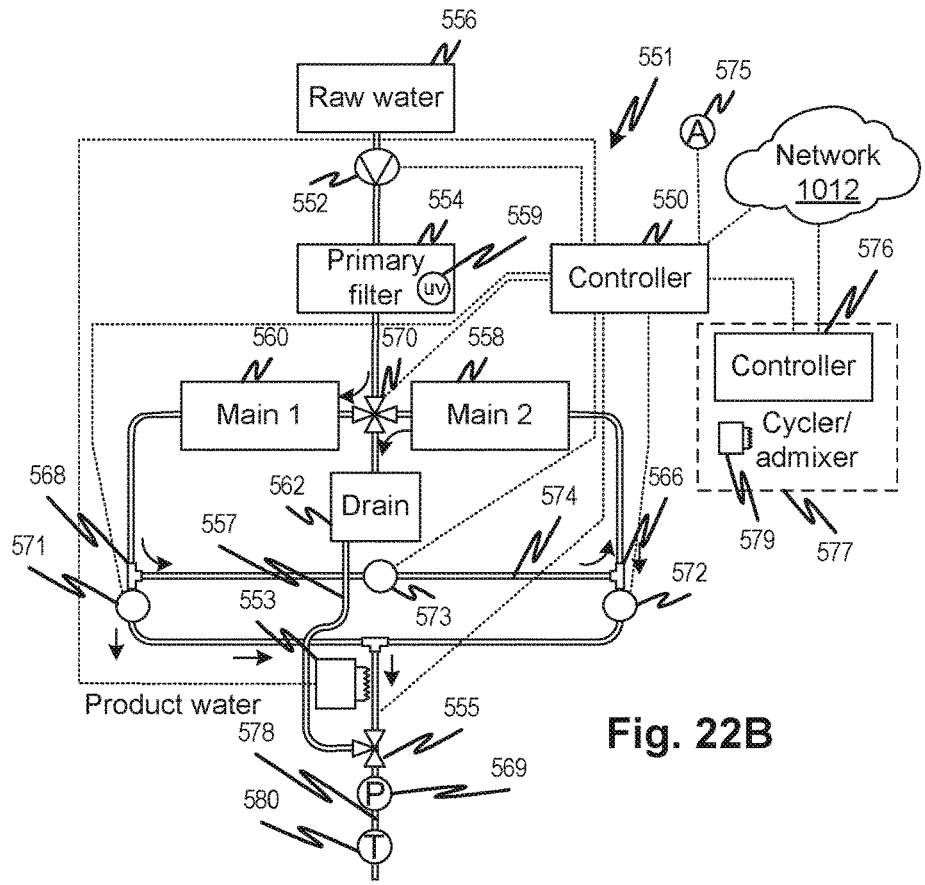

FIGS. 22A and 22B show a water filtration system 551 with cleaning and priming modes controlled by a water system controller 550 which is commanded by a proportioner/cycler controller 576 according to embodiments of the disclosed subject matter. A source of raw water 556, such as a source of potable water, is pumped by a pump 552 through a primary filter 554 which is not cleaned or regenerated, and then through a selected one of a pair of filters 558 and 560 which can be cleaned or regenerated. At any given time, the water system controller 550 controls the pump, a four-way reversing valve 570, and flow restrictors 571, 572, and 573 to direct a forward flow of the output of primary filter 554 through one of the filters 558 and 560, and directs a reverse output flow through the other of the filters 558 and 560 to the drain 562, depending on its setting. Output of one the filters 558 and 560 is divided at a respective one of the junctions at flow restrictors 571 and 572 depending on settings of variable flow restrictors 571, 572, and 573 such that a fraction (from 0 to 100%) is directed through the branch 574 and a remainder toward the outlet 578 so that one filter can produce product water to clean the other and for release through outlet 578 while the other is being cleaned with product water. The settings of the flow restrictors 571, 572, and 573 make it possible to clean one filter with all the product water or for both filters to produce product water until a cleaning is required. In FIG. 22A, the arrows show the flow for forward flow through filter 558 and reverse flow of filtered product water from valve 566 and 568 flowing through the filter 560. In FIG. 22B, the arrows show the flow for forward flow through filter 560 and reverse flow of filtered product water from valve 566 and 568 flowing through the filter 558. The flow restrictors 571, 572, and 573 may be controlled by the water system controller 550 which in turn may be commanded by the proportioner/cycler controller 576 of the proportioner/cycler 576 which may be configured according to any of the embodiments disclosed or referenced herein or others.

In addition to the cleaning mode, the water filtration system 551 may also have a flushing mode in which water that has remained for too long in the system is diverted by a diverting valve 555 to the drain 562. This operation may be performed on a periodic basis or in response to a condition (such as a time since last use) under control of the water system controller 550 of the cycler controller 576. In addition to cleaning and flushing modes, the water filtration system 551 may also have priming mode wherein raw water is pumped through both filters 558 and 560 in a forward direction with flow restrictor 573 set to fully open and flow restrictors 571 and 572 alternating between fully open and partially restricting so that the branch line 574 is primed. In this mode, all flow may be directed through the drain line 557 by a diverting valve 555. An air or other type of detector may be provided in the drain line 557 to indicate when the water passing through has been sufficiently cleared by priming. The filters 558 and 560 may also be reverse flushed to drain during the priming sequence.

The filtration system 551 may also have a primary filter stage 554 with, for example, an ultraviolet lamp 559 that is controlled by the water system controller 550. The water system controller 550 may optimize lamp life by regulating the lamp's 559 output so that it is cycled on when required (e.g., when water is flowing) and turned off when water is not flowing. The controller 550 or 576 may be configured to turn the ultraviolet lamp 559 on just prior to the water pump activation to ensure that its output is applied to all water flowing through the stage.

The filtration system 551 may have an off mode, a sleep mode, and an operating mode. In the off mode, the water system controller 550 and controlled flow restrictors 571, 572, and 573, the pump 552, the valves 555 and 570 may all be powered down. From the sleep mode, these may be powered up with the water system controller 550 in a mode in which it can immediately accept commands and act accordingly. The sleep mode may also include regulating the pressure and primed state of the water lines such that there is minimal delay from the receipt of the command to pump and deliver product water and the actual output. The water source controller 550 may transmit to the proportioner/cycler controller 576 a signal indicating a ready status. The water source controller 550 may transmit a signal, either unprompted or in response to a request from the proportioner/cycler controller 576 indicating its operating state. For unprompted signaling, the water source controller 550 may transmit a heartbeat signal that contains the state of the water filtration system 551. This heartbeat signal may be periodically cast to the proportioner/cycler controller 576 where communication is unidirectional from the water source controller 550 to the proportioner/cycler controller 576. Such cases may be relevant for configurations in which the water source controller responds to direct measurements such as pressure signals as described in connection with FIGS. 19A through 19M embodiments. A state signal can indicate various state information such when the water filtration system 551 is performing a flushing or priming operation or in another non-ready state, the water source controller 550 may transmit a state signal indicating so. Additional state information may include time left on the filters, expiration of filters, diagnostic information such as time taken for priming and flushing operations, smoothness of pressure regulation, power consumption, duty cycle of the system over a predefined period, and other information.

The water source controller 550 may regulate the pump and flow restrictors 571, 572, and 573 to maintain a target pressure at the product water outlet 578. This may be based on a closed loop control method with a target pressure which may include and range (deadband). At 569 a pressure sensor is indicated in the product water outlet line 578.

The water source controller 550 and proportioner/cycler controller 576 may communicate by any suitable device or system. That communication may unidirectional or bidirectional as indicated above. Either or both of the water source controller 550 and proportioner/cycler controller 576 may be of the various forms described with reference to FIG. 14.

The water source controller 550 may activate an alarm 575 in response to any conditions indicating a need for intervention or change of configuration. For example, the water source controller 550 may activate an alarm output 575 such as a general purpose user interface (See for example, display 1018 and speaker 1024) or special purpose output such as a lamp or annunciator. The water source controller 550 may also, concurrently, output any alarms to its communications link to the proportioner/cycler controller 576. The latter may command the water source controller 550 to suppress alarm outputs, delay alarm outputs by a predefined interval, or to perform other actions associated with alarms such as the suppression of the local output from the alarm output 575. In addition to outputting alarms to the proportioner/cycler controller 576, the water source controller 550 may also transmit instructions for use or instructions for alarm condition recovery to the proportioner/cycler controller 576 for output and use by a user interface of the proportioner/cycler controller 576. The user interface of the proportioner/cycler controller 576 may transmit commands back to water source controller 550 as well by generating an alarm handler input/output session on the proportioner/cycler controller 576. One mechanism for doing this is for the water source controller 550 to generate a remote session on the user interface of the proportioner/cycler controller 576 whereby the water source controller 550 has an ability to control the output and respond to inputs such as mouse and keyboard input, directly, by replicating an adapted model of the user interface it generates internally on the user interface of the proportioner/cycler controller 576 functioning as a thin client, effectively. The user interfaces of the water source controller 550 and proportioner/cycler controller 576 are not shown but may be understood to have one or more of the aspects described with reference to FIG. 14. The water source controller 550 may also generate a troubleshooting session on the proportioner/cycler controller 576 in the same manner or by simply outputting informational data and instructions in the form of a decision tree for output and control by the water source controller 550.

In alternative embodiments, the water source controller 550 outputs a uniform resource locator (URL) with metadata indicating the condition to which it pertains, for example, a set of conditions may indicate an urgency or priority of the information contained in the URL. The metadata may be sent in preceding message or may be combined with the URL. The proportioner/cycler controller 576 may have a priority table stored within that indicates how the proportioner/cycler controller 576 handles the URL (or other alarm data) to allow the proportioner/cycler controller 576 to determine whether the URL should be accessed and displayed immediately, right after a current input/output session, or output only after a certain condition is detected by the proportioner/cycler controller 576. In embodiments, the instructions for troubleshooting the water filtration system 551 are stored in the proportioner/cycler controller 576 and their output is initiated by the receipt of alarm data from the water source controller 550.

In addition to the above functions, the proportioner/cycler controller 576 may indirectly control the water source controller 550 to control a product water heater 553 according to certain commands from the proportioner/cycler controller 576. For example, the proportioner/cycler 577 may be provided with a fluid heater 579. Such a fluid heater, as known in various prior art embodiments of peritoneal dialysis cyclers, may be provided to raise the peritoneal dialysis fluid to body temperature. Such heaters as 579 may be instantaneous or batch heaters. The heater 579 may heat incoming water, mixtures of concentrate and water such as ready-to-use medicament, or precursor fluids such as partially diluted concentrate, or combinations of these. The power requirement of a cycler-based heater must be sufficient to raise the temperature from room temperature to body temperature because typically ready-to-use bagged dialysis fluid is used for treatment. However, in the system of FIG. 22A/22B, the water temperature may be lower than that, for example it may be at ground temperature or even near freezing as may come from a domestic tap. In order to reduce the peak power requirement of the proportioner/cycler 577 heater, at least part of the heating burden may be shared by the product water heater 553. Note that product water heater 553 may be located at other positions in the flow of water such as the raw water inlet or elsewhere. The product water heater 553 may be commanded indirectly by the proportioner/cycler controller 576 to provide a predefined power output or delivery temperature. In the case of the latter, the product water heater 553 may be closed-loop controlled by the water source controller 550 or another controller on a detected output temperature by a temperature sensor 580.

The proportioner/cycler controller 576 may also receive status information from water source controller 550. Such information may include indications that the water filtration system 551 is in flushing, priming, or cleaning mode. Other information may include water temperature, estimate of time till ready, estimated time left till filter replacement (estimated time to exhaustion), time on the UV lamp 559, time till next flush or cleaning cycle, and whether the water filtration system 551 is in sleep mode and how long the before it is available to produce water. This information, because it may indicate reasons for delay, may be useful to provide in real time to a connected patient through the user interface of the proportioner/cycler controller 576. Additional information output to the proportioner/cycler controller 576 user interface may also include forecasting of maintenance tasks such as filter replacement and ultraviolet bulb 559 replacement. One or more resistivity sensors may be provided in the product water outlet line 578, which may be connected to the water source controller 550 with the resistivity transmitted as status information to the proportioner/cycler controller 576 and relevant synthesis of this information output on a user interface. For example, such a synthesis may be the display of an alert when the resistivity is out of bounds. The raw water resistivity may be similarly monitored. Since the lifespan of the filters may be affected by the raw water quality, this information may be provided to the proportioner/cycler controller 576 and relevant outputs generated in response to it. For example, the proportioner/cycler controller 576 may alert the user to a low water quality level in the supply which may be mitigated by changes in infrastructure and at least warn the user that filter replacement may need to be frequent.

Some of the functions of the water filtration system 551 can be scheduled with some flexibility without seriously impairing its ability provide purified water or causing premature exhaustion or failure of components such as filters. For example, functions whose timing may interfere with a patient's lifestyle may be moved up or delayed in order to permit the patient to be treated on a schedule that better fits the patient's life schedule. The user interface of the water source controller 550 or the proportioner/cycler controller 576 may provide a control to allow the user to enter scheduled events such as treatment time, treatment duration (e.g., wakeup time), and time ready for treatment (which requires the line to be primed and connected to the patient). In embodiments, relevant data such as the patient's treatment schedule may be entered in the controller, e.g., the proportioner/cycler controller 576. In further embodiments, the patient's treatment schedule may be stored over time and used to estimate future treatment schedules including connect time, bedtime, treatment start time, wake time, treatment end time and any other events associated with treatment and maintenance normally indicated by the respective controllers (550, 576). The respective controllers 550 (or indirectly as commanded through proportioner/cycler controller 576) may be controlled to run flushing and cleaning modes at times that lie between certain interfering events such as treatment or to prime the water system a certain interval ahead of a predicted connection of the patient to the proportioner/cycler 577. Note that in embodiments, the water filtration system 551 may have a reservoir to receive product water for use on-demand by the proportioner/cycler 577. The heater 553 may, in such embodiments, be a batch heater that applies heat to the reservoir. In such embodiments, the water source controller 550 or proportioner/cycler controller 576 may schedule production and storage of purified water in the reservoir and heating thereof according to an estimated time of use for treatment. Such a reservoir may be a disposable component, for example a plastic bag. The reservoir may be sized to receive water for a single cycle, part of a cycle, or multiple cycles of a full treatment. A reservoir may be provided with a sterilizing filter on its inlet (for touch contamination), its outlet (to block back-growth contamination), or both. Check valves may be provided on inlets or outlets or both to prevent backflow. A predefined pressure at the outlet of the reservoir may be maintained at a constant level by means of a recirculation loop with a check valve having the predefined cracking pressure.

The water filtration system 551 illustrated shows a very basic example. Many purifiers that create water suitable for peritoneal dialysis involve many stages, each with filters having different lifetimes which may be affected by the quality of the raw water. In embodiments, the controllers 550, 576 indicate estimated exhaustion events for filters such as reverse osmosis membranes, carbon filters, ultrafilters, deionization resin beds, sediment filters, or other consumable types of filters. The indications may be based on time, raw water quality, number of cleaning cycles, etc. Either controller 550 or 576 may be programmed to order replacements for such consumable components and/or consumable supplies used for treatment automatically. For example, commands for ordering supplies may be sent to a server by means of the network 1012 (which may include the Internet). Failed components that are not consumables may also be reported and replacement parts ordered automatically along with repair orders in the same way.

Figure 22C:
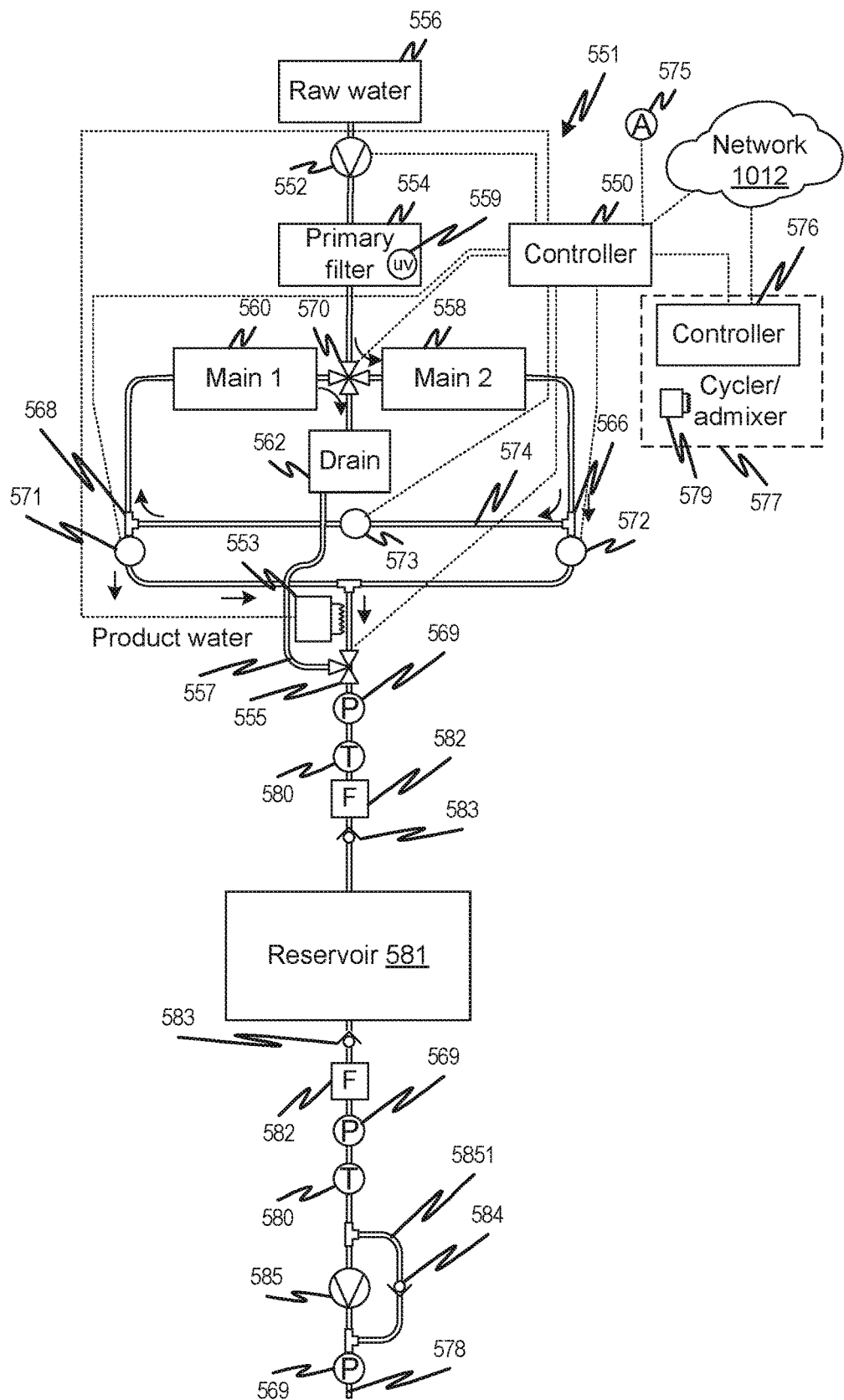
FIG. 22C shows multiple additional features that may be added to form variations of the various embodiments disclosed herein, including those of FIGS. 22A and 22B.

FIG. 22C shows the water source and associated systems similar to the embodiment of water filtration system 551 described with reference to FIGS. 21A and 21B. A reservoir 581 is fluidly connected to receive product water filtered through a sterilizing filter 582 and a check valve 583. The water is supplied to the proportioner/cycler 577 through an outlet 578 under a predefined pressure maintained by a loop S851 containing a pump 585 and a check valve 584 with cracking pressure set at the predefined pressure. Pressure 569 and temperature 580 sensors may be located at various positions, including one located to monitor the predefined pressure. An error in the detected versus expected predefined pressure may be output as an alarm condition. Other filters 582 and check valves 583 may be provided to prevent grow-back contamination and to prevent back flow, respectively.

Note that where both controllers are referenced together as controllers 550, 576 it is intended to refer to either water source controller 550 or the proportioner/cycler controller 576 acting as a command controller and the other acting as a slave depending on whether the function is performed directly or indirectly by the controller and on whether the function is performed by the proportioner/cycler 577 or the water filtration system 551.

Note that in all the embodiments herein where a cycler is described, a proportioner/cycler may be substituted, i.e., a device that performs as a peritoneal cycler as well as a fluid proportioning device (aka a proportioning device). Note that in all the embodiments herein where a proportioner/cycler is described or identified, a cycler or proportioning device (also called proportioner) may be substituted. Note that in all the embodiments herein where a proportioner or proportioning device or system is described or identified, a cycler or a proportioner/cycler may be substituted.

Note that the present application has generally avoided the terms such as "admixing" to make the present application clearer. The term "admixing" is suggestive of an intermediate mixture of fluids rather than a final mixture such as ready-to-use peritoneal dialysis fluid.

For example, in the present application, applicants have used the term proportioning instead admixing because admixing implies the making of an intermediate product. The term proportioning implies a more general process such as the making of an intermediate product (an admixture) or a final product such as a ready-to-use peritoneal dialysis fluid. Thus, the term proportioning suggests something more general and is adopted in the present application where in the priority application, the term admixing was also used in this broader sense. Thus usages of terms such as "admix," "admixing," and "admixer" in the priority applications refer to corresponding terms such as "proportion," "proportioning," and "proportioner" in the present application. The differences in the terms does not modify the subject matter relative to the priority applications. The priority applications simply used "admix," "admixing," and "admixer" and related terms in a broader sense.

According to the above embodiments, especially those discussed with reference to FIGS. 19A-19M and 22A-22C, there are provided the following features and embodiments of a system that includes a water source system with a controller in combination with a proportioner/cycler or cycler, also with its own controller.

The water system pumps water in response to a demand signal communicated via a fluid connection between the water system and the proportioner/cycler. The demand signal may be a detection by the water system controller of a change in pressure generated by the proportioner/cycler. The pressure change may be generated by the cycler pump operation, where the cycler pump is one that is used for fill and drain of a patient peritoneal cavity, or a pump (if different) used for proportioning, or some other pump controlled by a proportioner/cycler controller. The pressure may be a draw-down of pressure caused by forward operation of the proportioner/cycler pump. The water source may have a pump which may start when a pressure sensor in a connection to the proportioner/cycler water system passes a particular (negative) threshold. The water source may have a pressure sensor that detects and conveys signals by way of pressure pulses to the water source controller which decodes them into specific predefined commands One command may be for the water source to start pumping product water into the connection to the proportioner/cycler. Another command may communicate a value and command to which a closed-loop control pressure target of the water source outlet should be reset. Other aspects of the water source may be commanded, such as a time for the water system to flush, clean, or prime, a future time of treatment, and other parameters identified above. As for closed-loop control of a water source pump, the speed of a water pump that pushes water through one or more filters may be adjusted automatically in response to an outlet (outlet being the interface to the proportioner/cycler) or other intermediate pressure of the water system. The pressure pulses may be generated by a selected one (or more if present) cycler/admixer pump(s) that is/are positioned to influence the pressure at the outlet of the water source. For example, pulses may be generated by modulating driving power of a pump actuator in a stepwise fashion.

In other embodiments, the water source receives commands from the proportioner/cycler. In embodiments, such commands are transmitted and/or exchanged between the water source and the proportioner/cycler by any suitable means for exchanging digital data including wired and wireless. In embodiments, the proportioner/cycler may control the timing, duration, and type of all water source functions including priming and flushing operations. In embodiments, the water source controller indicates to the proportioner/cycler controller its status including an indication that it is ready to output product water. In embodiments, the proportioner/cycler controller starts and stops water production. In embodiments, the proportioner/cycler transmits commands to start and stop an ultraviolet (germicidal) lamp in the water source. In embodiments, the commands may be adapted for extending the life of such an ultraviolet lamp by ensuring it is operated and ready only when required for treatment of water. The proportioner/cycler may use two-way communication with the water source to place it in a sleep mode at end of a treatment such that some or all power functions are switched off to save power and reduce wear. The proportioner/cycler may send commands to wake up the water source so that it is ready at a time of a predefined treatment stored in the proportioner/cycler. Commands from the proportioner/cycler may also be used to regulate the pressure and flow rate at which product water is delivered. As indicated above, closed loop control based on a pressure signal may be provided by the water source controller. The two-way communication may support the transmission of alarms generated by the water source and the proportioner/cycler may respond by ceasing dialysate preparation in response to predefined alarms. Alarm or status outputs of the water source may be used to generate specific outputs through the proportioner/cycler user interface which may have audio and visual output capability. The proportioner/cycler user interface may output guided troubleshooting steps in response to and related to the water source outputs and alarms, and these may be output to a patient or operator. The output may be attended by the presentation of input controls to receive relevant feedback to create a guided session. Feedback may include answers to questions about the system such as the observations about the status of the parameters being checked, such as closure of fluid connections, proper electrical connections, proper mating of tubing with actuators, and instructions to skip to certain steps.

The proportioner/cycler may control the water source heater and receive indications of power output, temperature, and ready status. The total heat required by the product dialysate may be shared by the water source and the proportioner/cycler so that the power required of either is split between the water source and the proportioner/cycler. This may be relevant where the proportioner/cycler heater power is sized to raise the temperature of premixed dialysate from room temperature to body temperature so that the additional power required to raise the temperature of water from a tap temperature (which may be very low in some cases, such as in northern climates where water mains can have temperatures near freezing) to room temperature may be borne by the water source heater. The water source consumable component status (predicted or indicated by sensors) including carbon filters, deionization resins, ultrafilters and others may be indicated by the water source to the proportioner/cycler and output by the latter's user interface to inform a user or patient of the need for maintenance and resupply. The controller of the water source or proportioner/cycler may be programmed to auto-order replacements through the Internet. The timing of such auto-order replacements may be done to effect the required change-out before exhaustion. The estimated time for a needed replacement may be responsive to the disposable consumption rate, therapy frequency, raw water quality, and order processing/delivery lead times.

The priming of the proportioner/cycler may include priming and flushing with water from the water source. The proportioner/cycler controller may transmit commands to the water source controller to output water at pressures and flow rates required for the proportioner/cycler to perform these functions. The priming may be preceded by a flushing operation with purified water to reduce the potential presence of endotoxins in the disposable fluid circuit.

The water source may include a reservoir sized to provide water sufficient for a fill/drain cycle or for a full treatment (multiple fill/drain cycles). The reservoir may have one or more sterilizing-grade filters on its inlet (and/or outlet) lines to prevent touch contamination or back-growth contamination. The reservoir may include one or more check valves on its outlet lines to prevent backflow. The disposable reservoir outlet may include a recirculation loop with a pump that maintains a target head pressure useful to maintain consistent dosing.

Figure 24:
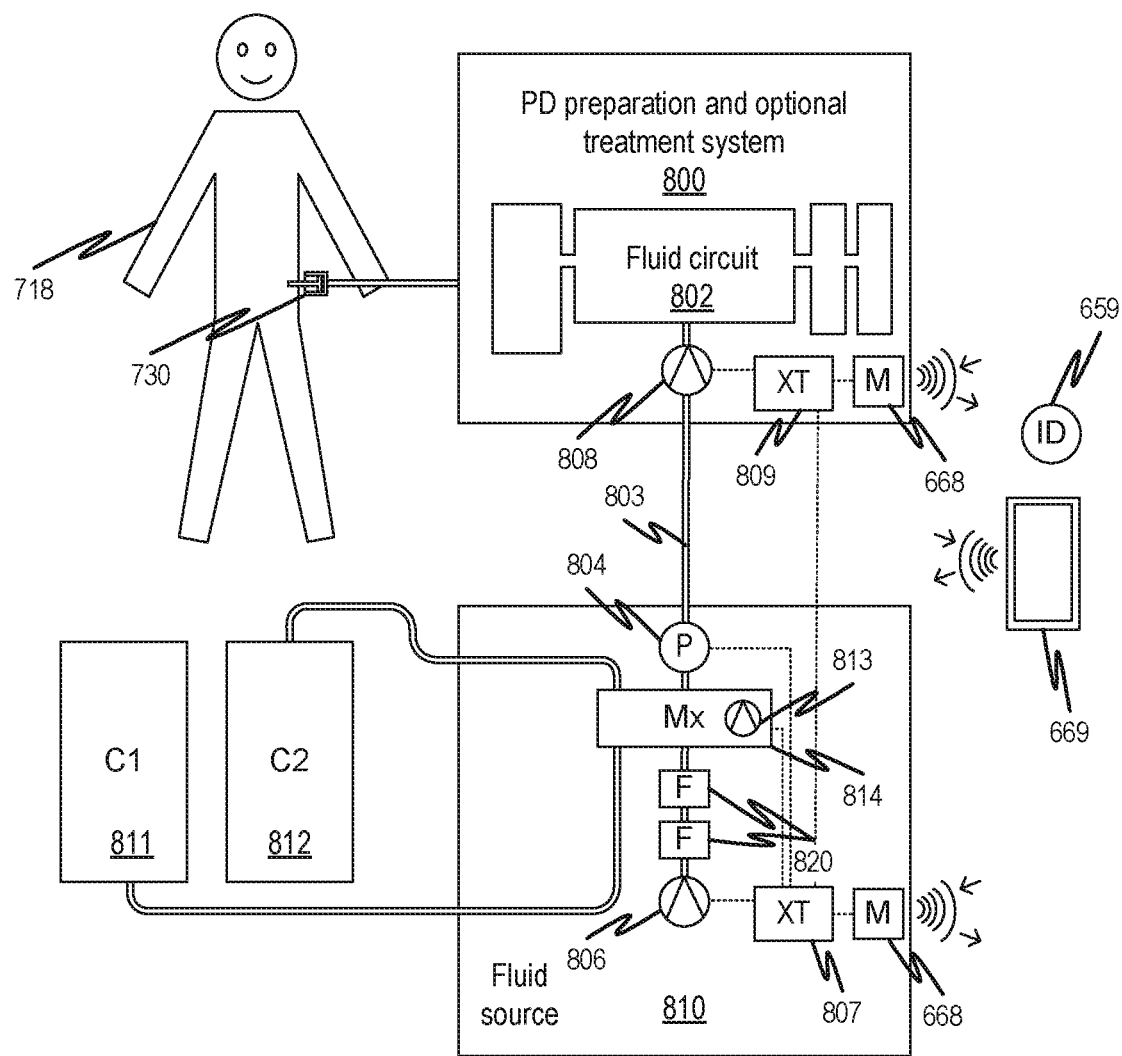
FIG. 24 shows a peritoneal dialysis system connected to a remote device for purposes of describing various features that may be used with the disclosed embodiments to form additional disclosed embodiments.

Referring now to FIG. 24, the proportioner/cycler 800 with the pump 808 and fluid circuit 802 is provided for mixing fluids and for performing a peritoneal dialysis treatment. The proportioner/cycler 800 has a controller 809 for controlling operations involving the fluid circuit directed at generating dialysate and performing an automated treatment. The fluid source 810 pump 806 conveys fluid to the peritoneal dialysis fluid preparation device 800 through a fluid line 803. A pressure sensor 804 detects pressure in the fluid line and applies a corresponding signal to a controller 807 of the fluid source 810. The controller 807 controls a fluid multiplexer 814 that direct a selected one of water, a first concentrate 811 and a second concentrate 812. The multiplexer 814 may have a pump 813. The controller 807 also controls the pump 806 or pumps 806, 813. It will be observed that this is a generalization of embodiments described elsewhere herein. Each of the controllers 807 and 809 has a respective communications modem 668 to permit each to communicate wirelessly with a mobile terminal 669 using a wireless protocol such as near field communication (NFC). In other embodiments, the mobile terminal is substituted with another type of data-bearing device such as a bar code, a QR code, a radio frequency identification device (RFID), or a battery powered transponder. Note that in embodiments, only one modem is used to transfer information to one of the controllers 807, 809 which transfers information to the other of the controllers 807, 809 by other means. The mobile terminal 669 may be a general or special purpose device such as an embedded system device, a tablet or a smart phone. The mobile terminal 669 may have an internal modem to permit it to communicate with the controllers 807 and 809.

In embodiments, the mobile terminal 669 stores prescriptions for a treatment that can be uploaded wirelessly to the controller 807 and 809. The prescriptions may contain parameters including proportions and dilutions of concentrate, tolerance of the proportions, and other information. The prescription may be encoded with information specifying the identity of a particular patient. A user of the mobile terminal 669 may be a patient, a caregiver, or a doctor. The mobile terminal may have a biometric authentication component such as an iris scanner, a fingerprint scanner, a face recognition algorithm, or other. A user may authenticate himself to enable the capability for a prescription transfer to a modem 668.

A token 659 may incorporate a NFC, Bluetooth, or other type of communications device to identify and track a person. For example, such a device may be worn by a patient. The controller(s) 807, 809 may confirm the identity of the patient before implementing an uploaded prescription. Such tokens may take the form of tags or labels. The token 659 may identify consumable materials used for treatment such as concentrates and fluid circuits.

As mentioned above, methods above may be based on the premise that the volume of concentrate is incorrect if a conductivity measurement indicates the target is not matched. This may instead be changed to a presumption that the error arises in the concentration (or strength) of the concentrates. Here the presumption is based on the observation that a long storage interval may cause evaporative loss from a typical bag-type container. This causes the concentration of the concentrate to be excessive. If the storage interval is much too high, the concentration may be non-uniform or the conductivity measurement may indicate excessive time in storage in which case the batch may be failed. The embodiment of FIG. 25 describes an example of a procedure based on this presumption.

Figure 25:
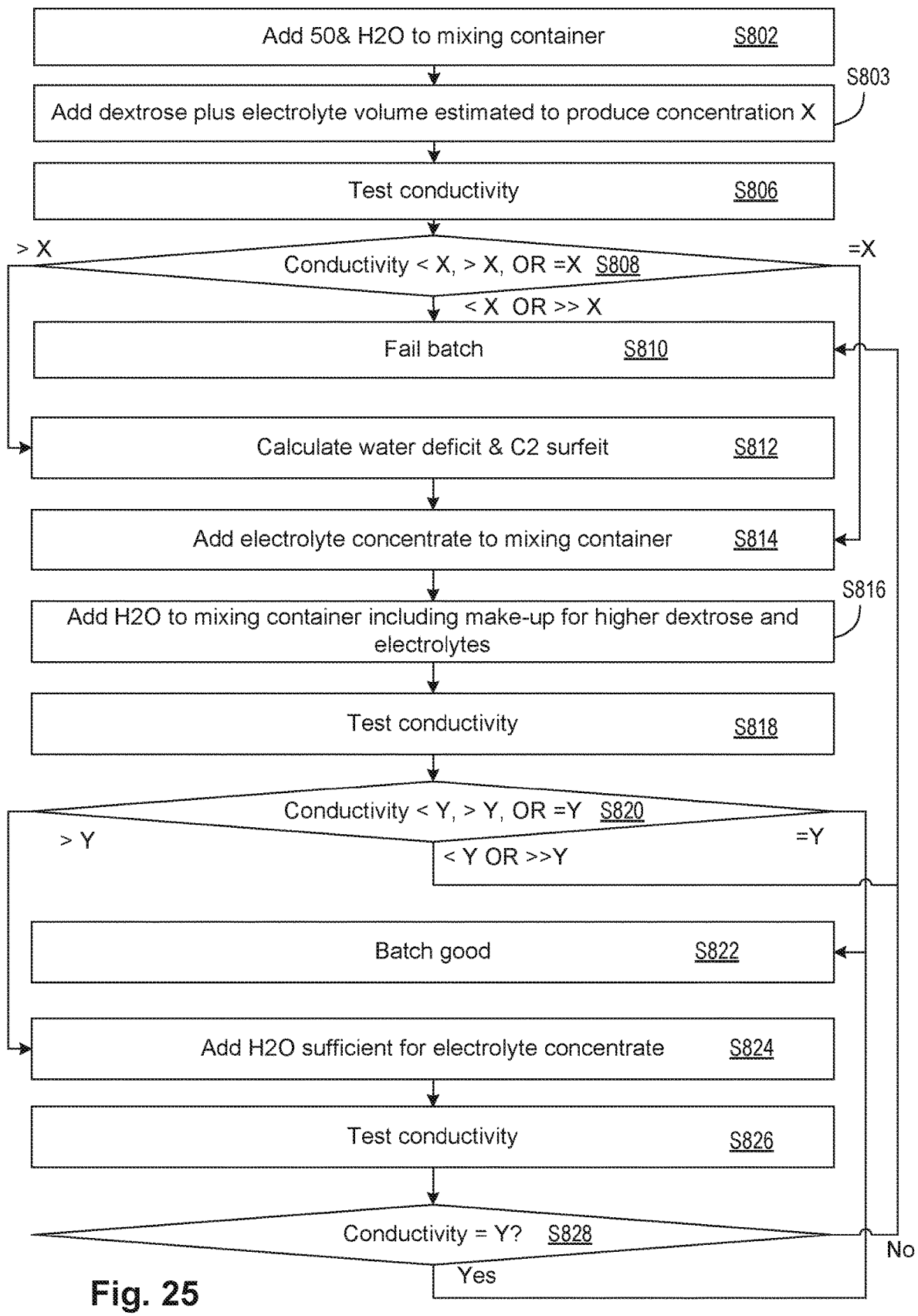
FIG. 25 shows a flow chart for describing an embodiment based on the premise that discrepancies between a measured conductivity and the expected conductivity result from a reduction in moisture content of one or both of the prepackaged concentrates, such as may result from moisture loss due to evaporation, according to embodiments of the disclosed subject matter.

Referring now to FIG. 25, at S802, after a command is received or generated by a controller, a fraction (alternatively, all) of a target quantity of purified water is added to a mixing container. The apparatus may be as described according to any of the embodiments disclosed or claimed herein. At S803, a quantity of osmotic agent and partial electrolyte concentrate may be added. In alternative embodiments, the electrolyte concentrate may be added first and later the osmotic agent with or without electrolyte may be added. As discussed above, since osmotic agent can have a conductivity signal-suppressing effect, the osmotic agent conductivity change can be used as an indicator of concentration. At S806, the conductivity of the mixing container contents is tested.

It is determined at S808 whether the concentration of the mixing container contents is lower than an expected target (X) or higher than X by a predefined amount, in which case the mixing container contents may be failed and not used at S810. Although not presently shown, it should be understood that an error output to a user interface may be generated by the controller which may include instructions for checking for certain faults in the system and instructions for recovery. A measured conductivity that is too high may also be identified and failed. If the concentration of the mixing container surpasses such a threshold it may indicate that the contents of the mixing container are insufficiently mixed. Thus, in alternative embodiments a modification may be included to retry mixing a predefined number of times. The batch may also be subjected to remix trials if the mixing container contents have a conductivity that is too low. This is not illustrated but may be added readily as a short additional flow. If the mixing retry attempts fail, the additional flow may terminate (after the predefined number of retries) and proceed to S810. If the mixing container contents conductivity is above X (in embodiments, within a predefined conductivity range), then at S812 the water deficiency may be calculated from the magnitude of the overage and used as a basis for estimating the water loss for the first concentrate (in this example, osmotic agent, but as indicated above, it could be electrolyte concentrate instead), as well as the second concentrate. The amount of the second concentrate (C2 in the figure) is also adjusted by this measure since to maintain the correct ratio of the two solutes, the amount of the second concentrate needs to be adjusted as well. This is discussed above. This overage estimate may thus be used to calculate the amount of additional water required to add in a final completion step in order to bring the conductivity to the desired level for a final treatment fluid. That is, the same estimate for water deficiency may be used to calculate a water deficiency for both concentrates (or the total number of separate concentrates according to the embodiment).

At S814, the proper quantity of the second concentrate, in the present example, the electrolyte concentrate, is added to the mixing container. As indicated, the quantity of the second concentrate is adjusted to account for the first concentrate overage as calculated in S812. At S816, water sufficient to make up for any deficiency calculated in S812 is added to the mixing container. Then at S818, the conductivity of the mixing container contents is tested, and at S820 the flow branches responsively to the result. The batch is failed if the target conductivity (Y) is too low or, optionally higher than a predefined level beyond the target Y. If the target Y is found, the batch is ready to use. If the conductivity is too high, at S824, additional water may be calculated and added. Then the conductivity may tested again and if it fails (< >Y) S828, the batch may be failed. S824-S828 may be omitted in embodiments.

Any of the methods for treatment fluid preparation described herein may be modified based in part on an analysis of the tolerance stacking. Such a stacking may take into account different kinds of variability, some of which are not straightforward to derive from the process itself. For example, the process analyzed may be defined between the manufacture of the input constituents, water and concentrates, and the provision of a final treatment fluid. However, the analyzed process here is defined to include detectable and correctable errors during the process that provisions the final treatment fluid and errors that result in alarms during treatment. The final impact of errors on the patient's safety along with any correction techniques may also be included in the analysis.

Tolerances may also include ranges resulting from variability in the manufacture of concentrate, which cannot be influenced, tolerances in testing of intermediate and final conductivities, measurement error, and the required tolerance range of the final product and any other sources of variability. The analysis can benefit from creative input and ultimately may result in an alteration of the methods. So, an effort was made to analyze the above methods based on tolerances throughout.

Note that in the above processes, adjustments to the C2 as a result of water loss may not be necessary. That is because the upward adjustment due to the higher concentration of C1 may be canceled by the downward adjustment due to predicted higher concentration of C2. So, the adjustments may be removed from the procedure of FIG. 25 in embodiments. However, in other embodiments, the cancelation may be incomplete if differences in the propensity for water loss of the two concentrates or their packaging are different.

Note that in embodiments, average preparation time for batches may be minimized by optimizing the initial quantity of water added to the mixing container at S802. In embodiments, adjustments may be found to be rare occurrences such that close to 100% of the water may be added initially with the expectation that few adjustments and retries will be required. In practice, time saved by adding 100% of the water at S802 may totally compensate for any occasional failed batches that cannot be adjusted to the expected concentration.

In any of the embodiments, where the description refers to the conductivity being equal to the target, it should be understood that "equal to" refers to a predefined range around the target. In embodiments, the range may be +/−5%, for example.

In any of the embodiments in which conductivity is measured, it should be understood that the conductivity may be numerically compensated for temperature deviation from a standard conductivity. In any embodiments in which the conductivity of the mixing container is tested, a mixing operation may be inserted. In addition, any mixing operation may include multiple mixing, testing, and remixing trials until a predefined number of retries is reached.

In any of the embodiments, any of the pumps may be, or include, any of a variety of types including peristaltic pumps, diaphragm pumps, screw pumps, gear pumps, centrifugal pumps, turbine pumps, syringe pumps, or piston pumps. The foregoing is a list of examples and is not intended to limit the scope of the present disclosure or the claims below.

In any of the embodiments, the containers of concentrate may be replaced with online sources of concentrate such as proportioning systems in a large-scale installation that mixes component ingredients to form concentrates and provides them from a fixed connector. In any of the embodiments, other sources of fluids may be connected to the fluid flow director embodiments described herein. Examples include cleaning fluids, reference testing fluids for calibrating the conductivity sensor or sensors, sample fluids, and fluids for testing membranes such as air. In any of the embodiments, such other fluids may flow through various parts of the fluid circuit including the drain as described with reference to other fluids.

As the term is used herein, "flow director" is a fluid circuit and associated actuators effective for selectively creating flow paths and moving fluids through the flow paths in order to connect fluid channels or vessels including those connected to sources and consumers, repositories, or other receiving elements. A "fluid circuit" is may be any line or branching element and may contain vessels, chambers, sensor portions, actuator portions, or any other type of fluid confining and controlling element.

Any embodiment which recites or shows tubes as portions of a fluid circuit, fluid channel, or other equivalent may have instead other types of fluid channel elements such as channels defined in a casting with a bonded film layer to close the channels, panels with welded patterns to form fluid channels, non-round ducts, or other types of elements. The disclosed tubes may be replaced with such alternative elements to form additional embodiments.

Any embodiment which identifies peritoneal dialysis fluid may be modified to form additional embodiments by replacing the components identified with that particular fluid with corresponding fluids to form other medicaments.

Any component or element identified herein as "disposable" may be sterile. Sterility may be readily provided and assured at a time of use, by providing components as disposable elements as is known in the relevant field of medical devices.

As used herein, "pre-connected" may refer to the integral combination of elements or to their connection in such a manner as to form a sterile boundary or permit the provision of a sterile boundary around their interior. For example, if a connection of connectors of two elements is made (i.e., they are pre-connected or pre-connected) and the connected elements are sterilized as a unit thereafter, the pre-connected or pre-connected elements may protect against the touch contamination that would be required if the corresponding connection were made in the field, for example. When elements are integral they may provide the same benefit.

As the terms are used herein, electrolyte concentrate may include various ionic species as well as non-ionic species as required. As used herein, osmotic agent concentrate may include any osmotic agent such as glucose or dextrose and may include other species including ionic species that may be characterized by the term "electrolytes."

Any of the embodiments expressly limited to "peritoneal dialysis fluid" may be modified to form additional embodiments by substitution of the term "dialysate" and making appropriate substitutions for the constituents. Any embodiments limited to multiple concentrates, including two, may be changed to employ a single concentrate that is diluted to form a ready-to-use medicament.

Any of the valves or pumps recited herein may be substituted for any of a variety of types of flow directing and fluid conveying devices. For example, a variety of pump and valve types are known and may be substituted for those described herein. Variations based on substitutions of these elements may be made to form additional embodiments.

As the term is used herein, "in-line" means that an element is in a flow path. For example, a flow channel with an in-line sterilizing filter is such that fluid flowing in the flow channel is filtered by the in-line filter.

A port is any transition for a fluid conveyance such as a channel, tube, integral connection, or connector. Any recitation of "port" may be replaced with the term "connector" to form variations of the disclosed embodiments.

As used herein, a window is any opening in a curved or flat element. A drain is any outlet to an external element and may include a storage vessel.

Any sterilizing filter may be embodied as a channel blocked by a microporous membrane. Such a microporous membrane may have pores whose maximum size is no greater than a minimum pathogen size. Known threshold pore sizes are, for example, 0.2 microns.

Any embodiment element identified with the term "daily" may be changed by substitution of other time intervals to form additional embodiments.

Integral or integrally attached refers to elements that are formed of a single piece or bonded together so as to create a single unit. Elements identified as integral may be changed to identify them as "connected" or "attached" to define additional embodiments.

As used herein, a "source" is any container or plant capable of supplying a recited fluid. A sink is any destination for a fluid such as a container, a consuming device, or a drain.

As user herein, a "line" is tube or other type of fluid channel. In any of the embodiments, lines may be tubes such as polymer tubing commonly used for medical disposable devices.

A "recess" is any concavity. A recess has two ends, an "access" which is the open end, and a "blind end," which is the closed end.

Any détente mechanism identified herein may be substituted with any type of frictional or interference-based mechanism for locking or restraining one element relative to another to form additional embodiments.

In any of the embodiments, including in the claims, where the integrity of a sterilizing filter is tested, the filter membrane may be subjected to a pressure-decay test or a bubble-point test. Other types of tests such as diffusion test and other known techniques may be used.

Any of the embodiments of a dialysis device may have a digital controller that directs the sequence of operation to perform a treatment on a patient may have a wireless interface that communicates with a transmitter such as a radio frequency identification (RFID) tag, Bluetooth, or a NFC device. Such a device may communicate with a wireless-capable appliance such as a cellular phone, tablet, or other computer. Using the transmitter, the dialysis device may transfer a digital record of therapy data, such as a treatment log, from the transmitter. If the transmitter includes a receiver or if a separate receiver is provided, then the dialysis device may be enabled to receive a prescription for a therapy. For example, a NFC tag or mobile phone may be used to upload data such as a prescription from a mobile or a passive NFC tag to the dialysis device. The upload of a data to the dialysis device may be accomplished using a passive tag such as an RFID or a passive NFC device.

Other information that may be uploaded to the dialysis device includes patient-identifying information as well as patient classifying information. The dialysis device may upload information about the dialysis system for diagnostic purposes using any of the wireless protocols. The dialysis device may transfer data by wireless protocols such as 802.11 a/b/g/ac/n and Bluetooth. The dialysis device may download system logging or diagnostic data from the dialysis device to the cellular phone, tablet, or other computer using any of the wireless protocols. The dialysis device may download treatment summary data to the cellular phone, tablet, or other computer using any of the wireless protocols.

According to first embodiments, the disclosed subject matter includes a method for making a batch of peritoneal dialysis solution sufficient for at least a single patient fill operation, the batch being a final mixture of constituents, the constituents including a final quantity of water, a final quantity of osmotic agent concentrate, and a final quantity of electrolyte concentrate. The method includes using a fluid proportioning device with a controller, actuators, and a conductivity sensor and attaching a fluid circuit to the actuators, the fluid circuit having a mixing container. The method includes using the controller to control the actuators: pumping a fraction of the final quantity of water into the mixing container; pumping more than the final quantity, plus or minus an error, of electrolyte concentrate into the mixing container; mixing contents of the mixing container; sampling the contents of the mixing container in a manner that reduces volume of fluid in the mixing container and measuring the conductivity thereof; calculating and storing data responsive to a deviation of the measured conductivity from a predefined expected conductivity resulting from the error; calculating an adjusted quantity of water and/or osmotic agent concentrate required to achieve predefined proportions of the constituent final quantities responsive to the data; and pumping the adjusted quantity of water or osmotic agent concentrate into the mixing container.

In variations thereof, the first embodiments include ones in which the method is performed at a location of a peritoneal dialysis treatment. In variations thereof, the first embodiments include ones in which the method is performed at a time of a peritoneal dialysis treatment. In variations thereof, the first embodiments include ones in which the method is performed such that it is completed within a day, within 12 hours, within 6 hours, within 3 hours, or within an hour of a start of a peritoneal dialysis treatment. In variations thereof, the first embodiments include ones in which the fluid proportioning device is located in a same room, within 100 meters, within 10 meters, within 5 meters, or within 2 meters as a patient receiving a peritoneal dialysis treatment.

In variations thereof, the first embodiments include ones in which the electrolyte concentrate is pumped into the mixing concentrate after the fraction of the final quantity of water; the mixing takes place after the pumping of the more than the final quantity of electrolyte concentrate; the sampling takes place after the mixing; the calculating and storing data take place after the sampling; the calculating the adjusted quantity takes place after the calculating and storing the data; and the pumping the adjusted quantity takes place after the calculating the adjusted quantity.

In variations thereof, the first embodiments include ones in which the using a fluid proportioning device includes providing a peritoneal dialysis cycler. In variations thereof, the first embodiments include ones that include, after pumping the adjusted quantity of water and/or osmotic agent concentrate, sampling the contents of the mixing container and measuring a final conductivity thereof. In variations thereof, the first embodiments include ones that include comparing a final conductivity to a predefined final conductivity and permitting use of the batch or preventing use of the batch responsively to a result thereof. In variations thereof, the first embodiments include ones in which the fraction of the final quantity of water pumped into the mixing container is less than 60%. In variations thereof, the first embodiments include ones in which the controller samples the mixing container contents by pumping a sample from the mixing container across a conductivity sensor in a drain line. In variations thereof, the first embodiments include ones in which the fraction of the final quantity of water pumped into the mixing container is less than 90%. In variations thereof, the first embodiments include ones in which the pumping more than the final quantity, plus or minus an error, of electrolyte concentrate occurs before the pumping the adjusted quantity of water or osmotic agent concentrate into the mixing container.

According to second embodiments, the disclosed subject matter includes a method for making a batch of peritoneal dialysis solution sufficient for a patient fill operation, the batch being a mixture of constituents in target proportions, the constituents including water, osmotic agent concentrate, and electrolyte concentrate. The method includes using a fluid proportioning device with a controller, actuators, and a conductivity sensor. The method includes attaching a fluid circuit to the actuators, the fluid circuit having a mixing container. The method includes using the controller to control the actuators: pumping water into the mixing container; pumping electrolyte concentrate into the mixing container in an amount intended to create a predefined ratio of the electrolyte concentrate and the water; mixing contents of the mixing container; sampling the contents of the mixing container and measuring a conductivity thereof; calculating and storing data responsive to a deviation of a measured conductivity of the mixing container contents from one corresponding to the predefined ratio; calculating an adjusted quantity of water or osmotic agent concentrate responsively to the data; and pumping the adjusted quantity of water or osmotic agent concentrate into the mixing container.

In variations thereof, the second embodiments include ones in which the method is performed at a time of a peritoneal dialysis treatment. In variations thereof, the second embodiments include ones in which the using a fluid proportioning device includes providing a peritoneal dialysis cycler. In variations thereof, the second embodiments include ones that include, after pumping the adjusted quantity of water or osmotic agent concentrate, sampling the contents of the mixing container and measuring a final conductivity thereof. In variations thereof, the second embodiments include ones that include, comparing the measured final conductivity to a predefined final conductivity and permitting use of the contents of the mixing container or preventing use of the contents of the mixing responsively to a result thereof. In variations thereof, the second embodiments include ones that include adding further water to the mixing container to create ready-to-use dialysate therein, wherein the adding water into the mixing container transfers less than 60% of the quantity of water in the ready-to-use dialysate in the mixing container. In variations thereof, the second embodiments include ones in which the controller samples the mixing container contents by pumping a sample from the mixing container across a conductivity sensor in a drain.

According to third embodiments, the disclosed subject matter includes method for making a batch of peritoneal dialysis solution sufficient for least a single patient fill operation, the batch being a final mixture of constituents, the constituents including a final quantity of water, a final quantity of osmotic agent concentrate, and a final quantity electrolyte concentrate, wherein the osmotic agent concentrate includes a predefined proportion of electrolyte. The method includes providing a fluid proportioning device with a controller, actuators, and a conductivity sensor. The method includes attaching a fluid circuit to the actuators, the fluid circuit having a mixing container. The method includes using the controller to control the actuators: pumping a fraction of the final quantity of water into the mixing container; pumping more than the final quantity, plus or minus an error, of osmotic agent concentrate into the mixing container; mixing contents of the mixing container; sampling the contents of the mixing container in a manner that reduces volume of fluid in the mixing container and measuring the conductivity thereof; calculating and storing data responsive to a deviation of the measured conductivity from a predefined expected conductivity resulting from the error; calculating an adjusted quantity of water and/or electrolyte concentrate required to achieve predefined proportions of the constituent final quantities; and pumping the adjusted quantity of water and/or electrolyte concentrate into the mixing container.

In variations thereof, the third embodiments include ones in which the method is performed at a location of a peritoneal dialysis treatment. In variations thereof, the third embodiments include ones in which the method is performed at a time of a peritoneal dialysis treatment. In variations thereof, the third embodiments include ones in which the method is performed such that it is completed within a day, within 12 hours, within 6 hours, within 3 hours, or within an hour of a start of a peritoneal dialysis treatment. In variations thereof, the third embodiments include ones in which the fluid proportioning device is located in a same room, within 100 meters, within 10 meters, within 5 meters, or within 2 meters as a patient receiving a peritoneal dialysis treatment. In variations thereof, the third embodiments include ones that include providing a peritoneal dialysis cycler. In variations thereof, the third embodiments include ones that include, after pumping the adjusted quantity of water and/or electrolyte concentrate, sampling the contents of the mixing container and measuring a final conductivity thereof. In variations thereof, the third embodiments include ones that include comparing the final conductivity to a predefined final conductivity and permitting use of the batch or preventing use of the batch responsively to a result thereof. In variations thereof, the third embodiments include ones in which the fraction of the final quantity of water pumped into the mixing container is less than 60%. In variations thereof, the third embodiments include ones in which the controller samples the mixing container contents by pumping a sample from the mixing container across a conductivity sensor in a drain line. In variations thereof, the third embodiments include ones in which the fraction of the final quantity of water pumped into the mixing container is less than 90%. In variations thereof, the third embodiments include ones in which the pumping more than the final quantity, plus or minus an error, of osmotic agent concentrate occurs before occurs before the pumping the adjusted quantity of water and/or electrolyte concentrate into the mixing container.

According to fourth embodiments, the disclosed subject matter includes method for making a batch of peritoneal dialysis solution sufficient for at least a single patient fill operation, the batch being a final mixture of constituents, the constituents including a final quantity of water, a final quantity of osmotic agent concentrate, and final quantity of electrolyte concentrate, the method, using a controller of a peritoneal dialysis treatment delivery system. The method includes (a) adding a fraction of the final quantity of water and a first concentrate, the first concentrate being one of osmotic agent concentrate or electrolyte concentrate, to a mixing container and mixing contents of the mixing container;

(b) measuring a conductivity of the contents of the mixing container and if within a first predefined range, skipping to (d);

(c) computing a new final quantity of a second concentrate, the second concentrate being the other of osmotic agent concentrate or electrolyte concentrate to add to the mixing container responsively to an error of the measuring, the error being in a proportion of the first concentrate detected and the fraction of the final quantity of water measured in (b);

(d) adding the second concentrate to the mixing container and mixing the contents of the mixing container;

(e) measuring a conductivity of the contents of the mixing container and if the measured conductivity is within a second predefined range, skipping to (h)

(f) generating a command to terminate the making of the batch if a new final quantity of the second concentrate was computed in (c); otherwise, computing a first supplemental amount of the second concentrate or water to bring the conductivity to a second predefined range;

(g) measuring a conductivity of the contents of the mixing container and if not within a third predefined range, computing a second supplemental amount of the first and second concentrates or water to add to bring the conductivity within the predefined range; and (h) adding one or more further quantities of water, the first concentrate, and/or the second concentrate sufficient to achieve the proportions of the final mixture, responsively to the first and/or second supplemental amounts if computed.

In variations thereof, the fourth embodiments include ones in which the method is performed at a time of a peritoneal dialysis treatment. In variations thereof, the fourth embodiments include ones in which the method is performed at a location of a peritoneal dialysis treatment. In variations thereof, the fourth embodiments include ones in which, if the contents of the mixing container are not within the third predefined range in (g) then generating a command to terminate the making of the final mixture. In variations thereof, the fourth embodiments include ones that include, in response to the command to terminate the making of the batch, preventing the use of the final mixture. In variations thereof, the fourth embodiments include ones that include using the final mixture to perform a fill cycle of a peritoneal dialysis treatment. In variations thereof, the fourth embodiments include ones that include testing a sterilizing filter through which at least one component of the contents of the mixing container flows and generating a command to terminate the method if the test indicates a failure. In variations thereof, the fourth embodiments include ones in which the testing includes applying pressurized air to a wetted membrane and measuring a pressure.

According to fifth embodiments, the disclosed subject matter includes method of making a dialysate. The method includes adding water and a first concentrate (C1) to a mixing container, measuring a first conductivity of the mixing container contents, and if the first conductivity of the contents of the mixing container is in a first range, adding a second concentrate (C2), measuring a second conductivity of the contents of the mixing container, and if the second conductivity is in a second range further diluting the contents of the mixing container. The method includes measuring a third conductivity of the contents of the mixing container and if the third conductivity is in a third range, using the contents of the mixing container for a treatment; otherwise, if the third conductivity is lower than the third range, adding C1 and C2, and if the third conductivity is higher than the third range, further diluting the contents of the mixing container. The method includes, if the second conductivity of the contents of the mixing container is higher than the second range, adding C1 and water in amounts that are responsive to the second conductivity and if the second conductivity of the contents of the mixing container is lower than the second range, adding C2 in an amount that is responsive to the second conductivity.

In variations thereof, the fifth embodiments include ones that include, if after adding C1 to the mixing container the first conductivity higher than the first range, calculating an additional amount of C2 to add to the mixing container responsive to the first conductivity. In variations thereof, the fifth embodiments include ones that include, if after adding C1 to the mixing container the first conductivity higher than the first range, calculating an additional amount of C1 to add to the mixing container responsive to the first conductivity. In variations thereof, the fifth embodiments includes ones that include if after adding C1 to the mixing container the first conductivity higher than the first range, calculating an additional amount of C1 to add to the mixing container responsive to the first conductivity. In variations thereof, the fifth embodiments include ones that include mixing the contents of the mixing container prior to determining the first or the second conductivity.

According to sixth embodiments, the disclosed subject matter includes a method of generating a batch of treatment fluid, the method including using a controller that stores a treatment prescription, and according to the prescription, pumping a calculated ratio of water and electrolyte concentrate into a mixing container by regulating a pump to control a net volume of each that is transferred to the mixing container. The controller further stores reference data indicating conductivity of predefined dilution ratios of water and the electrolyte concentrate. The method includes testing a conductivity of the contents of the mixing container resulting from the pumping and further pumping water or electrolyte concentrate responsively to the testing if the conductivity differs by more than a defined threshold from the conductivity indicated by the stored reference data and controlling a further use of a pump to permit the contents of the mixing container to be used thereafter, or immediately controlling a further use of the pump to permit the contents of the mixing container to be used if the conductivity differs by less than the defined threshold.

In variations thereof, the sixth embodiments include ones that include, after the pumping a predefined quantity of water and electrolyte concentrate, mixing contents of the mixing container. In variations thereof, the sixth embodiments include ones that include using the controller to measure temperature of the fluid from the mixing container. In variations thereof, the sixth embodiments include ones that include using the controller to measure temperature of the fluid from the mixing container, temperature-compensate the conductivity, calculate whether the conductivity falls under the threshold to generate a pass/fail result, and outputting one of a command to change a later addition of water or concentrate responsively to the pass/fail result and a command to stop preparation of the batch responsively to the pass/fail result. In variations thereof, the sixth embodiments include ones that include, using the controller to measure temperature of the fluid from the mixing container, temperature-compensating the conductivity, calculating whether the conductivity falls under the threshold to generate a pass/fail result, and outputting one of a command to change the later addition of water or concentrate responsively the pass/fail result and a command to stop preparation of the batch responsively to the pass/fail result, wherein the threshold indicates a conductivity of a diluted osmotic agent electrolyte concentrate.

According to seventh embodiments, the disclosed subject matter includes method of making a batch of peritoneal dialysis fluid. The method includes providing a controller connected to receive signals from a conductivity sensor, the controller storing target conductivities of predefined target ratios of first and second fluids at a body temperature of a human, the controller further storing a correction factor that indicates a rate of change of conductivity with temperature. The method includes using the controller, in no particular order, adding a predefined volume of the first fluid to a container and adding the second fluid to the container having a composition different from the first. The method includes mixing the first and second fluids in the container to create an in-process mixture. The method includes warming the first and second fluids to a temperature within a predefined range of the body temperature either prior to, during, or after the adding or mixing. The method includes measuring a current conductivity and a current temperature of the in-process mixture from the container. The method includes using the controller, selecting one of the predefined target ratios corresponding to a current target in-process mixture and calculating an additional amount of the first or second fluid to add to the container to achieve the selected one of the predefined target ratios responsively to the current conductivity, the current temperature, and the correction factor; and adding the additional amount to the container.

In variations thereof, the seventh embodiments include ones in which the controller stores correction factors for each of the predefined target ratios and the calculating an additional amount is responsive to a correction factor corresponding to the selected one of the predefined target ratios. In variations thereof, the seventh embodiments include ones in which the container stores a batch of peritoneal dialysis fluid. In variations thereof, the seventh embodiments include ones that include adding a predefined volume of a third fluid at a time before, during, or after the adding the additional amount. In variations thereof, the seventh embodiments include ones in which the adding the additional amount includes adding one of water and electrolyte concentrate. In variations thereof, the seventh embodiments include ones in which the adding the additional amount includes adding one of water and a concentrate including an osmotic agent. In variations thereof, the seventh embodiments include ones in which the osmotic agent concentrate includes electrolyte. In variations thereof, the seventh embodiments include ones in which the first fluid is water and the second fluid is a mixture of electrolytes for peritoneal dialysis fluid. In variations thereof, the seventh embodiments include ones in which the first fluid is water and the second fluid is a mixture of electrolytes and osmotic agent for peritoneal dialysis fluid. In variations thereof, the seventh embodiments include ones in which the predefined target ratios are concentrations of electrolytes in water.

According to eighth embodiments, the disclosed subject matter includes medicament preparation system. A proportioning element that prepares medicament from concentrate and water. A proportioning element controller connects to the proportioning element and configured to control functions thereof. A water preparation element is configured to purify water and has a product water output connected to convey water to the proportioning element. A water preparation element controller connects to the water preparation element and is configured to control functions thereof. The water preparation element controller is controlled by the proportioning controller such that functions of the water preparation element are controlled by the proportioning controller.

In variations thereof, the eighth embodiments include ones in which the water preparation element functions include a filter regeneration function and the filter regeneration function is controlled by the proportioning element controller. eighth the water preparation element has a reversing valve and the proportioning element controller controls the reversing valve.

In variations thereof, the eighth embodiments include ones in which the water preparation element is configured to divert at least a fraction of its product water through a one of multiple filter units therein to regenerate the one of multiple filter units. In variations thereof, the eighth embodiments include ones in which the water preparation element includes an ultraviolet lamp, the proportioning element controller being configured to cycle the ultraviolet lamp in order to eliminate or reduce output when water is not being filtered. In variations thereof, the eighth embodiments include ones in which the water preparation element has a product water heater and the proportioning element controller is configured to regulate a temperature of product water received by it by cycling the product water heater. In variations thereof, the eighth embodiments include ones in which the proportioning element has a proportioning heater that heats fluid flowing therethrough. In variations thereof, the eighth embodiments include ones in which the proportioning element controller controls the product water heater and the proportioning heater to share a net heating demand between the product water heater and the proportioning heater. In variations thereof, the eighth embodiments include ones in which the water preparation element has a product water heater and the proportioning element controller is configured to regulate a temperature of product water received by it by cycling the water heater. In variations thereof, the eighth embodiments include ones in which the proportioning element has a proportioning heater that heats fluid flowing therethrough. In variations thereof, the eighth embodiments include ones in which the proportioning element controller controls the product water heater and the proportioning heater to share a net heating demand between the product water heater and the proportioning heater. In variations thereof, the eighth embodiments include ones in which the proportioning element includes a treatment element.

In variations thereof, the eighth embodiments include ones in which the treatment element includes a dialysis machine. In variations thereof, the eighth embodiments include ones in which the treatment element includes a dialysis cycler. In variations thereof, the eighth embodiments include ones in which the treatment element includes a peritoneal dialysis cycler. In variations thereof, the eighth embodiments include ones in which the proportioning element controller receives status information from the water preparation element controller. In variations thereof, the eighth embodiments include ones in which the proportioning element controller includes a user interface and the proportioning element controller derives information from the status information and outputs derived data on the user interface, the derived data including indications that a filter of the water preparation element is in a flushing, priming, or cleaning mode. In variations thereof, the eighth embodiments include ones in which the proportioning element controller includes a user interface and the proportioning element controller derives information from the status information and outputs derived data on the user interface, the derived data including indications of water temperature or estimate of time delay till product water is available. In variations thereof, the eighth embodiments include ones in which the proportioning element controller includes a user interface and the proportioning element controller derives information from the status information and outputs derived data on the user interface, the derived data including indications of estimated time left till filter replacement (estimated time to exhaustion).

In variations thereof, the eighth embodiments include ones in which the proportioning element controller receives status information from the water preparation element controller, the proportioning element controller includes a user interface, and the proportioning element controller derives information from the status information and outputs derived data on the user interface, the derived data including indications or amount of life left on the ultraviolet lamp. In variations thereof, the eighth embodiments include ones in which the proportioning element controller includes a user interface and the proportioning element controller derives information from the status information and outputs derived data on the user interface, the derived data including indications time till a next flush or a next cleaning cycle of the water preparation element. In variations thereof, the eighth embodiments include ones in which the proportioning element controller includes a user interface and the proportioning element controller derives information from the status information and outputs derived data on the user interface, the derived data including an indication whether the water preparation element is in a sleep mode and/or how long the before it is available to produce water.

In variations thereof, the eighth embodiments include ones in which the proportioning element controller includes a user interface and the proportioning element controller derives information from the status information and outputs derived data on the user interface, the derived data including forecasts of maintenance tasks such as filter replacement. In variations thereof, the eighth embodiments include ones in which the proportioning element controller receives status information from the water preparation element controller, the proportioning element controller includes a user interface, and the proportioning element controller derives information from the status information and outputs derived data on the user interface, the derived data including a forecast of a time for ultraviolet lamp replacement. In variations thereof, the eighth embodiments include ones in which the proportioning element controller includes a user interface and the proportioning element controller derives information from the status information and outputs derived data on the user interface, one or more resistivity sensors being provided in a product water outlet line the derived data including resistivity of the product water. In variations thereof, the eighth embodiments include ones in which the proportioning element controller includes a user interface and the proportioning element controller derives information from the status information and outputs derived data on the user interface, one or more resistivity sensors being provided in a product water outlet line the derived data including an alert when the resistivity is out of a predefined range.

In variations thereof, the eighth embodiments include ones in which the proportioning element controller includes a user interface and the proportioning element controller derives information from the status information and outputs derived data on the user interface, one or more resistivity sensors being provided in a tap water inlet line the derived data including an alert when the resistivity is out of a predefined range. In variations thereof, the eighth embodiments include ones in which the derived data may be an estimate of filter life based on resistivity of water in the water inlet line. In variations thereof, the eighth embodiments include ones in which the water preparation element has an off mode, a sleep mode, and an operating mode. In variations thereof, the eighth embodiments include ones in which the proportioning element controller and the water preparation element controller communicate over a network. In variations thereof, the eighth embodiments include ones in which the proportioning element controller and the water preparation element controller communicate over a signal cable. In variations thereof, the eighth embodiments include ones in which the proportioning element controller and the water preparation element controller communicate over a wireless connection. In variations thereof, the eighth embodiments include ones in which the water preparation element controller indicates to the proportioning element controller its status including an indication that the water preparation element is ready to output product water.

In variations thereof, the eighth embodiments include ones in which the proportioning element controller starts and stops water production by applying commands to the water preparation element controller. In variations thereof, the eighth embodiments include ones in which the proportioning element controller transmits commands to start and stop an ultraviolet (germicidal) lamp in the water preparation element. In variations thereof, the eighth embodiments include ones in which the commands are effective for extending a life of such an ultraviolet lamp by ensuring the lamp is operated only when required for treatment of water. In variations thereof, the eighth embodiments include ones in which the commands are effective for extending a life of such an ultraviolet lamp by ensuring the lamp is operated only when water is being filtered. In variations thereof, the eighth embodiments include ones in which the proportioning element controller employs two-way communication with the water preparation element to place the water preparation element in a sleep mode at an end of a treatment such that some or all power functions thereof are switched off to save power and reduce wear. In variations thereof, the eighth embodiments include ones in which the proportioning element controller may send commands to wake up the water preparation element so that it is ready at a time of a predefined treatment stored in the proportioning element controller. In variations thereof, the eighth embodiments include ones in which commands from the proportioning element controller regulate a pressure and flow rate at which product water is delivered by the water preparation element.

In variations thereof, the eighth embodiments include ones in which closed loop control based on a pressure signal is provided by the water preparation element controller. In variations thereof, the eighth embodiments include ones in which the proportioning element controller employs two-way communication with the water preparation element to transmit alarms generated by the water preparation element and the proportioning responds by ceasing dialysate proportioning in response to predefined alarms. In variations thereof, the eighth embodiments include ones in which alarm or status outputs of the water preparation element are effective to generate specific outputs through a user interface of the proportioning element controller. In variations thereof, the eighth embodiments include ones in which the proportioning element controller has a user interface that outputs guided troubleshooting steps in response to and related to outputs and alarms of the water preparation element controller. In variations thereof, the eighth embodiments include ones in which the water preparation element has a water heater and the proportioning element controller controls the water heater and receives indications from the water preparation element controller of a power output of the water heater, water temperature, and status of the water preparation element.

In variations thereof, the eighth embodiments include ones in which the water preparation element controller is configured to auto-order replacements filters through the Internet. In variations thereof, the eighth embodiments include ones in which a timing of the auto-order replacements is such as to effect a required change-out before exhaustion of the filters being replaced. In variations thereof, the eighth embodiments include ones in which the proportioning element has a priming mode in which flushes a fluid circuit thereof with water from the water preparation element. In variations thereof, the eighth embodiments include ones in which the proportioning element controller transmits commands to the water preparation element controller to output water at pressures and flow rates required for the proportioning element. In variations thereof, the eighth embodiments include ones in which the priming is preceded by a flushing operation with purified water to minimize endotoxins in the fluid circuit. In variations thereof, the eighth embodiments include ones in which the water preparation element includes a reservoir sized to provide water sufficient for a fill/drain cycle or for a full treatment (multiple cycles). In variations thereof, the eighth embodiments include ones in which the reservoir has one or more sterilizing-grade filters on its inlet (and/or outlet) lines to prevent touch contamination or back-growth contamination. In variations thereof, the eighth embodiments include ones in which the reservoir includes one or more check valves on its outlet lines to prevent backflow. In variations thereof, the eighth embodiments include ones in which an outlet of the reservoir includes a recirculation loop with a pump that maintains a target head pressure.

According to ninth embodiments, the disclosed subject matter includes system for performing peritoneal dialysis with a fluid circuit with at least one fluid inlet and a mixing container. A peritoneal dialysis system has a peritoneal dialysis system controller, valve actuators, one or more pumps, to pump and direct concentrate and water selectively through at least at times and through portions of the fluid circuit to transfer concentrate and water, through the at least one fluid inlet, to the mixing container to form dialysis fluid. A water supply source has a water pump, the water pump being controlled by a water supply controller and being connected to a purified water outlet which is in turn connected to the at least one fluid inlet. A command interface is between the peritoneal dialysis system controller and the water supply controller, the peritoneal dialysis system controller transmitting one or more commands to the water supply controller to start and stop the water pump.

In variations thereof, the ninth embodiments include ones in which the one or pumps are configured to pump concentrate and water from one or more sources.

According to tenth embodiments, the disclosed subject matter includes system for performing peritoneal dialysis. A fluid circuit has a single fluid inlet and a mixing container. A peritoneal dialysis system has a peritoneal dialysis system controller, valve actuators, and a cycler pump that pumps concentrate and water within the fluid circuit. A water source with a water pump and a concentrate source with a concentrate pump are connected to pump water and concentrate through the fluid inlet under control of a fluid source controller connected to control the water and concentrate pumps. A command interface is connected between the peritoneal dialysis system controller and the fluid source controller, the peritoneal dialysis system controller transmitting one or more commands to the fluid source controller to start and stop the water source and concentrate source pumps.

According to eleventh embodiments, the disclosed subject matter includes system for performing peritoneal dialysis. A fluid circuit has at least one fluid inlet and a mixing container. A peritoneal dialysis system has a controller, valve actuators, one or more pumps, to pump and direct concentrate and water selectively through the fluid circuit to transfer concentrate and water, through the fluid inlet, to the mixing container to form dialysis fluid. A peritoneal dialysis cycler has actuators, including a cycler pump actuator, to direct concentrate and water selectively through the fluid circuit to transfer concentrate and water from one or more external sources, through the fluid inlet, to the mixing container to form dialysis fluid. A water supply source with a water pump having a purified water outlet connected to the at least one fluid inlet. The water supply source has a water source controller that controls the water pump responsively to at least one sensor that detects at least one operating condition of the peritoneal dialysis cycler. The water source controller activates the water pump when the operating condition indicates a requirement for water by the peritoneal dialysis cycler.

In variations thereof, the eleventh embodiments include ones in which operating condition includes an activation of an actuator of the peritoneal dialysis cycler that controls the opening of the fluid inlet. In variations thereof, the eleventh embodiments include ones in which the operating condition includes the activation of the peritoneal dialysis cycler pump actuator. In variations thereof, the eleventh embodiments include ones in which the at least one sensor includes a pressure sensor that provides pressure signals to the water source controller, the water pump being controlled responsively to the pressure signals such that when the cycler pump actuator is activated to draw water from the at least one fluid inlet thereby generating a reduction in pressure in the at least one fluid inlet while the water pump is off, the water pump is turned on by the water source controller In variations thereof, the eleventh embodiments include ones in which the water pump is turned on by the water source controller when the reduction reaches a predefined magnitude stored by the water source controller. In variations thereof, the eleventh embodiments include ones in which the water source controller controls the water pump to maintain the pressure of the at least one fluid inlet within a predefined range of pressures.

According to twelfth embodiments, the disclosed subject matter includes a system for performing peritoneal dialysis. A fluid circuit has a fluid inlet and a mixing container. A peritoneal dialysis cycler has a cycler controller, actuators, including a cycler pump actuator, to direct concentrate and water selectively through the fluid circuit to transfer concentrate and water, through the fluid inlet, to the mixing container to form dialysis fluid. A water supply source has a water pump having a purified water outlet connected to the at least one fluid inlet. The purified water outlet has a pressure sensor and a water source controller that receives pressure signals from the pressure sensor and controls the water pump responsively to the pressure signals, the cycler pump actuator generating coded pressure pulses in the fluid inlet that are received by the pressure sensor and decoded by the water source controller to command the water source controller to activate and deactivate the water pump responsively to decoded commands encoded in the pressure signals.

In variations thereof, the twelfth embodiments include ones in which the coded pressure pulses encode changes to operating parameters of the water source controller including a closed-loop pressure set point at the fluid inlet. In variations thereof, the twelfth embodiments include ones in which the coded pressure pulses encode changes to operating parameters of the water source controller. In variations thereof, the twelfth embodiments include ones in which the water source controller controls the water pump to maintain the pressure of the at least one fluid inlet within a predefined range of pressures.

According to thirteenth embodiments, the disclosed subject matter includes method for making a peritoneal dialysis fluid, the method including connecting a fluid circuit to a proportioning machine, the fluid circuit including a mixing container. The proportioning machine has actuators that engage with the fluid circuit when received thereby. The method includes connecting a water source and one or more fresh containers of concentrate to the fluid circuit, each of the one or more fresh containers of concentrate having sufficient concentrate for multiple treatments. The method includes using a controller of the proportioning machine, flowing purified water from the water source and concentrate from the one or more containers through the fluid circuit to the mixing container to prepare a dialysis fluid in the mixing container by proportioning the water and concentrate. The flowing includes flowing water and concentrate through at least one sterilizing filter to ensure sterility of the water and concentrate. The at least one sterilizing filter includes serially-connected redundant sterilizing filters or the method including, using the controller, testing the integrity of a membrane of the at least one sterilizing filter and preventing a use of contents of the mixing container responsively to a result of the testing. The method includes using the controller, treating a patient using the dialysis fluid from the mixing container, the treating including performing multiple fill and drain cycles of a peritoneal dialysis treatment. The method includes replacing the fluid circuit with a new fluid circuit. The method includes repeating the connecting a fluid circuit, flowing purified water and concentrate, and repeating the treating a patient, without replacing the one or more fresh containers of concentrate, whereby the one or more fresh concentrate containers are replaced once every multiple treatments.

In variations thereof, the thirteenth embodiments include ones in which the at least one filter is integrally attached to the fluid circuit. In variations thereof, the thirteenth embodiments include ones in which the flowing water and concentrate through at least one sterilizing filter includes flowing water and concentrate through separate filters. In variations thereof, the thirteenth embodiments include ones in which the at least one filter includes a testable filter with an air line, the method including, using the controller, applying a pressure to the air line to test an ability of a wetted membrane of the testable filter to withstand pressure and thereby indicate the membrane's integrity. In variations thereof, the thirteenth embodiments include ones in which the connecting a water source and one or more containers of concentrate to the fluid circuit includes: at a first time, replacing one or more spent containers of concentrate with the one or more fresh containers of concentrate; at a second time, connecting a fluid inlet line of the fluid circuit with the at least one sterilizing filter to a common fluid outlet of a fluid source module; the fluid source module having automatic valves connected to a water source and the one or more fresh containers of concentrate, the automatic valves selecting, under control of the controller, only one of the water source and the one or more fresh containers of concentrate for connection to the fluid inlet line at a given time.

In variations thereof, the thirteenth embodiments include ones in which the flowing water and concentrate includes pumping the water and concentrate by the fluid source module.

According to fourteenth embodiments, the disclosed subject matter includes treatment method including connecting a fluid circuit to a proportioning machine, the fluid circuit including a mixing container. The proportioning machine has actuators that engage with the fluid circuit when received thereby. The method includes connecting one or more containers of medicament concentrate to the fluid circuit, each container having sufficient medicament concentrate for multiple treatments. The method includes using the proportioning machine, flowing purified water and concentrate through the fluid circuit to the mixing container to prepare a medicament in the mixing container by proportioning the purified water and medicament concentrate. The flowing includes flowing water and concentrate through at least one sterilizing filter to ensure sterility of the water and concentrate. The method includes ensuring an integrity of the at least one sterilizing filter by testing the at least one sterilizing filter or providing serially-connected redundant sterilizing filters. The method includes treating a patient using the prepared medicament in the mixing container. The method includes replacing the fluid circuit with a new fluid circuit and repeating the connecting a fluid circuit, flowing purified water and concentrate, treating a patient, without replacing the one or more containers of medicament concentrate.

In variations thereof, the fourteenth embodiments include ones in which the at least one filter is integrally attached to the fluid circuit. In variations thereof, the fourteenth embodiments include ones in which the flowing water and concentrate through at least one sterilizing filter includes flowing water and concentrate through separate filters.

According to fifteenth embodiments, the disclosed subject matter includes a system for preparation of sterile medical treatment fluid. The system includes t least one fluid circuit with a pumping tube segment and multiple valve segments, at least one pumping actuator, and multiple valve actuators positioned to engage the multiple valve segments. The at least one pumping actuator engages the at least one pumping tube segment. A controller is connected to control the multiple valve actuators and the at least one pumping actuator. A first of the multiple valve segments is along a fluid inlet line with a sterilizing filter. A first multi-treatment concentrate container has sufficient concentrate for preparation of enough peritoneal dialysis fluid to perform multiple peritoneal dialysis treatments, each treatment including multiple fill/drain cycles. The system has a water source. The at least one fluid circuit has, integrally-attached thereto, a first single-treatment concentrate container and a mixing container, the mixing container being sized to hold sufficient peritoneal dialysis fluid for at least a single fill cycle. Ones of the multiple valve segments is/are connected between the fluid inlet line and the water source and between the first multi-treatment concentrate container and the fluid inlet line. The controller, controlling the ones of the multiple valve segments and the at least one pumping actuator, sequentially connects the first single-treatment concentrate container and the water source to the fluid inlet line and controls flow such that water is conveyed from the water source to the mixing container and concentrate is conveyed from the first multi-treatment concentrate container to the first single-treatment concentrate container, and subsequently incorporated in a dialysis fluid formed in the mixing container.

In variations thereof, the fifteenth embodiments include ones in which the controller is configured to perform a fill/drain cycle including draining spent fluid from a patient line and pumping the dialysis fluid from the mixing container to the patient line. In variations thereof, the fifteenth embodiments include ones that include a second multi-treatment concentrate container, wherein, ones of the multiple valve segments are connected the second multi-treatment concentrate container and the fluid inlet line. In variations thereof, the fifteenth embodiments include ones that include a second single-treatment concentrate container connected to the fluid circuit, the controller transferring concentrate from the second multi-treatment concentrate container to the second single-treatment concentrate container to form the dialysis fluid. In variations thereof, the fifteenth embodiments include ones in which the sterilizing filter has an air port to allow a membrane of the sterilizing filter to be pressure tested, the controller being programmed to test the sterilizing filter membrane by applying pressure to the air port and measuring the pressure after pumping water therethrough. In variations thereof, the fifteenth embodiments include ones in which controller generates an alarm signal responsively to a result of a test of the sterilizing filter membrane if the test indicates a loss of integrity of the sterilizing filter membrane.

According to sixteenth embodiments, the disclosed subject matter includes fluid circuit for dialysis solution preparation. A valve network has interconnected channels that can be opened and closed by opening and closing valve portions of the interconnected channels. A fluid inlet line has an inline sterilizing filter, a mixing container, a first concentrate container, a drain line, a patient fill/drain line all empty and pre-connected to the valve network to form a unit and sealed from an external environment. The valve network has a pumping portion to pump fluid between the interconnected channels.

In variations thereof, the sixteenth embodiments include ones in which the patient fill/drain line includes separate branch lines that connect to the valve network which branch lines merge to form a single line that connects to a patient. In variations thereof, the sixteenth embodiments include ones in which the inline sterilizing filter has an air line attached thereto, the air line being connected such that air forced through the air line applies pressure to a membrane of the inline sterilizing filter to permit an integrity test thereof. In variations thereof, the sixteenth embodiments include ones in which the valve network is attached to a rigid manifold member, the air line being connecting to a port fixedly attached to the rigid manifold member. In variations thereof, the sixteenth embodiments include ones in which the air line is collinear with the fluid inlet line. In variations thereof, the sixteenth embodiments include ones in which valve network is supported by a panel. In variations thereof, the sixteenth embodiments include ones in which the valve network is supported by a panel, the pumping portion being supported by a rigid manifold portion of the valve network which is spaced from the panel. In variations thereof, the sixteenth embodiments include ones in which the rigid manifold portion has pressure sensing diaphragms integrated in and supported thereby.

In variations thereof, the sixteenth embodiments include ones in which the air line is integral with at least a portion of the fluid inlet line. In variations thereof, the sixteenth embodiments include ones in which the rigid manifold portion pressure sensing diaphragms are located one at each end of the pumping portion. In variations thereof, the sixteenth embodiments include ones in which the pumping portion is straight. In variations thereof, the sixteenth embodiments include ones that include a second concentrate container pre-connected to the valve network. In variations thereof, the sixteenth embodiments include ones in which the mixing container and first and second concentrate containers are polymer bags. In variations thereof, the sixteenth embodiments include ones in which the mixing container has a larger internal volume than the first and second concentrate containers. In variations thereof, the sixteenth embodiments include ones in which the panel has windows that overlie the valve portions. In variations thereof, the sixteenth embodiments include ones in which the valve network includes a manifold portion with a pumping tube segment. In variations thereof, the sixteenth embodiments include ones in which the valve portions are portions of a bank of tubes stemming from the manifold portion. In variations thereof, the sixteenth embodiments include ones in which the valve portions are portions of a bank of parallel tubes stemming from the manifold portion. In variations thereof, the sixteenth embodiments include ones that include a second sterilizing filter connected in series with the inline sterilizing filter such that the second and inline sterilizing filters are separated by a flow channel. In variations thereof, the sixteenth embodiments include ones in which the mixing container and first concentrate container are defined by two bonded flexible panels along seams to define the mixing container and concentrate container. In variations thereof, the sixteenth embodiments include ones in which the valve network fluidly interconnects the fluid inlet line to the concentrate container. In variations thereof, the sixteenth embodiments include ones in which the valve network fluidly interconnects the concentrate container with the mixing container. In variations thereof, the sixteenth embodiments include ones in which the valve network fluidly interconnects the mixing container with the patient fill and patient drain lines.

According to seventeenth embodiments, the disclosed subject matter includes system for performing a peritoneal dialysis treatment. At least two multi-treatment concentrate containers have concentrate supply connectors, the at least two multi-treatment concentrate containers having sufficient concentrate to perform multiple dialysis treatments, where each treatment includes multiple fill/drain cycles. A valve network has interconnected channels that can be opened and closed by opening and closing valve portions of the interconnected channels. A fluid inlet line has an inline sterilizing filter, a mixing container, first and second single-treatment concentrate containers, a drain line, a patient fill/drain line all empty and pre-connected to the valve network to form a unit and sealed from an external environment. The valve network has a pumping portion to pump fluid between the interconnected channels.

In variations thereof, the seventeenth embodiments include ones that include a connection platform that mechanically supports the at least two multi-treatment concentrate containers and selectively couples them to the fluid inlet line. In variations thereof, the seventeenth embodiments include ones that include a connection platform with a water source and attachments for the at least two multi-treatment concentrate containers, the connection platform having a valve system that fluidly couples the at least two multi-treatment concentrate containers and the water source to the fluid inlet line. In variations thereof, the seventeenth embodiments include ones in which the inline sterilizing filter has an air line attached thereto, the air line being connected such that air forced through the air line applies pressure to a membrane of the inline sterilizing filter to permit an integrity test thereof. In variations thereof, the seventeenth embodiments include ones in which the air lines are each collinear with at least a portion of the fluid inlet line. In variations thereof, the seventeenth embodiments include ones in which the air lines are each attached along at least a portion of the fluid inlet line. In variations thereof, the seventeenth embodiments include ones in which the valve network is supported by a panel, the pumping portion being supported by a rigid manifold portion of the valve network which is spaced from the panel. In variations thereof, the seventeenth embodiments include ones in which the manifold portion has pressure sensors integrated therein, one at each end of a pumping tube segment of the pumping portion. In variations thereof, the seventeenth embodiments include ones in which the pumping tube segment is straight. In variations thereof, the seventeenth embodiments include ones in which the pressure sensor includes a pressure pod with a diaphragm that serves as a portion of a wall of a respective one of two separate chambers of the rigid manifold portion. In variations thereof, the seventeenth embodiments include ones in which the valve network is attached to a rigid manifold, the air line being connecting to a port fixedly attached to the rigid manifold. In variations thereof, the seventeenth embodiments include ones in which the air line is collinear with the fluid inlet line. In variations thereof, the seventeenth embodiments include ones in which the valve network is supported by a panel. In variations thereof, the seventeenth embodiments include ones that include a second concentrate container pre-connected to the valve network.

In variations thereof, the seventeenth embodiments include ones in which the mixing container and first and second concentrate containers are polymer bags. In variations thereof, the seventeenth embodiments include ones in which the mixing container has a larger internal volume than the first and second single-treatment concentrate containers. In variations thereof, the seventeenth embodiments include ones in which the panel has windows that overlie the valve portions. In variations thereof, the seventeenth embodiments include ones in which the valve network includes a manifold portion with a pumping tube segment. In variations thereof, the seventeenth embodiments include ones in which the valve portions are portions of a bank of tubes stemming from the manifold. In variations thereof, the seventeenth embodiments include ones in which the valve portions are portions of a bank of parallel tubes stemming from the manifold. In variations thereof, the seventeenth embodiments include ones that include a second sterilizing filter connected in series with the inline sterilizing filter such that the second and inline sterilizing filters are separated by a flow channel.

In variations thereof, the seventeenth embodiments include ones in which the mixing container and first and second single-treatment concentrate containers are defined by two bonded flexible panels along seams to define the mixing container and first and second single-treatment concentrate containers. In variations thereof, the seventeenth embodiments include ones in which the valve network fluidly interconnects the fluid inlet line to the first and second single-treatment concentrate containers. In variations thereof, the seventeenth embodiments include ones in which the valve network fluidly interconnects the first and second single-treatment concentrate containers with the mixing container. In variations thereof, the seventeenth embodiments include ones in which the valve network fluidly interconnects the mixing container with the patient fill/drain line. In variations thereof, the seventeenth embodiments include ones in which the at least two multi-treatment concentrate containers are contained in a single package. In variations thereof, the seventeenth embodiments include ones in which the single package is housed by a single box. In variations thereof, the seventeenth embodiments include ones that include a connection platform with a water source and attachments for the at least two multi-treatment concentrate containers, the connection platform fluidly coupling the at least two multi-treatment concentrate containers and the water source to the fluid inlet line using control valves that include one for each of the at least two multi-treatment concentrates containers and one the water source, the water source having a water pump. In variations thereof, the seventeenth embodiments include ones that include a connection platform with a water source and attachments for the at least two multi-treatment concentrate containers, the connection platform fluidly coupling the at least two multi-treatment concentrate containers and the water source to the fluid inlet line using control valves that include one for each of the at least two concentrates and one the water source, the at least two concentrates containers connecting to a common line having a concentrate pump. In variations thereof, the seventeenth embodiments include ones that include a connection platform with a water source and attachments for the at least two multi-treatment concentrate containers, the connection platform fluidly coupling the at least two multi-treatment concentrate containers and the water source to the fluid inlet line using control valves that include one for each of the at least two concentrates and one the water source, and the water source having a pump, the at least two concentrates containers connecting to a common line having a concentrate pump.

In variations thereof, the seventeenth embodiments include ones that include a controller programmed to control the connection platform controls valves to connect the at least two multi-treatment concentrate containers sequentially to the fluid inlet line to fill the at least two multi-treatment concentrate containers with concentrate. In variations thereof, the seventeenth embodiments include ones in which the controller controls the connection platform water pump to convey water to the mixing container through the fluid inlet line. In variations thereof, the seventeenth embodiments include ones that include a controller programmed to control the connection platform control valves and the concentrate pump to connect the at least two multi-treatment concentrate containers sequentially to the fluid inlet line to fill the first and second single-treatment concentrate containers with concentrate. In variations thereof, the seventeenth embodiments include ones in which the controller controls the connection platform water pump to convey water to the mixing container through the fluid inlet line. In variations thereof, the seventeenth embodiments include ones that include a controller programmed to control the connection platform control valves and the concentrate pump to connect the at least two multi-treatment concentrate containers sequentially to the fluid inlet line to fill the first and second single-treatment concentrate containers with concentrate and to control the connection platform control valves and the connection platform water pump to fill the mixing container with water.

According to eighteenth embodiments, the disclosed subject matter includes system for performing peritoneal dialysis. A peritoneal dialysis cycler has a fluid circuit with a fluid inlet, a mixing container, and at least two concentrate containers. The peritoneal dialysis cycler has actuators to pump and direct concentrate and water selectively through the fluid circuit to transfer concentrate from an external source, through the fluid inlet, to the at least two concentrate containers, to transfer water through the fluid inlet to the mixing container, and to transfer concentrate from the at least two concentrate containers to the mixing container to form dialysis fluid. The peritoneal dialysis cycler actuators also transferring dialysis fluid to a patient line.

In variations thereof, the eighteenth embodiments include ones in which the at least two concentrate containers are empty. 203. In variations thereof, the eighteenth embodiments include ones that include a programmable controller that controls the actuators. In variations thereof, the eighteenth embodiments include ones in which the actuators include pumping and valve actuators. In variations thereof, the eighteenth embodiments include ones in which the fluid circuit includes valve segments that are pinched by the valve actuators. In variations thereof, the eighteenth embodiments include ones in which the fluid inlet has an inline sterilizing filter. In variations thereof, the eighteenth embodiments include ones in which the inline sterilizing filter includes two filters or a single testable filter having an air line for applying air pressure to a membrane thereof. In variations thereof, the eighteenth embodiments include ones that include a fluid source module with input connections for concentrate and water and an outlet connection connectable to the fluid inlet. In variations thereof, the eighteenth embodiments include ones in which the fluid source module has actuators that sequentially connect concentrate and water to the outlet connection. In variations thereof, the eighteenth embodiments include ones in which the peritoneal dialysis cycler controls the fluid source module actuators. In variations thereof, the eighteenth embodiments include ones in which the fluid source module actuators include valve and pump actuators. In variations thereof, the eighteenth embodiments include ones in which the fluid source pump actuators include a water pump that pumps water through a filter system to generate purified water flowing through a purified water supply line connected to the outlet connection and the fluid source module valve actuators include a water valve actuator that selectively closes and opens the purified water supply line. In variations thereof, the eighteenth embodiments include ones in which the fluid source pump actuators include a concentrate pump that pumps concentrate from concentrate containers connected through respective concentrate feed lines to a common concentrate line that connect to the outlet connection, the fluid source module valve actuators including concentrate valve actuators that selectively close and open the respective concentrate feed lines. In variations thereof, the eighteenth embodiments include ones in which the peritoneal dialysis cycler has a programmable controller that controls the peritoneal dialysis cycler actuators.

In variations thereof, the eighteenth embodiments include ones in which the fluid source module pump actuators include a water pump, controlled by the programmable controller, that pumps water through a filter system to generate purified water flowing through a purified water supply line connected to the outlet connection and the fluid source module valve actuators include a water valve actuator that selectively closes and opens the purified water supply line under control of the programmable controller. In variations thereof, the eighteenth embodiments include ones in which the fluid source module pump actuators include a concentrate pump, controlled by the programmable controller, that pumps concentrate from concentrate containers connected through respective concentrate feed lines to a common concentrate line that connect to the outlet connection, the fluid source module valve actuators including concentrate valve actuators that selectively close and open the respective concentrate feed lines under the control of the programmable controller.

In variations thereof, the eighteenth embodiments include ones in which the fluid source module pump actuators include a concentrate pump, controlled by the programmable controller, that pumps concentrate from concentrate containers connected through respective concentrate feed lines to a common concentrate line that connect to the outlet connection, the fluid source module valve actuators including concentrate valve actuators that selectively close and open the respective concentrate feed lines under the control of the programmable controller and wherein the fluid source pump actuators include a water pump, controlled by the programmable controller, that pumps water through a filter system to generate purified water flowing through a purified water supply line connected to the outlet connection and the fluid source module valve actuators include a water valve actuator that selectively closes and opens the purified water supply line under the control of the programmable controller.

According to nineteenth embodiments, the disclosed subject matter includes fluid system for peritoneal dialysis and dialysis solution preparation. A pre-connected fluid circuit has a disposable mixing container of polymeric material, an empty concentrate container of polymeric material, a fluid multiplexer that includes a valve network that has junctions and valve portions that mechanically interface with valve actuators to define selectable flow paths in the valve network. The valve network further includes a concentrate line connected to the concentrate container, a fluid inlet line terminated by a fluid inlet line connector, and a pair of lines connected to the mixing container to permit simultaneous flow into, and flow out from, the mixing container. The fluid circuit is preconnected and sealed as a unit to isolate an internal volume thereof from an external environment to preserve sterility. An actuator device has valve actuators, sensors, and a pumping actuator. The fluid circuit has sensor and pumping portions that engage, respectively, along with the valve portions, with effectors of the actuator device.

In variations thereof, the nineteenth embodiments include ones in which the fluid inlet line has an inline sterilizing filter with an air line attached thereto, the air line being connected such that air forced through the air line applies pressure to a membrane of the inline sterilizing filter to permit an integrity test thereof. In variations thereof, the nineteenth embodiments include ones in which the fluid inlet line has respective sterilizing filters serially-connected sterilizing filter elements. In variations thereof, the nineteenth embodiments include ones in which the valve network is positioned and held in a cartridge that has a pumping portion supported by a rigid manifold member, the manifold member being hollow and defining at least some of the junctions and the air line connecting to a port fixedly attached to the manifold member. In variations thereof, the nineteenth embodiments include ones in which the valve network is in a cartridge with the pumping portion held by a rigid manifold member thereof, the manifold member being hollow and defining at least some of the junctions. In variations thereof, the nineteenth embodiments include ones in which the air line connects to a port fixedly attached to the manifold member. In variations thereof, the nineteenth embodiments include ones in which the manifold member is rigid and has two separate chambers connected by the pumping portion.

In variations thereof, the nineteenth embodiments include ones in which the valve network is supported by a panel providing support for the cartridge, the manifold member being connected to the panel. In variations thereof, the nineteenth embodiments include ones in which the valve network is supported by a panel, the manifold member being spaced apart from the panel. In variations thereof, the nineteenth embodiments include ones in which at least one of the two separate chambers has pressure sensors integrated therein, one at each end of the pumping portion. In variations thereof, the nineteenth embodiments include ones in which the pressure sensor includes a pressure pod with a diaphragm that serves as a portion of a wall of a respective one of the two separate chambers. In variations thereof, the nineteenth embodiments include ones in which the respective concentrate line connectors are connected by a frame that support a portion of the concentrate line. In variations thereof, the nineteenth embodiments include ones in which frame has a window and the portion of the concentrate line passes across the window. In variations thereof, the nineteenth embodiments include ones in which valve network has a drain line. In variations thereof, the nineteenth embodiments include ones in which valve network has a dialysis solution fill/drain line connectable to a peritoneal catheter. In variations thereof, the nineteenth embodiments include ones in which fill/drain line is sealed by a removable end cap. In variations thereof, the nineteenth embodiments include ones in which the dialysis solution fill/drain line has a second air line collinear with the dialysis solution fill/drain line, connected at an end of the dialysis solution fill/drain line to a pressure pod connected to the dialysis solution fill/drain line to measure a pressure therewithin. In variations thereof, the nineteenth embodiments include ones in which drain and fluid inlet lines are connected by a frame that support portions of the drain and fluid inlet lines. In variations thereof, the nineteenth embodiments include ones in which frame has a window and portions of the drain and fluid inlet lines pass across the window. In variations thereof, the nineteenth embodiments include ones in which the valve portions are supported by a planar element. In variations thereof, the nineteenth embodiments include ones in which planar element includes a pair of sheets shaped to hold the valve portions in predefined positions. In variations thereof, the nineteenth embodiments include ones in which the planar element includes a pair of sheets shaped to hold the valve portions in predefined positions, at least one of the pair of sheets having holes in it to permit valve actuators to contact the valve portions. In variations thereof, the nineteenth embodiments include ones in which the valve portions are tube segments. In variations thereof, the nineteenth embodiments include ones in which the valve portions are tube segments. In variations thereof, the nineteenth embodiments include ones in which the concentrate line is sealed by a frangible seal. In variations thereof, the nineteenth embodiments include ones in which the mixing container and concentrate container are defined by two bonded flexible panels along seams to define the mixing container and concentrate container. In variations thereof, the nineteenth embodiments include ones in which the seams are a result of thermal welding. In variations thereof, the nineteenth embodiments include ones in which the fluid circuit encloses a sterile internal volume. In variations thereof, the nineteenth embodiments include ones in which the actuator device includes a peritoneal dialysis cycler.

According to twentieth embodiments, the disclosed subject matter includes a system for administering a peritoneal dialysis treatment. A peritoneal dialysis system component is connectable to one or more long-term containers of dialysis fluid concentrate and a water source. A disposable fluid circuit has a pumping portion, a mixing container, and one or more short-term concentrate containers. Pumping and valve actuators are controlled by a controller, which controls them to engage the disposable fluid circuit to create a mixed batch of peritoneal dialysis fluid by transferring sufficient concentrate for multiple cycles of a single treatment from the one or more long-term containers of dialysis fluid concentrate to the one or more short-term concentrate containers and, for each cycle of a treatment, transferring sufficient concentrate for a fill cycle from the one or more short-term concentrate containers to the mixing container and transferring sufficient water to form a ready-to-use dialysate to the mixing container from the water source.

In variations thereof, the twentieth embodiments include ones in which the mixing container and the short-term concentrate containers are polymeric bags. In variations thereof, the twentieth embodiments include ones in which the pumping and valve actuators are controlled to perform a fill cycle of an automated peritoneal dialysis treatment using the contents of the mixing container. In variations thereof, the twentieth embodiments include ones that include at least one conductivity sensor connected to a drain line of the fluid circuit, wherein the pumping and valve actuators are controlled to sample contents of the mixing container to obtain a conductivity measurement thereof.

According to twenty-first embodiments, the disclosed subject matter includes a fluid circuit for peritoneal dialysis and dialysis solution preparation. A pre-connected fluid circuit has a disposable mixing container of polymeric material, a concentrate container of polymeric material, a fluid multiplexer that includes a valve network that has junctions and valve portions that mechanically interface with valve actuators to define selectable flow paths in the valve network. The valve network further includes a concentrate line connected to the concentrate container, a fluid inlet line terminated by a fluid inlet line connector, and a pair of lines connected to the mixing container to permit simultaneous flow into, and flow out from, the mixing container. The fluid inlet line has an inline sterilizing filter. The valve network is positioned and held in a cartridge that has a pumping portion supported by a manifold member, the manifold member being hollow and defining at least some of the junctions. The fluid circuit is preconnected and sealed as a unit to isolate an internal volume thereof from an external environment to preserve sterility.

In variations thereof, the twenty-first embodiments include ones in which the manifold member is rigid and defines two separate chambers connected by the pumping portion. In variations thereof, the twenty-first embodiments include ones in which fluid inlet line has an air line that is collinear with the fluid inlet line and connects to the inline sterilizing filter. In variations thereof, the twenty-first embodiments include ones in which the valve network is supported by a panel, the manifold member being connected to the panel. In variations thereof, the twenty-first embodiments include ones in which the valve network is supported by a panel, the manifold member being spaced apart from the panel. In variations thereof, the twenty-first embodiments include ones in which the manifold has pressure sensors integrated therein, one at each end of a pumping tube segment. In variations thereof, the twenty-first embodiments include ones in which the pumping tube segment is straight. In variations thereof, the twenty-first embodiments include ones in which the pressure sensors include a pressure pod with a diaphragm that serves as a portion of a wall of a respective one of the two separate chambers. In variations thereof, the twenty-first embodiments include ones in which the valve network has a drain line. In variations thereof, the twenty-first embodiments include ones in which the drain and fluid lines are connected by a frame that support portions of the drain and fluid lines. In variations thereof, the twenty-first embodiments include ones in which the frame has a window and the portion of the drain and fluid lines passes across the window. In variations thereof, the twenty-first embodiments include ones in which the valve network has a dialysis solution fill/drain line connectable to a peritoneal catheter. In variations thereof, the twenty-first embodiments include ones in which the fill/drain line is sealed by a removable end cap. In variations thereof, the twenty-first embodiments include ones in which the valve network has a dialysis solution fill/drain line connectable to a peritoneal catheter and the dialysis solution fill/drain line has a second air line collinear with the dialysis solution fill/drain line, connected at an end of the dialysis solution fill/drain line to a pressure pod connected to the dialysis solution fill/drain line to measure a pressure therewithin. In variations thereof, the twenty-first embodiments include ones in which the drain and fluid inlet lines are connected by a frame that support portions of the drain and fluid inlet lines. In variations thereof, the twenty-first embodiments include ones in which the frame has a window and portions of the drain and fluid inlet lines pass across the window. In variations thereof, the twenty-first embodiments include ones in which the valve portions are supported by a planar element. In variations thereof, the twenty-first embodiments include ones in which the planar element includes a pair of sheets shaped to hold the valve portions in predefined positions. In variations thereof, the twenty-first embodiments include ones in which the planar element includes a pair of sheets shaped to hold the valve portions in predefined positions, at least one of the pair of sheets having holes in it to permit valve actuators to contact the valve portions. In variations thereof, the twenty-first embodiments include ones in which the valve portions are tube segments. In variations thereof, the twenty-first embodiments include ones in which the valve portions are tube segments. In variations thereof, the twenty-first embodiments include ones in which the mixing container and concentrate container are defined by two bonded flexible panels along seams to define the mixing container and concentrate container. In variations thereof, the twenty-first embodiments include ones in which the seams are a result of thermal welding. In variations thereof, the twenty-first embodiments include ones in which the fluid circuit encloses a sterile internal volume.

According to twenty-second embodiments, the disclosed subject matter includes a fluid circuit for peritoneal dialysis and dialysate preparation. A disposable mixing container of polymeric material has a pre-attached fluid circuit, the mixing container and fluid circuit being sealed from an external environment. A concentrate container of polymeric material is pre-attached to the fluid circuit, the concentrate container being sealed from an external environment. The fluid circuit includes a fluid multiplexer that includes a valve network that has junctions and valve portions that mechanically interface with valve actuators to define selectable flow paths in the valve network. The valve network further including a concentrate line connected to the concentrate container, a water line terminated by a water line connector, and a at least one mixing container line connected to the mixing container to permit simultaneous flow into, and flow out from, the mixing container. The water line has an inline sterilizing filter. The valve network is positioned and held in a cartridge that has a pumping portion supported by a manifold member, the manifold member being hollow and defining at least some of the junctions. The manifold member defines two separate chambers connected by a pumping tube segment.

In variations thereof, the twenty-second embodiments include ones in which the water line has an air line attached thereto, the air line being connected such that air forced through the air line applies pressure to a membrane of the inline sterilizing filter to permit an integrity test thereof. In variations thereof, the twenty-second embodiments include ones in which the valve network is supported by a panel, the manifold member being connected to the panel. In variations thereof, the twenty-second embodiments include ones in which the valve network is supported by a panel, the manifold member being spaced apart from the panel. In variations thereof, the twenty-second embodiments include ones in which the air line is integral with at least a portion of a respective one of the concentrate and water lines. In variations thereof, the twenty-second embodiments include ones in which the manifold has pressure sensors integrated therein, one at each end of the pumping portion. In variations thereof, the twenty-second embodiments include ones in which the pumping portion is straight. In variations thereof, the twenty-second embodiments include ones in which the pressure sensor includes a pressure pod with a diaphragm that serves as a portion of a wall of a respective one of the two separate chambers. In variations thereof, the twenty-second embodiments include ones in which the valve network has a drain line and the respective water and drain lines are connected by a frame that support portions thereof. In variations thereof, the twenty-second embodiments include ones in which the frame has a window and the portions pass across the window. In variations thereof, the twenty-second embodiments include ones in which the valve network has a drain line. In variations thereof, the twenty-second embodiments include ones in which the valve network has a dialysate fill/drain line connectable to a peritoneal catheter. In variations thereof, the twenty-second embodiments include ones in which the fill/drain line is sealed by a removable end cap. In variations thereof, the twenty-second embodiments include ones in which the valve network has a dialysate fill/drain line connectable to a peritoneal catheter and wherein the dialysate fill/drain line has a second air line collinear with the dialysate fill/drain line, connected at an end of the dialysate fill/drain line to a pressure pod connected to the dialysate fill/drain line to measure a pressure therewithin. In variations thereof, the twenty-second embodiments include ones in which the drain and water lines are connected by a frame that support portions of the drain and water lines. In variations thereof, the twenty-second embodiments include ones in which the frame has a window and portions of the drain and water lines pass across the window. In variations thereof, the twenty-second embodiments include ones in which the valve portions are supported by a planar element. In variations thereof, the twenty-second embodiments include ones in which the planar element includes a pair of sheets shaped to hold the valve portions in predefined positions. In variations thereof, the twenty-second embodiments include ones in which the planar element includes a pair of sheets shaped to hold the valve portions in predefined positions, at least one of the pair of sheets having holes in it to permit valve actuators to contact the valve portions.

In variations thereof, the twenty-second embodiments include ones in which the valve portions are tube segments. In variations thereof, the twenty-second embodiments include ones in which the valve portions are tube segments. In variations thereof, the twenty-second embodiments include ones in which the concentrate line is sealed by a frangible seal. In variations thereof, the twenty-second embodiments include ones in which the cartridge includes parallel panels with the valve network sandwiched between them, the frangible seal held in the cartridge aligned with windows in at least one of the panels to permit an actuator to fracture them prior to use thereby allowing the concentrate to flow through the concentrate line. In variations thereof, the twenty-second embodiments include ones in which the cartridge includes a single folded panel forming parallel panel portions with the valve network sandwiched between them, the frangible seal being held in the cartridge aligned with windows in at least one of the panels to permit an actuator to fracture them prior to use thereby allowing the concentrate to flow through the concentrate line. In variations thereof, the twenty-second embodiments include ones in which the valve network includes the concentrate line which is sealed by a frangible seal thereby separating the concentrate from the rest of the fluid circuit until the frangible seal is fractured. In variations thereof, the twenty-second embodiments include ones that include a second sterilizing filter connected in series with the inline sterilizing filter such that the second and inline sterilizing filters are separated by a flow channel to prevent grow-through contamination between membranes thereof. In variations thereof, the twenty-second embodiments include ones in which the mixing container and concentrate container are defined by two bonded flexible panels along seams to define the mixing container and concentrate container. In variations thereof, the twenty-second embodiments include ones in which seams are a result of thermal welding. In variations thereof, the twenty-second embodiments include ones in which the fluid circuit encloses a sterile internal volume.

According to twenty-third embodiments, the disclosed subject matter includes a fluid system for peritoneal dialysis and dialysate preparation. A disposable mixing container of polymeric material has a pre-attached fluid circuit, the mixing container and fluid circuit being sealed from an external environment. A concentrate container of polymeric material is pre-attached to the fluid circuit, the concentrate container being sealed from an external environment. The fluid circuit includes a fluid multiplexer that includes a valve network that has junctions and valve portions that mechanically interface with valve actuators to define selectable flow paths in the valve network. The valve network further includes a concentrate line connected to the concentrate container, a water line terminated by a water line connector, and a pair of lines connected to the mixing container to permit simultaneous flow into, and flow out from, the mixing container. The water line has an inline sterilizing filter with an air line attached thereto, the air line being connected such that air forced through the air line applies pressure to a membrane of the inline sterilizing filter to permit an integrity test thereof. An actuator device has valve actuators, sensors, and a pumping actuator. The fluid circuit has sensor and pumping portions that engage, respectively, along with the valve portions, with effectors of the actuator device.

In variations thereof, the twenty-third embodiments include ones in which the valve network is in a cartridge with the pumping portion held by a rigid manifold member thereof, the manifold member being hollow and defining at least some of the junctions. In variations thereof, the twenty-third embodiments include ones in which the air line connects to a port fixedly attached to the manifold member. In variations thereof, the twenty-third embodiments include ones in which the manifold member is rigid and has two separate chambers connected by the pumping portion. In variations thereof, the twenty-third embodiments include ones in which the valve network is supported by a panel providing support for the cartridge, the manifold member being connected to the panel. In variations thereof, the twenty-third embodiments include ones in which the valve network is supported by a panel, the manifold member being spaced apart from the panel. In variations thereof, the twenty-third embodiments include ones in which the manifold has pressure sensors integrated therein, one at each end of the pumping portion. In variations thereof, the twenty-third embodiments include ones in which pressure sensor includes a pressure pod with a diaphragm that serves as a portion of a wall of a respective one of the two separate chambers. In variations thereof, the twenty-third embodiments include ones in which respective concentrate line connectors are connected by a frame that support a portion of the concentrate line. In variations thereof, the twenty-third embodiments include ones in which frame has a window and the portion of the concentrate line passes across the window. In variations thereof, the twenty-third embodiments include ones in which valve network has a drain line.

In variations thereof, the twenty-third embodiments include ones in which valve network has a dialysate fill/drain line connectable to a peritoneal catheter. In variations thereof, the twenty-third embodiments include ones in which fill/drain line is sealed by a removable end cap. In variations thereof, the twenty-third embodiments include ones in which dialysate fill/drain line has a second air line collinear with the dialysate fill/drain line, connected at an end of the dialysate fill/drain line to a pressure pod connected to the dialysate fill/drain line to measure a pressure therewithin. In variations thereof, the twenty-third embodiments include ones in which drain and water lines connected by a frame that support portions of the drain and water lines. In variations thereof, the twenty-third embodiments include ones in which In variations thereof, the twenty-third embodiments include ones in which frame has a window and portions of the drain and water lines pass across the window. In variations thereof, the twenty-third embodiments include ones in which the valve portions are supported by a planar element. In variations thereof, the twenty-third embodiments include ones in which the planar element includes a pair of sheets shaped to hold the valve portions in predefined positions. In variations thereof, the twenty-third embodiments include ones in which planar element includes a pair of sheets shaped to hold the valve portions in predefined positions, at least one of the pair of sheets having holes in it to permit valve actuators to contact the valve portions. In variations thereof, the twenty-third embodiments include ones in which the valve portions are tube segments. In variations thereof, the twenty-third embodiments include ones in which valve portions are tube segments. In variations thereof, the twenty-third embodiments include ones in which the concentrate line is sealed by a frangible seal. In variations thereof, the twenty-third embodiments include ones in which the cartridge includes parallel panels with the valve network sandwiched between them, the frangible seal held in the cartridge aligned with windows in at least one of the panels to permit an actuator to fracture them prior to use thereby allowing the concentrate to flow through the concentrate line. In variations thereof, the twenty-third embodiments include ones in which the cartridge includes a single folded panel forming parallel panel portions with the valve network sandwiched between them, the frangible seal being held in the cartridge aligned with windows in at least one of the panels to permit an actuator to fracture them prior to use thereby allowing the concentrate to flow through the concentrate line. In variations thereof, the twenty-third embodiments include ones in which the valve network includes the concentrate line which is sealed by a frangible seal thereby separating the concentrate from the rest of the fluid circuit until the frangible seal is fractured. In variations thereof, the twenty-third embodiments include ones that include a second sterilizing filter connected in series with the inline sterilizing filter such that the second and inline sterilizing filters are separated by a flow channel to prevent grow-through contamination between membranes thereof. In variations thereof, the twenty-third embodiments include ones in which the batch container and concentrate container are defined by two bonded flexible panels along seams to define the batch container and concentrate container. In variations thereof, the twenty-third embodiments include ones in which the seams are a result of thermal welding. In variations thereof, the twenty-third embodiments include ones in which the fluid circuit encloses a sterile internal volume. In variations thereof, the twenty-third embodiments include ones in which actuator device includes a peritoneal dialysis cycler. In variations thereof, the twenty-third embodiments include ones in which the drain and water lines connected by a frame that support portions of the drain and water lines and the actuator device has a cut-and-seal device and a receiving slot that receives the frame and aligns a windows of the frame with the cut-and-seal device. In variations thereof, the twenty-third embodiments include ones in which the actuator device has a controller programmed to activate the cut-and-seal device to cut and seal the concentrate line thereby permitting the fluid circuit to be separated from the frame and a concentrate line connector as well as a stub portion of the concentrate line, which collectively remain in place on the actuator device to act as a seal on connectors of the actuator device.

According to twenty-fourth embodiments, the disclosed subject matter includes a treatment method. The method includes using a peritoneal cycler device with a fluid circuit having valve, container, and pumping portions, the peritoneal cycler device having actuators and sensors controlled by a controller that interface with the valve and pumping portions for preparing peritoneal dialysis fluid, and under control of the controller: accessing a priming bolus comprising a first volume of a first fluid; priming at least a patient fill line with the priming bolus; preparing a treatment batch comprising a second volume of a second fluid, wherein the second volume is larger than the first volume; and performing at least one fill/drain cycle of a renal replacement therapy through the fluid circuit and using the treatment batch.

In variations thereof, the twenty-fourth embodiments include ones in which the accessing a priming bolus and the preparing a treatment batch both include diluting and mixing at least one concentrate and the preparing the accessing a priming bolus takes less time than the preparing of the treatment batch. In variations thereof, the twenty-fourth embodiments include ones that include, prior to the preparing a treatment batch, determining that a fluid circuit is connected to a patient and preventing the preparing a treatment batch until a fluid circuit is connected to a patient. In variations thereof, the twenty-fourth embodiments include ones in which the first fluid and the second fluid have a same composition according to a same prescription. In variations thereof, the twenty-fourth embodiments include ones in which first fluid and the second fluid have different compositions. In variations thereof, the twenty-fourth embodiments include ones in which first fluid is a non-prescription fluid. In variations thereof, the twenty-fourth embodiments include ones in which the first fluid is water or saline.

In variations thereof, the twenty-fourth embodiments include ones that include receiving by the controller an indication through a user interface that quick priming is desired or determining whether a patient is full or empty and if not, skipping the accessing and the priming. In variations thereof, the twenty-fourth embodiments include ones in which the priming bolus and the treatment batch are stored in a same mixing container of the container portions. In variations thereof, the twenty-fourth embodiments include ones in which at least one of the priming bolus and the treatment batch is prepared by flowing purified water and a medicament concentrate to the mixing container to proportion and dilute the medicament concentrate. In variations thereof, the twenty-fourth embodiments include ones in which mixing container is disposable. In variations thereof, the twenty-fourth embodiments include ones in which fluid circuit is disposable and includes a pumping tube segment and multiple valve segments of the valve portions, wherein peritoneal cycler device includes at least one pumping actuator positioned to engage the pumping tube segment, wherein the peritoneal cycler device further includes multiple valve actuators positioned to engage the valve segments. In variations thereof, the twenty-fourth embodiments include ones in which the preparing of the priming bolus comprises drawing a concentrate and water through a sterilizing filter in predefined quantities to make the first volume of the first fluid. In variations thereof, the twenty-fourth embodiments include ones in which the preparing of the treatment batch comprises drawing a concentrate and water through a sterilizing filter in predefined quantities to make the second volume of the second fluid, wherein the second fluid is peritoneal dialysis fluid, wherein the second volume provides a sufficient quantity of peritoneal dialysis fluid for at least a single fill of a treatment cycle.

In variations thereof, the twenty-fourth embodiments include ones in which the drawing includes, using an interconnection module, connecting water and concentrate at different times to a common inlet of the fluid circuit to which the sterilizing filter is integrally attached. In variations thereof, the twenty-fourth embodiments include ones that include testing the sterilizing filter by an air pressure test and using, or preventing use of, the quantity for a peritoneal dialysis fill and drain cycle depending on a result of the testing. In variations thereof, the twenty-fourth embodiments include ones that include connecting a long-term concentrate container to the interconnection module once every multiple peritoneal dialysis treatments. In variations thereof, the twenty-fourth embodiments include ones in which the fluid circuit, having a sterilizing filter integrally attached thereto, is connected to the interconnection module once every single peritoneal dialysis treatment.

According to twenty-fifth embodiments, the disclosed subject matter includes a system for administering a peritoneal dialysis treatment. A peritoneal dialysis cycler portion is connectable to a source of priming fluid. A controller, with a user interface, controls a fill/drain pump of the peritoneal dialysis cycler portion. The controller requests input through the user interface indicating whether a patient is full or empty. In response to the controller receiving input through the user interface indicating the patient is empty, preparing a full batch of peritoneal dialysis fluid prior to beginning a treatment. In response to the controller receiving input through the user interface indicating the patient is full, initiating a quick prime mode prior to beginning a treatment. The quick prime mode including preparing or accessing a quick prime bolus and using it to prime a patient line.

In variations thereof, the twenty-fifth embodiments include ones in which the quick prime bolus is of a different composition from a peritoneal dialysis fluid. In variations thereof, the twenty-fifth embodiments include ones in which the quick prime bolus is of water. In variations thereof, the twenty-fifth embodiments include ones that include, after the quick prime mode, using the controller, draining a patient. In variations thereof, the twenty-fifth embodiments include ones that include, in response to the controller receiving input through the user interface indicating the patient is empty, generating a command to prevent access by a user to the quick prime mode.

According to twenty-sixth embodiments, the disclosed subject matter includes a treatment method that includes preparing a priming batch comprising a first volume of a first fluid and priming a patient fill/drain line with the priming batch. The method includes determining that a fluid circuit is connected to a patient. The method includes preparing a treatment batch comprising a second volume of a second fluid, wherein the second volume is larger than the first volume. The method includes performing at least one fill/drain cycle of a renal replacement therapy through the fluid circuit and using the treatment batch.

In variations thereof, the twenty-sixth embodiments include ones in which the preparing of the priming batch takes less time than the preparing of the treatment batch. In variations thereof, the twenty-sixth embodiments include ones in which the first fluid and the second fluid have a same composition according to a same prescription. In variations thereof, the twenty-sixth embodiments include ones in which first fluid and the second fluid have different compositions. In variations thereof, the twenty-sixth embodiments include ones in which the first fluid is a non-prescription fluid. In variations thereof, the twenty-sixth embodiments include ones in which the first fluid is water or saline. In variations thereof, the twenty-sixth embodiments include ones in which the method is performed after receiving an indication from the patient to perform quick priming. In variations thereof, the twenty-sixth embodiments include ones in which the priming batch and the treatment batch are stored in a same mixing container. In variations thereof, the twenty-sixth embodiments include ones in which at least one of the priming batch and the treatment batch is prepared by flowing purified water and a medicament concentrate to the mixing container to proportion and dilute the medicament concentrate.

In variations thereof, the twenty-sixth embodiments include ones in which the method is performed by a proportioning and treatment device having actuators that engage with the fluid circuit when received thereby. In variations thereof, the twenty-sixth embodiments include ones in which the mixing container is disposable. In variations thereof, the twenty-sixth embodiments include ones in which the fluid circuit is disposable and includes a pumping tube segment and multiple valve segments, wherein the proportioning and treatment device includes at least one pumping actuator positioned to engage the pumping tube segment, wherein the proportioning and treatment device further includes multiple valve actuators positioned to engage the valve segments. In variations thereof, the twenty-sixth embodiments include ones in which the preparing of the priming batch comprises drawing a concentrate and water through a sterilizing filter in predefined quantities to make the first volume of the first fluid. In variations thereof, the twenty-sixth embodiments include ones in which the preparing of the treatment batch comprises drawing a concentrate and water through a sterilizing filter in predefined quantities to make the second volume of the second fluid, wherein the second fluid is peritoneal dialysate, wherein the second volume provides a sufficient quantity of peritoneal dialysate for a single fill of a treatment cycle. In variations thereof, the twenty-sixth embodiments include ones in which the drawing includes, using an interconnection module, connecting water and concentrate at different times to a common inlet of the fluid circuit to which the sterilizing filter is integrally attached. In variations thereof, the twenty-sixth embodiments include ones that that include testing the sterilizing filter by an air pressure test and using, or preventing use of, the quantity for a peritoneal dialysis fill and drain cycle depending on a result of the testing. In variations thereof, the twenty-sixth embodiments include ones that include connecting a long-term concentrate container to the interconnection module once every multiple peritoneal dialysis treatments. In variations thereof, the twenty-sixth embodiments include ones in which the fluid circuit having the sterilizing filter integrally attached thereto is connected to the interconnection module once every single peritoneal dialysis treatment.

According to twenty-seventh embodiments, the disclosed subject matter includes a system for preparation of sterile medical treatment fluid with a disposable fluid circuit with a pumping tube segment and multiple valve segments. A proportioning and treatment device with a pumping actuator is shaped to engage the pumping tube segment and multiple valve actuators positioned to engage the valve segments. A first of the multiple valve segments is connected to a water inlet. A second of the multiple valve segments being connected to a first concentrate inlet. The disposable fluid circuit has a sterilizing filter connected between each of the water inlet and the first concentrate inlet and respective ones of the first and second of the multiple valve segments. A first concentrate container has sufficient concentrate for preparation of enough peritoneal dialysate to perform multiple peritoneal dialysis treatments, each treatment including multiple fill/drain cycles. The disposable fluid circuit has a first concentrate inlet connector for the first concentrate inlet which is adapted to be connected to the first concentrate container. The disposable fluid circuit having an integrally-attached mixing container sized to hold sufficient peritoneal dialysate for at least a single fill/drain cycle. The proportioning and treatment device has a programmable controller programmed to control the pumping actuator to pump concentrate and water into the mixing container to make a batch of peritoneal dialysate and subsequently to perform a fill/drain cycle including draining spent peritoneal dialysate and pumping a fill of the peritoneal dialysate from the mixing container.

In variations thereof, the twenty-seventh embodiments include ones in which the disposable fluid circuit has a second concentrate inlet with a sterilizing filter connected between the second concentrate inlet and a third of the multiple valve segments. In variations thereof, the twenty-seventh embodiments include ones that include a second concentrate container having concentrate for the preparation of enough peritoneal dialysate to perform multiple peritoneal dialysis treatments each treatment including multiple fill/drain cycles, wherein the first and second concentrate inlets are connected to the first and second concentrate containers by a double connector that carries the first concentrate inlet connector and a second concentrate inlet connector of the disposable fluid circuit, the double connector making connections for the first concentrate inlet connector and the second concentrate inlet simultaneously to the first and second concentrate containers. In variations thereof, the twenty-seventh embodiments include ones that include an interconnection module that has a primary connector, to which the first concentrate container is connected once every multiple treatments, and a secondary connector to which the disposable fluid circuit first concentrate inlet connector is connected once every treatment. In variations thereof, the twenty-seventh embodiments include ones in which the water inlet has a sterilizing filter with an air port controller to allow a membrane of the sterilizing filter to be pressure tested such as by a bubble point test, the controller being programmed to test the sterilizing filter membrane by applying pressure to the air port controller and measuring the pressure after pumping water therethrough. In variations thereof, the twenty-seventh embodiments include ones in which the controller generates an alarm signal responsively to a result of a test of the sterilizing filter membrane if the test indicates a disintegration of the sterilizing filter membrane.

According to twenty-eighth embodiments, the disclosed subject matter includes a fluid circuit for peritoneal dialysis and dialysate preparation. A disposable mixing container of polymeric material has a pre-attached fluid circuit, the mixing container and fluid circuit being sealed from an external environment. The fluid circuit includes a fluid multiplexer that has junctions and valve portions that mechanically interface with valve actuators to define selectable flow paths in the fluid circuit. The fluid circuit includes at least two concentrate lines terminated by respective concentrate line connectors, a water line terminated by a water line connector, and one or more lines connected to permit flow into and out of the mixing container. Each of the concentrate and water lines has a testable inline sterilizing filter or a redundant serially-connected pair of sterilizing filters. The fluid circuit has a pumping portion.

In variations thereof, the twenty-eighth embodiments include ones in which the testable inline sterilizing filters each have air lines that are each collinear with at least a portion of a respective one of the concentrate and water lines. In variations thereof, the twenty-eighth embodiments include ones in which the testable inline sterilizing filters each have air lines that are each integral with at least a portion of a respective one of the concentrate and water lines. In variations thereof, the twenty-eighth embodiments include ones that include a rigid manifold chamber with pressure sensors integrated therein, one at each end of a pumping tube segment of the pumping portion. In variations thereof, the twenty-eighth embodiments include ones in which the pumping tube segment is straight. In variations thereof, the twenty-eighth embodiments include ones in which the rigid manifold has two separate chambers and the pressure sensor includes a pressure pod with a diaphragm that serves as a portion of a wall of a respective one of the two separate chambers. In variations thereof, the twenty-eighth embodiments include ones in which the respective concentrate line connectors are connected by a frame that support portions of the concentrate lines. In variations thereof, the twenty-eighth embodiments include ones in which the frame has a window and the portions of the concentrate lines pass across the window. In variations thereof, the twenty-eighth embodiments include ones in which the fluid circuit has a drain line. In variations thereof, the twenty-eighth embodiments include ones in which the drain and water lines connected by a frame that support portions of the drain and water lines. In variations thereof, the twenty-eighth embodiments include ones in which the frame has a window and portions of the drain and water lines pass across the window. In variations thereof, the twenty-eighth embodiments include ones in which the valve portions are supported by a planar element. In variations thereof, the twenty-eighth embodiments include ones in which the planar element includes a pair of sheets shaped to hold the valve portions in predefined positions. In variations thereof, the twenty-eighth embodiments include ones in which the planar element includes a pair of sheets shaped to hold the valve portions in predefined positions, at least one of the pair of sheets having holes in it to permit valve actuators to contact the valve portions. In variations thereof, the twenty-eighth embodiments include ones in which the valve portions are tube segments. In variations thereof, the twenty-eighth embodiments include ones in which the valve portions are tube segments.

In variations thereof, the twenty-eighth embodiments include ones in which the fluid circuit is held by a cartridge that includes parallel panels with the valve portions sandwiched between them, at least two frangible seals being held in the cartridge aligned with windows in at least one of the panels to permit an actuator to fracture them prior to use thereby allowing the concentrate to flow through the at least two concentrate lines.

According to twenty-ninth embodiments, the disclosed subject matter includes a method of making a peritoneal dialysis fluid including drawing a concentrate and water through a sterilizing filter in predefined quantities and proportioning the concentrate and water to make a sufficient quantity of peritoneal dialysis fluid for at least a single fill of a peritoneal dialysis treatment. The drawing includes, using an interconnection module, connecting water and concentrate at different times to a common inlet of a disposable fluid circuit to which the sterilizing filter is integrally attached and testing the sterilizing filter by an air pressure test and using, or preventing use of, the quantity for a peritoneal dialysis fill and drain cycle depending on a result of the testing.

In variations thereof, the twenty-ninth embodiments include ones in which connecting a long-term concentrate container to the interconnection module once every multiple peritoneal dialysis treatments. In variations thereof, the twenty-ninth embodiments include ones that include connecting a treatment circuit having the sterilizing filter integrally attached thereto, to the interconnection module once every single peritoneal dialysis treatments. In variations thereof, the twenty-ninth embodiments include ones that include mixing the water and the concentrate. In variations thereof, the twenty-ninth embodiments include ones in which the drawing and the mixing are performed using a single common pump. In variations thereof, the twenty-ninth embodiments include ones in which the disposable fluid circuit has at least one concentrate container that is initially empty and the drawing a concentrate includes filling the at least one concentrate container with concentrate. In variations thereof, the twenty-ninth embodiments include ones in which the proportioning includes transferring concentrate from the at least one concentrate container to a mixing container. In variations thereof, the twenty-ninth embodiments include ones in which the proportioning includes transferring water through the common inlet to a mixing container. In variations thereof, the twenty-ninth embodiments include ones in which the proportioning includes transferring concentrate from the at least one concentrate container to a mixing container and transferring water through the common inlet to a mixing container.

According to thirtieth embodiments, the disclosed subject matter includes a method of performing a peritoneal dialysis treatment including drawing a concentrate and water through a sterilizing filter in predefined quantities to make a sufficient quantity of peritoneal dialysate for a single fill of a peritoneal dialysis treatment. The drawing includes connecting water and concentrate at different times to a common inlet of a disposable fluid circuit to which the sterilizing filter is integrally attached.

In variations thereof, the thirtieth embodiments include ones in which the sterilizing filters includes separate filter elements connected in series by a flow channel. In variations thereof, the thirtieth embodiments include ones that include testing the sterilizing filter by an air pressure test and using, or preventing use of, the quantity for a peritoneal dialysis fill and drain cycle depending on a result of the testing. In variations thereof, the thirtieth embodiments include ones that include connecting a long term concentrate container to an interconnection module once every multiple peritoneal dialysis treatments. In variations thereof, the thirtieth embodiments include ones that include connecting a treatment circuit having the sterilizing filter integrally attached thereto, to the interconnection module once every single peritoneal dialysis treatments. In variations thereof, the thirtieth embodiments include ones that include mixing the water and the concentrate. In variations thereof, the thirtieth embodiments include ones in which the drawing and the mixing are performed using a single common pump.

According to thirty-first embodiments, the disclosed subject matter includes a method of performing a peritoneal dialysis treatment including drawing a concentrate and water through respective sterilizing filters in predefined quantities to make a sufficient quantity of peritoneal dialysate for a single fill of a peritoneal dialysis treatment. The drawing includes, using an interconnection module, flowing water and concentrate in succession to a mixing container the flowing water and concentrate in succession including switching flow paths in a peritoneal dialysis cycler. The method includes ensuring an integrity of the respective sterilizing filters by testing them or providing the respective sterilizing filters as serially-connected redundant sterilizing filter elements.

In variations thereof, the thirty-first embodiments include ones that include connecting a long term concentrate container to the interconnection module once every multiple peritoneal dialysis treatments. In variations thereof, the thirty-first embodiments include ones that include connecting a treatment circuit having the respective sterilizing filters integrally attached thereto, to the interconnection module once every single peritoneal dialysis treatments. In variations thereof, the thirty-first embodiments include ones that include mixing the water and the concentrate. In variations thereof, the thirty-first embodiments include ones in which the drawing and the mixing are performed using a single common pump. In variations thereof, the thirty-first embodiments include ones in which the connecting a treatment circuit includes removing at least one sterile seal from water and concentrate connectors and connecting one or more new connectors of the treatment circuit to water and concentrate connectors and wherein following the using the quantity, cutting one or more portions of the one or more new connectors to create at least one new sterile seal. In variations thereof, the thirty-first embodiments include ones in which the interconnection module supports a connector of the concentrate container, the connecting a long term concentrate connector including replacing the connector of the concentrate container and the connecting a treatment circuit includes connecting the treatment circuit to the connector of the concentrate container. In variations thereof, the thirty-first embodiments include ones in which the flowing water and concentrate in succession using the interconnection module includes washing a fixed volume of concentrate from a common outlet of the interconnection module and an inlet of a disposable fluid circuit, the method further comprising, using a controller used to make the sufficient quantity, calculating an amount of the fixed volume and controlling an amount of water pumped to form the sufficient quantity responsively to a result of the calculating.

According to thirty-second embodiments, the disclosed subject matter includes a system for preparation of sterile medical treatment fluid. A disposable fluid circuit has a pumping tube segment and multiple valve segments. A proportioning and treatment device has at least one pumping actuator positioned to engage the at least one pumping tube segment and multiple valve actuators positioned to engage the multiple valve segments. A first of the multiple valve segments is connected to a fluid inlet. The disposable fluid circuit has a sterilizing filter connected between a fluid inlet connector and the first of the multiple valve segments. A first concentrate container has sufficient concentrate for preparation of enough peritoneal dialysate to perform multiple peritoneal dialysis treatments, each treatment including multiple fill/drain cycles. The disposable fluid circuit having an integrally-attached mixing container sized to hold sufficient peritoneal dialysate for at least a single fill/drain cycle. An interconnection module has a primary concentrate connector and a primary water connector, to which the first concentrate container is connected once every multiple treatments. The interconnection module also has a common secondary connector to which the disposable fluid circuit fluid inlet connector is connected once every treatment. The interconnection module has a valve network controlled by a programmable controller that selects water or concentrate to flow through the common secondary connector. The proportioning and treatment device has a programmable controller programmed to control the at least one pumping actuator to pump concentrate and water into the mixing container to make a batch of peritoneal dialysate and subsequently to perform a fill/drain cycle including draining spent peritoneal dialysate and pumping a fill of the peritoneal dialysate from the mixing container.

In variations thereof, the thirty-third embodiments include ones that include a controller, the controller being programmed to calculate and store data representing a volume of water or concentrate remaining in a portion of the valve network after selecting water or concentrate to be drawn by the proportioning and treatment device and to control the pump responsively to the data representing a volume of water or concentrate.

According to thirty-fourth embodiments, the disclosed subject matter includes a method of making a fluid circuit having a chamber prefilled with medicament concentrate. The method includes integrally connecting a fluid circuit with a chamber and connecting a sterilizing filter with the chamber. The integrally connecting and connecting a sterilizing filter forms an assembly with a sealed volume that is separated from an outside environment by walls thereof, a frangible plug in a concentrate outlet line stemming from the chamber, and a membrane of the sterilizing filter. The method includes sterilizing the assembly. The method includes sterile-filling the chamber with concentrate through the sterilizing filter. The method includes permanently sealing and then cutting a line connecting the sterilizing filter and the chamber and subjecting the fluid circuit and chamber to gamma or e-beam sterilization.

According to thirty-fifth embodiments, the disclosed subject matter includes a method of making a fluid circuit having a chamber prefilled with medicament concentrate. The method includes integrally connecting a fluid circuit with a chamber. The method includes connecting a sterilizing filter with the chamber. The integrally connecting and connecting a sterilizing filter form an assembly with a sealed volume that is separated from an outside environment by walls thereof, a frangible plug in a concentrate outlet line stemming from the chamber, and a membrane of the sterilizing filter. The method includes sterilizing the assembly. The method includes sterile-filling the chamber with concentrate through the sterilizing filter. The method includes heat welding and cutting a line connecting the sterilizing filter and the chamber and subjecting the fluid circuit and chamber to gamma or e-beam sterilization.

According to thirty-fifth embodiments, the disclosed subject matter includes a fluid line connector with at least one thermoplastic tube supported in a frame such that the at least one thermoplastic tube is accessible from opposite sides of the frame. The frame has an overhanging ridge at one end and at least one connector that is fluidly coupled at an opposite end to the at least one thermoplastic tube. A cap is fitted to the frame to cover the at least one connector. The at least one tube extends through holes in the frame at end thereof adjacent the overhanging ridge.

In variations thereof, the thirty-fifth embodiments include ones in which the frame has a recess shaped to engage a détente pin along an elongate side thereof. In variations thereof, the thirty-fifth embodiments include ones in which the frame has an oval-shaped recess, the at least one connector being located within the oval-shaped recess. In variations thereof, the thirty-fifth embodiments include ones in which the cap fits in the oval-shaped recess to define a tortuous path between the at least one connector and an access of the oval-shaped recess. In variations thereof, the thirty-fifth embodiments include ones in which at least one connector and the at least one thermoplastic tubes are at least two.

According to thirty-sixth embodiments, the disclosed subject matter includes a connector system. A connector component has at least one thermoplastic tube supported in a frame such that the at least one thermoplastic tube is accessible from opposite sides of the frame. The frame has an overhanging ridge at one end and at least one connector that is fluidly coupled at an opposite end to the at least one thermoplastic tube. A cap is fitted to the frame to cover the at least one connector. The at least one tube extends through holes in the frame at an end thereof adjacent the overhanging ridge. A fluid supply device has at least one supply connector that mates with the at least one connector, the fluid supply device having a portion shaped to engage the frame to align the at least one thermoplastic tube with a tube cut-and-seal device.

In variations thereof, the thirty-sixth embodiments include ones in which the cut-and-seal device cuts the at least one thermoplastic tube and seals it at both ends, the connector component being configured to permit the at least one thermoplastic tube to be withdrawn from the one end leaving the frame and at least one connector in place on the at least one supply connector to cover and protect it from contamination until it is replaced by another connector component. In variations thereof, the thirty-sixth embodiments include ones in which the frame has a recess shaped to engage a détente pin along an elongate side thereof. In variations thereof, the thirty-sixth embodiments include ones in which the frame has an oval-shaped recess, the at least one connector being located within the oval-shaped recess. In variations thereof, the thirty-sixth embodiments include ones in which the cap fits in the oval-shaped recess to define a tortuous path between the at least one connector and an access of the oval-shaped recess. In variations thereof, the thirty-sixth embodiments include ones in which at least one connector and the at least one thermoplastic tubes are at least two. In variations thereof, the thirty-sixth embodiments include ones in which the frame has a recess shaped to engage a détente pin along an elongate side thereof. In variations thereof, the thirty-sixth embodiments include ones in which the frame has an oval-shaped recess, the at least one connector being located within the oval-shaped recess.

In variations thereof, the thirty-sixth embodiments include ones in which the cap fits in the oval-shaped recess to define a tortuous path between the at least one connector and an access of the oval-shaped recess. In variations thereof, the thirty-sixth embodiments include ones in which at least one connector and the at least one thermoplastic tubes are at least two.

According to thirty-seventh embodiments, the disclosed subject matter includes a fluid proportioning system with first and second manifolds connected by a pump. A port on the first manifold is provided for connection of a last-fill medicament and/or an auxiliary fluid. A controller is programmed to control the pump to draw, according to a command generated by the controller, a last fill or an auxiliary fluid.

In variations thereof, the thirty-seventh embodiments include ones that include a mixing container, the controller being programmed to transfer the auxiliary fluid to the mixing container and to use contents thereof to fill a peritoneum. In variations thereof, the thirty-seventh embodiments include ones in which the controller fills the mixing container with a fill of peritoneal dialysate prior to controlling the pump to draw a last fill or an auxiliary fluid. In variations thereof, the thirty-seventh embodiments include ones in which the controller is programmed to use contents of the mixing container to perform a peritoneal dialysis treatment.

According to thirty-eighth embodiments, the disclosed subject matter includes a method of mixing a medicament, the method including using a controller, combining respective quantities of water and liquid first medicament concentrate in a first target concentration calculated by the controller responsively to a map of allowed and disallowed ratios and a final prescribed concentration of the first medicament to generate an initial mixture. The method includes using the controller, testing the concentration of the initial mixture including measuring a conductivity of thereof. The method includes using the controller, responsively to the testing, diluting the initial mixture to a second target concentration of first medicament and further testing the concentration of a resulting second mixture including measuring a conductivity thereof.

In variations thereof, the thirty-eighth embodiments include ones that include, using the controller, adding a second medicament concentrate to the second mixture.

In variations thereof, the thirty-eighth embodiments include ones in which the first target is based on an optimization of total pumping time to minimize the time it to prepare a completed mixed batch of medicament.

According to thirty-ninth embodiments, the disclosed subject matter includes a system for making a peritoneal dialysis fluid. The system includes a peritoneal dialysis system component connectable to first and second containers of first and second concentrates and a water source and a disposable fluid circuit with a pumping portion and a mixing container. The system includes pumping and valve actuators controlled by a controller, which controls them to engage the disposable fluid circuit to create a predefined mixture of water, a first concentrate, and a second concentrate to form a ready-to-use peritoneal dialysate by:

(a) pumping a first quantity of water into the mixing container;

(b) pumping an amount of the first concentrate into the mixing container estimated to achieve a target conductivity of contents of the mixing container;
(c) testing a conductivity of the mixing container contents and, responsively to a result of the testing, adjusting a target amount of water and a target amount of a second concentrate to add to the mixing container if a result of the testing indicates a conductivity above the target conductivity;
(d) outputting an indication of a failed in-process mixture if the conductivity is below the target conductivity;
(e) adding an adjusted target amount of water and an adjusted target amount of second concentrate to the mixing container; and
(f) testing a conductivity of contents of the mixing container and depending on a result of the testing, outputting an indication of a successful or failed in-process mixture.

In variations thereof, the thirty-ninth embodiments include ones in which, after the adding an adjusted target amount of water, testing a conductivity of the contents of the mixing container and adding a further amount of water if a conductivity resulting from the testing is higher than a target. In variations thereof, the thirty-ninth embodiments include ones in which an amount of water added by the adding a further amount of water is responsive to the conductivity resulting from the testing.

According to fortieth embodiments, the disclosed subject matter includes a method of forming a batch of treatment fluid. The method includes adding water to a mixing container. The method includes adding a first concentrate to the mixing container and testing a conductivity of its contents. The method includes outputting an indication of a failed batch in the mixing container if the conductivity is below a first predefined level. The method includes, responsively to the conductivity, calculating an additional quantity of water and an additional quantity of a second concentrate to be added to the mixing container if the conductivity is above the predefined level. The method includes adding water and the second concentrate, including the additional quantities, to the mixing container.

In variations thereof, the fortieth embodiments include ones that include testing the conductivity of the mixing container contents and responsively to the conductivity outputting an indication of a failed batch in the mixing container if the conductivity is below a second predefined level.

According to forty-first embodiments, the disclosed subject matter includes a method of preparing a batch of treatment fluid. The method includes adding a quantity of an osmotic agent to a mixing container containing an electrolyte and detecting quantity of the added osmotic agent by a reduction in a conductivity of a solution in the mixing container.

In variations thereof, the forty-first embodiments includes ones that include adjusting a concentration of water or electrolyte responsively to a result of the detecting in order to achieve a target mixture of electrolyte and osmotic agent.

According to forty-second embodiments, the disclosed subject matter includes a method of preparing a batch of treatment fluid. The method includes
adding a fraction of a final quantity of water plus a first concentrate to a mixing container;
mixing the contents of the mixing container and testing a first conductivity of the contents;
if the first conductivity is below a first predefined range, outputting an indication of a failure of the mixing container contents;
if the first conductivity is above the first predefined range, calculating a first additional amount of water, to add to the final quantity, responsive to the first conductivity, plus an additional quantity beyond a final quantity of a second concentrate and add the second concentrate to the mixing container;
if the first conductivity is in the first predefined range, add the second concentrate to the mixing container;
adding a remainder of the final quantity of water plus the additional amount of water, if calculated, to the mixing container;
mixing the contents of the mixing container and testing a second conductivity of the contents;
if the second conductivity is below a second predefined range, outputting an indication of a failure of the mixing container contents; and
if the second conductivity is within the second predefined range, making the contents of the mixing container available for a treatment.

In variations thereof, the forty-second embodiments include ones in which, if the second conductivity is above the second predefined range, adding the first additional amount of water plus a second additional amount of water responsive to the second conductivity. In variations thereof, the forty-second embodiments include ones that include using the contents of the mixing container for a dialysis treatment. In variations thereof, the forty-second embodiments include ones that include using the contents of the mixing container for a peritoneal dialysis treatment.

According to forty-third embodiments, the disclosed subject matter includes method of making a batch of peritoneal dialysis fluid. The method includes:
(a) adding a first amount of water to a mixing container that is less than required to make the batch of peritoneal dialysis fluid;
(b) adding a first concentrate to the mixing container, mixing the mixing container contents, measuring a resulting first conductivity of the mixing container contents, and determining if the first conductivity is in a first range;
(c) if the first conductivity is in the first range, adding a second concentrate to the mixing container, mixing the mixing container contents, and measuring a resulting second conductivity of the mixing container contents;
(d) if the second conductivity is in a second range, adding water to the mixing container, mixing and measuring a resulting third conductivity of the mixing container contents;
(e) if the third conductivity falls in a third range, generating a signal indicating the contents of the mixing container form a usable batch of peritoneal dialysis fluid;
(f) if the first conductivity is outside the first range, calculating an amount of water or first concentrate responsively to the first conductivity and an estimated quantity of fluid in the mixing container and adding the amount of water or first concentrate to the mixing container, mixing the mixing container contents, and measuring a resulting fourth conductivity of the mixing container contents;
(g) if the fourth conductivity is in the first range, adding the second concentrate to the mixing container, mixing the mixing container contents, and measuring a resulting fifth conductivity of the mixing container contents;

(h) if the fifth conductivity is in the second range, adding water to the mixing container, mixing the mixing container contents, measuring a resulting sixth conductivity of the mixing container;

(i) if the sixth conductivity is in the third range, generating a signal indicating the contents of the mixing container form a usable batch of peritoneal dialysis fluid; and (j) if the second conductivity is outside the second range, the third conductivity is outside the third range, the fourth conductivity is outside the first range, the fifth conductivity is outside the second range, or the sixth conductivity is outside the third range, generating a signal indicating to terminate the making of a batch.

In variations thereof, the forty-third embodiments include ones in which the first concentrate is electrolyte concentrate and the second concentrate is osmotic agent concentrate. In variations thereof, the forty-third embodiments include ones in which the first concentrate is osmotic agent concentrate and the second concentrate is electrolyte concentrate.

According to forty-fourth embodiments, the disclosed subject matter includes a method for making a batch of peritoneal dialysis fluid. The method includes:

(a) adding water to a mixing container;

(b) adding electrolyte concentrate to the mixing container;

(c) mixing contents of the mixing container and measuring the conductivity of its contents;

(d) if the conductivity measured at (c) is in a first range, performing step (h) and if the conductivity measured at (c) is outside the first range performing step (e);

(e) estimating an amount of water or electrolyte concentrate, responsively to the conductivity measured in step (c), to bring the conductivity of the contents of the mixing container within the first range;

(f) adding the amount of water estimated in (e) to the mixing container, mixing the contents of the mixing container, and measuring the conductivity of its contents;

(g) if the conductivity measured in step (f) is outside a second range, generating a command to abort the making of the batch and performing step (p);

(h) calculating a quantity of a second concentrate according to a predefined ratio of the first and second concentrates responsively to a calculated quantity of fluid held by the mixing container and the conductivity measured at step (d) if the conductivity measured at step (c) was in the first range or the conductivity measured at (f) if not;

(i) adding the quantity of the second concentrate calculated at step (h) to the mixing container, mixing the contents of the mixing container, and measuring the conductivity thereof;

(j) if the conductivity measured at step (i) is outside the second range, generating a command to abort the making of the batch and going to step (p);

(k) if the conductivity measured at step (i) is in the second range, then calculating a quantity of water to add to the mixing container responsively to the conductivity measured at step (i) and a calculated quantity of fluid held by the mixing container;

(m) adding the quantity of water calculated at step (k) to the mixing container, mixing the contents of the mixing container, and measuring the conductivity of its contents;

(n) if the conductivity measured at step (m) falls in a third range, generating a command indicating the mixing container contents are usable;

(o) if the conductivity measured at step (m) fall outside the third range, generating a command to abort the making of the batch; and (p) terminating the method.

In variations thereof, the forty-fourth embodiments include ones in which the first concentrate is electrolyte concentrate and the second concentrate is osmotic agent concentrate. In variations thereof, the forty-fourth embodiments include ones in which the first concentrate is osmotic agent concentrate and the second concentrate is electrolyte concentrate. In variations thereof, the forty-fourth embodiments include ones in which a quantity of the adding electrolyte at step (b) is responsive to an estimate of an amount required for a completed batch. In variations thereof, the forty-fourth embodiments include ones in which each of the measuring the conductivity includes draining a portion of the contents of the mixing container. In variations thereof, the forty-fourth embodiments include ones in which the quantity of the adding electrolyte at step (b) is responsive to an estimate of a quantity of every instance of draining a portion.

According to forty-fifth embodiments, the disclosed subject matter includes a method of preparing a batch of treatment fluid. The method includes adding a quantity of an osmotic agent to a mixing container containing an electrolyte and detecting quantity of the added osmotic agent by a reduction in a conductivity of a solution in the mixing container.

In variations thereof, the forty-fifth embodiments include ones in which adjusting a concentration of water or electrolyte responsively to a result of the detecting in order to achieve a target mixture of electrolyte and osmotic agent.

According to forty-sixth embodiments, the disclosed subject matter includes a method of performing a peritoneal dialysis treatment. The method includes performing a fill cycle of a peritoneal dialysis treatment. The method includes performing a drain cycle of a peritoneal dialysis treatment and during the drain cycle, diverting at least one fraction of spent peritoneal dialysis fluid to a sample container to collect a sample.

In variations thereof, the forty-sixth embodiments include ones in which the sample includes multiple fractions of spent peritoneal dialysis diverted at different times during the drain cycle. In variations thereof, the forty-sixth embodiments include ones in which the different times, stored in a controller, are calculated to make the sample representative of the composition of all of the spent peritoneal dialysis fluid of a full drain cycle. In variations thereof, the forty-sixth embodiments include ones in which the diverting includes filling a container of less than 500 ml. In variations thereof, the forty-sixth embodiments include ones that include, using a controller, outputting instructions for handling the sample container. In variations thereof, the forty-sixth embodiments include ones that include, using a controller, outputting instructions for handling the sample container. In variations thereof, the forty-sixth embodiments include ones that include, using a controller, outputting instructions for removing, sealing, and delivering a sample collected in the sample container.

According to forty-seventh embodiments, the disclosed subject matter includes a method of performing a peritoneal dialysis treatment. The method includes using a controller, during a peritoneal dialysis drain cycle, according to a schedule of fractioning times stored in a controller, diverting fractions of spent peritoneal dialysis fluid from spent peritoneal dialysis fluid to a sample container. The schedule is responsive to predicted variations in the composition of the spent peritoneal dialysis fluid during a drain cycle and the fractioning times indicate times and durations of the fractions.

In variations thereof, the forty-seventh embodiments include ones in which the times and durations are independent of each other. In variations thereof, the forty-seventh embodiments include ones in which at least two of the durations are different from each other. In variations thereof, the forty-seventh embodiments include ones that include, diverting spent dialysis fluid other than the fractions to a drain responsively to the schedule.

According to forty-eighth embodiments, the disclosed subject matter includes a method of performing a peritoneal dialysis treatment. The method includes, using a controller, performing multiple drain cycles over the course of a peritoneal dialysis treatment and, for at least one of the drain cycles, diverting one or more fractions of spent peritoneal dialysis fluid from one or more of the multiple drain cycles and to a respective sample container for each of the multiple drain cycles. The method includes diverting one or more portions of the spent peritoneal dialysis fluid other than the one or more fractions, to a drain or waste collection container. The timings of the diverting of the one or more fractions are selected such that the resulting composition of the contents of each sample represent a composition of all, or a portion, of the entire contents of a respective one of the drain cycles.

In variations thereof, the forty-eighth embodiments include ones that include comparing the contents of one or more of the respective sample containers to a model that estimates the composition of all, or a portion, of the entire contents of a respective one of the drain cycles. In variations thereof, the forty-eighth embodiments include ones that include accepting input from a user interface of the controller indicating a total volume of the one or more fractions for each of the one or more of the multiple drain cycles, the controller using the input to control the total volume during the peritoneal dialysis treatment. In variations thereof, the forty-eighth embodiments include ones that include accepting input from a user interface of the controller indicating spacings of timings of the one or more fractions for each of the one or more of the multiple drain cycles, the controller using the input to control the spacings of timings during the peritoneal dialysis treatment.

In variations thereof, the forty-eighth embodiments include ones in which the one or more fractions is a plurality of fractions, the method further comprising accepting input from a user interface of the controller indicating a timing of a first of the plurality of fractions for each of the one or more of the multiple drain cycles, the controller using the input to control the timing of a first of the plurality of fractions during the peritoneal dialysis treatment. In variations thereof, the forty-eighth embodiments include ones in which the one or more fractions is a single fraction, the method further comprising accepting input from a user interface of the controller indicating a timing of the single fraction for each of the one or more of the multiple drain cycles, the controller using the input to control the timing of the single fraction during the peritoneal dialysis treatment. In variations thereof, the forty-eighth embodiments include ones that include accepting input from a user interface of the controller indicating a quantity of an initial one of the portions of the spent peritoneal dialysis other than the one or more fractions, the controller using the input to control the quantity of an initial one of the portions during the peritoneal dialysis treatment. In variations thereof, the forty-eighth embodiments include ones that include accepting input from a user interface of the controller indicating treatment days on which to collect the one or more fractions and corresponding combinations of parameters for each of the treatment days to create a sampling schedule, the controller using the schedule to control the collection of the one or more fractions according to corresponding combinations of parameters over successive peritoneal dialysis treatments.

In variations thereof, the forty-eighth embodiments include ones in which a user interface of the controller accepts input indicating a maximum number of reschedulings of days on which to collect the one or more fractions, the method further comprising, using the controller, preventing input attempting to reschedule more than the maximum number of days on which to collect the one or more fractions. In variations thereof, the forty-eighth embodiments include ones in which a user interface of the controller accepts input indicating a schedule of days on which to collect the one or more fractions by date, day of week, day of month, or number of times in a predefined interval, the method further comprising, using the controller, controlling the days on which the one or more fractions are collected over successive peritoneal dialysis treatments. In variations thereof, the forty-eighth embodiments include ones in which the controller controls a number of the one or more fractions per drain cycle, a number of sample containers to fill with corresponding ones of the one or more fractions during a treatment, or a flow rate of draining, or any combination thereof, responsively to input received from a user interface.

According to forty-ninth embodiments, the disclosed subject matter includes a dialysis system. A dialysis device has a proportioning element configured to generate dialysis fluid and a cycler to deliver dialysis fluid to a patient to perform dialysis therapy. The dialysis device further has a digital controller configured to direct a sequence of operations for the therapy. The dialysis device further includes a wireless interface configured to communicate with a wireless device or to write to or read from a data carrier including one of a near field communication (NFC) device and a radio frequency identification (RFID) device.

In variations thereof, the forty-ninth embodiments include ones in which the dialysis device is configured to upload a prescription for a peritoneal dialysis therapy through the wireless interface. In variations thereof, the forty-ninth embodiments include ones in which the wireless interface is configured to transfer a digital record of therapy data following a treatment to the wireless device. In variations thereof, the forty-ninth embodiments include ones in which the wireless interface is configured to read a prescription or peritoneal dialysis therapy from the wireless device. In variations thereof, the forty-ninth embodiments include ones in which the wireless interface is configured to read patient identifying information from a phone, a tablet, a computer, NFC, or RFID device. In variations thereof, the forty-ninth embodiments include ones in which the wireless interface is configured to read patient information from the wireless device. In variations thereof, the forty-ninth embodiments include ones in which the wireless interface is configured to transfer system logging information to the wireless device. In variations thereof, the forty-ninth embodiments include ones in which the wireless interface is configured to transfer diagnostic system logging information to the wireless device. In variations thereof, the forty-ninth embodiments include ones in which the wireless device includes a phone, a tablet, and NFC device or an RFID device or a computer.

According to fiftieth embodiments, the disclosed subject matter includes a method of priming a dialysis fluid circuit. The method includes priming a dialysis fluid circuit with priming fluid using a pump having a pumping tube segment and running the pump with priming fluid by recirculating the priming fluid for a predetermined period of time beyond that required for priming the dialysis fluid circuit.

In variations thereof, the fiftieth embodiments include ones in which the pump is a peristaltic pump. In variations thereof, the fiftieth embodiments include ones in which the predetermined period of time is effective to break-in the pumping tube segment. In variations thereof, the fiftieth embodiments include ones in which the predetermined period of time is determined based on an estimate of the time or number of pump rotations required to cause a relationship between pump cycles and flow rate to vary by less than a predetermined rate. In variations thereof, the fiftieth embodiments include ones in which the priming includes recirculating priming fluid in a loop through the pumping tube segment. In variations thereof, the fiftieth embodiments include ones in which the predetermined period of time is determined responsive to an estimate of a relationship between pump cycles and flow rate to vary by less than a predetermined rate.

It will be appreciated that the modules, processes, systems, and sections described above can be implemented in hardware, hardware programmed by software, software instruction stored on a non-transitory computer readable medium or a combination of the above. For example, a method for preparing a treatment fluid and/or treating a patient can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their subcomponents or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

It will be evident from the context that in many instances that a water source may be, or include, a water purifier or a water filtration system. See for example, water filtration system 551 in FIGS. 22A through 22C.

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control system, fluid handling systems, medical treatment and/or computer programming arts.

Moreover, embodiments of the disclosed method, system, and computer program product can be implemented in software executed on a programmed general purpose computer, a special purpose computer, a microprocessor, or the like.

Figure 14:
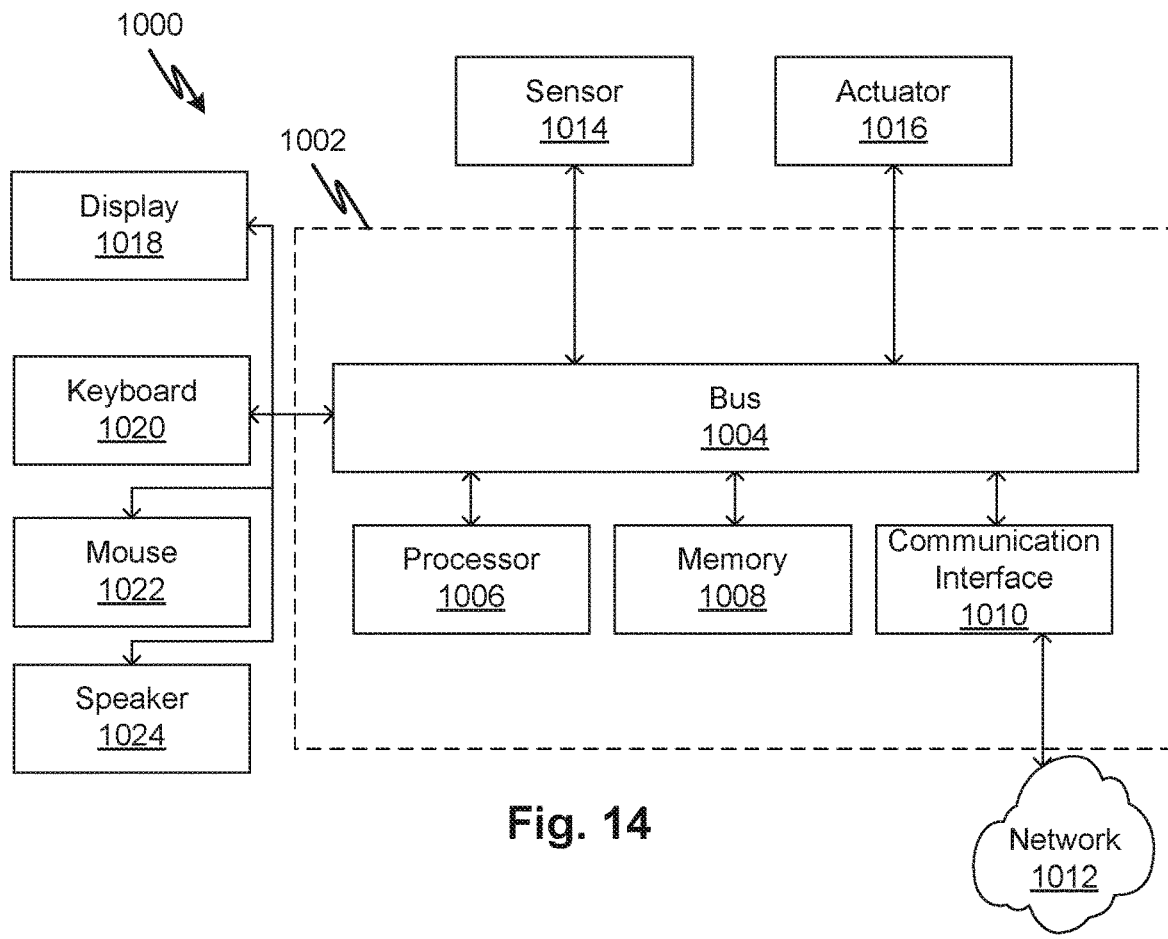
FIG. 14 shows a block diagram of an example computer system according to embodiments of the disclosed subject matter.

FIG. 14 shows a block diagram of an example computer system according to embodiments of the disclosed subject matter. In various embodiments, all or parts of system 1000 may be included in a medical treatment device/system such as a renal replacement therapy system. In these embodiments, all or parts of system 1000 may provide the functionality of a controller of the medical treatment device/systems. In some embodiments, all or parts of system 1000 may be implemented as a distributed system, for example, as a cloud-based system.

System 1000 includes a computer 1002 such as a personal computer or workstation or other such computing system that includes a processor 1006. However, alternative embodiments may implement more than one processor and/or one or more microprocessors, microcontroller devices, or control logic including integrated circuits such as ASIC.

Computer 1002 further includes a bus 1004 that provides communication functionality among various modules of computer 1002. For example, bus 1004 may allow for communicating information/data between processor 1006 and a memory 1008 of computer 1002 so that processor 1006 may retrieve stored data from memory 1008 and/or execute instructions stored on memory 1008. In one embodiment, such instructions may be compiled from source code/objects provided in accordance with a programming language such as Java, C++, C#, .net, Visual Basic™ language, LabVIEW, or another structured or object-oriented programming language. In one embodiment, the instructions include software modules that, when executed by processor 1006, provide renal replacement therapy functionality according to any of the embodiments disclosed herein.

Memory 1008 may include any volatile or non-volatile computer-readable memory that can be read by computer 1002. For example, memory 1008 may include a non-transitory computer-readable medium such as ROM, PROM, EEPROM, RAM, flash memory, disk drive, etc. Memory 1008 may be a removable or non-removable medium.

Bus 1004 may further allow for communication between computer 1002 and a display 1018, a keyboard 1020, a mouse 1022, and a speaker 1024, each providing respective functionality in accordance with various embodiments disclosed herein, for example, for configuring a treatment for a patient and monitoring a patient during a treatment.

Computer 1002 may also implement a communication interface 1010 to communicate with a network 1012 to provide any functionality disclosed herein, for example, for alerting a healthcare professional and/or receiving instructions from a healthcare professional, reporting patient/device conditions in a distributed system for training a machine learning algorithm, logging data to a remote repository, etc. Communication interface 1010 may be any such interface known in the art to provide wireless and/or wired communication, such as a network card or a modem.

Bus 1004 may further allow for communication with a sensor 1014 and/or an actuator 1016, each providing respective functionality in accordance with various embodiments disclosed herein, for example, for measuring signals indicative of a patient/device condition and for controlling the operation of the device accordingly. For example, sensor 1014 may provide a signal indicative of a viscosity of a fluid in a fluid circuit in a renal replacement therapy device, and actuator 1016 may operate a pump that controls the flow of the fluid responsively to the signals of sensor 1014.

It is, thus, apparent that there is provided, in accordance with the present disclosure, methods, devices, and system for preparing fluids, managing fluids, sterilizing fluids, treating patients and other functions. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A system for performing peritoneal dialysis, comprising:
    a fluid circuit with at least one fluid inlet and a mixing container;
    a peritoneal dialysis system having a peritoneal dialysis system controller, valve actuators, one or more pumps, to pump and direct concentrate and water selectively through at least at times and through portions of the fluid circuit to transfer concentrate and water, through the at least one fluid inlet, to the mixing container to form dialysis fluid;
    a water supply source with a water pump, the water pump being controlled by a water supply controller, the water supply source having a water outlet which is fluidly connected to the at least one fluid inlet of the fluid circuit by a water line; and
    a command interface between the peritoneal dialysis system controller and the water supply controller, wherein
    the peritoneal dialysis system controller is configured to transmit one or more commands to the water supply controller through the water line to start and stop the water pump.

2. The system according to claim 1, wherein
    the peritoneal dialysis system controller transmits the one or more commands by generating a pressure drop in the water line, and
    the water supply source is configured to detect the pressure drop as the one or more commands.

3. The system according to claim 1, wherein
    the peritoneal dialysis system further comprises a pressure modulator configured to generate pulses in the water line, and
    the peritoneal dialysis system controller transmits the one or more commands by controlling the pressure modulator to generate one or more pulses in the water line.

* * * * *